US010676534B2

(12) United States Patent
Rome et al.

(10) Patent No.: US 10,676,534 B2
(45) Date of Patent: Jun. 9, 2020

(54) VAULTS ENGINEERED FOR HYDROPHOBIC DRUG DELIVERY

(71) Applicant: The Regents of the University of California, Oakland, CA (US)

(72) Inventors: Leonard H. Rome, Los Angeles, CA (US); Daniel Buehler, Los Angeles, CA (US); Heather D. Maynard, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 202 days.

(21) Appl. No.: 15/027,467

(22) PCT Filed: Oct. 17, 2014

(86) PCT No.: PCT/US2014/061019
§ 371 (c)(1),
(2) Date: Apr. 6, 2016

(87) PCT Pub. No.: WO2015/058025
PCT Pub. Date: Apr. 23, 2015

(65) Prior Publication Data
US 2016/0235862 A1    Aug. 18, 2016

Related U.S. Application Data

(60) Provisional application No. 62/028,247, filed on Jul. 23, 2014, provisional application No. 61/939,130, filed on Feb. 12, 2014, provisional application No. 61/892,951, filed on Oct. 18, 2013.

(51) Int. Cl.
| *C12N 7/00* | (2006.01) |
| *C07K 14/47* | (2006.01) |
| *C07K 16/28* | (2006.01) |
| *C07K 16/30* | (2006.01) |
| *C07K 14/31* | (2006.01) |
| *A61K 47/69* | (2017.01) |
| *A61K 47/56* | (2017.01) |
| *A61K 9/00* | (2006.01) |
| *A61K 31/203* | (2006.01) |
| *A61K 31/365* | (2006.01) |
| *A61K 31/704* | (2006.01) |
| *A61K 31/7048* | (2006.01) |

(52) U.S. Cl.
CPC ............ *C07K 16/30* (2013.01); *A61K 9/0019* (2013.01); *A61K 31/203* (2013.01); *A61K 31/365* (2013.01); *A61K 31/704* (2013.01); *A61K 31/7048* (2013.01); *A61K 47/56* (2017.08); *A61K 47/6903* (2017.08); *A61K 47/6949* (2017.08); *C07K 14/31* (2013.01); *C07K 14/4702* (2013.01); *C07K 16/28* (2013.01); *C12N 7/00* (2013.01); *C07K 2317/76* (2013.01); *C07K 2319/00* (2013.01); *C07K 2319/30* (2013.01); *C07K 2319/33* (2013.01); *C07K 2319/705* (2013.01); *C07K 2319/74* (2013.01); *C12N 2770/24233* (2013.01); *C12N 2770/24271* (2013.01)

(58) Field of Classification Search
CPC .. A61K 31/203; A61K 31/365; A61K 31/704; A61K 31/7048; A61K 47/48961; A61K 47/56; A61K 47/6903; A61K 47/6949; A61K 9/0019; C07K 14/31; C07K 16/28; C07K 16/30; C07K 2317/76; C07K 2319/00; C07K 2319/30; C07K 2319/33; C07K 2319/705; C07K 2319/74; C07K 14/4702; C12N 2770/24233; C12N 2770/24271; C12N 7/00
See application file for complete search history.

(56) References Cited

U.S. PATENT DOCUMENTS

| 7,236,536 B2 | 6/2007 | Hochwald et al. |
| 8,551,781 B2 | 10/2013 | Rome et al. |
| 2011/0201112 A1* | 8/2011 | Rome .................. C07K 14/005 435/375 |

FOREIGN PATENT DOCUMENTS

WO    WO-2013036622 A2 *    3/2013    ............. A61K 38/08

OTHER PUBLICATIONS

Daniel C. Buehler, Vaults Engineered for Hydrophobic Drug Delivery, Small. May 23, 2011; 7(10): 1432-1439.*
Devin M Nelson, Extended and Sequential Delivery of Protein from Injectable Thermoresponsive Hydrogels , Published in final edited form as: J Biomed Mater Res A. Mar. 1, 2012; 100(3): 776-785.*
Nicholas M. Matsumoto,Smart Vaults: Thermally-Responsive Protein Nanocapsules, vol. 7, No. 1 , pp. 867-874, published online 2012, ACS Nano.*

(Continued)

*Primary Examiner* — Rachael E Bredefeld
*Assistant Examiner* — Erinne R Dabkowski
(74) *Attorney, Agent, or Firm* — Suzannah K. Sundby, Esq.; Canady + Lortz LLP

(57) ABSTRACT

The invention relates to compositions of vault complexes for use as delivery agents for hydrophobic and/or aqueous insoluble therapeutic compounds. In one aspect, provided herein is a vault complex comprising a modified major vault protein (MVP), wherein the modified major vault protein comprises a fusion peptide, wherein said fusion peptide is fused to the N-terminus of the major vault protein, and wherein said peptide provides enhanced sequestering of a hydrophobic and/or aqueous insoluble therapeutic compound within the vault complex.

14 Claims, 9 Drawing Sheets
Specification includes a Sequence Listing.

(56) References Cited

OTHER PUBLICATIONS

International Search Report received in PCT/US2014/061019, dated Jan. 30, 2015.
Written Opinion received in PCT/US2014/061019, dated Jan. 30, 2015.

* cited by examiner

VAULTS ENGINEERED FOR HYDROPHOBIC DRUG DELIVERY

REFERENCE TO A SEQUENCE LISTING SUBMITTED VIA EFS-WEB

The content of the ASCII text file of the sequence listing named "20141008_034044_142WO1_seq" which is 160 kb in size was created on Oct. 8, 2014, and electronically submitted via EFS-Web herewith the application is incorporated herein by reference in its entirety.

FIELD OF THE INVENTION

The present invention relates generally to a vault complex and compositions thereof for the delivery of therapeutic compounds, such as therapeutic compounds that are hydrophobic and/or have poor aqueous solubility.

BACKGROUND OF THE INVENTION

Although chemically produced drugs have a long record of success as therapeutic agents, they are not without serious limitations. The vast majority are small hydrophobic molecules that are limited in use due to their poor pharmacokinetic and pharmacodynamic properties. While much attention has focused on generating new compounds or modifying existing ones for improved efficacy, a new paradigm has emerged within the existing dogma of drug therapy. The development of nanoparticle based platforms enhances the delivery of current compounds and circumvents the adverse pharmacological properties of conventional drugs. These new drug delivery systems (DDS) overcome current limitations by offering environments for improved solubility, thereby eliminating the need for toxic organic solvents. Common examples include the use of dendrimers, liposomes, or conjugation to polymers, such as polyethylene glycol (PEG). Although the latter two have had success and have been approved for clinical use, they are not without pitfalls, such as size limitations and lack of tissue targeting. Therefore, new nanoparticles and new strategies for drug delivery are needed.

Vaults are cytoplasmic ubiquitous ribonucleoprotein particles first described in 1986 that are found in most eukaryotic cells (Kedersha et al., J Cell Biol, 103(3):699-709 (1986)). Native vaults are 12.9±1 MDa ovoid spheres with overall dimensions of approximately 40 nm in width and 70 nm in length (Kong et al., Structure, 7(4):371-379 (1999); Kedersha et al., J Cell Biol, 112(2):225-235 (1991)), present in nearly all eukaryotic organisms with between $10^4$ and $10^7$ particles per cell (Suprenant, Biochemistry, 41(49):14447-14454 (2002)). Despite their cellular abundance, vault function remains elusive, although they have been linked to many cellular processes, including the innate immune response, multidrug resistance in cancer cells, multifaceted signaling pathways, and intracellular transport (Berger et al., Cell Mol Life Sci, 66(1):43-61 (2009)).

Vaults are highly stable structures in vitro, and a number of studies indicate that the particles are non-immunogenic (Champion et al., PLoS One, 4(4):e5409 (2009)). Vaults can be engineered and expressed using a baculovirus expression system and heterologous proteins can be encapsulated inside of these recombinant particles using a protein-targeting domain termed INT for vault INTeraction domain. Several heterologous proteins have been fused to the INT domain (e.g., fluorescent and enzymatic proteins) and these fusion proteins can be added to the recombinant vaults and, due to the dynamic nature of the vaults, the fused INT proteins access the interior of the particle where they bind non-covalently and retain their native characteristics, thus conferring new properties onto these vaults (Stephen et al., J Biol Chem, 276(26):23217-23220 (2001); Kickhoefer et al., Proc Natl Acad Sci USA, 102(12):4348-4352 (2005)).

Vaults have also been engineered to contain a discoidal phospholipid bilayer nanodisks (NDI), by the self-assembly of a small discoidal lipid bilayer lipoprotein complex, which absorbed ATRA (Buehler, D. C., et al., Small, 2011, 7(10): 1432-9). As these nanodisks of Δapo-AI protein were conjugated with the INT domain, ATRA did not directly interact with the vault but was rather carried into the vault indirectly via this nanodisk conjugation with INT. The formation of NDI lipoprotein complexes followed by vault packaging remains a time consuming and complicated multi-step process. Furthermore, as Δapo-AI is expressed in E. coli, there is the possibility that during purification it may bind liberated host bacterial membrane constituents such as Lipopolysaccharide (LPS), an endotoxin which elicits a strong pro-inflammatory immune response and poses a risk if administered to humans (Erridge, et al., Microbes and infection/Institut Pasteur, 2002, 4(8): 837-51). Apo-AI naturally binds LPS in order to mitigate host inflammatory response thru rapid clearance via the liver (Henning, et al., Innate immunity, 2011, 17(3): p. 327-37). As such, NDI produced in bacteria may act to carry LPS to the targeted cells, possibly inducing a harmful pro-inflammatory response.

Vaults are generally described in U.S. Pat. No. 7,482,319, filed on Mar. 10, 2004; U.S. Pat. No. 6,156,879, filed on Jun. 3, 1998; U.S. Pat. No. 6,555,347, filed on Jun. 28, 2000; U.S. Pat. No. 6,110,740, filed on Mar. 26, 1999; and PCT Publication No. WO 1999/62547 filed on Jun. 3, 1998. Vault compositions for immunization against chlamydia genital infection are described in U.S. Pat. No. 8,124,109, filed on May 15, 2009. The entire contents of these applications are incorporated herein by reference in their entirety for all purposes.

SUMMARY OF THE INVENTION

In one aspect, provided herein is a vault complex comprising a modified major vault protein (MVP), wherein the modified major vault protein comprises a fusion peptide, wherein said fusion peptide is fused to the N-terminus of the major vault protein, and wherein said peptide provides enhanced sequestering of a hydrophobic and/or aqueous insoluble therapeutic compound within the vault complex.

In some embodiments, the fusion peptide binds the therapeutic compound non-covalently and/or binds a lipophilic substance non-covalently, providing an increased affinity of the therapeutic compound to the inside of the vault complex as compared to a control vault complex, thereby providing the enhanced sequestering of the therapeutic compound.

In some embodiments, the fusion peptide comprises one or more amphipathic α-helix structures. In some embodiments, the one or more amphipathic α-helix structures bind the therapeutic compound non-covalently and/or bind a lipophilic substance non-covalently, providing an increased affinity of the therapeutic compound to the inside of the vault complex, thereby providing the enhanced sequestering of the therapeutic compound. In some embodiments, the fusion peptide has 1 to 10 amphipathic α-helix structures, 1 to 9 amphipathic α-helix structures, 1 to 8 amphipathic α-helix structures, 1 to 7 amphipathic α-helix structures, 1 to 6 amphipathic α-helix structures, 1 to 5 amphipathic α-helix structures, 1 to 4 amphipathic α-helix structures, 1 to 3 amphipathic α-helix structures, 1 or 2 amphipathic α-helix structures, or 1 amphipathic α-helix structure. In some embodiments, each amphipathic α-helix structure of the fusion peptide has 10 to 50 amino acids, 10 to 40 amino acids, or 18 to 35 amino acids.

In some embodiments, the modified major vault protein comprises a fusion peptide fused to the N-terminus of the major vault protein, and a fusion peptide fused to the C-terminus of the major vault protein, wherein said fusion peptide fused to the N-terminus of the major vault protein provides enhanced sequestering of a hydrophobic and/or aqueous insoluble therapeutic compound within the vault complex, and wherein said fusion peptide fused to the C-terminus of the major vault protein provides a targeting domain.

In another aspect, provided herein is a composition for delivery of a hydrophobic and/or aqueous insoluble therapeutic compound comprising the therapeutic compound and a vault complex, wherein the vault complex comprises a modified major vault protein, wherein the modified major vault protein comprises a fusion peptide, wherein said fusion peptide is fused to the N-terminus of the major vault protein, and wherein said peptide provides enhanced sequestering of the therapeutic compound within the vault complex.

In another aspect, provided herein is a method for delivery of a hydrophobic and/or aqueous insoluble therapeutic compound comprising administering a composition comprising the therapeutic compound and a vault complex, wherein the vault complex comprises a modified major vault protein, wherein the modified major vault protein comprises a fusion peptide, wherein said fusion peptide is fused to the N-terminus of the major vault protein, and wherein said peptide provides enhanced sequestering of the therapeutic compound within the vault complex.

In one aspect, provided herein is a composition comprising: a) a vault complex comprising a modified major vault protein, wherein the modified major vault protein comprises a fusion peptide, wherein said fusion peptide is fused to the N-terminus of the major vault protein, and wherein said peptide provides enhanced sequestering of a hydrophobic and/or aqueous insoluble therapeutic compound within the vault complex; and b) the therapeutic compound sequestered inside the vault complex.

In another aspect, provided herein is a composition comprising a) a vault complex comprising a modified major vault protein, wherein the modified major vault protein comprises a fusion peptide, wherein said fusion peptide is fused to the N-terminus of the major vault protein, and wherein said peptide provides enhanced sequestering of a hydrophobic and/or aqueous insoluble therapeutic compound within the vault complex; b) the therapeutic compound sequestered inside the vault complex and c) a hydrogel. In some embodiments, the vault complex is covalently attached to the hydrogel. In some embodiments, the vault complex is covalently attached to the hydrogel by one or more linkers. In some embodiments, the one or more linkers comprises one or more labile bonds, wherein the one or more labile bonds break in vivo, resulting in detachment of the vault complex from the hydrogel. In some embodiments, the one or more linkers comprises one or more labile bonds selected from the group consisting of an ester bond, an amide bond, a disulfide bond, an ether bond and a thioether bond. In some embodiments, the one or more labile bonds are ester bonds. In some embodiments, the one or more linkers are covalently bound to the vault complex by an amide bond, and the one or more linkers are covalently bound to the hydrogel by an amide bond. In some embodiments, the one or more linkers are covalently bound to the vault complex by an amide bond, and the one or more linkers are covalently bound to the hydrogel by an amide bond, wherein the linkers further comprise one or more labile bonds selected from the group consisting of an ester bond, an amide bond, a disulfide bond, an ether bond and a thioether bond. In some embodiments, the one or more linkers are covalently bound to the vault complex by an amide bond, and the one or more linkers are covalently bound to the hydrogel by an amide bond, wherein the linkers further comprise one or more ester bonds.

In another aspect, provided herein is a composition comprising a) a vault complex comprising a modified major vault protein, wherein the modified major vault protein comprises a fusion peptide, wherein said fusion peptide is fused to the N-terminus of the major vault protein, and wherein said peptide provides enhanced sequestering of a hydrophobic and/or aqueous insoluble therapeutic compound within the vault complex; b) the therapeutic compound sequestered inside the vault complex and c) a thermally responsive polymer covalently attached to the vault complex, wherein vault complexes attached to the thermally responsive polymer do not aggregate at room temperature, and wherein vault complexes attached to the thermally responsive polymer aggregate at body temperature.

In an embodiment, the vault complex comprises MVP fused to an amphipathic α-helix peptide, such as NS5A1-31 peptide from Hepatitis C. In a further embodiment, the MVP is fused to Z domain of Staphylococcal Protein A (SpA). In a further embodiment, the MVP is fused to the amphipathic α-helix peptide NS5A1-31 from Hepatitis C at the N-terminus of MVP.

In another embodiment, the MVP is fused to the Z domain of Staphylococcal Protein A (SpA) at the C-terminus of MVP. In a further embodiment, the MVP is fused to an amphipathic α-helix NS5A1-31 from Hepatitis C at the N-terminus of MVP and is fused to Z domain of Staphylococcal Protein A (SpA) at the C-terminus of MVP. In a further embodiment, the sequence of the amphipathic α-helix NS5A1-31 from Hepatitis C comprises SEQ ID NO:17. In a further embodiment, the sequence of the Z domain of Staphylococcal Protein A (SpA) comprises SEQ ID NO:18.

In further embodiments of the above, the hydrophobic agent is selected from the group consisting of All-trans Retinoic Acid (ATRA), amphotericin B, bryostatin 1, GSK744, MK-2048, IQP0528, CSIS, and dapivirine.

In some embodiments, provided herein is a vault complex comprising a modified major vault protein (MVP), wherein the modified MVP comprises a fusion peptide, wherein said fusion peptide is fused to the N-terminus of the MVP, and wherein said fusion peptide provides enhanced sequestering of a hydrophobic and/or aqueous insoluble therapeutic compound within the vault complex. In some embodiments of the vault complex the fusion peptide binds the therapeutic compound non-covalently and/or binds a lipophilic substance non-covalently. In some embodiments of the vault complex wherein the fusion peptide binds the therapeutic compound non-covalently and/or binds a lipophilic substance non-covalently, the therapeutic compound has an increased affinity to the inside of the vault complex as compared to a control vault complex. In some embodiments of the vault complex, the fusion peptide has one or more amphipathic α-helix structures. In some embodiments of the vault complex, the fusion peptide has 1 to 10 amphipathic α-helix structures. In some embodiments of the vault complex, the fusion peptide has 1 to 5 amphipathic α-helix structures. In some embodiments of the vault complex, the fusion peptide has 1 amphipathic α-helix structure.

In some embodiments, provided herein is a vault complex comprising a modified major vault protein (MVP), wherein the modified MVP comprises a fusion peptide, wherein said fusion peptide is fused to the N-terminus of the MVP, and wherein said fusion peptide provides enhanced sequestering of a hydrophobic and/or aqueous insoluble therapeutic compound within the vault complex, and wherein the fusion peptide has 1 to 10 NS5A amphipathic α-helix structures. In some embodiments of the vault complex, the fusion peptide having 1 to 10 NS5A amphipathic α-helix structures binds the therapeutic compound non-covalently and/or binds a lipophilic substance non-covalently. In some embodiments of the vault complex wherein the fusion peptide having 1 to 10 NS5A amphipathic α-helix structures binds the therapeutic compound non-covalently and/or binds a lipophilic substance non-covalently, the therapeutic compound has an increased affinity to the inside of the vault complex as compared to a control vault complex. In some embodiments of the vault complex, the fusion peptide has 1 to 5 NS5A amphipathic α-helix structures. In some embodiments of the vault complex, the fusion peptide has 1 NS5A amphipathic α-helix structure. In some embodiments, the fusion peptide comprises SEQ ID NO:17. In some embodiments, the NS5A amphipathic α-helix structure comprises SEQ ID NO:19.

In some embodiments, the vault complex of any one of the above embodiments further comprises a second fusion peptide fused to the C-terminus of the MVP, wherein the second fusion peptide provides targeting of the vault complex to a cell. In some embodiments, the second fusion peptide provides targeting of the vault complex to the cell by binding to a cell receptor. In some embodiments, the second fusion peptide provides targeting of the vault complex to the cell by binding to an antibody, wherein the antibody binds to the cell. In some embodiments, the second fusion peptide comprises the Z domain of Staphylococcal Protein A (SpA). In some embodiments, the second fusion peptide comprises SEQ ID NO:18.

In some embodiments, provided herein is a composition for delivery of a hydrophobic and/or aqueous insoluble therapeutic compound comprising the therapeutic compound and the vault complex according to any of the above embodiments. In some embodiments of the composition, the therapeutic compound is selected from the group consisting of All-trans Retinoic Acid (ATRA), amphotericin B, bryostatin 1, GSK744, MK-2048, IQP0528, CSIS, and dapivirine. In some embodiments of the composition, the composition further comprises a hydrogel. In some embodiments of the composition comprising a hydrogel, the vault complex is covalently attached to the hydrogel. In some embodiments, the vault complex is covalently attached to the hydrogel by a linker, wherein the linker comprises one or more labile bonds. In some embodiments, the one or more labile bonds breaks in vivo, resulting in detachment of the vault complex from the hydrogel. In some embodiments of the composition, the vault complex is covalently attached to a thermally responsive polymer.

In some embodiments, provided herein is a method for delivery of a therapeutic compound comprising administering an effective amount of the composition of any of the above embodiments to a subject in need thereof. In some embodiments, the composition is injected into a solid tumor. In some embodiments, the composition is administered to a mucosal surface.

BRIEF DESCRIPTION OF THE DRAWINGS

These and other features, aspects, and advantages of the present invention will become better understood with regard to the following description, and accompanying drawings, where:

FIG. 1A) NS5A1-31 consists of an amphipathic α-helix with asymmetrical charge distribution along the polar face. FIG. 1B) Solved structure of NS5A domain I reveals NS5A1-31 anchors the remainder of the protein to the plasma membrane surface as covalently linked Zinc binding dimer motif suspected of accommodating viral RNA during replication.

FIG. 8A) Negative stain TEM of AH1 vault complexes before treatment with 5% Tween 20 show significant internalized mass with a majority of the nanoparticles (arrowheads). FIG. 8B) Negative stain TEM of AH1 vault complexes after treatment with 5% Tween 20 indicate a loss in the internalized mass prominence and frequency suggesting dynamic, detergent soluble nature.

FIG. 10A) In vitro latent HIV activation using bryostatin 1 sequestered in AH1 vault complexes compared to empty vault complexes on J-Lat 10.6 cells for 48 hrs. In these assays 50 nM of byrostatin 1 (without vaults) was used as a positive control and induced GFP expression in 30.6% (±0.6%) of cells. Error bars indicate ±1 SD (N=3). NS not significant, **p<0.0001 empty vault vs. Vault+Byrostatin 1 (2-sided t-test). FIG. 10B) In vitro stimulation of CD69 HIV provirus latency activation biomarker using bryostatin 1 sequestered in AH1 vault complexes compared to empty vault complexes on primary human PBMCs for 24 hrs. Positive control stimulations with 50 nM of byrostatin 1 compound (without vaults) induced CD69 expression in 69.4% (±31.3%) of cells. Error bars indicate ±1 SD (N=4 different cell donors).

NS not significant, * p<0.01 empty vault vs. Vault+Byrostatin 1 (2-sided t-test). FIG. 10C) In vivo CD69 stimulation in C57/b16 mouse splenocytes 24 hours post i.v. injection of control media, bryostatin 1, or bryostatin 1 sequestered in AH1 vault complexes, or empty AH1 vaults. Error bars indicate ±1 SD (3-5 mice per group).

DETAILED DESCRIPTION OF THE INVENTION

Figure 1A:
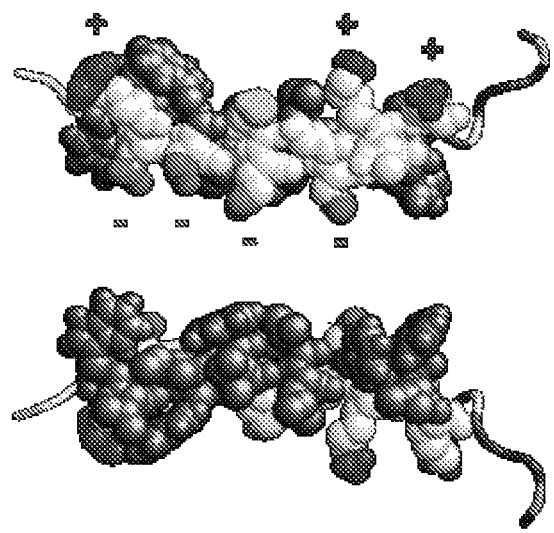
FIGS. 1A and 1B.

Provided herein are vault complexes comprising a modified major vault protein, wherein the modified major vault protein comprises a fusion peptide, wherein said fusion peptide is fused to the N-terminus of the major vault protein, and wherein said peptide provides enhanced sequestering of a hydrophobic and/or aqueous insoluble therapeutic compound within the vault complex. Also provided are compositions thereof for use in delivering the therapeutic compound to a subject, i.e., to deliver a therapeutic amount of the compound to a subject in need thereof for treating a disease. Further provided are compositions comprising the vault complex and a hydrogel or a thermally responsive polymer, and uses thereof for use in delivering the therapeutic compound to a subject, i.e., to deliver a therapeutic amount of the compound to a subject in need thereof for treating a disease.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as BIOTECHNOLOGY: A TEXTBOOK OF INDUSTRIAL MICROBIOLOGY (Brock, Sinauer Associates, Inc., Second Edition, 1989), MOLECULAR CLONING: A LABORATORY MANUAL (Sambrook et al., 1989, $2^{nd}$ ed.); OLIGONUCLEOTIDE SYNTHESIS (M. J. Gait, ed., 1984); METHODS IN ENZYMOLOGY (Academic Press, Inc.); CURRENT PROTOCOLS IN MOLECULAR BIOLOGY (F. M. Ausubel et al., eds., 1987, and periodic updates); PCR: THE POLYMERASE CHAIN REACTION (Mullis et al., eds., 1994), DICTIONARY OF MICROBIOLOGY AND MOLECULAR BIOLOGY (Singleton et al., $2^{nd}$ ed., J. Wiley and Sons, New York, N.Y., 1994); and ADVANCED ORGANIC CHEMISTRY REACTIONS, MECHANISMS AND STRUCTURE (March, $4^{th}$ ed., John Wiley and Sons, New York, N.Y., 1992), which provide one skilled in the art with a general guide to many of the terms and methods used in the present disclosure. Additional methods used in the Examples are described in manuals including ADVANCED BACTERIAL GENETICS (Davis, Roth and Botstein, Cold Spring Harbor Laboratory, 1980), EXPERIMENTS WITH GENE FUSIONS (Silhavy, Berman and Enquist, Cold Spring Harbor Laboratory, 1984), EXPERIMENTS IN MOLECULAR GENETICS (Miller, Cold Spring Harbor Laboratory, 1972) EXPERIMENTAL TECHNIQUES IN BACTERIAL GENETICS (Maloy, in Jones and Bartlett, 1990), and A SHORT COURSE IN BACTERIAL GENETICS (Miller, Cold Spring Harbor Laboratory 1992).

Unless defined otherwise, technical and scientific terms used herein have the same meaning as commonly understood by one of ordinary skill in the art to which this invention belongs.

Definitions

Terms used in the claims and specification are defined as set forth below unless otherwise specified.

As used herein, the term "vault" or "vault particle" refers to a large cytoplasmic ribonucleoprotein (RNP) particle found in eukaryotic cells. The naturally-occurring vault or vault particle found in higher eukaryotic cells, including humans, is composed of MVP, VPARP, and/or TEP1 proteins and one or more untranslated vRNA molecules.

As used herein, the term "vault complex" and "recombinant vault" refers to a vault that is engineered to sequester a small molecule or protein of interest inside of the vault. A vault complex can include all the components of a vault or vault particle or just a subset, including any modified components, such as MVP modified with a fusion peptide at either or both of the C-terminus or N-terminus of the MVP, as described herein. A vault complex with just a subset of the components found in vaults or vault particles can also be termed a "vault-like particle" or a "vault complex particle". Examples of vault-like particles include: 1) MVP without VPARP, TEP1 and vRNA; 2) MVP and either VPARP or a portion of VPARP, without TEP1 and vRNA; 3) MVP and TEP1 or a portion of TEP1 with or without the one or more than one vRNA, and without VPARP; 4) MVP without VPARP, TEP1 and vRNA, where the MVP is modified to attract a specific substance within the vault-like particle, or modified to attract or target the vault complex to a specific tissue, cell type or environmental medium, or modified both to attract a specific substance within the vault complex and to attract/target the vault-like particle to a specific tissue, cell type or environmental medium; and 5) MVP, and either VPARP or a portion of VPARP, or TEP1 or a portion of TEP1 with or without the one or more than one vRNA, or with both VPARP or a portion of VPARP, and TEP1, with or without the one or more than one vRNA, where one or more than one of the MVP, VPARP or portion of VPARP and TEP1 is modified to attract a specific substance within the vault-like particle, or modified to attract the vault-like particle to a specific tissue, cell type or environmental medium, or modified both to attract a specific substance within the vault complex and to attract the vault complex to a specific tissue, cell type or environmental medium. As used herein, a vault complex is sometimes referred to as a "vault nanoparticle". Vault complexes include, without limitation, those as described in the Examples, such as AH1, AH1Z, AH2, or AH2Z.

As used herein, the term "sequestered" inside the vault complex, or "sequestering" of a compound inside the vault complex refers to the increase in concentration of a substance within the vault complex, with retention of the compound within the vault complex. The substance being sequestered inside the vault complex, such as a lipophilic substance, or a hydrophobic and/or aqueous insoluble therapeutic compound, will have an affinity to the internal environment of the vault, and will therefor bind preferentially inside the vault such that the sequestered material is at a much higher concentration than would be due to diffusion in and out of the vault interior. The compound sequestered inside the vault complex is retained within the vault complex, and is slowly released by the vault complex. The slow release provides a level of safety for delivery of the drug to a specific location, for example by targeting of the vault complex to a specific cell type, or by directly injecting the vault complex into, for example, a solid tumor. The slow release of the compound provides localized delivery of the compound to the targeted site, such that the systemic exposure to the compound is very low, while delivering a therapeutically effective amount as it is released at the target site. The compound levels sequestered inside the vault complexes as described herein can be measured by comparison to a control vault complex, e.g., a similar vault complex that lacks the fusion peptide on the MVP, or that has a fusion peptide that does not provide enhanced binding of the lipophilic substance or hydrophobic and/or aqueous insoluble therapeutic compound. A therapeutic compound as described herein is sequestered at a level that is greater than 20, greater than 40, greater than 60, greater than 80, greater than 100, greater than 200, greater than 500, or greater than 1000 molecules of compound per vault complex particle.

As used herein, the term "hydrogel" refers to a network of polymer chains that are hydrophilic, forming a colloidal gel dispersed in water. In one aspect, a hydrogel as described herein is a "diblock copolypeptide hydrogel (DCH)", in which the polymer chains are polypeptides. Such diblock copolypeptide hydrogels are described in US Patent Application Publication No. 2012/0093722, the disclosure of which is hereby incorporated herein by reference as it relates to DCH.

As used herein, the term "fusion peptide" refers to a polypeptide sequence that is fused to the major vault protein, or to the INT domain. In some aspects, the fusion peptide is a peptide having an amphipathic α-helical structure, wherein the peptide is fused to the N-terminus of the major vault protein. The major vault protein fused to a fusion peptide at either or both of the C-terminus and N-terminus is an example of a "fusion protein", i.e., wherein the fused peptide/protein are expressed so that they are covalently joined by a peptide bond within the resulting protein. Such recombinant fusion proteins are generated by methods known to those of skill in the art, e.g., by recombinant DNA methods to join two or more genes or portions of genes that are translated to generate the fusion protein.

As used herein, the term "amphipathic α-helix peptide" or "amphipathic α-helix structure" or the like, refers to peptides as are known in the art that have a sequence that forms an α-helix such that one face of the α-helix contains primarily hydrophobic amino acids. Such peptides as known in the art can be readily adapted to make fusion peptides and the corresponding vault complexes as described herein. Such amphipathic α-helix peptides include, but are not limited to, those described in (Mishra et al., Journal of Biological Chemistry, 1994, 269(10): 7185-7191; Epand et al., Journal of Biological Chemistry, 1989, 264(8): 4628-4635; Maass et al., Journal of Cell Science, 2009, 122(5): 625-635; Gouttenoire et al., Journal of Virology, 2009, 83(21): 11378-11384; and Wang et al., Journal of Biological Chemistry, 2005, 280(6): 4154-4165; Segrest et al., Journal of Lipid Research, 1992, 33: 141-166; Segrest et al., Adv Protein Chem, 1994, 45: 303-69), including fusion peptides readily derived therefrom, or analogs thereof, the disclosures of which are hereby incorporated herein by reference as they relate to amphipathic α-helical peptides.

As used herein, the term "vault packaging domain" or "vault interaction domain" is a domain that is responsible for interaction or binding of a heterologous fusion protein with a vault protein, or interaction of a VPARP with a vault protein, such as a MVP. As used herein, the term "INT domain" is a vault interaction domain from a vault poly ADP-ribose polymerase (VPARP) that is responsible for the interaction of VPARP with a major vault protein (MVP). The term "INT domain" refers to a major vault protein (MVP) interaction domain comprising amino acids 1563-1724 of VPARP.

As used herein, the term "MVP" is major vault protein. The term "CP-MVP" is a fusion protein with a cysteine-rich peptide fused to the N-terminus of the major vault protein.

The term "VPARP" refers to a vault poly ADP-ribose polymerase.

As used herein, the term "TEP-1" is a telomerase/vault associated protein 1.

As used herein, the term "vRNA" is an untranslated RNA molecule found in vaults.

As used herein, the term "vector" is a DNA or RNA molecule used as a vehicle to transfer foreign genetic material into a cell. The four major types of vectors are plasmids, bacteriophages and other viruses, cosmids, and artificial chromosomes. Vectors can include an origin of replication, a multi-cloning site, and a selectable marker.

As used herein, a "cell" includes eukaryotic and prokaryotic cells.

As used herein, the terms "organism", "tissue", and "cell" include naturally occurring organisms, tissues and cells, genetically modified organisms, tissues and cells, and pathological tissues and cells, such as tumor cell lines in vitro and tumors in vivo.

As used herein, the term "extracellular environment" is the environment external to the cell.

As used herein, the term "in vivo" refers to processes that occur in a living organism.

A "subject" referred to herein can be any animal, including a mammal (e.g., a laboratory animal such as a rat, mouse, guinea pig, rabbit, primates, etc.), a farm, or commercial animal (e.g., a cow, horse, goat, donkey, sheep, etc.), a domestic animal (e.g., cat, dog, ferret, etc.), an avian species, or a human.

The term "mammal" as used herein includes both humans and non-humans and include but is not limited to humans, non-human primates, canines, felines, murines, bovines, equines, and porcines.

As used herein, the term "human" refers to "*Homo sapiens.*"

As used herein, the term "agents" or "pharmaceutical agents" refers to any compound that can be used as a therapeutic, i.e., that can be dosed to a subject in need thereof at a therapeutically effective amount, so as to treat a disease, for example resulting in ameliorating a symptom of a disease. While generally a pharmaceutical agent can be any therapeutic agent, include a biological molecule such as an antibody, peptide, nucleic acid or the like, preferred pharmaceutical agents for use in the vault complexes and methods as described herein are small molecule pharmaceutical agents.

As used herein, the term "hydrophobic agent" or "hydrophobic pharmaceutical agent" or "hydrophobic therapeutic compound" refers to a compound that has a therapeutic effect, i.e., can be delivered in a therapeutically effective amount to treat a disease, which is generally insoluble in aqueous solutions and which has a greater solubility in a non-polar solvent. Such compounds as described herein as insoluble in aqueous solution or aqueous insoluble does not necessarily mean that the compound is incapable of being dissolved in an aqueous solution, but that it is soluble only to a very slight degree. In one aspect a therapeutic compound that is "hydrophobic and/or aqueous insoluble" refers to such therapeutic compound having a log P of greater than 0, greater than 0.5, greater than 1.0, greater than 1.5, greater than 2.0, greater than 2.5, greater than 3.0, greater than 3.5, greater than 4.0, greater than 4.5, or greater than 5.0 or an aqueous solubility of less than 10 mg/mL, less than 5 mg/mL, less than 2 mg/mL, less than 1 mg/mL, less than 0.5 mg/mL, less than 0.2 mg/mL, less than 0.1 mg/mL, less than 0.05 mg/mL, less than 0.02 mg/mL or less than 0.01 mg/mL, or to such compounds having a log P of greater than 0, greater than 0.5, greater than 1.0, greater than 1.5, greater than 2.0, greater than 2.5, greater than 3.0, greater than 3.5, greater than 4.0, greater than 4.5, or greater than 5.0 and aqueous solubility of less than 10 mg/mL, less than 5 mg/mL, less than 2 mg/mL, less than 1 mg/mL, less than 0.5 mg/mL, less than 0.2 mg/mL, less than 0.1 mg/mL, less than 0.05 mg/mL, less than 0.02 mg/mL or less than 0.01 mg/mL.

As used herein, the term "sufficient amount" is an amount sufficient to produce a desired effect, e.g., an amount sufficient to stimulate a cellular immune response.

As used herein, the term "therapeutically effective amount" is an amount that is effective to ameliorate a symptom of a disease, such as cancer.

A "prophylactically effective amount" refers to an amount that is effective for prophylaxis.

As used herein, the term "stimulating" refers to activating, increasing, or triggering a molecular, cellular, or enzymatic activity or response in a cell or organism, e.g., a cellular immune response.

As used herein, the term "inhibiting" refers to deactivating, decreasing, or shutting down a molecular, cellular, or enzymatic activity or response in a cell or organism.

As used herein, the term "administering" includes any suitable route of administration, as will be appreciated by one of ordinary skill in the art with reference to this disclosure, including direct injection into a solid organ, direct injection into a cell mass such as a tumor, inhalation, intraperitoneal injection, intravenous injection, topical application on a mucous membrane, or application to or dispersion within an environmental medium, and a combination of the preceding.

As used herein, the term "treating" or "treatment" refers to the reduction or elimination of symptoms of a disease, e.g., cancer.

As used herein, the term "preventing" or "prevention" refers to the reduction or elimination of the onset of symptoms of a disease, e.g., cancer.

As used herein, the term "regressing" or "regression" refers to the reduction or reversal of symptoms of a disease after its onset, e.g., cancer remission.

As used in this disclosure, the term "modified" and variations of the term, such as "modification," means one or more than one change to the naturally occurring sequence of MVP, VPARP, or TEP1 selected from the group consisting of addition of a polypeptide sequence to the C-terminal, addition of a polypeptide sequence to the N-terminal, deletion of between about 1 and 100 amino acid residues from the C-terminal, deletion of between about 1 and 100 amino acid residues from the N-terminal, substitution of one or more than one amino acid residue that does not change the function of the polypeptide, as will be appreciated by one of ordinary skill in the art with reference to this disclosure, such as for example, an alanine to glycine substitution, and a combination of the preceding.

As used herein, the term percent "identity," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

As used in this disclosure, the term "comprise" and variations of the term, such as "comprising" and "comprises," are not intended to exclude other additives, components, integers or steps.

It must be noted that, as used in the specification and the appended claims, the singular forms "a," "an" and "the" include plural referents unless the context clearly dictates otherwise.

The vault nanoparticle is one of the largest known ribonucleoprotein complexes in the sub-100 nm range. Highly conserved and almost ubiquitously expressed in eukaryotes, vaults form a large nanocapsule with a barrel-shaped morphology surrounding a large hollow interior. These properties make vaults an ideal candidate for development into a drug delivery vehicle. As disclosed herein, we have engineered recombinant vaults to sequester highly aqueous insoluble hydrophobic compounds.

Therapeutic agents are predominantly small hydrophobic compounds that exhibit various degrees of solubility due to their hydrophobicity and/or lipophilicity. These compounds can be loaded into the vault lumen and retained within the vaults, where the sequestering of these compounds into the vault lumen requires altering vault properties to provide environments with enhanced non-covalent binding of hydrophobic and/or aqueous insoluble therapeutic compounds. As disclosed herein, the major vault protein can be modified by fusion of a suitable peptide to the N-terminus. The modified major vault protein forms a vault complex with the fusion peptide internal to the vault, forming a ring of hydrophobic binding region inside the vault. As a result, the fusion peptide provides either enhanced non-covalent binding of the therapeutic compound inside the vault, or enhanced non-covalent binding of a lipophilic substance, resulting in enhanced binding of the therapeutic compound inside the vault. As such, the fusion peptide provides a vault internal environment with an enhanced binding affinity for the hydrophobic and/or aqueous insoluble therapeutic compound, and the therapeutic can be sequestered inside the vault at high concentrations to be delivered by the vault complex.

The descriptions of various aspects of the invention herein are presented for purposes of illustration, and are not intended to be exhaustive or to limit the invention to the forms disclosed. Persons skilled in the relevant art can appreciate that many modifications and variations are possible in light of the embodiment teachings.

It should be noted that the language used herein has been principally selected for readability and instructional purposes, and it may not have been selected to delineate or circumscribe the inventive subject matter. Accordingly, the disclosure is intended to be illustrative, but not limiting, of the scope of invention.

Any terms not directly defined herein shall be understood to have the meanings commonly associated with them as understood within the art of the invention. Certain terms are discussed herein to provide additional guidance to the practitioner in describing the compositions, devices, methods and the like of embodiments of the invention, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the embodiments of the invention herein.

Compositions of the Invention

As described in more detail below, provided are vault complexes, and compositions and methods of using vault complexes. In some embodiments, the composition comprises recombinant vaults having a recombinant MVP fused with an amphipathic α-helix and a hydrophobic therapeutic compound contained in the vault complex. Such vault complexes can be used for delivery of hydrophobic compounds, e.g., delivery to a subject for treating a disease.

Vaults and Vault Complexes

The compositions of the invention comprise a vault complex. A vault complex is a recombinant particle that sequesters a small molecule (drug, sensor, toxin, etc.), or a protein of interest, e.g., a peptide, or a protein, including an endogenous protein, a heterologous protein, a recombinant protein, or recombinant fusion protein. Vault complexes as described herein can include, in particular, a vault complex enhanced for sequestering of a hydrophobic therapeutic compound inside the vault complex.

Vaults, e.g., vault particles are ubiquitous, highly conserved ribonucleoprotein particles found in nearly all eukaryotic tissues and cells, including dendritic cells (DCs), endometrium, and lung, and in phylogeny as diverse as mammals, avians, amphibians, the slime mold *Dictyostelium discoideum*, and the protozoan *Trypanosoma brucei* (Izquierdo et al., *Am. J. Pathol.*, 148(3):877-87 (1996)). Vaults have a hollow, barrel-like structure with two protruding end caps, an invaginated waist, and regular small openings surround the vault cap. These openings are large enough to allow small molecules and ions to enter the interior of the vault. Vaults have a mass of about 12.9±1 MDa (Kedersha et al., *J. Cell Biol.*, 112(2):225-35 (1991)) and overall dimensions of about 42×42×75 nm (Kong et al., *Structure*, 7(4):371-9 (1999)). The volume of the internal vault cavity is approximately $50×10^3$ nm$^3$, which is large enough to enclose an entire ribosomal protein.

Vaults comprise three different proteins, designated MVP, VPARP and TEP1, and comprise one or more different untranslated RNA molecules, designated vRNAs. The number of vRNA can vary. For example, the rat *Rattus norvegicus* has only one form of vRNA per vault, while humans have three forms of vRNA per vault. The most abundant protein, major vault protein (MVP), is a 95.8 kDa protein in *Rattus norvegicus* and a 99.3 kDa protein in humans which is present in 78 copies per vault and accounts for about 75% of the total protein mass of the vault particle. The two other proteins, the vault poly-ADP ribose polymerase, VPARP, a 193.3 kDa protein in humans, and the telomerase/vault associated protein 1, TEP1, a 292 kDa protein in *Rattus norvegicus* and a 290 kDa protein in humans, are each present in between about 2 and 16 copies per vault.

A vault complex can be formed from just the MVP, without any VPARP, TEP1 or vRNA. A vault complex for use as described herein comprises a modified MVP (i.e., recombinant MVP), and optionally comprises one or more of VPARP, TEP1 and vRNA. In some embodiments, the vault complex as described herein comprises modified MVP as a fusion protein, wherein the fusion protein comprises a fusion peptide fused to the N-terminus of the MVP. In some embodiments the modified MVP is modified human MVP or modified rat MVP. In some embodiments, the fusion peptide fused to the N-terminus comprises an amphipathic α-helix. In some embodiments, the fusion peptide fused to the N-terminus has 1 to 10 amphipathic α-helix structures, 1 to 9 amphipathic α-helix structures, 1 to 8 amphipathic α-helix structures, 1 to 7 amphipathic α-helix structures, 1 to 6 amphipathic α-helix structures, 1 to 5 amphipathic α-helix structures, 1 to 4 amphipathic α-helix structures, 1 to 3 amphipathic α-helix structures, 1 to 2 amphipathic α-helix structures, or 1 amphipathic α-helix structure. In some embodiments, the fusion peptide fused to the N-terminus has 10 amphipathic α-helix structures. In some embodiments, the fusion peptide fused to the N-terminus has 9 amphipathic α-helix structures. In some embodiments, the fusion peptide fused to the N-terminus has 8 amphipathic α-helix structures. In some embodiments, the fusion peptide fused to the N-terminus has 7 amphipathic α-helix structures. In some embodiments, the fusion peptide fused to the N-terminus has 6 amphipathic α-helix structures. In some embodiments, the fusion peptide fused to the N-terminus has 5 amphipathic α-helix structures. In some embodiments, the fusion peptide fused to the N-terminus has 4 amphipathic α-helix structures. In some embodiments, the fusion peptide fused to the N-terminus has 3 amphipathic α-helix structures. In some embodiments, the fusion peptide fused to the N-terminus has 2 amphipathic α-helix structures. In some embodiments, the fusion peptide fused to the N-terminus has 1 amphipathic α-helix structure. In some embodiments, the amphipathic α-helix is a portion of NS5A. In some embodiments the fusion peptide comprises the sequence RDIWDWICEVLSDFKTWLKA (SEQ ID NO:19). In some embodiments the fusion peptide comprises the sequence GSWLRDIWDWICEVLSDFKTWLKAKLMP (SEQ ID NO:20). In some embodiments the fusion peptide comprises the sequence MAGSWLRDIWDWICEVLSDFKTWLKAKLMPT (SEQ ID NO:17). In some embodiments, the MVP fusion protein comprises SEQ ID NO:23.

VPARP, INT Domain, and INT Fusion Proteins

A vault poly ADP-ribose polymerase (VPARP) includes a region of about 350 amino acids that shares 28% identity with the catalytic domain of poly ADP-ribosyl polymerase, PARP, a nuclear protein that catalyzes the formation of ADP-ribose polymers in response to DNA damage. VPARP catalyzes an NAD-dependent poly ADP-ribosylation reaction, and purified vaults have poly ADP-ribosylation activity that targets MVP, as well as VPARP itself. VPARP includes a INT domain (major vault protein (MVP) interaction domain). The INT domain is responsible for the interaction of VPARP with a major vault protein (MVP).

A vault complex of the invention can include an INT domain. The INT domain is responsible for interaction of a protein of interest with a vault protein such as a MVP. In some embodiments, the INT domain is expressed as a fusion protein with a protein of interest. Alternatively, a protein of interest can be covalently or non-covalently attached. The INT of the vault complexes of the invention are derived from VPARP sequences. Exemplary VPARP sequences and INT sequences can be found in Table 1. One of skill in the art understands that the INT can have the entire naturally occurring sequence or portions of the sequence or fragments thereof. In other embodiments, the INT has at least 50%, 60%, 70%, 80%, 90%, 95%, 96%, 97%, 98% or 99% sequence identity to any of the VPARP and/or INT sequences disclosed in Table 1.

In one embodiment, the INT is derived from a human VPARP, SEQ ID NO:3, GenBank accession number AAD47250, encoded by the cDNA, SEQ ID NO:4, GenBank accession number AF158255. In some embodiments, the vault packaging domain comprises or consists of the INT domain corresponding to residues 1473-1724 of human VPARP protein sequence (full human VPARP amino acid sequence is SEQ ID NO:3). In other embodiments, the vault packaging domain comprises or consists of the INT domain comprising residues 1563-1724 (SEQ ID NO:2) of the human VPARP protein sequence. In certain embodiments, the vault packaging domain is at least 90%, 91%, 92%, 93%, 94%, 95%, 96%, 97%, 98%, or 99% identical to SEQ ID NO:2 or SEQ ID NO:3.

In alternative embodiments, as with VPARP, a major vault protein (MVP) interaction domain can be derived from TEP1 sequences. Such interaction domains can be termed, for example INT2, to distinguish them from a VPARP interaction domain. One of skill in the art understands that the INT2 can have the entire naturally occurring sequence of the vault interaction domain in TEP1 or portions of the sequence or fragments thereof.

MVP

A vault complex of the invention includes an MVP. Exemplary MVP sequences can be found in Table 1. One of skill in the art understands that the MVP can have the entire naturally occurring sequence or portions of the sequence or fragments thereof. In other embodiments, the MVP has at least 50%, 60%, 70%, 80%, 90%, 95%, 96%, 97%, 98% or 99% sequence identity to any of the MVP sequences disclosed in Table 1.

In one embodiment, the MVP is human MVP, SEQ ID NO:5, GenBank accession number CAA56256, encoded by the cDNA, SEQ ID NO:6, GenBank accession number X79882. In one embodiment, the MVP is rat MVP, SEQ ID NO:24, GenBank accession number AAC52161, encoded by the cDNA, SEQ ID NO:25, GenBank accession number U09870. In other embodiments, the MVP is at least 90%, 91%, 92%, 93%, 94%, 95%, 96%, 97%, 98%, or 99% identical to the MVP sequences described herein.

In one embodiment, there is provided a vault complex comprising, consisting essentially of, or consisting of an MVP modified by adding an amphipathic peptide to the N-terminal to create sites that allow either the direct or indirect binding (e.g., via a lipid bilayer formed in association with the amphipathic peptide) of hydrophobic compounds. In some embodiments, these peptides form amphipathic α-helices, such as that formed by NS5A1-31 from Hepatitis C.

Any of the vault complexes described herein can include MVPs or modified MVPs disclosed herein.

TEP1

In some embodiments, a vault complex of the invention can include a TEP1 protein. Exemplary TEP1 sequences can be found in Table 1. One of skill in the art understands that the TEP1 can have the entire naturally occurring sequence or portions of the sequence or fragments thereof. In other embodiments, the TEP1 has at least 50%, 60%, 70%, 80%, 90%, 95%, 96%, 97%, 98% or 99% sequence identity to any of the TEP1 sequences disclosed in Table 1.

The TEP1 can be human TEP1, SEQ ID NO:10, GenBank accession number AAC51107, encoded by the cDNA, SEQ ID NO:11, GenBank accession number U86136. Any of the vault complexes described herein can include TEP1 or modifications thereof.

vRNA

A vault complex of the invention can include a vRNA. Exemplary vRNA sequences can be found in Table 1. One of skill in the art understands that the vRNA can have the entire naturally occurring sequence or portions of the sequence or fragments thereof. In other embodiments, the vRNA has at least 50%, 60%, 70%, 80%, 90%, 95%, 96%, 97%, 98% or 99% sequence identity to any of the vRNA sequences disclosed in Table 1.

In one embodiment, the vRNA can be a human vRNA, SEQ ID NO:12, GenBank accession number AF045143, SEQ ID NO:13, GenBank accession number AF045144, or SEQ ID NO:14, GenBank accession number AF045145, or a combination of the preceding.

As will be appreciated by one of ordinary skill in the art with reference to this disclosure, the actual sequence of any of MVP, VPARP, TEP1 and vRNAs can be from any species suitable for the purposes disclosed in this disclosure, even though reference or examples are made to sequences from specific species. Further, as will be appreciated by one of ordinary skill in the art with reference to this disclosure, there are some intraspecies variations in the sequences of MVP, VPARP, TEP1 and vRNAs that are not relevant to the purposes of the present invention. Therefore, references to MVP, VPARP, TEP1 and vRNAs are intended to include such intraspecies variants.

Fusion Peptides for Fusing to N-Terminus of MVP

The fusion peptides described herein, when fused to the N-terminus of MVP, are located in the interior of the vault complex when the vault complex is assembled. Such fusion peptides fused to the N-terminus of MVP in the vault complexes as described herein provide a hydrophobic environment inside the vault, such that therapeutic compounds that are hydrophobic and/or aqueous insoluble preferably bind inside the vault complex. The nature of the fusion peptide provides an internal vault environment that enhances sequestering of the therapeutic compound inside of the vault. In some instances, the fusion peptide has a binding affinity for the therapeutic compound, i.e., binds the therapeutic compound non-covalently. In some instances, the fusion peptide binds to a lipophilic substance non-covalently, such that the therapeutic compound binds to the lipophilic substance inside the vault complex. As such, in some instances the enhanced sequestering of the therapeutic compound results from binding to the fusion peptide non-covalently, and/or binding to a lipophilic substance that binds the fusion peptide non-covalently. This enhanced sequestering can be measured, for example, by incubating the vault particles in a solution containing the therapeutic compound and isolating the vault particles from the solution, for example by semi-discontinuous gradient, followed by ultracentrifugation to isolate the vault particles. The amount of vault complex and amount of compound associated with the vault complex fraction can be determined by various methods, such as by spectrophotometric analysis or HPLC coupled with multiple reaction monitoring tandem mass spectrometry (MRM-LC-MS/MS). The amount of compound associated with the vault complex as described herein can be compared to that of a vault complex that is not engineered to enhance the binding of the therapeutic compound, for example using a control vault complex, e.g., a vault complex comprising an MVP that does not include a fusion protein on the N-terminus, or that may include a fusion protein on the N-terminus that does not provide enhanced binding of the therapeutic compound. Ideally the control vault complex comprises unmodified MVP, although the vault complex prepared with CP-MVP (e.g., human, SEQ ID NO:8; rat, SEQ ID NO:32) or CP-MVP-Z (e.g., rat, SEQ ID NO:34) can also be used as a suitable control. Thus a suitable control vault complex is one that does not sequester the therapeutic compound inside the vault complex. In some embodiments, the vault complex with the therapeutic compound sequestered inside can be determined as the amount (e.g., molecules) of therapeutic compound per vault complex particle. The fusion peptides for use in the vault complex as described herein will provide sequestering of the vault complex to a level of greater than 20, greater than 40, greater than 60, greater than 80, greater than 100, greater than 200, greater than 500, greater than 1000 molecules of the therapeutic compound per vault complex particle. In some embodiments, the fusion peptide for use in the vault complex as described herein will provide sequestering of the vault complex to a level of between 20 and 10000 molecules per vault particle, between 40 and 10000 molecules per vault particle, between 60 and 10000 molecules per vault particle, between 80 and 10000 molecules per vault particle, between 100 and 10000 molecules per vault particle, between 200 and 10000 molecules per vault particle, between 500 and 10000 molecules per vault particle, between 1000 and 10000 molecules per vault particle. In some embodiments, the fusion peptide for use in the vault complex as described herein will provide sequestering of the vault complex to a level of between 20 and 5000 molecules per vault particle, between 40 and 5000 molecules per vault particle, between 60 and 5000 molecules per vault particle, between 80 and 5000 molecules per vault particle, between 100 and 5000 molecules per vault particle, between 200 and 5000 molecules per vault particle, between 500 and 5000 molecules per vault particle, between 1000 and 5000 molecules per vault particle. In some embodiments, the fusion peptide for use in the vault complex as described herein will provide sequestering of the vault complex to a level of between 20 and 2000 molecules per vault particle, between 40 and 2000 molecules per vault particle, between 60 and 2000 molecules per vault particle, between 80 and 2000 molecules per vault particle, between 100 and 2000 molecules per vault particle, between 200 and 2000 molecules per vault particle, between 500 and 2000 molecules per vault particle, between 1000 and 2000 molecules per vault particle.

The fusion peptide can be any suitable peptide that provides sequestering of a therapeutic compound inside the vault complex. The fusion peptide can be fused to the N-terminus of MVP, and the vault complex prepared by methods as described herein, and assessed for enhanced sequestering of the therapeutic compound by methods as described herein. In some embodiments, the fusion peptide results in a hydrophobic environment inside of the vault complex so that either a lipophilic substance is sequestered within the vault complex and provides sequestering of the therapeutic compound, or the therapeutic compound is sequestered inside the vault complex directly, i.e., without a lipophilic substance sequestered within the vault complex. In some embodiments, the fusion peptide is an amphipathic peptide, such as an amphipathic α-helix peptide a peptide that includes an amphipathic α-helix structure. In some embodiments, the fusion peptide includes more than one amphipathic α-helix structure, where each amphipathic α-helix can have the same amino acid sequence, or can have a different amino acid sequence. In some embodiments, the fusion peptide has 1 to 10 amphipathic α-helix structures, 1 to 9 amphipathic α-helix structures, 1 to 8 amphipathic α-helix structures, 1 to 7 amphipathic α-helix structures, 1 to 6 amphipathic α-helix structures, 1 to 5 amphipathic α-helix structures, 1 to 4 amphipathic α-helix structures, 1 to 3 amphipathic α-helix structures, 1 to 2 amphipathic α-helix structures, or 1 amphipathic α-helix structure. As described herein, the fusion peptide is readily determined by one skilled in the art in providing suitable hydrophobic surface area to the inside of the vault, i.e., using the methods and compositions provided herein to optimize the amphipathic α-helix structure and the number of amphipathic α-helix structures per fusion peptide, to provide the desired sequestering of a desired pharmaceutical compound within the vault complex.

The fusion peptides provided herein include, without limitation, a fusion peptide comprising an amphipathic α-helical structure. In some embodiments, the fusion peptide comprises a peptide sequence of 10 to 50 amino acids, 10 to 40 amino acids, or 18 to 35 amino acids that forms an amphipathic α-helix. In some embodiments, the fusion peptide comprises one or more peptide sequences that form an amphipathic α-helix, wherein each of the one or more peptide sequences that forms an amphipathic α-helix independently comprises 10 to 50 amino acids, 10 to 40 amino acids, or 18 to 35 amino acids that forms the amphipathic α-helix. In some embodiments, the fusion peptide comprises 1 to 10 peptide sequences that form an amphipathic α-helix, wherein each of the 1 to 10 peptide sequences that forms an amphipathic α-helix independently comprises 10 to 50 amino acids, 10 to 40 amino acids, or 18 to 35 amino acids that forms the amphipathic α-helix. In some embodiments, the fusion peptide comprises 1 to 9 peptide sequences that form an amphipathic α-helix, wherein each of the 1 to 9 peptide sequences that forms an amphipathic α-helix independently comprises 10 to 50 amino acids, 10 to 40 amino acids, or 18 to 35 amino acids that forms the amphipathic α-helix. In some embodiments, the fusion peptide comprises 1 to 8 peptide sequences that form an amphipathic α-helix, wherein each of the 1 to 8 peptide sequences that forms an amphipathic α-helix independently comprises 10 to 50 amino acids, 10 to 40 amino acids, or 18 to 35 amino acids that forms the amphipathic α-helix. In some embodiments, the fusion peptide comprises 1 to 7 peptide sequences that form an amphipathic α-helix, wherein each of the 1 to 7 peptide sequences that forms an amphipathic α-helix independently comprises 10 to 50 amino acids, 10 to 40 amino acids, or 18 to 35 amino acids that forms the amphipathic α-helix. In some embodiments, the fusion peptide comprises 1 to 6 peptide sequences that form an amphipathic α-helix, wherein each of the 1 to 6 peptide sequences that forms an amphipathic α-helix independently comprises 10 to 50 amino acids, 10 to 40 amino acids, or 18 to 35 amino acids that forms the amphipathic α-helix. In some embodiments, the fusion peptide comprises 1 to 5 peptide sequences that form an amphipathic α-helix, wherein each of the 1 to 5 peptide sequences that forms an amphipathic α-helix independently comprises 10 to 50 amino acids, 10 to 40 amino acids, or 18 to 35 amino acids that forms the amphipathic α-helix. In some embodiments, the fusion peptide comprises 1 to 4 peptide sequences that form an amphipathic α-helix, wherein each of the 1 to 4 peptide sequences that forms an amphipathic α-helix independently comprises 10 to 50 amino acids, 10 to 40 amino acids, or 18 to 35 amino acids that forms the amphipathic α-helix. In some embodiments, the fusion peptide comprises 1 to 3 peptide sequences that form an amphipathic α-helix, wherein each of the 1 to 3 peptide sequences that forms an amphipathic α-helix independently comprises 10 to 50 amino acids, 10 to 40 amino acids, or 18 to 35 amino acids that forms the amphipathic α-helix. In some embodiments, the fusion peptide comprises 1 or 2 peptide sequences that form an amphipathic α-helix, wherein each of the 1 or 2 peptide sequences that forms an amphipathic α-helix independently comprises 10 to 50 amino acids, 10 to 40 amino acids, or 18 to 35 amino acids that forms the amphipathic α-helix. In some embodiments, the fusion peptide comprises 1 peptide sequence that forms an amphipathic α-helix, wherein the 1 peptide sequence that forms an amphipathic α-helix comprises 10 to 50 amino acids, 10 to 40 amino acids, or 18 to 35 amino acids that forms the amphipathic α-helix. In some embodiments, the amphipathic α-helix comprises an amphipathic α-helix derived from NS5A. In some embodiments, the fusion peptide comprises the sequence RDIWDWICEVLSDFKTWLKA (SEQ ID NO:19).

Figure 1B:
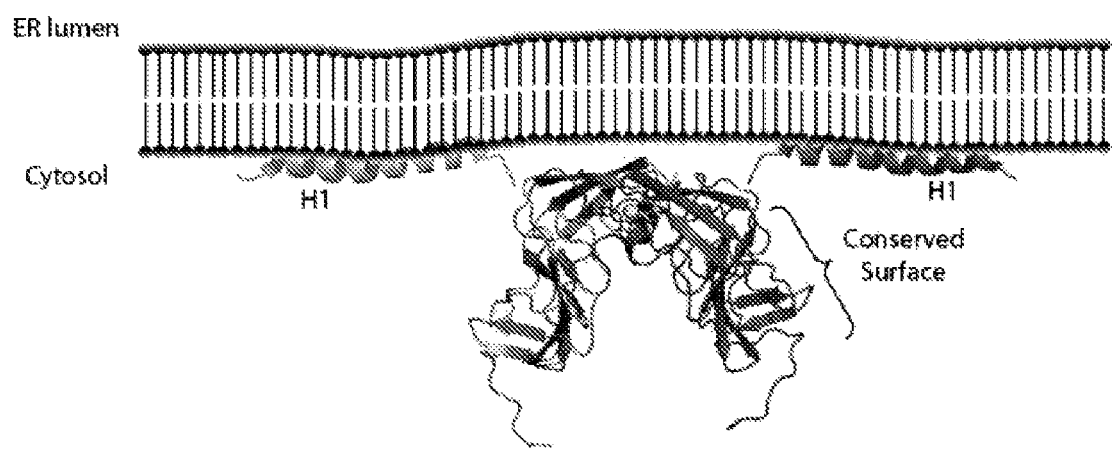

The non-structural protein 5A (NS5A) is a viral protein essential in the viral replication process (Pawlotsky, et al., Journal of viral hepatitis, 1999, 6(5): 343-56; Macdonald, A. and M. Harris, M., The Journal of General Virology, 2004, 85(Pt 9): 2485-502; McLauchlan, J., Biochemical Society Transactions, 2009, 37(Pt 5): 986-90). The full NS5A protein associates with host membranes along with other Hepatitis C proteins involved with the viral replication machinery. Furthermore, NS5A is implicated in altering host cytokine production (Khabar, K. S. and S. J. Polyak, Journal of Interferon & Cytokine Research: the Official Journal of the International Society for Interferon and Cytokine Research, 2002, B(10): 1005-12). Interestingly, the membrane interaction region of NS5A has been mapped to the first 31 amino acids of the protein (Penin, F., et al., The Journal of Biological Chemistry, 2004, 279(39): 40835-43; Moradpour, et al., Hepatology, 2005, 42(3): 732-5). Analysis of this region revealed it is an amphipathic α-helix that functions as an in-plane membrane anchor domain on the cytoplasmic leaflet of host-cell membranes via hydrophobic interactions between helix tryptophan residues and the acyl chains of the neighboring host phospholipids (FIG. 1A). The polar face of the amphipathic helix shows an asymmetrical charge distribution, which suggests a possible functional role through binding interactions with other aspects of the viral replication complex (Brass, V., et al., The Journal of Biological Chemistry, 2002, 277(10): 8130-9). Recently, structural studies have modeled the first full domain of NS5A as a Zinc coordinating dimer motif covalently linked by a single cysteine disulfide bridge (FIG. 1B) (Tellinghuisen, et al., Nature, 2005, 435(7040): 374-9). The solved structure reveals an interesting "claw-like" morphology that may accommodate RNA during viral replication.

The NS5A1-31 amphipathic α-helix was recombinantly fused to the amino terminus of MVP. In some embodiments, a short peptide domain derived from staphylococcal Protein A (SpA) known as the Z domain was also attached to the carboxyl terminus of MVP to generate recombinant vaults capable of binding IgG antibodies for direct cell targeting (Nilsson, B., et al., Protein Engineering, 1987, 1(2): 107-13; Braisted, A. C. and Wells, J. A., Proceedings of the National Academy of Sciences of the United States of America, 1996, 93(12): 5688-92; Kickhoefer, V. A., et al., ACS Nano, 2009, 3(1): 27-36). These NS5A1-31 Amphipathic α-Helix-MVP-Z or AHZ vaults generate a suitable hydrophobic environment within the vault lumen capable of packaging small hydrophobic compounds for therapeutic applications using direct cell targeting.

NS5A amino acids 1-31 have the sequence SGSWLRDIWDWICEVLSDFKTWLKAKLMPQL (SEQ ID NO:16), where the bolded amino acids represent the portion of the peptide that forms the amphipathic α-helix. As such, this sequence, or a similar sequence that includes the bolded amino acids, can be fused to the N-terminus of MVP to provide a vault complex having the desired properties that result in sequestering the therapeutic compound inside of the vault complex. The fusion protein can include this sequence repeated in the fusion peptide, to provide more than one amphipathic α-helix. In some embodiments this sequence is modified to provide the fusion peptide of M AGSWLRDIWDWICEVLSDFKTWLKAKLMPT (SEQ ID NO:17). In some embodiments, the fusion peptide is (MAGSWLRDIWDWICEVLSDFKTWLKAKLMPT (SEQ ID NO:17))$_n$, where n is 1 to 10, 1 to 9, 1 to 8, 1 to 7, 1 to 6, 1 to 5, 1 to 4, 1 to 3, 1 to 2, or 1. Fusion peptides can be similarly prepared using any known amphipathic α-helix peptide sequence, or analogs thereof. Analogs thereof includes modification to the sequence such that the amphipathic α-helix structure of the fusion peptide remains intact. As in the example of NS5A, for example, the amino acids that are not directly involved in the amphipathic α-helix structure can be changed and the amphipathic α-helix structure will be maintained. Similarly, those amino acids involved in the amphipathic α-helix structure can be modified, provided that the nature of the amino acid is conserved. For example, hydrophobic amino acids such as Leucine, Valine, and Isoleucine can be substituted for each other, or charged amino acids such as Lysine, Histidine, and Arginine can be substituted for each other, to provide fusion peptides useful for making the vault complexes as described herein. As such, one skilled in the art can readily determine the optimal fusion peptide, and using the methods as described herein, determine the optimal number of such sequences per fusion peptide.

In addition to the modified MVP comprising a fusion peptide at the N-terminus, the MVP comprises a further modification comprising a fusion peptide at the C-terminus. When fused to the C-terminus of MVP, the fusion peptide is found external to the vaults, on each end of the vault complex in the assembled vault complex. The fusion peptides that are fused to the C-terminus of MVP provide targeting of the vault complex to a particular cell. The fusion peptide can provide a peptide on the surface that directly targets the vault complex to a particular cell, e.g., by binding a cell receptor, for example the fusion peptide comprises EGF, such that the resulting vault is targeted to cells having an EGF receptor. The fusion peptide can also be engineered to provide an antibody binding domain, such as the Staphyloccucus Z domain that binds IgG. In this instance, the vault complex can be bound to a suitably targeted IgG antibody, such as an anti-CD4 antibody, or anti-dendritic cell antibody, such that the vault complex will have targeted delivery to cells having a CD4 or dendritic cell marker on its surface, including CD1a, CD1b, CD1c, CD11c, CD83, CD207, CD208, CD103, CD209, or CD123. The antibody could also be targeted to treat a cancer, such as an antibody directed to CD52, CD30, CD33, CD20, CTLA4, ErbB2, VEGF, EGFR, and the like. The fusion peptide can also be engineered to provide a peptide that can be targeted to a bispecific antibody, i.e., an antibody engineered to bind the particular fusion peptide on one end, and a cell specific antibody on the other. Fusion peptides in this instance include, for example, a FLAG sequence, HIS sequence, or the like. The bispecific antibody binds the FLAG or HIS on one end, and is suitably targeted to the desired cell associated peptide on the other end, such as CD4, CD1a, CD1b, CD1c, CD11c, CD83, CD207, CD208, CD103, CD209, CD123, CD52, CD30, CD33, CD20, CTLA4, ErbB2, VEGF, or EGFR.

Pharmaceutical Compositions of the Invention

In one embodiment, provided herein are pharmaceutical compositions comprising the vault complexes as described herein, and methods of using pharmaceutical compositions comprising the vault complexes described herein. These compositions can comprise, in addition to one or more of the vault complexes, a pharmaceutically acceptable excipient, carrier, buffer, stabilizer, or other materials well known to those skilled in the art. Such materials should be non-toxic and should not interfere with the efficacy of the active ingredient. The precise nature of the carrier or other material can depend on the route of administration, e.g., oral, intravenous, cutaneous or subcutaneous, nasal, intramuscular, intraperitoneal routes. In some embodiments, the composition can be injected intra-tumorally, e.g., directly injected into a solid tumor.

In some aspects, the pharmaceutically acceptable excipient is a polymer, gel, hydrogel, or the like, where the vault complex is contained within a polymer, gel, or hydrogel, such that the vault complex and the therapeutic compound sequestered therein are slowly released from the polymer, gel, or hydrogel. In some embodiments, the vault complex is covalently attached to the polymer, gel, or hydrogel, where the covalent attachment can be broken under physiological conditions, resulting in the release of the vault complex and the therapeutic compound sequestered therein. In some embodiments, the polymer attached to the vault complex is a thermally responsive polymer, wherein the vault complex attached to the polymer, when at room temperature, does not aggregate, and wherein the vault complex attached to the polymer, when at physiological temperatures, aggregates, thereby forming aggregated vault complexes, resulting in slow release of the vault complex and the therapeutic compound sequestered therein. In some embodiments, the vault complexes covalently attached to the polymer, gel, or hydrogel are suitable for injection directly into a desired site for delivery of the therapeutic compound to the desired site, such as intra-tumoral injection.

In certain embodiments, the pharmaceutical compositions that are injected intra-tumorally comprise an isotonic or other suitable carrier fluid or solution.

For intravenous, cutaneous, or subcutaneous injection, or injection at the site of affliction, the active ingredient can be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

In other embodiments, pharmaceutical compositions for oral administration can be in tablet, capsule, powder, or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol, or polyethylene glycol can be included.

In some embodiments, administration of the pharmaceutical compositions may be topical, pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; or intracranial, e.g., intraparenchymal, intrathecal or intraventricular, administration. Formulations for parenteral administration may include sterile aqueous solutions which may also contain buffers, diluents and other suitable additives. Formulations may be reconstituted from freeze-dried (lyophilized) preparations. For intravenous use, the total concentration of solutes should be controlled to render the preparation isotonic.

I. Therapeutic Compounds

Examples of pharmaceutical agents, including hydrophobic and/or aqueous insoluble therapeutic compounds as described herein, useful in the preparation of compositions as described herein and in the methods of treatment as described herein include, but are not limited to, α-adrenergic agonists, β-adrenergic agonists, α-adrenergic blockers, β-adrenergic blockers, aldose reductase inhibitors, anabolics, analgesics (narcotic and non-narcotic), androgens, anesthetics, anorexics, anthelmintics (e.g., cestode, nematode, onchocerca, schistosoma, and the like), anti-allergics, anti-ameboics, anti-androgens, anti-anginals, anti-arrhythmics, anti-arteriosclerotics, anti-arthritics, antibiotics and other antibacterials, anti-cholinergics, anti-convulsants, anti-depressants, anti-diabetics agents, anti-diarrheals, anti-diuretics, anti-estrogens, antifungals, anti-yeast agents, anti-glaucomas, anti-gonadotropins, anti-gout agents, anti-histaminics, anti-hyperlipoproteinemics, anti-hypertensives, anti-hyperthyroid agents, anti-hypertrophy agents, anti-hypotensives, anti-hypothyroid agents, antiinflammatories, anti-malarials, antimicrobials, anti-migraine agents, anti-nausea agents, anti-neoplastics, antioxidants, antiparasitic agents, anti-parkinsonian agents, anti-pheochromocytoma agents, anti-pneumocytis agents, antiproliferative agents, anti-protozoals (e.g., leishmania, trichomonas, trypansoma, and the like), anti-pruritic agents, anti-psoratic agents, antipsychotic agents, anti-pyretics, anti-rheumatics, anti ricketts agents, anti-seborrheic agents, antiseptics, anti-spasmodic agents, anti-thrombotic agents, antitussives, anti-ulcer agents, anti-urolithic agents, anti-venins, antivirals, anxiolytics, benzodiazepine antagonists, bronchodilators, calcium channel blockers, calcium regulators, cardiotonics, chelating agents, chemotherapeutics, cholecystokinin antagonists, cholelitholytic agents, choleretics, cholinergics, cholinesterase inhibitors, cholinesterase reactivators, central nervous system stimulants and agents, decongestants, diuretics, dopamine receptor agonists, drugs for treating or preventing pain, ectoparasiticides, enzymes, enzyme inducers, estrogens, gastric secretion inhibitors, glucocorticoids, gonad-stimulating principles, gonadotropic hormones, growth hormones, growth hormone releasing factors, growth stimulants, hemolytics, heparin agonists, hepatoprotectants, hypnotics, immune system boosters, immunomodulators, immunosuppressants, kinase inhibitors, lactation stimulating hormones, LH-RH stimulating agonists, lipotropics, lupus erythmatosus suppressants, mineral corticoids, miotics, monoamine oxidase inhibitors, mucolytics, muscle relaxants, narcotic antagonists, neuroprotectives, neotropics, ovarian hormones, oxytocics, pepsin inhibitors, peristaltic stimulators, progestrogens, prolactin inhibitors, protoglandins, prostoglandin analogs, protease inhibitors, respiratory stimulants, sclerosing agents, sedatives, steroids, thrombolytics, thyrotropic hormones, transdermal penetration enhancers, uricosurics, vasoconstrictors, vasodilators (e.g., cerebral, coronary, peropheral, and the like), vasoprotectants, vitamins, vitamin source extracts, vulneraries (including, but not limited to, those listed in U.S. Pat. No. 5,719,197, the entire disclosure of which is incorporated herein by reference), and combinations thereof. Other additionally or alternately acceptable pharmaceutically active agents can be found, e.g., in U.S. Pat. No. 6,221,383, the entire disclosure of which is incorporated herein by reference.

Among the hydrophobic pharmaceutical agents that can be used in accordance with the present invention include, but are not limited to, the following.

Analgesics and anti-inflammatory agents: aloxiprin, auranofin, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxyphenbutazone, phenylbutazone, piroxicam, sulindac.

Anthelmintics: albendazole, bephenium hydroxynaphthoate, cambendazole, dichlorophen, ivermectin, mebendazole, oxamniquine, oxfendazole, oxantel embonate, praziquantel, pyrantel embonate, thiabendazole.

Anti-arrhythmic agents: amiodarone HCl, disopyramide, flecainide acetate, quinidine sulphate. Anti-bacterial agents: benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim.

Anti-coagulants: dicoumarol, dipyridamole, nicoumalone, phenindione.

Anti-depressants: amoxapine, maprotiline HCl, mianserin HCL, nortriptyline HCl, trazodone HCL, trimipramine maleate.

Anti-diabetics: acetohexamide, chlorpropamide, glibenclamide, gliclazide, glipizide, tolazamide, tolbutamide.

Anti-epileptics: beclamide, carbamazepine, clonazepam, ethotoin, methoin, methsuximide, methylphenobarbitone, oxcarbazepine, paramethadione, phenacemide, phenobarbitone, phenytoin, phensuximide, primidone, sulthiame, valproic acid.

Anti-fungal agents: amphotericin B, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid.

Anti-gout agents: allopurinol, probenecid, sulphin-pyrazone.

Anti-hypertensive agents: amlodipine, benidipine, darodipine, dilitazem HCl, diazoxide, felodipine, guanabenz acetate, isradipine, minoxidil, nicardipine HCl, nifedipine, nimodipine, phenoxybenzamine HCl, prazosin HCL, reserpine, terazosin HCL.

Anti-malarials: amodiaquine, chloroquine, chlorproguanil HCl, halofantrine HCl, mefloquine HCl, proguanil HCl, pyrimethamine, quinine sulphate.

Anti-migraine agents: dihydroergotamine mesylate, ergotamine tartrate, methysergide maleate, pizotifen maleate, sumatriptan succinate.

Anti-muscarinic agents: atropine, benzhexol HCl, biperiden, ethopropazine HCl, hyoscyamine, mepenzolate bromide, oxyphencylcimine HCl, tropicamide.

Anti-neoplastic agents and Immunosuppressants aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone.

Anti-protazoal agents: benznidazole, clioquinol, decoquinate, diiodohydroxyquinoline, diloxanide furoate, dinitolmide, furzolidone, metronidazole, nimorazole, nitrofurazone, ornidazole, tinidazole.

Anti-thyroid agents: carbimazole, propylthiouracil.

Antiviral agents: abacavir, acyclovir, adefovir, amantadine, amprenavir, ampligen, arbidol, atazanavir, atripla, bryostatin and bryostatin analogs (as well as other Protein Kinase C activators), boceprevir, cidofovir, combivir, dolutegravir, duranavir, delavirdine, didanosine, docosanol, edoxudine, efavirenz, emtricitabine, enfuvirtide, entecavir, famciclovir, fomovirsen, fosamprenavir, ganciclovir, ibacitabine, idoxuridine, imiquimod, indinavir, inosine, lamivudine, lopinavir, loviride, maraviroc, moroxydine, methisazone, nelfinavir, nevirapine, oseltamivir, penciclovir, peramivir, pleconaril, podophyllotoxin, raltegravir, ribavirin, rimantadine, ritonavir, saquinavir, sofosbuvir, stavudine, telaprevir, tenofovir, tipranavir, trifluridine, trizivir, tromantadine, valaciclovir, valganciclovir, vicriviroc, vidarabine, viramidine, zalcitabine, zanamivir, zidovudine, GSK744, MK-2048, IQP0528, CSIS (5-chloro-3-phenylsulfonylindole-2-carboxamide), dapivirine.

Anxiolytic, sedatives, hypnotics and neuroleptics: alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone.

β-Blockers: acebutolol, alprenolol, atenolol, labetalol, metoprolol, nadolol, oxprenolol, pindolol, propranolol.

Cardiac Inotropic agents: amrinone, digitoxin, digoxin, enoximone, lanatoside C, medigoxin.

Corticosteroids: beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone.

Diuretics: acetazolamide, amiloride, bendrofluazide, bumetanide, chlorothiazide, chlorthalidone, ethacrynic acid, frusemide, metolazone, spironolactone, triamterene.

Anti-parkinsonian agents: bromocriptine mesylate, lysuride maleate.

Gastro-intestinal agents: bisacodyl, cimetidine, cisapride, diphenoxylate HCl, domperidone, famotidine, loperamide, mesalazine, nizatidine, omeprazole, ondansetron HCL, ranitidine HCl, sulphasalazine.

Histamine H-Receptor Antagonists: acrivastine, astemizole, cinnarizine, cyclizine, cyproheptadine HCl, dimenhydrinate, flunarizine HCl, loratadine, meclozine HCl, oxatomide, terfenadine.

Lipid regulating agents: bezafibrate, clofibrate, fenofibrate, gemfibrozil, probucol.

Nitrates and other anti-anginal agents: amyl nitrate, glyceryl trinitrate, isosorbide dinitrate, isosorbide mononitrate, pentaerythritol tetranitrate.

Nutritional agents: betacarotene, vitamin A, vitamin B.sub.2, vitamin D, vitamin E, vitamin K.

Opioid analgesics: codeine, dextropropyoxyphene, diamorphine, dihydrocodeine, meptazinol, methadone, morphine, nalbuphine, pentazocine.

Sex hormones: clomiphene citrate, danazol, ethinyl estradiol, medroxyprogesterone acetate, mestranol, methyltestosterone, norethisterone, norgestrel, estradiol, conjugated oestrogens, progesterone, stanozolol, stibestrol, testosterone, tibolone.

Stimulants: amphetamine, dexamphetamine, dexfenfluramine, fenfluramine, mazindol.

Mixtures of hydrophobic drugs can, of course, be used where therapeutically effective.

Classes of anticancer agents suitable for targeting and delivery by the compositions and methods of the present disclosure include, but are not limited to: 1) alkaloids, including, microtubule inhibitors (e.g., Vincristine, Vinblastine, and Vindesine, etc), microtubule stabilizers (e.g., Paclitaxel (Taxol), and Docetaxel, etc), and chromatin function inhibitors, including, topoisomerase inhibitors, such as, epipodophyllotoxins (e.g., Etoposide (VP-16), and Teniposide (VM-26), etc), and agents that target topoisomerase I (e.g., Camptothecin and Isirinotecan (CPT-1 1), etc); 2) covalent DNA-binding agents (alkylating agents), including, nitrogen mustards (e.g., Mechlorethamine, Chlorambucil, Cyclophosphamide, Ifosphamide, and Busulfan (Myleran), etc), nitrosoureas (e.g., Carmustine, Lomustine, and Semustine, etc), and other alkylating agents (e.g., Dacarbazine, Hydroxymethylmelamine, Thiotepa, and Mitocycin, etc); 3) noncovalent DNA-binding agents (antitumor antibiotics), including, nucleic acid inhibitors (e.g., Dactinomycin (Actinomycin D), etc), anthracyclines (e.g., Daunorubicin (Daunomycin, and Cerubidine), Doxorubicin (Adriamycin), and Idarubicin (Idamycin), etc), anthracenediones (e.g., anthracycline analogues, such as, (Mitoxantrone), etc), bleomycins (Blenoxane), etc, and plicamycin (Mithramycin), etc; 4) antimetabolites, including, antifolates (e.g., Methotrexate, Folex, and Mexate, etc), purine antimetabolites (e.g., 6-Mercaptopurine (6-MP, Purinethol), 6-Thioguanine (6-TG), Azathioprine, Acyclovir, Ganciclovir, Chlorodeoxyadenosine, 2-Chlorodeoxyadenosine (CdA), and 2'-Deoxycoformycin (Pentostatin), etc), pyrimidine antagonists (e.g., fluoropyrimidines (e.g., 5-fluorouracil (Adrucil), 5-fluorodeoxyuridine (FdUrd) (Floxuridine)) etc), and cytosine arabinosides (e.g., Cytosar (ara-C) and Fludarabine, etc); 5) enzymes, including, L-asparaginase, and hydroxyurea, etc; 6) hormones, including, glucocorticoids, such as, antiestrogens (e.g., Tamoxifen, etc), nonsteroidal antiandrogens (e.g., Flutamide, etc), and aromatase inhibitors (e.g., anastrozole (Arimidex), etc); 7) platinum compounds (e.g., Cisplatin and Carboplatin, etc); 8) monoclonal antibodies conjugated with anticancer drugs, toxins, and/or radionuclides, etc; 9) biological response modifiers (e.g., interferons (e.g., IFN-y, etc) and interleukins (e.g., IL-2, etc), etc); 10) adoptive immunotherapy; 11) hematopoietic growth factors; 12) agents that induce tumor cell differentiation (e.g., all-trans-retinoic acid, etc); 13) gene therapy techniques; 14) antisense therapy techniques; 15) tumor vaccines; 16) therapies directed against tumor metastases (e.g., Batimistat, etc); 17) angiogenesis inhibitors, and the like.

Therapeutic compounds for use in the methods and compositions as described herein have characteristic solubilities and hydrophobicities that are readily measured by one skilled in the art. For example, aqueous solubility can be assessed by measuring the solubility in a suitable solution, where for example compound concentrations can be measured by HPLC, HPLC/MS, or the like. Hydrophobicity is typically assessed by measuring the portioning of the compound between water and an organic solvent such as octanol. As such, the log P value is a standard measurement of hydrophobicity known in the art. An example of such values for a number of therapeutic compounds that may be used in the methods and compositions as described herein can be found in Benet et al., AAPS Journal, 2011, 13(4): 519-547, the disclosure of which is hereby incorporated herein by reference in its entirety as it relates to therapeutic compounds, aqueous solubilities of the compounds, log P of the compounds, and other characteristics of the compounds.

In some embodiments, the therapeutic compound as described herein is aqueous insoluble, having an aqueous solubility of less than 10 mg/mL, less than 5 mg/mL, less than 2 mg/mL, less than 1 mg/mL, less than 0.5 mg/mL, less than 0.2 mg/mL, less than 0.1 mg/mL, less than 0.05 mg/mL, less than 0.02 mg/mL or less than 0.01 mg/mL. In some embodiments, the therapeutic compounds has an aqueous solubility of the less than 10 mg/mL, less than 5 mg/mL, less than 2 mg/mL, less than 1 mg/mL, less than 0.5 mg/mL, less than 0.2 mg/mL, less than 0.1 mg/mL, less than 0.05 mg/mL, less than 0.02 mg/mL or less than 0.01 mg/mL; where the range of solubility is to as low as $10^{-3}$ mg/mL, as low as $10^{-4}$ mg/mL, as low as $10^{-5}$ mg/mL, as low as $10^{-6}$ mg/mL, as low as $10^{-7}$ mg/mL, or as low as an undetectable level of solubility. In some embodiments, the therapeutic compound as described herein is hydrophobic, for example as determined by measuring the log P. In some embodiments, the therapeutic compound has a log P of greater than 0, greater than 0.5, greater than 1.0, greater than 1.5, greater than 2.0, greater than 2.5, greater than 3.0, greater than 3.5, greater than 4.0, greater than 4.5, or greater than 5.0. In some embodiments, the therapeutic compound has a log P ranging from 0 to 10.0, 0.5 to 10.0, 1.0 to 10.0, 1.5 to 10.0, 2.0 to 10.0, 2.5 to 10.0, 3.0 to 10.0, 3.5 to 10.0, 4.0 to 10.0, 4.5 to 10.0, 5.0 to 10.0, 0 to 7.0, 0.5 to 7.0, 1.0 to 7.0, 1.5 to 7.0, 2.0 to 7.0, 2.5 to 7.0, 3.0 to 7.0, 3.5 to 7.0, 4.0 to 7.0, 4.5 to 7.0, or 5.0 to 7.0.

In some embodiments, the therapeutic compound as described herein has an aqueous solubility of less than 10 mg/mL, less than 5 mg/mL, less than 2 mg/mL, less than 1 mg/mL, less than 0.5 mg/mL, less than 0.2 mg/mL, less than 0.1 mg/mL, less than 0.05 mg/mL, less than 0.02 mg/mL or less than 0.01 mg/mL and a log P greater than 0, greater than 0.5, greater than 1.0, greater than 1.5, greater than 2.0, greater than 2.5, greater than 3.0, greater than 3.5, greater than 4.0, greater than 4.5, or greater than 5.0. In some embodiments, the therapeutic compound as described herein has an aqueous solubility of less than 10 mg/mL, less than 5 mg/mL, less than 2 mg/mL, less than 1 mg/mL, less than 0.5 mg/mL, less than 0.2 mg/mL, less than 0.1 mg/mL, less than 0.05 mg/mL, less than 0.02 mg/mL or less than 0.01 mg/mL and a log P ranging from 0 to 10.0, 0.5 to 10.0, 1.0 to 10.0, 1.5 to 10.0, 2.0 to 10.0, 2.5 to 10.0, 3.0 to 10.0, 3.5 to 10.0, 4.0 to 10.0, 4.5 to 10.0, 5.0 to 10.0, 0 to 7.0, 0.5 to 7.0, 1.0 to 7.0, 1.5 to 7.0, 2.0 to 7.0, 2.5 to 7.0, 3.0 to 7.0, 3.5 to 7.0, 4.0 to 7.0, 4.5 to 7.0, or 5.0 to 7.0.

In some embodiments, the therapeutic compound as described herein has an aqueous solubility of less than 10 mg/mL, less than 5 mg/mL, less than 2 mg/mL, less than 1 mg/mL, less than 0.5 mg/mL, less than 0.2 mg/mL, less than 0.1 mg/mL, less than 0.05 mg/mL, less than 0.02 mg/mL or less than 0.01 mg/mL, where the range of solubility is to as low as $10^{-3}$ mg/mL, as low as $10^{-4}$ mg/mL, as low as $10^{-5}$ mg/mL, as low as $10^{-6}$ mg/mL, as low as $10^{-7}$ mg/mL, or as low as an undetectable level of solubility; and a log P greater than 0, greater than 0.5, greater than 1.0, greater than 1.5, greater than 2.0, greater than 2.5, greater than 3.0, greater than 3.5, greater than 4.0, greater than 4.5, or greater than 5.0. In some embodiments, the therapeutic compound as described herein has an aqueous solubility of less than 10 mg/mL, less than 5 mg/mL, less than 2 mg/mL, less than 1 mg/mL, less than 0.5 mg/mL, less than 0.2 mg/mL, less than 0.1 mg/mL, less than 0.05 mg/mL, less than 0.02 mg/mL or less than 0.01 mg/mL, where the range of solubility is to as low as $10^{-3}$ mg/mL, as low as $10^{-4}$ mg/mL, as low as $10^{-5}$ mg/mL, as low as $10^{-6}$ mg/mL, as low as $10^{-7}$ mg/mL, or as low as an undetectable level of solubility; and a log P ranging from 0 to 10.0, 0.5 to 10.0, 1.0 to 10.0, 1.5 to 10.0, 2.0 to 10.0, 2.5 to 10.0, 3.0 to 10.0, 3.5 to 10.0, 4.0 to 10.0, 4.5 to 10.0, 5.0 to 10.0, 0 to 7.0, 0.5 to 7.0, 1.0 to 7.0, 1.5 to 7.0, 2.0 to 7.0, 2.5 to 7.0, 3.0 to 7.0, 3.5 to 7.0, 4.0 to 7.0, 4.5 to 7.0, or 5.0 to 7.0.

II. Hydrogels and Polymers

The vault complexes as described herein, and compositions thereof comprising a sequestered therapeutic compound can be formulated to further comprise a hydrogel or polymer. The hydrogels and polymers can provide additional control of the dosing of the therapeutic compound, as the vault complex itself can be slowly released from the hydrogel or polymer. A variety of polymers and hydrogels are known in the art and can be used to formulate the compositions comprising vault complex and a therapeutic compound sequestered therein (Vilar et al., Curr Drug Deliv, 2012, 9(4): 367-94; Giri et al., Curr Drug Deliv, 2012; 9(6): 539-55; Elbert, Donald L., Acta Biomater., 2011, 7(1): 31-56).

A diblock copolypeptide hydrogel (DCH) is an example of a suitable hydrogel for the vault complex compositions as described herein (see Zhang et al., Biomaterials, 2014, 35(6): 1989-2000; US Patent Application Publication No. 2012/0093722, the disclosures of which are hereby incorporated herein by reference as they relate to DCH). Such hydrogels can administered to a particular site, such as intratumoral injection, or administration to a mucosal site, and will remain at an site of administration, so that the material will stay localized and provide the slow release of the vault complex and the therapeutic compound from the vault complex to act locally, with greater activity at the desired site of action, and fewer side effects due to the lack of systemic exposure.

DCH offer significant advantages over most biomaterials since many molecular variables can be used to readily adjust their physical properties (Deming, T. J., Soft Matter, 2005. 1:28-35; Li, Z. B., and Deming, T. J., Cancer Research, 2010, Soft Matter, 6:2546-51; Nowak, A. P., et al., Nature, 2002, 417:424-8; Yang, C. Y., et al., biomaterials, 2009, 30:2881-98; Breedveld, V., et al., Macromolecules, 2004, 37:3943-53; Deming, T. J., et al., Adv Drug Deliv Rev, 2002, 54:1145-55). While the stiffness of most hydrogels is mainly adjusted either by polymer concentration or crosslink density, DCH stiffness can be tuned by these methods and additionally by altering amino acid composition, hydrophilic to hydrophobic ratio, molecular weight, and block architecture of the polymers. Gel strength, porosity, functionality, and media stability can be controlled, and these properties can be adjusted independently of each other. The physical and biological properties of DCH can be varied almost limitlessly and adjusted for potential applications by altering copolymer chain length and composition. Moreover, DCH are physically associated gels that can be deformed and thinned by stress and either applied by smearing or injected through an applicator, after which they rapidly self-assemble into elastic gels with fibril-like nanostructures and porous microstructures. These can be readily adapted for use in compositions comprising the vault complexes, for site directed delivery. Further, a DCH formulation of $K_{180}L_{20}$ exhibits good deposit formation with desirable properties that could be varied according to weight percent concentration to give different degrees of deposit consistency and porosity suitable for drug delivery and scaffold applications.

General techniques exist for controlling the delivery of the vault complex from hydrogels, including physical entrapment, covalent tethering, and affinity-based sequestration. The vault complex can be physically entrapped within the mesh of the hydrogel, which impedes their diffusion, or, the vault complex can be covalently attached to the hydrogel network through degradable linkages (typically utilizing hydrolysis of esters or similarly labile bonds by water or enzymatic degradation). The vault complex can also be sequestered within the hydrogel by, for example, ionic interactions. These methods typically result in a sustained release profile. In one example, the DCH hydrogel can be covalently attached to the vault complex by a suitable linker, such as a polyglycolic acid linker. Thus, the lysines of $K_{180}L_{20}$ vaults can be covalently bound to one end of the polyglycolic acid linker by forming an amide bond with a carboxylic acid of the linker and the lysine amine. The other end of the linker can be similarly covalently bound to the vault complex, for example forming an amide with a lysine amine on the surface of the vault particle. The ester bonds within the polyglycolic acid linker will hydrolyze in vivo, resulting in detachment from the hydrogel and the slow release of the vault into the local environment. In one example, the vault complex can be modified by binding to a cationic dendronized polymer, and combined with a negatively charged hydrogel, such as $E_{180}L_{20}$ hydrogels. In this instance, the positively charged modified vault complex and negatively charged hydrogel have an ionic affinity attraction that results in sustained release of the vaults from the hydrogel.

In some instances, the therapeutic compound to be sequestered within the vault complex is an antiviral compound, including an antiviral compound for preventing an infection of HIV. Is this instance, the vault complex is delivered or administered to a mucosal surface, such as a vaginal or rectal mucosal surface. The hydrogels for use herein, in addition to controlling the delivery of the vault complex by physical entrapment, covalent attachment of the vault complex, or by affinity-based sequestration of the vault complex, are also targeted to the mucosal surface. In one example, the hydrogel comprises $K_{180}L_{20}$, wherein the cationic chains of lysine adhere to the mucosal tissue membranes, which are anionic. In one example, the vault complex can be modified by binding to a cationic dendronized polymer, and combined with a negatively charged hydrogel, such as $E_{180}L_{20}$ hydrogels. In this instance, the positively charged modified vault complex and negatively charged hydrogel have an ionic affinity attraction that results in sustained release of the vaults from the hydrogel. As the dendronized polymer bound to vault contains additional branches that are positively charged, the resulting composition comprising the $E_{180}L_{20}$ hydrogels and the vault bound to the dendronized polymer will be positively charged, and will adhere to the negatively charged mucosal tissue membranes. In one example, the polymers for use in preparing the hydrogels can be modified to include methionine residues, such as $(K_xM_y)_{180}L_{20}$, wherein x+y=180. The methionine residues can be further modified by chemoselective alkylation to introduce functional groups such as alkylation with 4-(bromomethyl)phenyl)boronic acid, which promotes hydrogel formation including functional groups that can bind to sugar groups present in the mucus and on HIV-1 Env glycoproteins. Such hydrogels comprising the vault complex when administered to the desired mucosal surface will not only be maintained at that surface due to the charge of the lysines in the hydrogel, the sugar binding functional group will also target the mucosal tissue membranes. Such hydrogels will also attract any HIV virus by attraction of the sugar binding function group of the hydrogel to the HIV envelope glycoproteins.

Another possible polymer system for use in delivering the vault complexes as described herein involves the use of a thermally responsive polymer. As an example, Poly(N-isopropyl acrylamide) undergoes a reversible phase transition, where it becomes insoluble in water above the lower critical solution temperature of 32° C. This can be covalently attached to the vault complex, for example, by attaching a linker that forms a disulfide bond with a cysteine on the surface of the vault. Details of this method can be found, for example, in Matsumoto et al., ACS Nano, 2013, 7:867-874, the disclosure of which is hereby incorporated herein by reference in its entirety. Upon delivery of the vault complex conjugated to the Poly(N-isopropyl acrylamide), the local delivery site of the subject, such as a human, is above the lower critical solution temperature, and the vault complexes aggregate at the delivery site, thereby maintaining the vault complex at the site of delivery, where the therapeutic compound is released from the vault to provide an optimal therapeutic effect with reduced side effects due to systemic exposure of the therapeutic compound.

The compositions described herein comprising the vault complex with a therapeutic compound sequestered therein, as well as compositions further comprising the polymer or hydrogel, such as a thermally responsive polymer, or suitable hydrogel as described herein, can be readily assessed for their ability to deliver the therapeutic compound to the desired site or cells. Such methods are known to one skilled in the art, and include, for example, the methods described herein in Examples 10 and 11.

Methods of Use

Vault complexes described herein can be used to deliver an agent of interest (e.g., a hydrophobic therapeutic compound) to a cell, a tissue, an environment outside a cell, a tumor, an organism, or a subject. In one embodiment, the vault complex comprises a therapeutic compound sequestered within the vault complex, and the vault complex is introduced to the cell, tissue, or tumor. In some embodiments, the vault complex is introduced into the extracellular environment surrounding the cell. In other embodiments, the vault complex is introduced into a subject. Delivery of the vault complex of the invention can include administering the vault complex to a specific tissue, specific cells, an environmental medium, or to the subject, such as a human.

The methods of the invention comprise delivering a therapeutic compound to a cell by contacting the cell with any of the vault complexes described herein. Cells of the invention can include, but are not limited to, any eukaryotic cell, mammalian cell, or human cells, including tumor cells.

Methods of the invention include delivery of the vault complex to a subject. The delivery of a vault complex to a subject in need thereof can be achieved in a number of different ways. In vivo delivery can be performed directly by administering a vault complex to a subject. In one embodiment, the vault complex is administered to a mammal, such as a mouse or rat. In another embodiment, the vault complex is administered to a human.

In another embodiment, the methods of delivery of the invention include systemic injection of vaults. In other embodiments, the methods of delivery of the invention include oral ingestion of vaults.

In some embodiments, the methods of delivery include oral, intravenous, cutaneous, subcutaneous, nasal, intramuscular, or intraperitoneal routes. In some embodiments, the composition can be injected intra-tumorally, e.g., directly into a solid tumor. In some embodiments, the composition can be administered directly to a surface, e.g., a topical administration, including topical administration to a mucosal surface, including a nasal, vaginal, or rectal mucosal surface.

Methods of Treatment

Provided herein is a method of treating or managing disease by administering the vault complex as described herein to a subject (e.g., human). In some embodiments, the method comprises treating a subject in need of such treatment or management by administering to the subject a therapeutically effective amount of the vault complexes described herein.

The data obtained from cell culture assays and animal studies can be used in formulating a range of dosage for use in humans. For any therapeutic compound used in the methods described herein, the therapeutically effective dose can be estimated initially from cell culture assays. A dose may be formulated in animal models to achieve a circulating plasma concentration range of the vault complex. Such information can be used to more accurately determine useful doses in humans.

The pharmaceutical composition according to the present invention to be given to a subject, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of the disease being treated. Prescription of treatment, e.g., decisions on dosage etc., is within the responsibility of general practitioners and other medical doctors, and typically takes account of the disorder to be treated, the condition of the individual patient, the site of delivery, the method of administration, and other factors known to practitioners. Examples of the techniques and protocols mentioned above can be found in Remington's Pharmaceutical Sciences, 16th edition, Osol, A. (ed), 1980. A composition can be administered alone or in combination with other treatments, either simultaneously or sequentially dependent upon the condition to be treated.

In certain embodiments, the dosage of vault complexes is between about 0.1 and 10,000 micrograms per kilogram of body weight or environmental medium. In another embodiment, the dosage of vault complexes is between about 1 and 1,000 micrograms per kilogram of body weight or environmental medium. In another embodiment, the dosage of vault complexes is between about 10 and 1,000 micrograms per kilogram of body weight or environmental medium. For intravenous injection and intraperitoneal injection, the dosage is preferably administered in a final volume of between about 0.1 and 10 mL. For inhalation the dosage is preferably administered in a final volume of between about 0.01 and 1 mL. As will be appreciated by one of ordinary skill in the art with reference to this disclosure, the dose can be repeated one or multiple times as needed using the same parameters to effect the purposes disclosed in this disclosure.

In some embodiments, the dosage of vault complexes including vault complexes further comprising a polymer or hydrogel, injected intra-tumorally is between about 0.1 and 10,000 micrograms per $cm^3$, or between about 10 and 1,000 micrograms per $cm^3$, wherein the dosage is administered in a volume that is between about 1% and 25% of the tumor volume.

In some embodiments, the dosage of vault complexes, including vault complexes further comprising a polymer or hydrogel, administered to a mucosal surface is between about 0.1 and 10,000 micrograms per $cm^2$ of mucosal surface area, or between about 10 and 1,000 micrograms per $cm^2$ of mucosal surface area, wherein the dosage is administered in a volume that is between about 0.001 cm to 1 cm times the mucosal surface area in $cm^2$ (i.e., administered to a surface area at a thickness of about 0.001 cm to 1 cm).

For instance, the pharmaceutical composition may be administered once to a subject, or the vault complex may be administered as two, three, or more sub-doses or injections at appropriate intervals. In that case, the vault complexes can be injected in sub-doses in order to achieve the total required dosage.

The vault complexes as described herein can be administered in combinations of vault complexes containing different therapeutic compounds, or in combination with other known agents or therapies effective in treatment of a particular condition. An administering physician can adjust the amount and timing of vault complex administration or injection on the basis of results observed using standard measures of efficacy known in the art or described herein. The skilled artisan will also appreciate that certain factors may influence the dosage and timing required to effectively treat a subject, including but not limited to the severity of the disease or disorder, previous treatments, the general health and/or age of the subject, and other diseases present.

Methods of Preparing Vault Complexes

The methods of the invention include preparing the vault complexes described herein.

In one embodiment, the vault complexes are derived or purified from natural sources, such as mammalian liver or spleen tissue, using methods known to those with skill in the art, such as for example tissue homogenization, differential centrifugation, discontinuous sucrose gradient fractionation and cesium chloride gradient fractionation. In another embodiment, the vault complexes are made using recombinant technology.

In the case of a recombinant protein, such as recombinant MVP, the polynucleotide sequences encoding the recombinant protein are used to generate a bacmid DNA, which is used to generate a baculovirus comprising the sequence. The baculovirus is then used to infect insect cells for protein production using an in situ assembly system, such as the baculovirus protein expression system, according to standard techniques, as will be appreciated by one of ordinary skill in the art with reference to this disclosure. Advantageously, the baculovirus protein expression system can be used to produce milligram quantities of vault complexes, and this system can be scaled up to allow production of gram quantities of vault complexes as described herein, e.g., for use in sequestering a therapeutic compound, and for use in compositions further comprising a polymer or hydrogel.

In another embodiment, therapeutic compound, e.g., a hydrophobic and/or aqueous insoluble therapeutic compound as described herein, is incorporated (i.e., sequestered) into the provided vault complex. In one embodiment, incorporation is accomplished by incubating the vaults with the agent of interest at an appropriate temperature and for an appropriate time, as will be appreciated by one of ordinary skill in the art with reference to this disclosure. The vaults containing the protein of interest are then purified, such as, for example sucrose gradient fractionation, as will be appreciated by one of ordinary skill in the art with reference to this disclosure.

In another embodiment, the vault complex comprising the therapeutic compound sequestered therein is used to prepare a composition further comprising a polymer or hydrogel. In some embodiments, the vault complex comprising the therapeutic compound sequestered therein is covalently attached to a thermally responsive polymer, a cationic dendronized polymer, or to a hydrogel by methods known to one skilled in the art or as described herein. In some embodiments, the vault complex comprising the therapeutic compound sequestered therein is entrapped within a hydrogel by methods known to one skilled in the art, or as described herein. In some embodiments, the vault complex comprising the therapeutic compound sequestered therein that is covalently attached to the cationic dendronized polymer is associated by ionic interaction within a negatively charged hydrogel, such as a hydrogel comprising $E_{180}L_{20}$, by methods known to one skilled in the art, or as described herein.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques, and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B (1992).

Example 1: AH1Z and AH2Z Cloning

NS5A 1-31 was PCR amplified from a genomic construct generously provided by Darius Moradpour M.D. at The Centre Hospitalier Universitaire Vaudois, University of Lausanne Switzerland. In order to generate recombinant MVP carrying the NS5A1-31 ampithathic α-helix at the amino terminus of MVP, a previously constructed vector containing rat MVP (pBluescript+ MVP) was used, which contained a NcoI restriction enzyme site at the start methionine codon of MVP allowing for in-frame insertion of sequences with complimentary 5' NcoI overhangs. Primers were designed as follows to generate NS5A1-31 carrying NcoI sequences at both ends (underlined, start Met in bold).

```
Forward:    5'GAATTCACCATGGCCGGTTCCTGGC3'
                                        (SEQ ID NO: 21)

Reverse:    5'CCTTGCTCACCCATGGTTGGCATGAG3'
                                        (SEQ ID NO: 22)
```

However, this resulted in two sequence codon changes of Ser2Ala and Arg31Trp, the latter being a more non-conservative point mutation, given previous data demonstrating, the first five and last five amino acids of NS5A1-31 are relatively unstructured as seen by NMR (Penin, F., et al., The Journal of Biological Chemistry, 2004, 279(39): 40835-43). As such, these changes were expected to have little to no consequential impact. The final amino acid sequence generated by PCR for NS5A1-31 is as follows with the point mutations underlined:

```
MAGSWLRDIWDWICEVLSDFKTWLKAKLMPT. SEQ ID NO: 17
```

The sequence of NS5A1-31 as reported in the literature is: SGSWLRDIWDWICEVLSDFKTWLKAKLMPQL (SEQ ID NO:16). Thus, in the present work, when NS5A1-31 was attached to MVP, a starting methionine was inserted followed by an alanine (MA underlined below). In addition, the Q is converted to a T before the starting methionine of MVP. The amphipathic helix itself is shown in bold (above and below) and remains unchanged upon attachment to MVP. The resulting sequence at the junction of NS5A1-31 with MVP (with the sequence of MVP in parentheses) is shown below:

```
                                        (SEQ ID NO: 23)
MAGSWLRDIWDWICEVLSDFKTWLKAKLMPT(MATEE----).
```

Purified pBluescript+ MVP plasmid DNA was digested with NcoI then gel purified on a 1% agarose gel followed by spin-column (QiaQuick PCR Purification Kit, Qiagen) and quantified by O.D.$_{260nm}$ (Nanodrop 2000, Thermo Scientific). Digested vector and PCR insert were ligated and transformed into TOP10 E. coli cells (Invitrogen) and plated overnight on LB agar plates containing 50 µg/mL Ampicillin at 37° C. with 5% CO$_2$. Colonies were collected and screened for plasmid constructs carrying in-frame and properly orientated NS5A1-31 fused to the start methionine of MVP (Laragen DNA sequencing). A singlet and doublet version was identified, providing a single NS5A fusion peptide fused to MVP (SEQ ID NO:26), or two NS5A fusion peptides fused to MVP (i.e., containing two of the amphipathic α-helices, SEQ ID NO:28) and the resulting vault complexes were accordingly renamed AH1 and AH2 vaults. AH1 and AH2 were subsequently sub-cloned from pBluescript into pFastbac 1 vector using EcoRI sites flanking the entire construct. Positive pFastBac1-AH1 and AH2 colonies were similarly identified and used for large scale Maxi-Prep (Sigma) plasmid DNA purification with storage at −20° C.

A previous vault construct containing the Z domain attached to MVP (pFastbac1 CP-MVP-Z) was used to transfer the Z domain to AH1 and AH2 via restriction enzyme digestion with XhoI and KpnI, which flank the Z domain. Transformed colonies were sequenced for AH1Z and AH2Z positive constructs and subsequently re-grown for large scale Maxi-prep plasmid purification (Sigma Kit). Aliquots were stored at −20° C. or −80° C. until further use.

Purified pFastBac1-AH1Z & AH2Z constructs were transformed into DH10Bac E. coli cells carrying baculovirus DNA (Invitrogen Bac-to-Bac kit). Recombination between pFastBac plasmid and the Bacmid leads to transposition of the AH1Z and AHZ2 DNA into the insect virus genome leading to disruption of a Lac Z gene selection marker. Positively identified colonies were isolated according to the Bac-to-Bac Kit manual and stored at −20° C. Insertion of AH1Z and AH2Z DNA was confirmed by PCR amplification and gel analysis.

AH1Z and AH2Z Bacmid DNA was used to transfect Sf9 (Spodoptera frugiperda) cells. Briefly, approximately 8×10$^5$ Sf9 cells were added to 6 well plates in 2 mL of un-supplemented Grace's Insect Media and allowed to adhere for 15 minutes. Eight µL of Cellfectin II was mixed with 100 µL of Grace's Media while 1 µL of Bacmid DNA was mixed with 100 µL of Grace's Media and then both mixed together gently and allowed to sit for 30 minutes at room temperature in the dark. This Cellfectin-Bacmid DNA mixture was added to the previously plated cells and incubated for 5 hrs at 27° C. Media was replaced with fresh Grace's Media supplemented with 10% FBS and Penicillin/Streptomycin. Cells were incubated for an additional 72 hrs at 27° C. Media was collected, spun for 5 minutes at 500×g to remove any contaminating cells and stored at 4° C. This P1 viral stock was subsequently used to infect a 10 mL Sf9 cell culture at 2106 cells/mL for 48 hrs at 27° C. in order to amplify the viral titer. Media was collected, spun to remove cells, stored at both 4° C. and −80° C. and designated as P2 virus.

50 mL of Sf9 cell cultures at 2×10$^6$ cells/mL in SfII-900 Media were infected with either: 2.5, 5, 10, 15, 20 or 25 µL of P2 virus for 3 days at 27° C. with shaking. Cells were collected and lysed in Buffer A containing 1% Tx-100 for 5 minutes on ice. Lysates were centrifuged at 20,000×g for 20 minutes. Aliquots from both resuspended pellets and supernatant were run on SDS-PAGE followed by Western Blotting with an anti-MVP polyclonal rabbit antibody to assess infection levels for AH1Z and AH2Z. Subsequent infections were carried out with the optimal amount of P2 virus for each AH1Z and AH2Z. Cell pellets were collected, weighed, and stored at −80° C. until ready for vault purification.

Example 2: AH1Z and AH2Z Expression, Purification, & Electron Microscopy

AH1Z and AH2Z vault complexes were purified by methods known in the art. See, e.g., Buehler, D. C., et al., Small, 2011, 7(10): 1432-9; and Stephen, A. G., et al., J Biol Chem, 2001, 276(26): 23217-20, the disclosures of which are hereby incorporated herein by reference as it relates to methods of making such recombinant vault complexes. Very briefly, cell pellets were lysed and subjected to multiple rounds of differential ultra-centrifugation in which the large vault nanoparticle pellets at 100,000×g. Lastly, vault samples were treated with either: 50 µL RNAse A+5 µL T1 RNA cocktail (Invitrogen) or 2% Streptomycin to degrade contaminating ribosomes prior to overnight centrifugation over a discontinuous step-wise sucrose gradient (1.5 mL of 20, 30, 40, 45, 50, and 60% sucrose in Buffer A) at 25,000 rpm (77,000×g) using a Beckman SW41 Ti swinging bucket rotor for 16 hrs at 4° C. Gradient fractions were collected, diluted and ultra-centrifuged for 2 hrs at 100,000×g to collect purified vaults. Vault fractions were resuspended in either 20 mM MES buffer or 1×PBS$^-$ buffer and assayed for purity by either SDS-PAGE with coomassie blue staining or by Western Blotting and quantitated by BCA. Purified AH1Z and AH2Z vault complexes were visualized under negative stain EM using uranyl acetate. The resulting AH1 vault complex thus comprises the modified NS5A-MVP-Z domain fusion protein (SEQ ID NO:30), and AH2Z vault complex comprises the modified NS5A-NS5A-MVP-Z domain fusion protein (SEQ ID NO:36).

Example 3: Altered AH1Z Cell Lysis & Purification

A 1 L Sf9 cell culture was infected with AH1Z baculovirus and collected after 72 hrs at 27° C. Cells were resuspended in Buffer A and split into 4 equal fractions. Cells were lysed with either Tx-100 (both with and without overnight sucrose gradient centrifugation step), 10 mM CHAPS (3-((3-Cholamidopropyl)dimethylamminio)-1-propanesulfate) or by sonication. Vault purification was conducted as per standard protocol. Fraction volumes were kept normalized relative to each at each step in vault purification and 100 µL aliquots were taken and tested for MVP by Western Blotting as described previously. A separate control 250 mL Sf9 cell infection with CPZ baculovirus (the resulting CPZ vaults comprise the fusion protein MVP modified by CP on the N-terminus and Z domain on the C-terminus, SEQ ID NO:34, also referred to as CP-MVP-Z) was also tested using 10 mM CHAPS.

Figure 2:
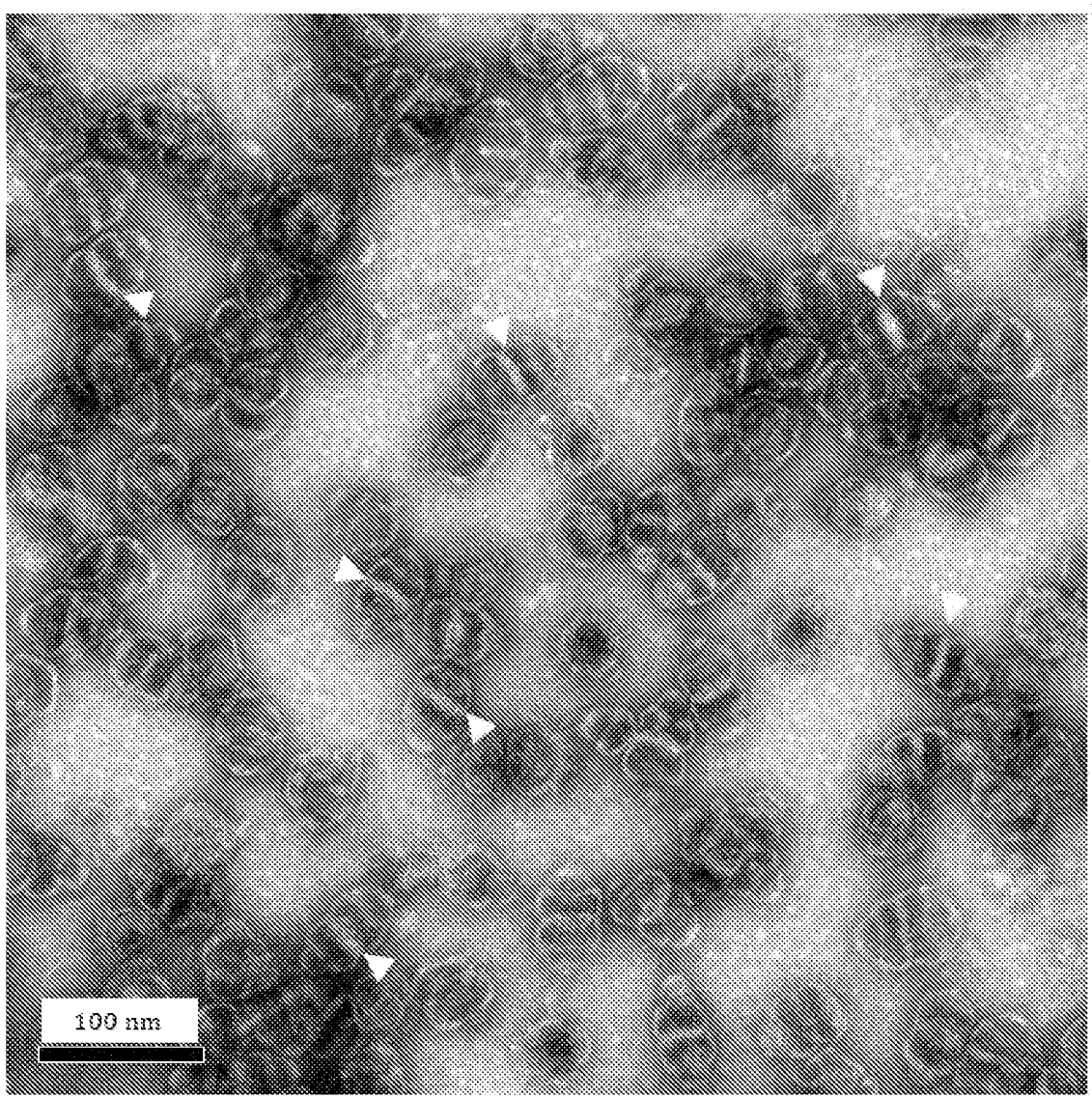
FIG. 2: Negative stain EM of purified AH1Z vault complexes show morphologically normal shaped vault nanoparticles except for the presence of a strong non stained additional band of density at the vault waistline (arrowheads).

The addition of NS5A1-31 amphipathic α-helix to the amino terminus did not prevent MVP expression and assembly into vault like particles. Like normal CPZ vaults, AH1Z and AH2Z vault complexes sediment during centrifugation into the denser fractions of the overnight sucrose gradient (40-60%) and appear morphologically intact by EM. The presence of a distinct non-stained band at the vault waist was apparent in many of the AH1Z and AH2Z vault complexes when viewed by EM (FIG. 2).

Both AH1Z and AH2Z vault complexes penetrate further into the denser 50 & 60% fractions of the gradient unlike that of control CPZ vaults, which are typically limited to the 40 & 45% fractions (data not shown). This altered gradient profile has been seen when larger vault aggregates known as vaultimers form. Indeed, both AH1Z and AH2Z samples contain these vaultimer structures. However, the majority of both AH1Z and AH2Z vault complexes remain relatively mono-dispersed with only approximately 5-10% existing as vaultimers. Lower yields were seen for cells infected with either AH1Z or AH2Z than compared to those infected with equivalent dosage of CPZ virus. Generally, a 50 mL (approximately 0.5 g) CPZ infection yielded an average of 300-400 µg of total vault protein, while a similar culture of AH1Z yield varied from 150-250 µg and AH2Z averaged less than 50 µg. Thus it was shown that AH1Z and AH2Z can be prepared and purified similarly to the CPZ vaults.

Figure 3:
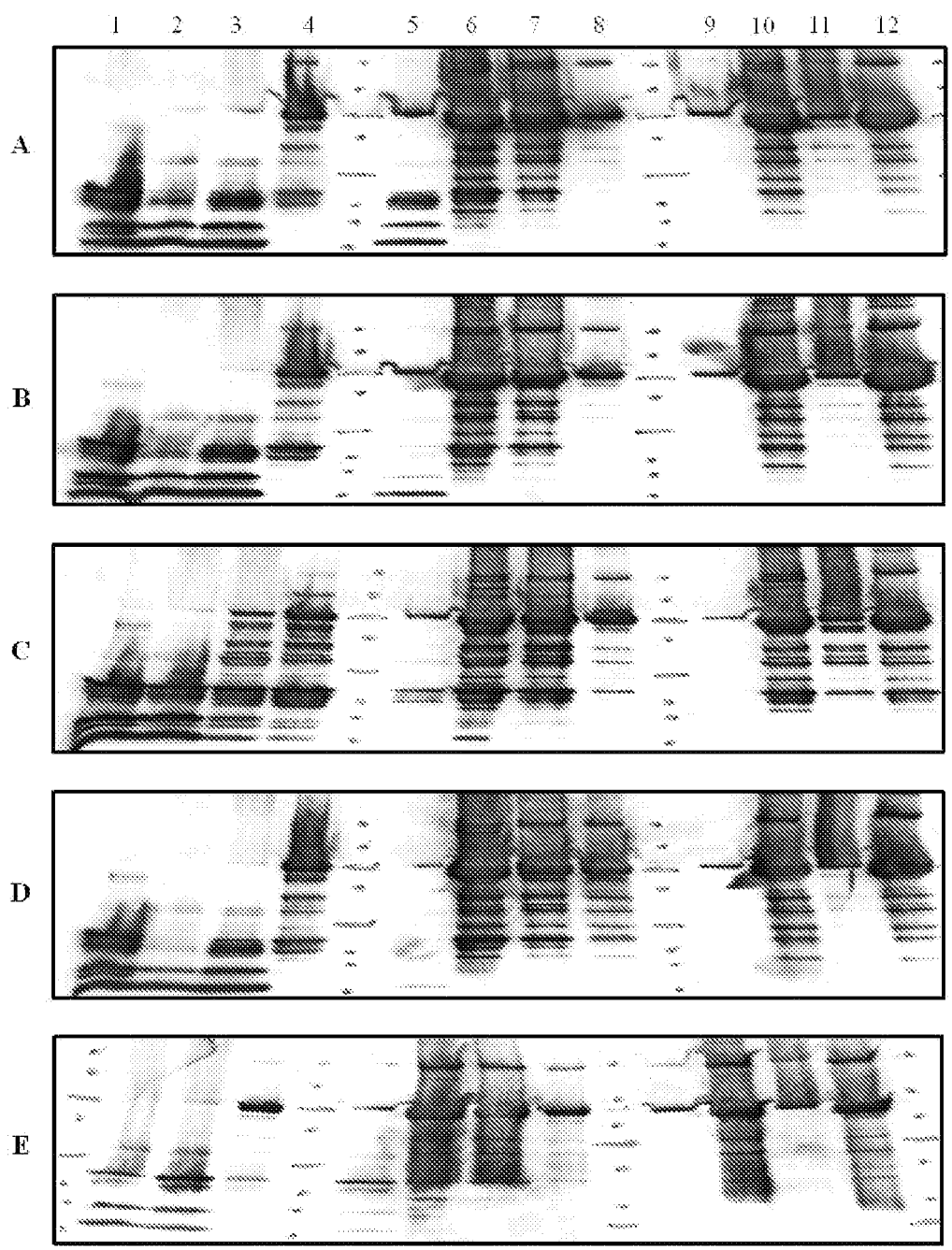
FIG. 3: Western blots of AH1Z vault complex purification steps using different cell lysis methods: Panel A) Tx-100 without overnight sucrose gradient, Panel B) Tx-100, Panel C) Sonication, and Panel D) CHAPS. Panel E) CHAPS lysis of control CPZ vaults.

Western blots profiling the pattern of MVP during each step of vault purification comparing lysis with Tx-100 or CHAPS or using sonication indicated that sonication resulted in a greater loss of AH1Z protein in the early 20,000×g pellet than that of traditional detergent based cell lysis with Tx-100 or alternatively with the zwitterion CHAPS mediated cell lysis (FIG. 3, Panels A-E). Furthermore, sonication leads to appearance of additional MVP breakdown bands not present in the other lysis conditions (FIG. 3, Panel C, lanes 3 & 4). While there was a loss of AH1Z for all cell lysis conditions which occurs at the 25,000×g centrifugation step where vaults are overlaid onto a 14% Ficoll/Sucrose step meant to remove microsomes (FIG. 3, Panels A-E, lane 7 vs. 8), this loss appeared to be consistent for both AH1Z and CPZ vaults. The recovered yields of AH1Z for each different cell lysis condition were approximately equivalent to anticipated values of 200-250 µg per 50 mL infection.

Figure 4:
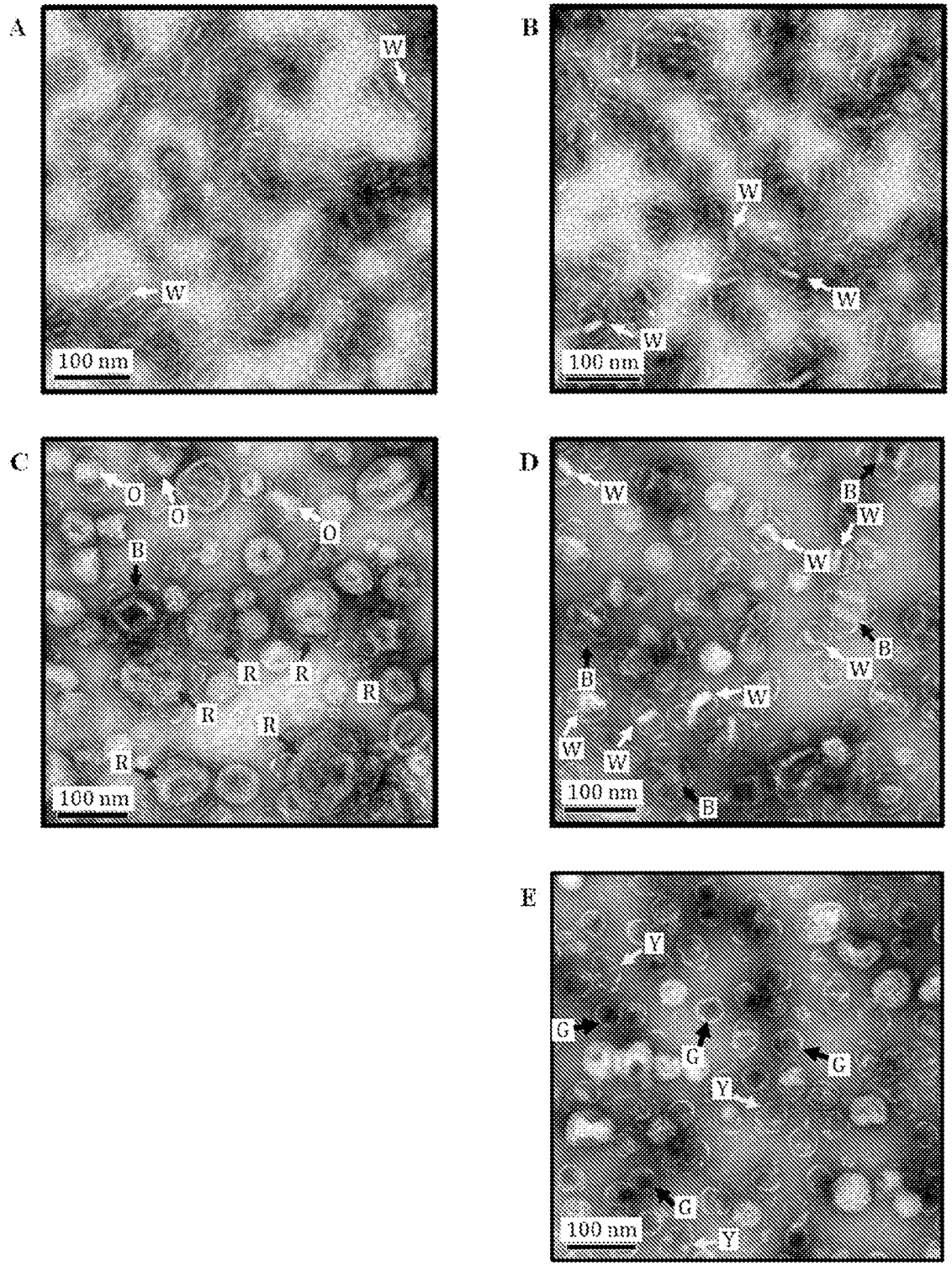
FIG. 4: Negative stain EM of purified AH1Z vault complexes using different cell lysis methods: Panel A) Tx-100 without overnight sucrose gradient, Panel B) Tx-100 C) Sonication, and Panel D) CHAPS. Panel E) Negative stain EM of control CPZ vaults using CHAPS mediated cell lysis.

Recovered vaults were examined by negative stain EM (FIG. 4, Panels A-E). AH1Z vault complexes purified using the standard approach using 1% Tx-100 detergent appear morphologically similar as before, both with or without the final overnight sucrose gradient centrifugation step (FIG. 4, Panels A & B). Additionally, the presence of the strong non-negatively stained band at the vault waist is present in many of the mono-dispersed AH1Z vault particles (FIG. 4, Panels A, B & D, white arrows (marked with "W")). Interestingly, vaults purified by sonication have distorted and bloated morphologies but retain a large non-stained area at the vault waist (FIG. 4, Panel C, orange arrows (marked with "O")). Furthermore, sonication not only leads to the presence of additional vaultimer structures (FIG. 4, Panels C & D, black arrows (marked with "B")) but the presence of large non-vaultimer like aggregates as well (FIG. 4, Panel C, red arrows (marked with "R")). These vault aggregates were previously unseen and are unique only to AH1Z purified by sonication. CHAPS mediated cell lysis results in AH1Z vault complexes possessing much stronger density bands at their waistline along with some vaultimers (FIG. 4, Panel D, white ("W") and black ("B") arrows, respectively). Control CPZ vaults purified with CHAPS show morphological normal CPZ vaults containing no additional interior density unlike that of AH1Z vault complex (FIG. 4, Panel E, yellow arrows (marked with "Y")). These vaults, like the AH1Z vault complexes recovered by sonication and CHAPS show additional unidentified co-purified objects. Thus, the AH1Z and CPZ vaults were similarly purified by the various methods, where the lysis methods are both preferable to sonication.

Example 4: Evaluating AH1Z Vault Complex for Hydrophobicity

Purified AH1Z vault complexes as described in Examples 1-3 were tested for hydrophobicity via incubation with the lipophilic dye 1,1'-dioctadecyl-3,3,3',3'-tetramethylindodicarbocyanine perchlorate (DiD) which has intense fluorescence (644 ex/665 em) only in the presence of lipophilic environments (Molecular Probes, Invitrogen). 5 µL of a 10 µg/µL DiD DMSO stock was added either alone or to 1 mg of pre-purified AH1Z, CPZ or BSA in 1×PBS⁻ buffer for 30 minutes at 4° C. with protection from light. Samples were overlaid onto 1 mL of 1×PBS⁻ buffer in a TLA100.1 rotor tubes (Beckman Coulter) and ultra-centrifuged at 100,000×g for 1 hr at 4° C. Pellets were resuspended in 100 µL of 1×PBS⁻ buffer.

Figure 6:
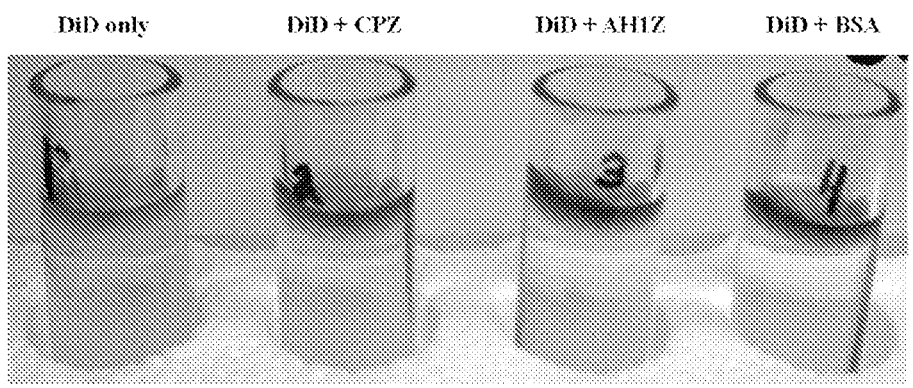
FIG. 6: Increased DiD fluorescence implicates improved hydrophobic properties of AH1Z vault complex (tube 3) over control CPZ vaults (tube 2).

Incubation of DiD alone or with either purified AH1Z, CPZ or BSA showed altered visual levels of dye fluorescence intensity. By itself, the DiD dye remains as an insoluble particulate clinging to the sides of the plastic tubing. Conversely, in the presence of the three different proteins, it displays varying levels of intensity. DiD shows moderately improved fluorescence when incubated with CPZ vaults. As a large protein complex consisting of numerous repeated sub-chains, there are numerous potential hydrophobic spots available for interaction with DiD. However, when incubated with an equal amount of AH1Z vault complexes, DiD fluorescence intensity increases greatly over that seen for CPZ (FIG. 6). The level of intensity roughly mirrors that seen when DiD is co-mixed with an equal amount of BSA, which is well known to contain numerous hydrophobic patches used for non-specific binding of serum sterols and fatty acids in vivo. This increase in DiD intensity between CPZ and AH1Z vaults supports that the addition of the NS5A 1-31 peptide provides an environment for sequestering small hydrophobic compounds such as DiD, as it is likely that this improved fluorescence of DiD is due to the presence of additional membrane lipids. The varying degrees of DiD fluorescence suggest that AH1Z vault complexes contain increased hydrophobic properties over that of control CPZ vaults as would be expected given the nature of the attachment of the amphipathic NS5A1-31 α-helix.

Example 5: Cryo-EM Tomography

Figure 5:
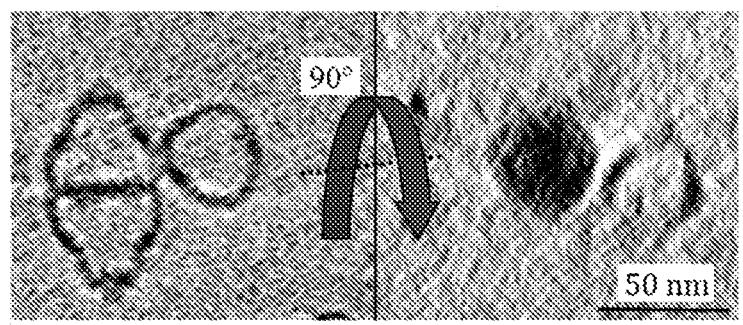
FIG. 5: High magnification tomography density slice of a single AH1Z vault complex obtained from cryo-EM data. Bisected along the x-plane, the waistline density band spans the entire vault lumen.

Cryo-EM tomography studies of purified AH1Z vault complex was conducted to generate tilt series images. The novel waistline density band seen in a majority of the AH1Z vault complexes is a unique anomaly. The tomography tilt slices which shows the additional density band at the vault waistline originally attributed to the addition of NS5A1-31 can actually span the entire width of the vault lumen (FIG. 5). Furthermore, additional density can be seen at both vault caps correlating with the attached Z domain. When the vault image is tilted perpendicularly and viewed as a slice at the waistline, the additional density remains spanning the entire vault lumen. Interestingly, some AH1Z vault complexes have additional density at the waistline that does not span the full width of the lumen but are in various levels of completeness, i.e., waxing to waning "crescent-moons" (data not shown).

Example 6: Transmission Electron Microscopy on AH1 Vault Complex

Figure 8A:
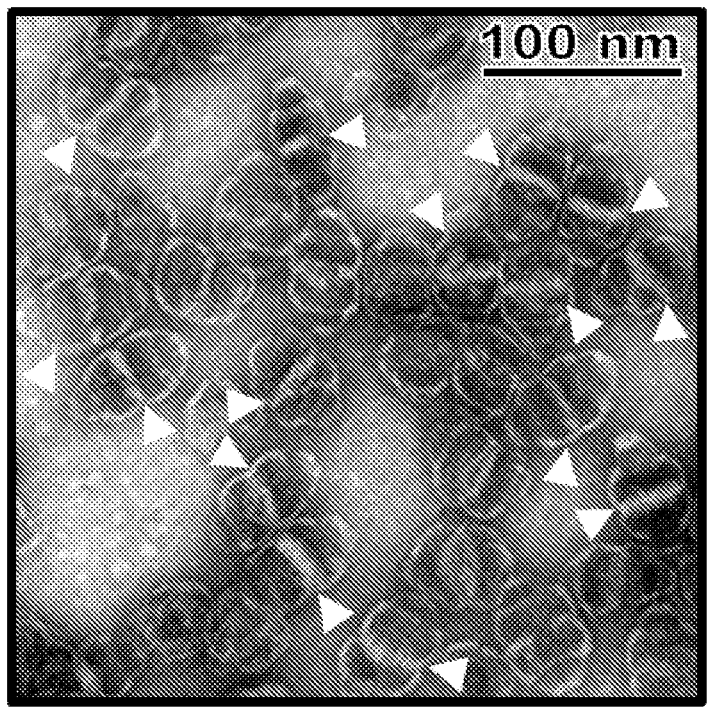
FIGS. 8A and 8B.
Figure 8B:
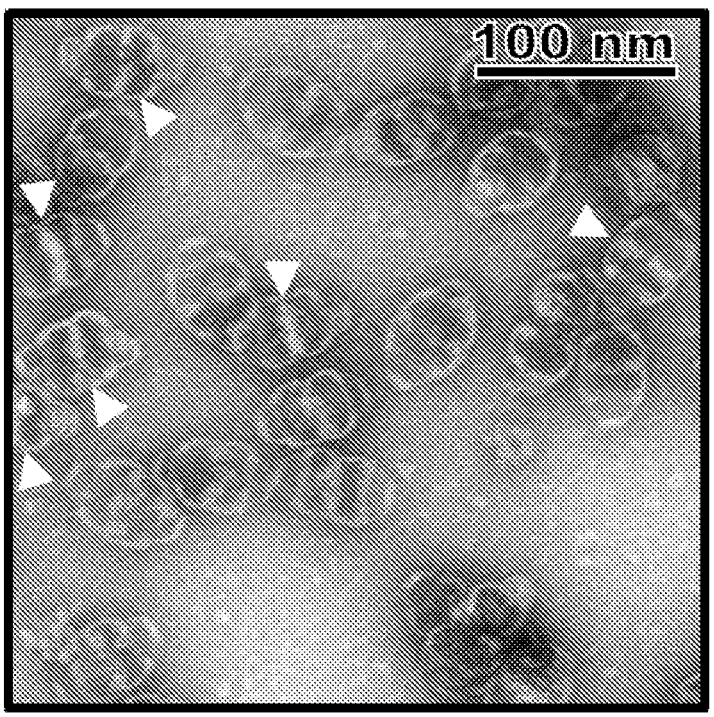

A vault complex without the Z domain, AH1 vault complex (comprising NS5A1-31 fused to the N-terminus of MVP, SEQ ID NO:26) were prepared similarly to Examples 1 and 2, without attachment of the Z domain. These vaults were examined by uranyl-acetate negatively stained transmission electron microscopy (TEM), which showed a high intensity non-staining region within the vaults not consistent with the additional mass attributable to the added NS5A (FIG. 8A). The purified AH1 vault complexes were further treated with 5% Tween 20 detergent followed by re-purification of the vault complex. The non-staining region of additional mass showed significantly less intensity (FIG. 8B). This supports that a lipophilic material bound to the NS5A1-31 amphipathic α-helix was removed by the detergent.

Example 7: Packaging ATRA into AH1Z Vault Complex

Packaging ATRA into AH1Z vault complexes (prepared per Examples 1-3) was conducted using 1 mg of pre-purified AH1Z vault complexes co-mixed with 10 µg of ATRA for 30 minutes at 4° C. followed by overnight centrifugation on a step-wise sucrose gradient. Fractions were collected and vaults pelleted at 100,000×g for 2 hrs at 4° C. Fractions 20-30, 40-45 and 50-60% were collected and resuspended in 300 µL 1×PBS⁻ and assayed for protein concentration. ATRA concentration was measure from UV/Vis absorbance spectra of each sample in a 1:10 dilution of 100% ethanol using a normalized concentration of AH1Z vault complex only as the blank with the long wavelength value being set to baseline. ATRA has a characteristic peak around 350 nm with a known extinction coefficient of 44,300 M⁻¹ cm⁻¹ (Ete Z. Surts, F.I.H., Archives of Biochemistry and Biophysics, 1991, 287(2): p. 297-304).

Figure 7:
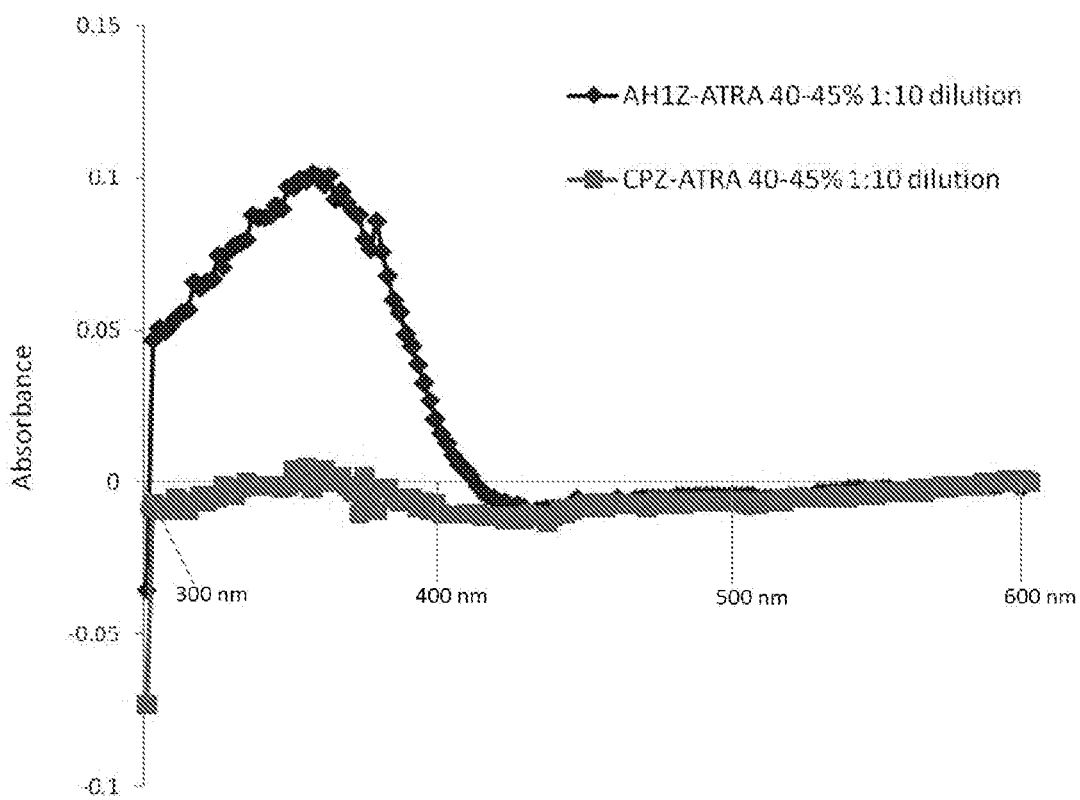
FIG. 7: AH1Z vault complexes preferentially bind and retain ATRA over non-engineered control CPZ vaults as shown by the absorbance spectra.

The ability of AH1Z vault complex to bind a specific therapeutic compound with poor solubility properties was tested using ATRA, which is aqueous insoluble, and has a log P of 6.30. Purified AH1Z or CPZ vaults were incubated with ATRA and non-vault associated drug was separated from the vaults via an overnight sucrose gradient. UV/Vis absorbance spectroscopy for ATRA alone shows no presence of the drug in any fractions as it does not pellet by itself at 100,000×g (Data not shown). Meanwhile, the 40-45% fraction collected from AH1Z incubated with ATRA shows a clear spectral peak centered on 350 nm in accordance with ATRAs normal spectra (FIG. 7). CPZ vaults mixed with ATRA collected from the 40-45% fraction showed no significant presence of ATRA. Using the absorbance spectra, approximately 6.8 ng/µL of ATRA was present within this sample of AH1Z vault complex, which was diluted to 1 µg/µL of vault protein prior to analysis. An extremely rough calculation indicates that 170 ATRA molecules are contained per single AH1Z vault for the tested sample reported in FIG. 7. This demonstrates the ability to directly engineer the vault complex to sequester a therapeutic small molecule compound that is hydrophobic and aqueous insoluble.

A similar study using AH1Z vault complex was done to assess the sequestering of doxorubicin within the vault complex. Doxorubicin is relatively aqueous soluble, with a solubility in water of over 50 mg/mL, and has a log P of 1.27. When incubated with AH1Z, no Doxorubicin was detected within the vault complex.

Figure 9:
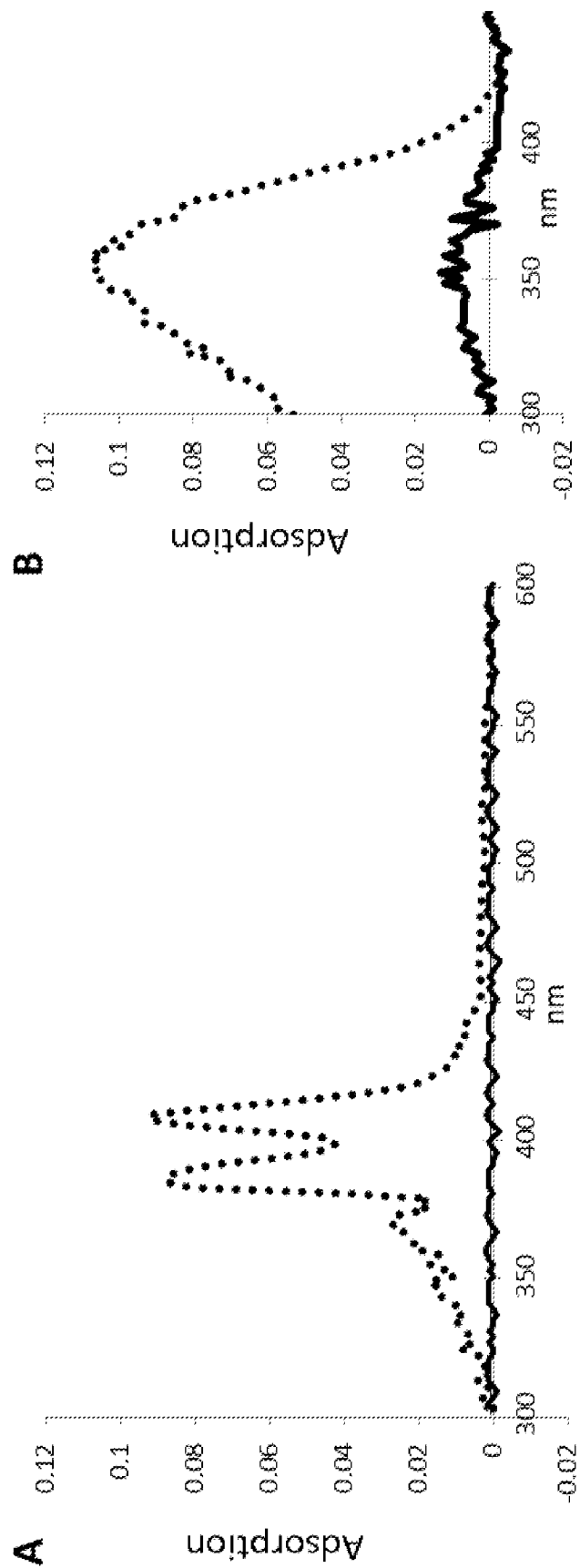
FIG. 9: Adsorption spectra of AH1 vault complex after co-incubation with amphotericin B (Panel A) or with ATRA (Panel B) after incubation with either control (solid line) or AH vaults (dotted line) with subsequent re-purification of vault nanoparticles via ultracentrifugation over a semi-discontinuous sucrose gradient. Spectrums represent the 40-45% layer where vault nanoparticles sediment.

Example 8: Packaging ATRA, Amphotericin B and Doxorubicin into AH1 Vault Complex Doxorubicin, ATRA and amphotericin B (AMB) were similarly assessed using the AH1 vault complex described in Example 6. Each compound was co-incubated with AH1 vault complex, or CP vault as a control (comprising CP-MVP, no Z domain, SEQ ID NO:32), the resultant complexes separated as described in Example 7, and the amount of compound sequestered in the vaults was determined. In the case of doxorubicin, as with AH1Z, neither control nor AH1 vault complex showed any detectable retention of compound in the collected vault fraction. AMB, an antifungal amphipathic polyene antibiotic with poor water solubility at physiological pH of less than 0.75 mg/mL despite a log P of 0.8, was selectively retained by AH1 vault complex during separation at ~5.64 ng AMB per 1 µg vault while control CP vault showed no detectable AMB association (FIG. 9, Panel A). Similarly, ATRA, displayed co-association with AH1 vault complex at ~7.32 ng ATRA per 1 µg vault (FIG. 9, Panel B). ATRA appears to have some non-specific association with the control CP vault (~10 fold lower). Quantitation of the amounts sequestered in the AH1 vault complex using known molar extinction coefficients ($AMB_{\varepsilon 406\ nm}$=150,000 M⁻¹ cm⁻¹$_{(methanol)}$, $ATRA_{\varepsilon 350\ nm}$=44,300 M⁻¹ cm¹$_{(Ethanol)}$) demonstrated ~48 molecules of AMB and ~182 molecules of ATRA per single AH1 vault complex.

Additional small scale studies were done with AMB using a higher titrated ratio of drug:vault. Instead of the 1 µg:100 µg ratio of AMB to AH1 vault complex or CP vault control, 100 µg of AH1 or CP vault was incubated with 10 µg or 50 µg of AMB. Following incubation, vaults and their associated drug cargo were recovered from excess, unbound material by passage through a micro-scale filtration spin column. Control vaults showed low levels of drug retention of 264 and 431 molecules of AMB per single control vault for the 10 µg and 50 µg load conditions, respectively. The AH1 vault complex showed 1,213 and 2,017 molecules of AMB per single AH1 vault for the 10 µg and 50 µg load conditions, respectively. These samples were also stored for one week at 4° C. and the drug bound vaults were reexamined. The control vault samples experienced 18% loss of AMB for the 10 µg load sample and 47% loss of AMB for the 50 µg load sample, while the AH1 vaults showed a minor loss, with 11% loss of AMB for the 10 µg load sample and 6% loss of AMB for the 50 µg sample. This data suggests that the control vaults, with non-specific binding of the drug, does not provide protection from the aqueous environment, allowing faster molecular decomposition of the AMB. The negligible loss of AMB in the AH1 vault samples likely results from the drug molecules being sequestered within the lipophilic core which provides greater overall stability and protection of the drug. Thus, the AH1 vaults have the ability to encapsulate >2,000 drug molecules per vault, while potentially offering a more stable microenvironment for the encapsulated drug. The results are summarized in the following table.

| Vault | AMB:vault starting ratio | AMB:vault ending ratio | AMB:vault ending ratio | % change |
|---|---|---|---|---|
| CP control | 10 µg:100 µg | 32.6 ng:1 µg | 26.8 ng:1 µg | −18% |
|  | 50 µg:100 µg | 53.0 ng:1 µg | 28.0 ng:1 µg | −47% |
| AH1 | 10 µg:100 µg | 149.2 ng:1 µg | 133.6 ng:1 µg | −11% |
|  | 50 µg:100 µg | 254.7 ng:1 µg | 240.8 ng:1 µg | −6% |

Example 9: Packaging Bryostatin 1 into AH1 Vault Complex

Bryostatin 1 (log P of 4.25-5.40, estimated) incorporation into AH1 vault complex was assessed similarly to Example 8, with detection of the Bryostatin 1 by high performance liquid chromatography (HPLC) coupled with multiple reaction monitoring (MRM) tandem mass spectrometry (MS/MS) in lieu of spectrophotometric analysis. MRM-LC-MS/MS allowed for sensitive detection (>0.009 ng/µL) of the sodiated bryostatin 1 ion at m/z 927.4, consistent with previous reports. AH1 vault complexes were co-incubated for 30 minutes at 4° C. with bryostatin 1 and subsequently collected from solution using ultracentrifugation at 100,000×g. Aliquots of the starting material, spin supernatant, and the re-suspended vaults were analyzed by HPLC-MRM-MS/MS and the bryostatin 1 concentration measured using a previously generated standard curve using known concentrations of bryostatin 1. The measurement of bryostatin 1 per 1 µg vault in the incubated, pre-centrifuged sample of measured 10.6±1.4 ng is in accordance with the known value of 10 ng/µL (1 µg of bryostatin 1 per 100 µg AH vault in 100 µL PBS−). The spin supernatant showed no bryostatin 1, while the re-suspended vault pellet value of 13.4±2.3 ng showed 100% retention of the bryostatin within the AH1 vault complex, within experimental error. This is ~83 molecules of bryostatin 1 per single AH1 vault complex.

Additional therapeutic compounds for the treatment of HIV can be similarly assessed for their ability to be sequestered within a vault complex as described herein. For example GSK744, MK-2048 (solubility <1 mg/mL in water), IQP0528 (solubility <66 ng/mL in water), CSIS (solubility 1.4 µg/mL in water), or dapivirine can be readily assessed and are expected to be sequestered by the vault complexes as described herein, for example by AH1Z vault complex.

Example 10: Latent HIV Provirus Activation by AH1 Vault Complex Containing Bryostatin 1

Figure 10A:
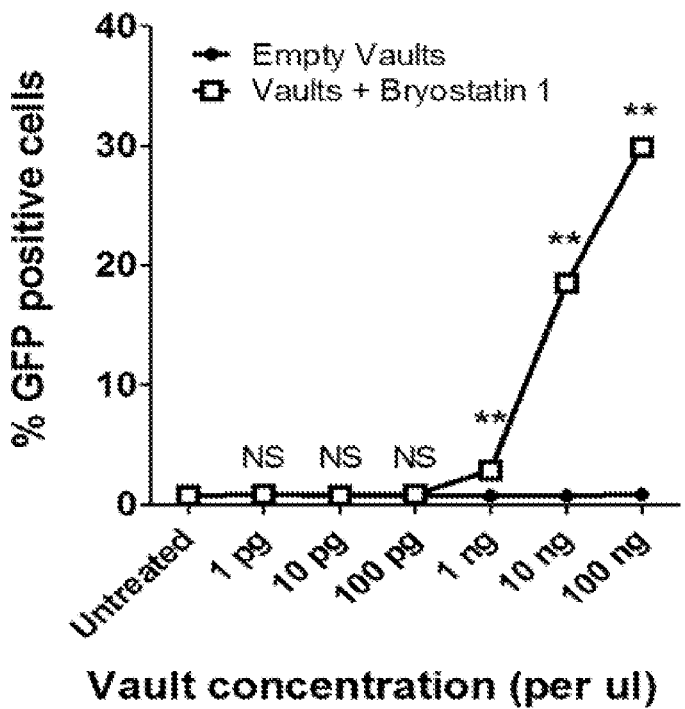
FIGS. 10A, 10B, and 10C.
Figure 10B:
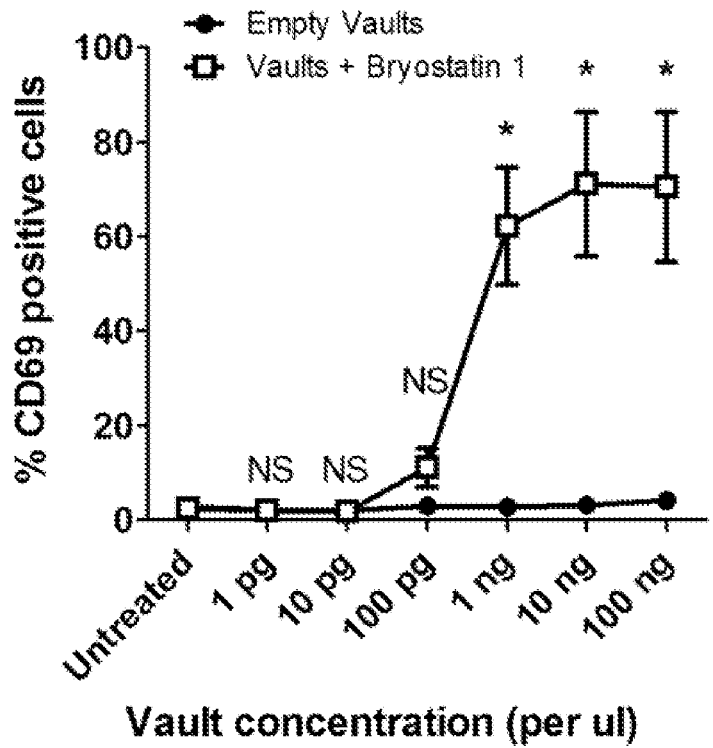

Bryostatin 1 is an effective HIV therapeutic as it activates latent HIV provirus that remains within cellular reservoirs. If these latent proviruses can be activated to express viral proteins, they would be susceptible to immune effector mechanisms, viral cytopathic effects and additional therapies directed toward viral proteins. The bryostatin 1 sequestered within AH1 vault complex (bryostatin/AH1) was assessed in vitro and in vivo for the ability to activate latent HIV provirus. The bryostatin/AH1 was used in a J-Lat 10.6 cell line assay, a well characterized model for the main T-lymphocyte cell reservoir (Jordan et al., EMBO J, 2003, 22:1868-1877; Beans, E. J., et al., Proc Natl Acad Sci USA, 2013, 110:11698-703), with activity starting at 1 ng/µL of bryostatin/AH1 (FIG. 10A). Alternatively, stimulation of T cells with PKC activating compounds, such as bryostatin 1, induces cell surface expression of CD69, which occurs at similar concentrations to those required to activate HIV from latency (Bear, H. D., et al., Anticancer Drugs, 1996, 7:299-306). As such, CD69 expression can be used as a biomarker for evaluating whether bryostatin 1 delivered via association with AH1 vaults remains bioactive in the desired T cell type. When tested for activity in this way, bryostatin/AH1 activated CD69 expression in primary human PBMC obtained from 4 different donors in a dose dependent manner with stimulation occurring at concentrations as low as 0.1 ng/µL AH1 vault complex as analyzed by flow cytometry (FIG. 10B).

Figure 10C:
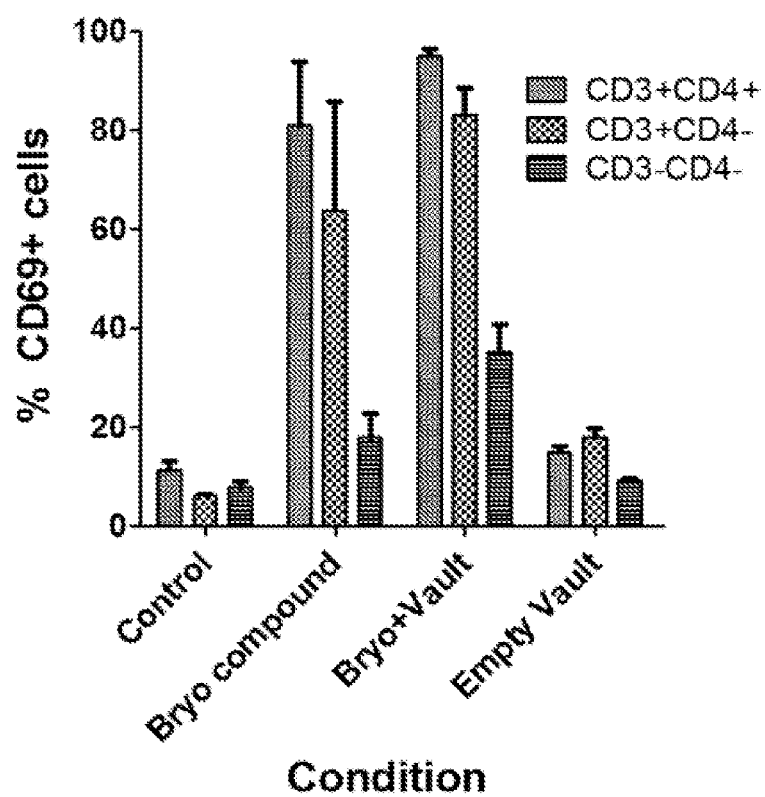

To evaluate whether the bryostatin/AH1 are also bioactive in vivo, they were injected intravenously into C57/bl6 mice at 1 µg bryostatin 1 per 100 µg AH1 vault complex per mouse. At 24 hrs post-injection, over 90% of CD4+ T cells present within harvested splenocytes had been induced to express CD69, demonstrating that the bryostatin/AH1 can successfully deliver compounds in vivo (FIG. 10C). Notably, these untargeted (e.g., not C-terminus modified) vault complexes also induced >70% of non-CD4+ T cells (primarily CD8+ T cells) and ~40% of non-T cells to express CD69. This activation of a broad spectrum of cell types illustrates the potential benefits of targeting the vaults more selectively to the cell type of interest (in this case, to CD4+ T cells). Further improvements to the HIV provirus latency activation could also be achieved by using more potent analogs of bryostatin or prostratin sequestered within a suitable vault complex (DeChristopher, B. A., et al., Nature Chemistry, 2012, 4:705-10; Beans, E. J., et al., Proc Natl Acad Sci USA, 2013, 110:11698-703).

Example 11: Measuring Delivery of Therapeutic Compound Sequestered in a Vault Complex The vault complexes as described herein, and compositions thereof comprising a therapeutic compound, and optionally further comprising a polymer or hydrogel, can be readily assessed for their targeting to certain cell types or physiological environments. For example, a rectal mucosal explant model or similar can be used to assess the effect on HIV-1 replication (Richardson-Harman, N., et al., J Clin Microbiol 47:3530-9). In one example, a large stock of HIV-1$_{BAL}$ is titered on fresh rectal biopsy tissue explants to determine dose that consistently yields infection of ~50% of explants (ID$_{50}$). To assess the vault complex/therapeutic composition, fresh biopsies are pre-treated with vault complex/therapeutic, empty vault complex or free therapeutic compound for 10 minutes, then infected with ID$_{50}$, and the infection rate assessed. The free therapeutic is used at the highest dose that has no effect on the infection rate of biopsies, with the same amount of therapeutic compound delivered by the vault complex to assess whether the targeted delivery provides an effect. The vault complex composition comprising a polymer (e.g., thermally responsive polymer) or hydrogel can be similarly assayed to determine the efficacy of delivery of the therapeutic compound.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents, and patent applications cited within the body of the instant specification are hereby incorporated herein by reference in their entirety, for all purposes.

TABLE 1

Sequences

SEQ ID NO: 1 INT DNA sequence tgcacacaac actggcagga tgctgtgcct tggacagaac tcctcagtct acagacagag
gatggcttct ggaaacttac accagaactg ggacttatat taaatcttaa tacaaatggt
ttgcacagct ttcttaaaca aaaaggcatt caatctctag gtgtaaaagg aagagaatgt
ctcctggacc taattgccac aatgctggta ctacagttta ttcgcaccag gttggaaaaa
gagggaatag tgttcaaatc actgatgaaa atggatgacc cttctatttc caggaatatt
ccctgggctt ttgaggcaat aaagcaagca agtgaatggg taagaagaac tgaaggacag
tacccatcta tctgcccacg gcttgaactg gggaacgact gggactctgc caccaagcag
ttgctgggac tccagcccat aagcactgtg tccctcttc atagagtcct ccattacagt
caaggctaa SEQ ID NO: 2 INT protein sequence (residues 1563-1724 of the human
VPARP protein sequence)

Cys Thr Gln His Trp Gln Asp Ala Val Pro Trp Thr Glu Leu Leu Ser Leu Gln
Thr Glu Asp Gly Phe Trp Lys Leu Thr Pro Glu Leu Gly Leu Ile Leu Asn Leu
Asn Thr Asn Gly Leu His Ser Phe Leu Lys Gln Lys Gly Ile Gln Ser Leu Gly
Val Lys Gly Arg Glu Cys Leu Leu Asp Leu Ile Ala Thr Met Leu Val Leu Gln
Phe Ile Arg Thr Arg Leu Glu Lys Glu Gly Ile Val Phe Lys Ser Leu Met Lys
Met Asp Asp Pro Ser Ile Ser Arg Asn Ile Pro Trp Ala Phe Glu Ala Ile Lys
Gln Ala Ser Glu Trp Val Arg Arg Thr Glu Gly Gln Tyr Pro Ser Ile Cys Pro
Arg Leu Glu Leu Gly Asn Asp Trp Asp Ser Ala Thr Lys Gln Leu Leu Gly Leu
Gln Pro Ile Ser Thr Val Ser Pro Leu His Arg Val Leu His Tyr Ser Gln Gly

SEQ ID NO: 3 VPARP protein sequence (Genbank #AAD47250)

Met Val Met Gly Ile Phe Ala Asn Cys Ile Phe Cys Leu Lys Val Lys Tyr Leu
Pro Gln Gln Gln Lys Lys Lys Leu Gln Thr Asp Ile Lys Glu Asn Gly Gly Lys
Phe Ser Phe Ser Leu Asn Pro Gln Cys Thr His Ile Ile Leu Asp Asn Ala Asp
Val Leu Ser Gln Tyr Gln Leu Asn Ser Ile Glu Gln Lys Asn His Val His Ile Ala
Asn Pro Asp Phe Ile Trp Lys Ser Ile Arg Glu Lys Arg Leu Leu Asp Val Lys
Asn Tyr Asp Pro Tyr Lys Pro Leu Asp Ile Thr Pro Pro Asp Gln Lys Ala
Ser Ser Ser Glu Val Lys Thr Glu Gly Leu Cys Pro Asp Ser Ala Thr Glu Glu
Glu Asp Thr Val Glu Leu Thr Glu Gly Met Gln Asn Val Glu Ile Pro His
Leu Pro Gln Asp Phe Glu Val Ala Lys Tyr Asn Thr Leu Glu Lys Val Gly Met
Glu Gly Gly Gln Glu Ala Val Val Glu Leu Gln Cys Ser Arg Asp Ser Arg
Asp Cys Pro Phe Leu Ile Ser Ser His Phe Leu Leu Asp Asp Gly Met Glu Thr
Arg Arg Gln Phe Ala Ile Lys Lys Thr Ser Glu Asp Ala Ser Glu Tyr Phe Glu
Asn Tyr Ile Glu Glu Leu Lys Lys Gln Gly Phe Leu Leu Arg Glu His Phe Thr
Pro Glu Ala Thr Gln Leu Ala Ser Glu Gln Leu Gln Ala Leu Leu Leu Glu Glu
Val Met Asn Ser Ser Thr Leu Ser Gln Glu Val Ser Asp Leu Val Glu Met Ile
Trp Ala Glu Ala Leu Gly His Leu His Met Leu Leu Lys Pro Val Asn Arg
Ile Ser Leu Asn Asp Val Ser Lys Ala Glu Gly Ile Leu Leu Leu Val Lys Ala
Ala Leu Lys Asn Gly Glu Thr Ala Glu Gln Leu Gln Lys Met Met Thr Glu Phe
Tyr Arg Leu Ile Pro His Lys Gly Thr Met Pro Lys Glu Val Asn Leu Gly Leu
Leu Ala Lys Lys Ala Asp Leu Cys Gln Leu Ile Arg Asp Met Val Asn Val Cys
Glu Thr Asn Leu Ser Lys Pro Asn Pro Ser Leu Ala Lys Tyr Arg Ala Leu
Arg Cys Lys Ile Glu His Val Glu Gln Asn Thr Glu Glu Phe Leu Arg Val Arg
Lys Glu Val Leu Gln Asn His His Ser Lys Ser Pro Val Asp Val Leu Gln Ile
Phe Arg Val Gly Arg Val Asn Glu Thr Thr Glu Phe Leu Ser Lys Leu Gly Asn
Val Arg Pro Leu Leu His Gly Ser Pro Val Gln Asn Ile Val Gly Ile Leu Cys
Arg Gly Leu Leu Pro Lys Val Val Glu Asp Arg Gly Val Gln Arg Thr Asp
Val Gly Asn Leu Gly Ser Gly Ile Tyr Phe Ser Asp Ser Leu Ser Thr Ser Ile
Lys Tyr Ser His Pro Gly Glu Thr Asp Gly Thr Arg Leu Leu Leu Ile Cys Asp
Val Ala Leu Gly Lys Cys Met Asp Leu His Glu Lys Asp Phe Ser Leu Thr Glu
Ala Pro Pro Gly Tyr Asp Ser Val His Gly Val Ser Gln Thr Ala Ser Val Thr
Thr Asp Phe Glu Asp Asp Glu Phe Val Val Tyr Lys Thr Asn Gln Val Lys Met
Lys Tyr Ile Ile Lys Phe Ser Met Pro Gly Asp Gln Ile Lys Asp Phe His Pro
Ser Asp His Thr Glu Leu Glu Glu Tyr Arg Pro Glu Phe Ser Asn Phe Ser Lys
Val Glu Asp Tyr Gln Leu Pro Asp Ala Lys Thr Ser Ser Ser Thr Lys Ala Gly
Leu Gln Asp Ala Ser Gly Asn Leu Val Pro Leu Glu Asp Val His Ile Lys Gly
Arg Ile Ile Asp Thr Val Ala Gln Val Ile Val Phe Gln Thr Tyr Thr Asn Lys
Ser His Val Pro Ile Glu Ala Lys Tyr Ile Phe Pro Leu Asp Asp Lys Ala Ala
Val Cys Gly Phe Glu Ala Phe Ile Asn Gly Lys His Ile Val Gly Glu Ile Lys
Glu Lys Glu Glu Ala Gln Gln Glu Tyr Leu Glu Ala Val Thr Gln Gly His Gly
Ala Tyr Leu Met Ser Gln Asp Ala Pro Asp Val Phe Thr Val Ser Val Gly Asn
Leu Pro Pro Lys Ala Lys Val Leu Ile Lys Ile Thr Tyr Ile Thr Glu Leu Ser
Ile Leu Gly Thr Val Gly Val Phe Phe Met Pro Ala Thr Val Ala Pro Trp Gln

TABLE 1-continued

Sequences

```
Gln Asp Lys Ala Leu Asn Glu Asn Leu Gln Asp Thr Val Glu Lys Ile Cys Ile
Lys Glu Ile Gly Thr Lys Gln Ser Phe Ser Leu Thr Met Ser Ile Glu Met Pro
Tyr Val Ile Glu Phe Ile Phe Ser Asp Thr His Glu Leu Lys Gln Lys Arg Thr
Asp Cys Lys Ala Val Ile Ser Thr Met Glu Gly Ser Ser Leu Asp Ser Ser Gly
Phe Ser Leu His Ile Gly Leu Ser Ala Ala Tyr Leu Pro Arg Met Trp Val Glu
Lys His Pro Glu Lys Glu Ser Glu Ala Cys Met Leu Val Phe Gln Pro Asp Leu
Asp Val Asp Leu Pro Asp Leu Ala Ser Glu Gly Ser Glu Val Ile Ile Cys Leu Asp
Cys Ser Ser Ser Met Glu Gly Val Thr Phe Leu Gln Ala Lys Gln Ile Thr Leu
His Ala Leu Ser Leu Val Gly Glu Lys Gln Lys Val Asn Ile Ile Gln Phe Gly
Thr Gly Tyr Lys Glu Leu Phe Ser Tyr Pro Lys His Ile Thr Ser Asn Thr Thr
Ala Ala Glu Phe Ile Met Ser Ala Thr Pro Thr Met Gly Asn Thr Asp Phe Trp
Lys Thr Leu Arg Tyr Leu Ser Leu Leu Tyr Pro Ala Arg Gly Ser Arg Asn Ile
Leu Leu Val Ser Asp Gly His Leu Gln Asp Glu Ser Leu Thr Leu Gln Leu Val
Lys Arg Ser Arg Pro His Thr Arg Leu Phe Ala Cys Gly Ile Gly Ser Thr Ala
Asn Arg His Val Leu Arg Ile Leu Ser Gln Cys Gly Ala Gly Val Phe Glu Tyr
Phe Asn Ala Lys Ser Lys His Ser Trp Arg Lys Gln Ile Glu Asp Gln Met Thr
Arg Leu Cys Ser Pro Ser Cys His Ser Val Ser Val Lys Trp Gln Gln Leu Asn
Pro Asp Ala Pro Glu Ala Leu Gln Ala Pro Ala Gln Val Pro Ser Leu Phe Arg
Asn Arg Leu Leu Val Tyr Gly Phe Ile Pro His Thr Gln Ala Thr Leu
Cys Ala Leu Ile Gln Glu Lys Glu Phe Cys Thr Met Val Ser Thr Thr Glu Leu
Gln Lys Thr Thr Gly Thr Met Ile His Lys Leu Ala Ala Arg Ala Leu Ile Arg
Asp Tyr Glu Asp Gly Ile Leu His Glu Asn Glu Thr Ser His Glu Met Lys Lys
Gln Thr Leu Lys Ser Leu Ile Ile Lys Leu Ser Val Glu Asn Ser Leu Ile Thr
Gln Phe Thr Ser Phe Val Ala Val Glu Lys Arg Asp Glu Asn Glu Ser Pro Phe
Pro Asp Ile Pro Lys Val Ser Glu Leu Ile Ala Lys Glu Asp Val Asp Phe Leu
Pro Tyr Met Ser Trp Gln Gly Glu Pro Gln Glu Ala Val Arg Asn Gln Ser Leu
Leu Ala Ser Ser Glu Trp Pro Glu Leu Arg Leu Ser Lys Arg Lys His Arg Lys Lys
Ile Pro Phe Ser Lys Arg Lys Met Glu Leu Ser Gln Pro Glu Val Ser Glu Asp
Phe Glu Glu Asp Gly Leu Gly Val Leu Pro Ala Phe Thr Ser Asn Leu Glu Arg
Gly Gly Val Glu Lys Leu Leu Asp Leu Ser Trp Thr Glu Ser Cys Lys Pro Thr
Ala Thr Glu Pro Leu Phe Lys Lys Val Ser Pro Gly Thr Ser Thr Ser Ser
Phe Phe Pro Ile Leu Ala Pro Ala Val Gly Ser Tyr Leu Thr Pro Thr Thr Arg
Ala His Ser Pro Ala Ser Leu Ser Phe Ala Ser Tyr Arg Gln Val Ala Ser Phe
Gly Ser Ala Ala Pro Pro Arg Gln Phe Asp Ala Ser Gln Phe Ser Gln Gly Pro
Val Pro Gly Thr Cys Ala Asp Trp Ile Pro Gln Ser Ala Ser Cys Pro Thr Gly
Pro Pro Gln Asn Pro Pro Ser Ala Pro Tyr Cys Gly Ile Val Phe Ser Gly Ser
Ser Leu Ser Ser Ala Gln Ser Ala Pro Leu Gln His Pro Gly Gly Phe Thr Thr
Arg Pro Ser Ala Gly Thr Phe Pro Glu Leu Asp Ser Pro Gln Leu His Phe Ser
Leu Pro Thr Asp Pro Asp Pro Ile Arg Gly Phe Gly Ser Tyr His Pro Ser Ala
Tyr Ser Pro Phe His Phe Gln Pro Ser Ala Ala Ser Leu Thr Ala Asn Leu Arg
Leu Pro Met ala Ser Ala Leu Pro Glu Ala Leu Cys Ser Gln Ser Arg Thr Thr
Pro Val Asp Leu Cys Leu Leu Glu Glu Ser Val Gly Ser Leu Glu Gly Ser Arg
Cys Pro Val Phe Ala Phe Gln Ser Ser Asp Thr Glu Ser Asp Glu Leu Ser Glu
Val Leu Gln Asp Ser Cys Phe Leu Gln Ile Lys Ser Asp Thr Lys Asp Asp Ser
Ile Pro Cys Phe Leu Glu Leu Lys Glu Glu Asp Glu Ile Val Cys Thr Gln His
Trp Gln Asp Ala Val Pro Trp Thr Glu Leu Leu Ser Leu Gln Thr Glu Asp Gly
Phe Trp Lys Leu Thr Pro Glu Leu Gly Leu Ile Leu Asn Leu Asn Thr Asn Gly
Leu His Ser Phe Leu Lys Gln Lys Gly Ile Gln Ser Leu Gly Val Lys Ser Arg
Glu Cys Leu Leu Asp Leu Ile Ala Thr Met Leu Val Leu Gln Phe Ile Arg Thr
Arg Leu Glu Lys Glu Gly Ile Val Phe Lys Ser Leu Met Lys Met Asp Asp Pro
Ser Ile Ser Arg Asn Ile Pro Trp Ala Phe Glu Ala Ile Lys Gln Ala Ser Glu
Trp Val Arg Arg Thr Glu Gly Gln Tyr Pro Ser Ile Cys Pro Arg Leu Glu Leu
Gly Asn Asp Trp Asp Ala Thr Lys Gln Leu Leu Gly Leu Gln Pro Ile Ser
Thr Val Ser Pro Leu His Arg Val Leu His Tyr Ser Gln Gly
```

SEQ ID NO: 4 VPARP cDNA, Genbank #AF158255

```
atggtgatgg gaatctttgc aaattgtatc ttctgtttga aagtgaagta cttacctcag
cagcagaaga aaaagctaca aactgacatt aaggaaaatg gcggaaagtt ttcctttcg
ttaaatcctc agtgcacaca tataatctta gataatgctg atgttctgag tcagtaccaa
ctgaattcta tccaaaagaa ccacgttcat attgcaaact cagattttat atggaaatct
atcagagaaa agagactctt ggatgtaaag aattatgatc cttataagcc cctggacatc
acaccacctc ctgatcagaa ggcgagcagt tctgaagtga aaacagaagg tctatgcccg
gacagtgcca cagaggagga agacactgtg gaactcactg agtttggtat gcagaatgtt
gaaattcctc atcttcctca agattttgaa gttgcaaaat ataacaccTt ggagaaagtg
ggaatggagg gaggccagga agctgtggtg gtggagcttc agtgttcgcg ggactccagg
gactgtcctt tcctgatatc ctcacacttc ctcctggatg atggcatgga gactagaaga
cagtttgcta taaagaaaac ctctgaagat gcaagtgaat actttgaaaa ttacattgaa
gaactgaaga aacaaggatt tctactaaga gaacatttca cacctgaagc aacccaatta
gcatctgaac aattgcaagc attgcttttg gaggaagtca tgaattcaag cactctgagc
caagaggtga gcgatttagt agagatgatt tgggcagagg ccctgggcca cctgaacac
atgcttctca agccagtgaa caggattagc ctcaacgatg tgagcaaggc agaggggatt
ctccttctag taaaggcagc actgaaaaat ggagaaacag cagagcaatt gcaaaagatg
atgacagagt ttacagact gatacctcac aaaggcacaa tgcccaaaga agtgaacctg
ggactattgg ctaagaaagc agaccctctgc cagctaataa agacatggt taatgtctgt
gaaactaatt tgtccaaacc caacccccaca tccctggcca ataccgagc tttgaggtgc
aaaattgagc atgttgaaca gaatactgaa gaatttctca gggttagaaa agaggttttg
cagaatcatc acagtaagag cccagtggat gtcttgcaga tatttagagt tggcagagtg
```

TABLE 1-continued

Sequences

```
aatgaaacca cagagttttt gagcaaactt ggtaatgtga ggcccttgtt gcatggttct
cctgtacaaa acatcgtggg aatcttgtgt cgagggttgc ttttacccaa agtagtggaa
gatcgtggtg tgcaaagaac agacgtcgga aaccttggaa gtgggattta tttcagtgat
tcgctcagta caagtatcaa gtactcacac ccgggagaga cagatggcac cagactcctg
ctcatttgtg acgtagccct cggaaagtgt atggacttac atgagaagga ctttcccttca
actgaagcac caccaggcta cgacagtgtg catggagttt cacaaacagc ctctgtcacc
acagactttg aggatgatga atttgttgtc tataaaacca atcaggttaa aatgaaatat
attattaaat tttccatgcc tggagatcag ataaaggact ttcatcctag tgatcatact
gaattagagg aatacagacc tgagttttca aatttttcaa aggttgaaga ttaccagtta
ccagatgcca aaacttccag cagcaccaag gccggcctcc aggatgcctc tgggaacttg
gttcctctgg aggatgtcca catcaaaggg agaatcatag acactgtagc ccaggtcatt
gtttttcaga catacacaaa taaaagtcac gtgcccattg aggcaaaata tatctttcct
ttggatgaca aggccgctgt gtgtggcttc gaagccttca tcaatgggaa gcacatagtt
ggagagatta aagagaagga agaagcccag caagagtacc tagaagccgt gacccagggc
catggcgctt acctgatgag tcaggatgct ccggacgttt ttactgtaag tgttggaaac
ttacccccta aggctaaggt tcttataaaa attacctaca tcacagaact cagcatcctg
ggcactgttg gtgtctttt catgcccgcc accgtagcac cctggcaaca ggacaaggct
ttgaatgaaa accttcagga tacagtagag aagatttgta taaagaaat aggaacaaag
caaagcttct ctttgactat gtctattgag atgccgtatg tgattgaatt cattttcagt
gatacacatg aactgaaaca aaagcgcaca gactgcaaag ctgtcattag caccatggaa
ggcagctcct tagacagcag tggatttttct ctccacatcg gtttgtctgc tgcctatctc
ccaagaatgt gggttgaaaa acatccagaa aaagaaagcg aggcttgcat gcttgtcttt
caacccgatc tcgatgtcga cctccctgac ctagccagtg agagcgaagt gattattttgt
cttgactgct ccagttccat ggagggtgtg acattcttgc aagccaagca aatcaccttg
catgcgctgt cctggtgggt tgagaagcag aaagtaaata ttatccagtt cggcacaggt
tacaaggagc tattttcgta tcctaagcat atcacaagca ataccacggc agcagagttc
atcatgtctg ccacacctac catggggaac acagacttct ggaaaacact ccgatatctt
agcttattgt accctgctcg agggtcacgg aacatcctcc tggtgtctga tgggcacctc
caggatgaga gcctgacatt acagctcgtg aagaggagcc gcccgcacac caggttattc
gcctgcggta tcggttctac agcaaatcgt cacgtcttaa ggattttgtc ccagtgtggt
gccggagtat ttgaatattt taatgcaaaa tccaagcata gttggagaaa acagatagaa
gaccaaatga ccaggctatg ttctccgagt tgccactctg tctccgtcaa atggcagcaa
ctcaatccag atgcgcccga ggccctgcag gccccagccc aggtgccatc cttgtttcgc
aatgatcgac tccttgtcta tggattcatt cctcactgca cacaagcaac tctgtgtgca
ctaattcaag agaaagaatt ttgtacaatg gtgtcgacta ctgagcttca gaagacaact
ggaactatga tccacaagct ggcagcccga gctctaatca gagattatga agatggcatt
cttcacgaaa atgaaaccag tcatgagatg aaaaaacaaa ccttgaaatc tctgattatt
aaactcagta agaaaactc tctcataaca caatttacaa gctttgtggc agttgagaaa
agggatgaga atgagtcgcc ttttcctgat attccaaaag tttctgaact tattgccaaa
gaagatgtag acttcctgcc ctacatgagc tggcaggggg agcccaaga agccgtcagg
aaccagtctc ttttagcatc ctctgagtgg ccagaattac gtttatccaa acgaaaacat
aggaaaattc cattttccaa aagaaaaatg gaattatctc agccagaagt ttctgaagat
tttgaagagg atggcttagg tgtactacca gcttttcacat caaatttgga acgtggaggt
gtggaaaagc tattggattt aagttggaca gagtcatgta aaccaacagc aactgaacca
ctatttaaga aagtcagtcc atgggaaaca tctacttcta gcttttttcc tatttttggct
ccggccgttg gttcctatct tacccccgact acccgcgctc acagtcctgc ttccttgtct
tttgcctcat atcgtcaggt agctagtttc ggttcagctg ctcctcccag acagtttgat
gcatctcaat tcagccaagg ccctgtgcct ggcacttgtg ctgactggat cccacagtcg
gcgtcttgtc ccacaggacc tccccagaac ccaccttctg cacccttattg tggcattgtt
ttttcaggga gctcattaag ctctgcacag tctgctccac tgcaacatcc tggaggcttt
actaccaggc cttctgctgg caccttccct gagctggatt ctccccagct tcatttctct
cttcctacag accctgatcc catcagaggt tttgggtctt atcatccctc tgcttactct
ccttttcatt ttcaaccttc cgcagcctct ttgactgcca accttaggct gccaatggcc
tctgctttac ctgaggctct ttgcagtcag tcccggacta cccccagtaga tctctgtctt
ctagaagaat cagtaggcag tctcgaagga agtcgatgtc ctgtctttgc ttttcaaagt
tctgacacag aaagtgatga gctatcagaa gtacttcaag acagctgctt tttacaaata
aagtgtgata caaaagtgca cagtatcccg tgctttctgg aattaaaaga agaggatgaa
atagtgtgca cacaacactg gcaggatgct gtgccttgga cagaactcct cagtctacag
acagaggatg gcttctggaa acttacacca gaactgggac ttatattaaa tcttaataca
aatggtttgc acagctttct taaacaaaaa ggcattcaat ctctaggtgt aaaaggaaga
gaatgtctcc tggacctaat tgccacaatg ctggtactac agtttattcg caccaggttg
gaaaagagg gaatagtgtt caaatcactg atgaaaatgg atgaccctttc tatttccagg
aatattccct gggcttttga ggcaataaag caagcaagtg aatgggtaag aagaactgaa
ggacagtacc catctatctg cccacggctt gaactgggga acgactggga ctctgccacc
aagcagttgc tgggactcca gcccataagc actgtgtccc ctcttcatag agtcctccat
tacagtcaag gctaa
```

SEQ ID NO: 5 hMVP (Genbank #CAA56256)

```
Met ala Thr Glu Glu Phe Ile Ile Arg Ile Pro Pro Tyr His Tyr Ile His Val
Leu Asp Gln Asn Ser Asn Val Ser Arg Val Glu Val Gly Pro Lys Thr Tyr Ile
Arg Gln Asp Asn Glu Arg Val Leu Phe Ala Pro Met Arg Met Val Thr Val Pro
Pro Arg His Tyr Cys Thr Val Ala Asn Pro Val Ser Arg Asp Ala Gln Gly Leu
Val Leu Phe Asp Val Thr Gly Gln Val Arg Leu Arg His Ala Asp Leu Glu Ile
Arg Leu Ala Gln Asp Pro Phe Pro Leu Tyr Pro Gly Glu Val Leu Glu Lys Asp
Ile Thr Pro Leu Gln Val Val Leu Pro Asn Thr Ala Leu His Leu Lys Ala Leu
Leu Asp Phe Glu Asp Lys Asp Gly Asp Lys Val Val Ala Gly Asp Glu Trp Leu
Phe Glu Gly Pro Gly Thr Tyr Ile Pro Arg Lys Glu Val Glu Val Val Glu Ile
```

TABLE 1-continued

Sequences

Ile Gln Ala Thr Ile Ile Arg Gln Asn Gln Ala Leu Arg Leu Arg Ala Arg Lys
Glu Cys Trp Asp Arg Asp Gly Lys Glu Arg Val Thr Gly Glu Glu Trp Leu Val
Thr Thr Val Gly Ala Tyr Leu Pro Ala Val Phe Glu Glu Val Leu Asp Leu Val
Asp Ala Val Ile Leu Thr Glu Lys Thr Ala Leu His Leu Arg Ala Arg Arg Asn
Phe Arg Asp Phe Arg Gly Val Ser Arg Arg Thr Gly Glu Glu Trp Leu Val Thr
Val Gln Asp Thr Glu Ala His Val Pro Asp Val His Gly Val Leu Glu Val Val
Val Pro Ile Thr Thr Leu Gly Pro His Asn Tyr Cys Val Ile Leu Asp Pro Val
Gly Pro Asp Gly Lys Asn Gln Leu Gly Gln Lys Arg Val Val Lys Gly Glu Lys
Ser Phe Leu Gln Pro Gly Glu Gln Leu Glu Gln Gly Ile Gln Asp Val Tyr
Val Leu Ser Glu Gln Gln Gly Leu Leu Leu Arg Ala Leu Gln Pro Leu Glu Glu
Gly Glu Asp Glu Glu Lys Val Ser His Gln Ala Gly Asp His Trp Leu Ile Arg
Gly Pro Leu Glu Tyr Val Pro Ser Ala Lys Val Glu Val Val Glu Glu Arg Gln
Ala Ile Pro Leu Asp Glu Asn Glu Gly Ile Tyr Val Gln Asp Val Lys Thr Gly
Lys Val Arg Ala Val Ile Gly Ser Thr Tyr Met Leu Thr Gln Asp Glu Val Leu
Trp Glu Lys Glu Leu Pro Pro Gly Val Glu Glu Leu Leu Asn Lys Leu Gln Asp
Pro Leu Ala Asp Arg Gly Glu Lys Asp Thr Ala Lys Ser Leu Gln Pro Leu Ala
Pro Arg Asn Lys Thr Arg Val Val Ser Tyr Arg Val Pro His Asn Ala Ala Val
Gln Val Tyr Asp Tyr Arg Glu Lys Arg Ala Arg Val Val Phe Gly Pro Glu Leu
Val Ser Leu Gly Pro Glu Glu Gln Phe Thr Val Leu Ser Leu Ser Ala Gly Arg
Pro Lys Arg Pro His Ala Arg Arg Ala Leu Cys Leu Leu Leu Gly Pro Asp Phe
Phe Thr Asp Val Ile Thr Ile Glu Thr Ala Asp His Ala Arg Leu Gln Leu Gln
Leu Ala Tyr Asn Trp His Phe Glu Val Asn Asp Arg Lys Asp Pro Gln Glu Thr
Ala Lys Leu Phe Ser Val Pro Asp Phe Val Gly Asp Ala Cys Lys Ala Ile Ala
Ser Arg Val Arg Gly Ala Val Ala Ser Val Thr Phe Asp Asp Phe His Lys Asn
Ser Ala Arg Ile Ile Arg Thr Ala Val Phe Gly Phe Glu Thr Ser Glu Ala Lys
Gly Pro Asp Gly Met ala Leu Pro Arg Pro Arg Asp Gln Ala Val Phe Pro Gln
Asn Gly Leu Val Val Ser Ser Val Asp Val Gln Ser Val Glu Pro Val Asp Gln
Arg Thr Arg Asp Ala Leu Gln Arg Ser Val Gln Leu Ala Ile Glu Ile Thr Thr
Asn Ser Gln Glu Ala Ala Lys His Glu Ala Gln Arg Leu Glu Gln Glu Ala
Arg Gly Arg Leu Glu Arg Gln Lys Ile Leu Asp Gln Ser Glu Ala Glu Lys Ala
Arg Lys Glu Leu Leu Glu Leu Glu Ala Leu Ser Met Ala Val Glu Ser Thr Gly
Thr Ala Lys Ala Glu Ala Glu Ser Arg Ala Glu Ala Ala Arg Ile Glu Gly Glu
Gly Ser Val Leu Gln Ala Lys Leu Lys Ala Gln Ala Leu Ala Ile Glu Thr Glu
Ala Glu Leu Gln Arg Val Gln Lys Val Arg Glu Leu Glu Leu Val Tyr Ala Arg
Ala Gln Leu Glu Leu Glu Val Ser Lys Ala Gln Gln Leu Ala Glu Val Glu Val
Lys Lys Phe Lys Gln Met Thr Glu Ala Ile Gly Pro Ser Thr Ile Arg Asp Leu
Ala Val Ala Gly Pro Glu Met Gln Val Lys Leu Leu Gln Ser Leu Gly Leu Lys
Ser Thr Leu Ile Thr Asp Gly Ser Thr Pro Ile Asn Leu Phe Asn Thr Ala Phe
Gly Leu Leu Gly Met Gly Pro Glu Gly Gln Pro Leu Gly Arg Arg Val Ala Ser
Gly Pro Ser Pro Gly Glu Gly Ile Ser Pro Gln Ser Ala Gln Ala Pro Gln Ala
Pro Gly Asp Asn His Val Val Pro Val Leu Arg SEQ ID NO: 6 hMVP cDNA, Genbank #X79882

```
atggcaactg aagagttcat catccgcatc ccccataac actatatcca tgtgctggac
cagaacagca acgtgtcccg tgtggaggtc gggccaaaga cctacatccg gcaggacaat
gagagggtac tgtttgcccc catgcgcatg gtgaccgtcc ccccacgtca ctactgcaca
gtggccaacc ctgtgtctcg ggatgccagg ggcttggtgc tgtttgatgt cacagggcaa
gttcggcttc gccacgctga cctcgagatc cggctggccc aggaccccct ccccctgtac
ccaggggagg tgctggaaaa ggacatcaca ccctgcagg tggttctgcc caacactgcc
ctccatctaa aggcgctgct tgattttgag gataaagatg gagacaaggt ggtggcagga
gatgagtggc ttttcgaggg acctggcacg tacatccccc ggaaggaagt ggaggtcgtg
gagatcattc aggccaccat catcaggcag aaccaggctc tgcggctcag ggcccgcaag
gagtgctggg accgggacgg caaggagagg gtgacagggg aagaatggct ggtcaccaca
gtaggggcgt acctcccagc ggtgtttgag gaggttctgg atttggtgga cgccgtcatc
cttacgggaa agacagccct gcacctccgg gctcggcgaa acttccggga cttcaggggga
gtgtcccgcc gcactgggga ggagtggctg gtaacagtgc aggacacaga ggcccacgtg
ccagatgtcc acgaggaggt gctggggggtt gtgcccatca ccaccctggg ccccacaac
tactgcgtga ttctcgaccc tgtcggaccg gatggcaaga tcagctgggg cagaagcgc
gtggtcaagg gagagaagtc ttttttcctc cagccaggag agcagctgga acaaggcatc
caggatgtgt atgtgctgtc ggagcagcag gggctgctgc tgagggccct gcagcccctg
gaggagggggg aggatgagga gaaggtctca caccaggctg ggaccactg gctcatccgc
ggacccctgg agtatgtgcc atctgccaaa gtggaggtgg tggaggagcg ccaggccatc
cctctagacg agaacgaggg catctatgtg caggatgtca agaccggaaa ggtgcgcgct
gtgattggaa gcacctacat gctgacccag gacgaagtcc tgtgggagaa agagctgcct
cccgggggtgg aggagctgct gaacaagggg caggaccctc tggcagacag gggtgagaag
gacacagcta agagcctcca gcccttggcg ccccggaaca gaccccgtgt ggtcagctac
cgcgtgcccc acaacgctgc ggtgcaggtg tacgactacc gagagaagcg agcccgcgtg
gtcttcgggc ctgagctggt gtcgctgggt cctgaggagc agttcacagt gttgtccctc
tcagctgggc ggcccaagcg tcccatgcc cgccgtgcgc tctgcctgct gctggggcct
gacttcttca cagacgtcat caccatcgaa acgcgcgatc atgccaggct gcaactgcag
ctggcctaca ctggcacttt tgaggtgaat gaccggaagg accccaagaa gacggccaag
ctcttttcag tgccagactt tgtaggtgat gcctgcaaag tcatcgcatc ccgggtgcgg
ggggccgtgg cctctgtcac tttcgatgac ttccataaga actcagcccg catcattcgc
actgctgtct ttggctttga gacctcggaa gcgaagggcc ccgatggcat ggccctgccc
aggcccgggg accaggctgt cttcccccaa aacgggctgg tggtcagcag tgtggacgtg
cagtcagtgg agcctgtgga tcagaggacc cggacgcccc tgcaacgcag cgtccagctg
gccatcgaga tcaccaccaa ctcccaggaa gcggcggcca agcatgaggc tcagagactg
```

TABLE 1-continued

Sequences gagcaggaag cccgcggccg gcttgagcgg cagaagatcc tggaccagtc agaagccgag
aaagctcgca aggaactttt ggagctggag gctctgagca tggccgtgga gagcaccggg
actgccaagg cggaggccga gtcccgtgcg gaggcagccc ggattgaggg agaagggtcc
gtgctgcagg ccaagctaaa agcacaggcc ttggccattg aaacggaggc tgagctccag
agggtccaga aggtccgaga gctggaactg gtctatgccc gggcccagct ggagctggag
gtgagcaagg ctcagcagct ggctgaggtg gaggtgaaga agttcaagca gatgacagag
gccataggcc ccagcaccat cagggacctt gctgtggctg ggcctgagat gcaggtaaaa
ctgctccagt ccctgggcct gaaatcaacc ctcatcaccg atggctccac tcccatcaac
ctcttcaaca cagcctttgg gctgctgggg atggggcccg agggtcagcc cctgggcaga
agggtggcca gtgggcccag ccctggggag gggatatccc cccagtctgc tcaggcccct
caagctcctg gagacaacca cgtggtgcct gtactgcgct aa SEQ ID NO: 7 CP Peptide Met ala Gly Cys Gly Cys Pro Cys Gly Cys Gly Ala SEQ ID NO: 8 CP-hMVP Met ala Gly Cys Gly Cys Pro Cys Gly Cys Gly Ala Met ala Thr Glu Glu Phe
Ile Ile Arg Ile Pro Pro Tyr His Tyr Ile His Val Leu Asp Gln Asn Ser Asn
Val Ser Arg Val Glu Val Gly Pro Lys Thr Tyr Ile Arg Gln Asp Asn Glu Arg
Val Leu Phe Ala Pro Met Arg Met Val Thr Val Pro Pro Arg His Tyr Cys Thr
Val Ala Asn Pro Val Ser Arg Asp Ala Gln Gly Leu Val Leu Phe Asp Val Thr
Gly Gln Val Arg Leu Arg His Ala Asp Leu Glu Ile Arg Leu Ala Gln Asp Pro
Phe Pro Leu Tyr Pro Gly Glu Val Leu Glu Lys Asp Ile Thr Pro Leu Gln Val
Val Leu Pro Asn Thr Ala Leu His Leu Lys Ala Leu Leu Asp Phe Glu Asp Lys
Asp Gly Asp Lys Val Val Ala Gly Asp Glu Trp Leu Phe Glu Gly Pro Gly Thr
Tyr Ile Pro Arg Lys Glu Val Glu Val Val Glu Ile Ile Gln Ala Thr Ile Ile
Arg Gln Asn Gln Ala Leu Arg Leu Arg Ala Arg Lys Glu Cys Trp Asp Arg Asp
Gly Lys Glu Arg Val Thr Gly Glu Glu Trp Leu Val Thr Thr Val Gly Ala Tyr
Leu Pro Ala Val Phe Glu Glu Val Leu Asp Leu Val Asp Ala Val Ile Leu Thr
Glu Lys Thr Ala Leu His Leu Arg Ala Arg Arg Asn Phe Arg Asp Phe Arg Gly
Val Ser Arg Arg Thr Gly Glu Glu Trp Leu Val Thr Val Gln Asp Thr Glu Ala
His Val Pro Asp Val His Glu Glu Val Leu Gly Val Val Pro Ile Thr Thr Leu
Gly Pro His Asn Tyr Cys Val Ile Leu Asp Pro Val Gly Pro Asp Gly Lys Asn
Gln Leu Gly Gln Lys Arg Val Val Lys Gly Glu Lys Ser Phe Phe Leu Gln Pro
Gly Glu Gln Leu Glu Gln Gly Ile Gln Asp Val Tyr Val Leu Ser Glu Gln Gln
Gly Leu Leu Leu Arg Ala Leu Gln Pro Leu Glu Glu Gly Glu Asp Glu Glu Lys
Val Ser His Gln Ala Gly Asp His Trp Leu Ile Arg Gly Pro Leu Glu Tyr Val
Pro Ser Ala Lys Val Glu Val Val Glu Glu Arg Gln Ala Ile Pro Leu Asp Glu
Asn Glu Gly Ile Tyr Val Gln Asp Val Lys Thr Gly Lys Val Arg Ala Val Ile
Gly Ser Thr Tyr Met Leu Thr Gln Asp Glu Val Leu Trp Glu Lys Glu Leu Pro
Pro Gly Val Glu Glu Leu Leu Asn Lys Gly Gln Asp Pro Leu Ala Asp Arg Gly
Glu Lys Asp Thr Ala Lys Ser Leu Gln Pro Leu Ala Pro Arg Asn Lys Thr Arg
Val Val Ser Tyr Arg Val Pro His Asn Ala Ala Val Gln Val Tyr Asp Tyr Arg
Glu Lys Arg Ala Arg Val Val Phe Gly Pro Glu Leu Val Ser Leu Gly Pro Glu
Glu Gln Phe Thr Val Leu Ser Leu Ser Ala Gly Arg Pro Lys Arg Pro His Ala
Arg Arg Ala Leu Cys Leu Leu Leu Gly Pro Asp Phe Phe Thr Asp Val Ile Thr
Ile Glu Thr Ala Asp His Ala Arg Leu Gln Leu Gln Leu Ala Tyr Asn Trp His
Phe Glu Val Asn Asp Arg Lys Asp Pro Gln Glu Thr Ala Lys Leu Phe Ser Val
Pro Asp Phe Val Gly Asp Ala Cys Lys Ala Ile Ala Ser Arg Val Arg Gly Ala
Val Ala Ser Val Thr Phe Asp Asp Phe His Lys Asn Ser Ala Arg Ile Ile Arg
Thr Ala Val Phe Gly Phe Glu Thr Ser Glu Ala Lys Gly Pro Asp Gly Met ala
Leu Pro Arg Pro Arg Asp Gln Ala Val Phe Pro Gln Asn Gly Leu Val Val Ser
Ser Val Asp Val Gln Ser Val Glu Pro Val Asp Gln Arg Thr Arg Asp Ala Leu
Gln Arg Ser Val Gln Leu Ala Ile Glu Ile Thr Thr Asn Ser Gln Glu Ala Ala
Ala Lys His Glu Ala Gln Arg Leu Glu Gln Glu Ala Arg Gly Arg Leu Glu Arg
Gln Lys Ile Leu Asp Gln Ser Glu Ala Glu Lys Ala Arg Lys Glu Leu Leu Glu
Leu Glu Ala Leu Ser Met ala Val Glu Ser Thr Gly Thr Ala Lys Ala Glu Ala
Glu Ser Arg Ala Glu Ala Ala Arg Ile Glu Gly Glu Gly Ser Val Leu Gln Ala
Lys Leu Lys Ala Gln Ala Leu Ala Ile Glu Thr Glu Ala Glu Leu Gln Arg Val
Gln Lys Val Arg Glu Leu Glu Leu Val Tyr Ala Arg Ala Gln Leu Glu Leu Glu
Val Ser Lys Ala Gln Gln Leu Ala Glu Val Glu Val Lys Lys Phe Lys Gln Met
Thr Glu Ala Ile Gly Pro Ser Thr Ile Arg Asp Leu Ala Val Ala Gly Pro Glu
Met Gln Val Lys Leu Leu Gln Ser Leu Gly Leu Val Ser Thr Leu Ile Thr Asp
Gly Ser Thr Pro Ile Asn Leu Phe Asn Thr Ala Phe Gly Leu Leu Gly Met Gly
Pro Glu Gly Gln Pro Leu Gly Arg Arg Val Ala Ser Gly Pro Ser Pro Gly Glu
Gly Ile Ser Pro Gln Ser Ala Gln Ala Pro Gln Ala Pro Gly Asp Asn His Val
Val Pro Val Leu Arg SEQ ID NO: 9 CP-hMVP cDNA atggcaggct gcggttgtcc atgcggttgt ggcgccatgg caactgaaga gttcatcatc
cgcatccccc cataccacta tatccatgtg ctggaccaga acagcaacgt gtcccgtgtg
gaggtcgggc caaagaccta catccggcag acaatgaga gggtactgtt tgccccatg
cgcatggtga ccgtcccccc acgtcactac tgcacagtgg caaccctgt gtctcgggat
gcccagggct tggtgctgtt tgatgtcaca gggcaagttc ggcttcgcca cgctgacctc
gagatccggc tggcccagga ccccttcccc ctgtacccag gggaggtgct ggaaaaggac

TABLE 1-continued

Sequences

```
atcacacccc tgcaggtggt tctgcccaac actgccctcc atctaaaggc gctgcttgat
tttgaggata aagatggaga caaggtggtg gcaggagatg agtggcttt cgagggacct
ggcacgtaca tccccggaa ggaagtggag gtcgtggaga tcattcaggc caccatcatc
aggcagaacc aggctctgcg gctcagggcc cgcaaggagt gctgggaccg ggacggcaag
gagagggtga caggggaaga atggctggtc accacagtag gggcgtacct cccagcggtg
tttgaggagg ttctggattt ggtggacgcc gtcatcctta cggaaaagac agccctgcac
ctccgggctc ggcggaactt ccgggacttc aggggagtgt cccgccgcac tggggaggag
tggctggtaa cagtgcagga cacagaggcc cacgtgccag atgtccacga ggaggtgctg
ggggttgtgc ccatcaccac cctgggcccc cacaactact gcgtgattct cgaccctgtc
ggaccggatg gcaagaatca gctggggcag aagcgcgtgg tcaagggaga gaagtctttt
ttcctccagc caggagagca gctggaacaa ggcatccagg atgtgtatgt gctgtcggaa
cagcaggggc tgctgctgag ggccctgcag ccctggagg aggggagga tgaggagaag
gtctcacacc aggctgggga ccactggctc atccgcggac ccctggagta tgtgccatct
gccaaagtgg aggtggtgga ggagcgccag gccatccctc tagacgagaa cgagggcatc
tatgtgcagg atgtcaagac cggaaaggtg cgcgctgtga ttggaagcac ctacatgctg
acccaggacg aagtcctgtg ggagaaagag ctgcctcccg gggtggagga gctgctgaac
aaggggcagg accctctggc agacaggggt gagaaggaca cagctaagag cctccagccc
ttggcgcccc ggaacaagac ccgtgtggtc agctaccgcg tgccccacaa cgctgcggtg
caggtgtacg actaccgaga gaagcgagcc cgcgtggtct tcgggcctga gctggtgtcg
ctgggtcctg aggagcagtt cacagtgttg tccctctcag ctgggcggcc caagcgtccc
catgcccgcc gtgcgctctg cctgctgctg gggcctgact tcttcacaga cgtcatcacc
atcgaaacgg cggatcatgc caggctgcaa ctgcagctgg cctacaactg cactttgag
gtgaatgacc ggaaggaccc ccaagagacg gccaagctct tttcagtgcc agactttgta
ggtgatgcct gcaaagccat cgcatcccgg gtgcgggggg ccgtgcctc tgtcactttc
gatgacttcc ataagaactc agcccgcatc attcgcactg ctgtctttgg ctttgagacc
tcggaagcga agggccccga tggcatggcc ctgcccaggc cccgggacca ggctgtcttc
ccccaaaacg ggctggtggt cagcagtgtg gacgtgcagt cagtggagcc tgtggatcag
aggacccggg acgccctgca acgcagcgtc cagctggcca tcgagatcac caccaactcc
caggaagcgg cggccaagca tgaggctcag agactggagc aggaagcccg cggccggctt
gagcggcaga agatcctgga ccagtcagaa gccgagaaag ctcgcaagga acttttggag
ctggaggctc tgagcatggc cgtggagagc accgggactg ccaaggcgga ggccgagtcc
cgtgcgcagg cagcccggat tgagggagaa gggtccgtgc tgcaggccaa gctaaaagca
caggccttgg ccattgaaac ggaggctgag ctccagaggg tccagaaggt ccgagagctg
gaactggtct atgcccgggc ccagctggag ctggaggtga gcaaggctca gcagctggct
gaggtggagg tgaagaagtt caagcagatg acagaggcca taggccccag caccatcagg
gaccttgctg tggctgggcc tgagatgcag gtaaaactgc tccagtccct gggcctgaaa
tcaaccctca tcaccgatgg ctccactccc atcaacctct tcaacacagc ctttgggctg
ctggggatgg ggcccgaggg tcagcccctg ggcagaaggg tggccagtgg gcccagccct
ggggagggga tatccccca gtctgctcag gcccctcaag ctcctggaga caaccacgtg
gtgcctgtac tgcgctaa
```

SEQ ID NO: 10 TEP1, Genbank #AAC51107

```
Met Glu Lys Leu His Gly His Val Ser Ala His Pro Asp Ile Leu Ser Leu Glu
Asn Arg Cys Leu Ala Met Leu Pro Asp Leu Gln Pro Leu Glu Lys Leu His Gln
His Val Ser Thr His Ser Asp Ile Leu Ser Leu Lys Asn Gln Cys Leu Ala Thr
Leu Pro Asp Leu Lys Thr Met Glu Lys Pro His Gly Tyr Val Ser Ala His Pro
Asp Ile Leu Ser Leu Glu Asn Gln Cys Leu Ala Thr Leu Ser Asp Leu Lys Thr
Met Glu Lys Pro His Gly His Val Ser Ala His Pro Asp Ile Leu Ser Leu Glu
Asn Arg Cys Leu Ala Thr Leu Pro Ser Leu Lys Ser Thr Val Ser Ala Ser Pro
Leu Phe Gln Ser Leu Gln Ile Ser His Met Thr Gln Ala Asp Leu Tyr Arg Val
Asn Asn Ser Asn Cys Leu Leu Ser Glu Pro Pro Ser Trp Arg Ala Gln His Phe
Ser Lys Gly Leu Asp Leu Ser Thr Cys Pro Ile Ala Leu Lys Ser Ile Ser Ala
Thr Glu Thr Ala Gln Glu Ala Thr Leu Gly Arg Trp Phe Asp Ser Glu Glu Lys
Lys Gly Ala Glu Thr Gln Met Pro Ser Tyr Ser Leu Ser Leu Gly Glu Glu Glu
Glu Val Glu Asp Leu Ala Val Lys Leu Thr His Ser Gly Asp Ser Glu Ser His Pro
Glu Pro Thr Asp His Val Leu Gln Leu Lys Lys Met ala Leu Leu Ser Leu Leu
Cys Ser Thr Leu Val Ser Glu Val Asn Met Asn Asn Thr Ser Asp Pro Thr Leu
Ala Ala Ile Phe Glu Ile Cys Arg Glu Leu Ala Leu Leu Glu Pro Glu Phe Ile
Leu Lys Ala Ser Leu Tyr Ala Arg Gln Gln Leu Asn Val Arg Asn Val Ala Asn
Asn Ile Leu Ala Ile Ala Ala Phe Leu Pro Ala Cys Arg Pro His Leu Arg Arg
Tyr Phe Cys Ala Ile Val Gln Leu Pro Ser Asp Trp Ile Gln Val Ala Glu Leu
Tyr Gln Ser Leu Ala Glu Gly Asp Lys Asn Lys Leu Val Pro Leu Pro Ala Cys
Leu Arg Thr Ala Met Thr Asp Lys Phe Ala Gln Phe Asp Glu Tyr Gln Leu Ala
Lys Tyr Asn Pro Arg Lys His Arg Ala Lys Arg His Pro Arg Pro Arg
Ser Pro Gly Met Glu Pro Pro Phe Ser His Arg Cys Phe Pro Arg Tyr Ile Gly
Phe Leu Arg Glu Glu Arg Lys Phe Glu Lys Ala Gly Asp Thr Val Ser Glu
Lys Lys Asn Pro Pro Arg Phe Thr Leu Lys Lys Leu Val Gln Arg Leu His Ile
His Ser Pro Ala Gln His Val Gln Ala Leu His Gly Tyr Arg Tyr Pro Ser Asn
Leu Gln Leu Phe Ser Arg Ser Arg Leu Pro Gly Pro Trp Asp Ser Ser Arg Ala
Gly Lys Arg Met Lys Leu Ser Arg Pro Glu Thr Trp Glu Arg Glu Leu Ser Leu
Arg Gly Asn Lys Ala Ser Val Trp Glu Glu Leu Ile Glu Asn Gly Lys Leu Pro
Phe Met ala Met Leu Arg Asn Leu Cys Asn Leu Arg Leu Arg Gly Ile Ser Ser
Arg His His Glu Leu Ile Leu Gln Arg Leu Gln His Gly Lys Ser Val Ile His
Ser Arg Gln Phe Pro Phe Arg Phe Leu Asn Ala His Asp Ala Ile Asp Ala Leu
Glu Ala Gln Leu Arg Asn Gln Ala Leu Pro Phe Pro Ser Asn Ile Thr Leu Met
Arg Arg Ile Leu Thr Arg Asn Glu Lys Asn Arg Pro Arg Arg Phe Leu Cys
His Leu Ser Arg Gln Gln Leu Arg Met ala Met Arg Ile Pro Val Leu Tyr Glu
```

TABLE 1-continued

Sequences

Gln Leu Lys Arg Glu Lys Leu Arg Val His Lys Ala Arg Gln Trp Lys Tyr Asp
Gly Glu Met Leu Asn Arg Tyr Arg Gln Ala Leu Gly Thr Ala Val Asn Leu Ser
Val Lys His Ser Leu Pro Leu Leu Pro Gly Arg Thr Val Leu Val Tyr Leu Thr
Asp Ala Asn Ala Asp Arg Leu Cys Pro Lys Ser Asn Pro Gln Gly Pro Pro Leu
Asn Tyr Ala Leu Leu Leu Ile Gly Met Met Ile Thr Arg Ala Glu Gln Val Asp
Val Leu Cys Gly Gly Asp Thr Leu Lys Thr Ala Val Leu Lys Ala Glu Glu
Gly Ile Leu Lys Thr Ala Ile Lys Leu Gln Ala Gln Gln Leu Glu Phe Asp Glu
Asn Asp Gly Trp Ser Leu Asn Thr Phe Gly Lys Tyr Leu Leu Ser Leu Ala Gly
Gln Arg Val Pro Val Asp Arg Val Ile Leu Leu Gly Gln Ser Met Asp Asp Gly
Met Ile Asn Val Ala Lys Gln Leu Tyr Trp Gln Arg Val Asn Ser Lys Cys Leu
Phe Val Gly Ile Leu Leu Arg Arg Val Gln Tyr Leu Ser Thr Asp Leu Asn Pro
Asn Asp Val Thr Leu Ser Gly Cys Thr Asp Ala Ile Leu Lys Phe Ile Ala Glu
His Gly Ala Ser His Leu Leu Glu His Val Gly Gln Met Asp Lys Ile Phe Lys
Ile Pro Pro Pro Gly Lys Thr Gly Val Gln Ser Leu Arg Pro Leu Glu Glu
Asp Thr Pro Ser Pro Leu Ala Pro Val Ser Gln Gly Trp Arg Ser Ile Arg
Leu Phe Ile Ser Ser Thr Phe Arg Asp Met His Gly Glu Arg Asp Leu Leu Leu
Arg Ser Val Leu Pro Ala Leu Gln Ala Arg Ala Ala Pro His Arg Ile Ser Leu
His Gly Ile Asp Leu Arg Trp Gly Val Thr Glu Glu Thr Arg Arg Asn Arg
Gln Leu Glu Val Cys Leu Gly Glu Val Glu Asn Ala Gln Leu Phe Val Gly Ile
Leu Gly Ser Arg Tyr Gly Tyr Ile Pro Pro Ser Tyr Asn Leu Pro Asp His Pro
His Phe His Trp Ala Gln Gln Tyr Pro Ser Gly Arg Ser Val Thr Glu Met Glu
Val Met Gln Phe Leu Asn Arg Asn Gln Arg Leu Gln Pro Ser Ala Gln Ala Leu
Ile Tyr Phe Arg Asp Ser Ser Phe Leu Ser Ser Val Pro Asp Ala Trp Lys Ser
Asp Phe Val Ser Glu Ser Glu Glu Ala Ala Cys Arg Ile Ser Glu Leu Lys Ser
Tyr Leu Ser Arg Gln Lys Gly Ile Thr Cys Arg Arg Tyr Pro Cys Glu Trp Gly
Gly Val Ala Ala Gly Arg Pro Tyr Val Gly Gly Leu Glu Glu Phe Gly Gln Leu
Val Leu Gln Asp Val Trp Asn Met Ile Gln Lys Tyr Leu Gln Pro Gly Ala
Leu Leu Glu Gln Pro Val Ser Ile Pro Asp Asp Asp Leu Val Gln Ala Thr Phe
Gln Gln Leu Gln Lys Pro Pro Ser Pro Ala Arg Pro Arg Leu Leu Gln Asp Thr
Val Gln Gln Leu Met Leu Pro His Gly Arg Leu Ser Leu Val Thr Gly Gln Ser
Gly Gln Gly Lys Thr Ala Phe Leu Ala Ser Leu Val Ser Ala Leu Gln Ala Pro
Asp Gly Ala Lys Val Ala Pro Leu Val Phe His Phe Ser Gly Ala Arg Pro
Asp Gln Gly Leu Ala Leu Thr Leu Leu Arg Arg Leu Cys Thr Tyr Leu Arg Gly
Gln Leu Lys Glu Pro Gly Ala Leu Pro Ser Thr Tyr Arg Ser Leu Val Trp Glu
Leu Gln Gln Arg Leu Leu Pro Lys Ser Ala Glu Ser Leu His Pro Gly Gln Thr
Gln Val Leu Ile Ile Asp Gly Ala Asp Arg Leu Val Asp Gln Asn Gly Gln Leu
Ile Ser Asp Trp Ile Pro Lys Lys Leu Pro Arg Cys Val His Leu Val Leu Ser
Val Ser Ser Asp Ala Gly Leu Gly Glu Thr Leu Glu Gln Ser Gln Gly Ala His
Val Leu Ala Leu Gly Pro Leu Glu Ala Ser Ala Arg Ala Arg Leu Val Arg Glu
Glu Leu Ala Tyr Gly Lys Arg Leu Glu Gly Ser Pro Phe Asn Asn Gln Met
Arg Leu Leu Leu Val Lys Arg Glu Ser Gly Arg Pro Leu Tyr Leu Arg Leu Val
Thr Asp His Leu Arg Leu Phe Thr Leu Tyr Glu Gln Val Ser Glu Arg Leu Arg
Thr Leu Pro Ala Thr Val Pro Leu Leu Gln His Ile Leu Ser Thr Leu Glu
Lys Glu His Gly Pro Asp Val Leu Pro Gln Ala Thr Ala Leu Glu Val Thr
Arg Ser Gly Leu Thr Val Asp Gln Leu His Gly Val Leu Ser Val Trp Arg Thr
Leu Pro Lys Gly Thr Lys Ser Trp Glu Glu Ala Val Ala Ala Gly Asn Ser Gly
Asp Pro Tyr Pro Met Gly Pro Phe Ala Cys Leu Val Gln Ser Leu Arg Ser Leu
Leu Gly Glu Gly Pro Leu Glu Arg Pro Gly Ala Arg Leu Cys Leu Pro Asp Gly
Pro Leu Arg Thr Ala Ala Lys Arg Cys Tyr Gly Lys Arg Pro Gly Leu Glu Asp
Thr Ala His Ile Leu Ile Ala Ala Gln Leu Trp Lys Thr Cys Asp Ala Asp Ala
Ser Gly Thr Phe Arg Ser Cys Pro Pro Glu Ala Leu Gly Asp Leu Pro Tyr His
Leu Leu Gln Ser Gly Asn Arg Gly Leu Leu Ser Lys Phe Leu Thr Asn Leu His
Val Val Ala Ala His Leu Glu Leu Gly Leu Val Ser Arg Leu Leu Glu Ala His
Ala Leu Tyr Ala Ser Ser Val Pro Lys Glu Glu Gln Lys Leu Pro Glu Ala Asp
Val Ala Val Phe Arg Thr Phe Leu Arg Gln Gln Ala Ser Ile Leu Ser Gln Tyr
Pro Arg Leu Leu Pro Gln Leu Ala Ala Asn Gln Pro Leu Asp Ser Pro Leu Cys
His Gln Ala Ser Leu Leu Ser Arg Arg Trp His Leu Gln His Thr Leu Arg Trp
Leu Asn Lys Pro Arg Thr Met Lys Asn Gln Ser Ser Ser Leu Ser Leu Ala
Val Ser Ser Ser Pro Thr Ala Val Ala Phe Ser Thr Asn Gly Gln Arg Ala Ala
Val Gly Thr Ala Asn Gly Thr Val Tyr Leu Leu Asp Leu Arg Thr Trp Gln Glu
Glu Lys Ser Val Val Ser Gly Cys Asp Gly Ile Ser Ala Cys Val Ser Phe Leu Ser
Asp Asp Thr Leu Phe Leu Thr Ala Phe Asp Gly Leu Leu Glu Leu Trp Asp Leu
Gln His Gly Cys Arg Val Leu Gln Thr Lys Ala His Gln Tyr Gln Ile Thr Gly
Cys Cys Leu Ser Pro Asp Cys Arg Leu Leu Ala Thr Val Cys Leu Gly Gly Cys
Leu Lys Leu Trp Asp Thr Val Arg Gly Gln Leu Ala Phe Gln His Thr Tyr Pro
Lys Ser Leu Asn Cys Val Ala Phe His Pro Glu Gly Gln Val Ile Ala Thr Gly
Ser Trp Ala Gly Ser Ile Ser Phe Phe Gln Val Asp Gly Leu Lys Val Thr Lys
Asp Leu Gly Ala Pro Gly Ala Ser Ile Arg Thr Leu Ala Phe Asn Val Pro Gly
Gly Val Val Ala Val Gly Arg Asp Ser Met Val Leu Leu Trp Ala Leu Trp Arg
Glu Gly Ala Arg Leu Ala Ala Phe Pro Ala His His Gly Phe Val Ala Ala Ala
Leu Phe Leu His Ala Gly Cys Gln Leu Leu Thr Ala Gly Glu Asp Gly Lys Val
Gln Val Trp Ser Gly Ser Leu Gly Arg Pro Arg Gly His Leu Gly Ser Leu Ser
Leu Ser Pro Ala Leu Ser Val Ala Leu Ser Pro Asp Gly Asp Arg Val Ala Val
Gly Tyr Arg Ala Asp Gly Ile Arg Ile Tyr Lys Ile Ser Ser Gly Ser Gln Gly
Ala Gln Gly Gln Ala Leu Asp Val Ala Val Ser Ala Leu Ala Trp Leu Ser Pro
Lys Val Leu Val Ser Gly Ala Glu Asp Gly Ser Leu Gln Gly Trp Ala Leu Lys
Glu Cys Ser Leu Gln Ser Leu Trp Leu Leu Ser Arg Phe Gln Lys Pro Val Leu
Gly Leu Ala Thr Ser Gln Glu Leu Leu Ala Ser Ala Ser Glu Asp Phe Thr Val

TABLE 1-continued

Sequences

```
Gln Leu Trp Pro Arg Gln Leu Leu Thr Arg Pro His Lys Ala Glu Asp Phe Pro
Cys Gly Thr Glu Leu Arg Gly His Glu Gly Pro Val Ser Cys Cys Ser Phe Ser
Thr Asp Gly Gly Ser Leu Ala Thr Gly Gly Arg Asp Arg Ser Leu Leu Cys Trp
Asp Val Arg Thr Pro Lys Thr Pro Val Leu Ile His Ser Phe Pro Ala Cys His
Arg Asp Trp Val Thr Gly Cys Ala Trp Thr Lys Asp Asn Leu Leu Ile Ser Cys
Ser Ser Asp Gly Ser Val Gly Leu Trp Asp Pro Glu Ser Gly Gln Arg Leu Gly
Gln Phe Leu Gly His Gln Ser Ala Val Ser Ala Val Ala Val His Glu Glu His
Val Val Ser Val Ser Arg Asp Gly Thr Leu Lys Val Trp Asp His Gln Gly Val
Glu Leu Thr Ser Ile Pro Ala His Ser Gly Pro Ile Ser His Cys Ala Ala Ala
Met Glu Pro Arg Ala Ala Gly Gln Pro Gly Ser Glu Leu Leu Val Val Thr Val
Gly Leu Asp Gly Ala Thr Arg Leu Trp His Pro Leu Val Cys Gln Thr His
Thr Leu Leu Gly His Ser Gly Pro Val Arg Ala Ala Ala Val Ser Glu Thr Ser
Gly Leu Met Leu Thr Ala Ser Glu Asp Gly Ser Val Arg Leu Trp Gln Val Pro
Lys Glu Ala Asp Asp Thr Cys Ile Pro Arg Ser Ser Ala Ala Val Thr Ala Val
Ala Trp Ala Pro Asp Gly Ser Met ala Val Ser Gly Asn Gln Ala Gly Glu Leu
Ile Leu Trp Gln Glu Ala Lys Ala Val Ala Thr Ala Gln Ala Pro Gly His Ile
Gly Ala Leu Ile Trp Ser Ser Ala His Thr Phe Phe Val Leu Ser Ala Asp Glu
Lys Ile Ser Glu Trp Gln Val Lys Leu Arg Lys Gly Ser Ala Pro Gly Asn Leu
Ser Leu His Leu Asn Arg Ile Leu Gln Glu Ala Ser Leu Gly Val Leu Thr Ser Leu
Asp Trp Ala Pro Asp Gly His Phe Leu Ile Leu Ala Lys Ala Asp Leu Lys Leu
Leu Cys Met Lys Pro Gly Asp Ala Pro Ser Glu Ile Trp Ser Ser Tyr Thr Glu
Asn Pro Met Ile Leu Ser Thr His Lys Glu Tyr Gly Ile Phe Val Leu Gln Pro
Lys Asp Pro Gly Val Leu Ser Phe Leu Arg Gln Lys Gly Leu Gly Leu Glu Glu
Glu Arg Leu Asn Phe Asp Ile Asn Leu Glu Asn Pro Ser Arg Thr Leu Ile Ser
Ile Thr Gln Ala Lys Pro Glu Ser Glu Ser Ser Phe Leu Cys Ala Ser Ser Asp
Gly Ile Leu Trp Asn Leu Ala Lys Cys Ser Pro Glu Gly Glu Trp Thr Thr Gly
Asn Met Trp Gln Lys Lys Ala Asn Thr Pro Glu Thr Gln Thr Pro Gly Thr Asp
Pro Ser Thr Cys Arg Glu Ser Asp Ala Ser Met Asp Ser Asp Ala Ser Met Asp
Ser Glu Pro Thr Pro His Leu Lys Thr Arg Gln Arg Arg Lys Ile His Ser Gly
Ser Val Thr Ala Leu His Val Leu Pro Glu Leu Leu Val Thr Ala Ser Lys Asp
Arg Asp Val Lys Leu Trp Glu Arg Pro Ser Met Gln Leu Leu Gly Leu Phe Arg
Cys Glu Gly Ser Val Ser Cys Leu Glu Pro Trp Leu Gly Ala Asn Ser Thr Leu
Gln Leu Ala Val Gly Asp Val Gln Gly Asn Val Tyr Phe Leu Asn Trp Glu
```

SEQ ID NO: 11 TEP1 cDNA, Genbank #U86136

```
atggaaaaac tccatgggca tgtgtctgcc catccagaca tcctctcctt ggagaaccgg
tgcctggcta tgctccctga cttacagccc ttggagaaac tacatcagca tgtatcctacc
cactcagata tcctctcctt gaagaaccag tgcctagcca cgcttcctga cctgaagacc
atggaaaaac cacatggata tgtgtctgcc cacccagaca tcctctcctt ggagaaccag
tgcctggcca cactttctga cctgaagacc atggagaaac cacatggaca tgtttctgcc
cacccagaca tcctctcctt ggagaaccgg tgcctggcca cctcccctag tctaaagagc
actgtgtctc cagcccctt gttccagagt ctacagatat ctcacatgac gcaagctgat
ttgtaccgtg tgaacaacag caattgcctg ctctctgagc ctccaagttg gagggctcag
catttctcta agggactaga cctttcaacc tgcccctatag ccctgaaatc catctctgcc
acagagacag ctcaggaagc aactttgggt cgttggtttg attcagaaga aagaagggg
gcagagaccc aaatgccttc ttatagtctg agcttgggag aggaggagga ggtggaggat
ctggccgtga agctcacctc tggagactct gaatctcatc cagagcctac tgaccatgtc
cttcaggaaa agaagatggc tctactgagc ttgctgtgct ctactctggt ctcagaagta
aacatgaaca atacatctga ccccacccctg gctgccattt ttgaaatctg tcgtgaactt
gccctcctgg agcctgagtt tatcctcaag gcatctttgt atgccaggca gcagctgaac
gtccggaatg tggccaataa catcttggcc attgctgctc tcttgccggc gtgtcgcccc
cacctgcgac gatatttctg tgccattgtc cagctgcctt ctgactggat ccaggtggct
gagctttacc agagcctggc tgagggagat aagaataagc tggtgccccct gcccgcctgt
ctccgtactg ccatgacgga caaatttgcc cagtttgacg agtaccagct ggctaagtac
aaccctcgga agcaccgggc caagagacac ccccgccggc cacccccgctc tccagggatg
gagcctccat tttctcacag atgtttttca aggtacatag ggtttctgag agaagagcag
agaaagtttg agaaggccgg tgatacagtg tcagagaaaa agaatcctcc aaggttcacc
ctgaagaagc tggttcagcg actgcacatc cacaagcctg cccagcacgt tcaagccctg
ctgggttaca gatacccctc caacctacag ctctttttctc gaagtcgcct tcctgggcct
tgggattcta gcagagctgg gaagaggatg aagctgtca ggccagagac ctgggagcgg
gagctgagcc tacgggggaa caaagcgtcg gtctgggagg aactcattga aaatgggaag
cttcccttca tggccatgct tcggaacctg tgcaacctgc tgcgggttgg aatcagttcc
cgccaccatg agctcattct ccagagactc cagcatggga agtcggtgat ccacagtcgg
cagtttccat tcagatttct taacgcccat gatgccattg atgcctctga ggctcaactc
agaaatcaag cattgccctt ccttcgaat ataacactga tgaggcggat actaactaga
aatgaaaaga accgtcccag gcggaggttt ctttgccacc taagccgtca gcagcttcgt
atggcaatga ggatacctgt gttgtatgag cagctcaaga gggaagaagct gagagtacac
aaggccagac agtggaaata tgatggtgag atgctgaaca ggtaccgaca ggccctagag
acagctgtga acctctctgt gaagcacagc ctgcccctgc tgccaggccg cactgtcttg
gtctatctga cagatgctaa tgcagacagg ctctgtccaa agagcaaccc acaagggccc
ccgctgaact atgcactgct gttgattggg atgatgatca cgagggcgga gcaggtggac
gtcgtgctgt gtgaggtga cactctgaag actgcagtcg ttaaggcaga agaaggcatc
ctgaagactg ccatcaagct ccaggctcaa gtccaggagt ttgatgaaaa tgatgatgg
tccctgaata cttttgggaa ataccgtctg tctctggctg gccaaggggt tcctgtggac
agggtcatcc tccttggcca aagcatggat gatggaatga taatgtggc caaacagctt
tactggcagc gtgtgaattc caagtgcctc tttgttggta tcctcctaag aagggtacaa
tacctgtcaa cagatttgaa tcccaatgat gtgacactct caggctgtac tgatgcgata
```

TABLE 1-continued

Sequences

```
ctgaagttca ttgcagagca tggggcctcc catcttctgg aacatgtggg ccaaatggac
aaaatattca agattccacc accccagga aagacagggg tccagtctct ccggccactg
gaagaggaca ctccaagccc cttggctcct gtttcccagc aaggatggcg cagcatccgg
cttttcattt catccacttt ccgagacatg cacggggagc gggacctgct gctgaggtct
gtgctgccag cactgcaggc ccgagcggcc cctcaccgta tcagccttca cggaatcgac
ctccgctggg gcgtcactga ggaggagacc cgtaggaaca gacaactgga agtgtgcctt
ggggaggtgg agaacgcaca gctgtttgtg gggattctgg gctcccgtta tggatacatt
cccccagct acaaccttcc tgaccatcca cacttccact gggcccagca gtacccttca
gggcgctctg tgacagagat ggaggtgatg cagttcctga accggaacca acgtctgcag
ccctctgccc aagctctcat ctacttccgg gattccagct cctcagctc tgtgccagat
gcctggaaat ctgactttgt ttctgagtct gaagaggccg catgtcggat ctcagaactg
aagagctacc taagcagaca gaaagggata acctgccgca gataccctg tgagtggggg
ggtgtggcag ctggccggcc ctatgttggc gggctggagg agtttgggca gttggttctg
caggatgtat ggaatatgat ccagaagctc tacctgcagc ctgggccct gctggagcag
ccagtgtcca tcccagacga tgacttggtc caggccacct tccagcagct gcagaagcca
ccgagtcctg cccggccacg ccttcttcag gacacagtgc aacagctgat gctgccccac
ggaaggctga gcctggtgac ggggcagtca ggacagggca agacagcctt cctggcatct
cttgtgtcag ccctgcaggc tcctgatggg gccaaggtgg caccattagt cttcttccac
ttttctgggg ctcgtcctga ccagggtctt gccctcactc tgctcagacg cctctgtacc
tatctgcgtg gccaactaaa agagccaggt gccctcccca gcacctaccg aagcctggtg
tgggagctgc agcagaggct gctgcccaag tctgctgagt ccctgcatcc tggccagacc
caggtcctga tcatcgatgg ggctgatagg ttagtggacc agaatgggca gctgatttca
gactggatcc caaagaagct tccccggtgt gtacacctgg tgctgagtgt gtctagtgat
gcaggcctag gggagaccct tgagcagagc cagggtgccc acgtgctggc cttgggcct
ctggaggcct ctgctcgggc ccggctggtg agagaggagc tggccctgta cgggaagcgg
ctggaggagt caccatttaa caaccagatg cgactgctgc tggtgaagcg ggaatcaggc
cggccgctct acctgcgctt ggtcaccgat cacctgaggc tcttcacgct gtatgagcag
gtgtctgaga gactccggac cctgcctgcc actgtccccc tgctgctgca gcacatcctg
agcacactgg agaaggagca cgggcctgat gtccttcccc aggccttgac tgccctagaa
gtcacacgga gtggtttgac tgtggaccag ctgcacggag tgctgagtgt gtggcggaca
ctaccgaagg ggactaagag ctgggaagaa gcagtggctg ctggtaacag tggagacccc
taccccatgg gcccgtttgc ctgcctcgtc cagagtctgc gcagtttgct aggggagggc
cctctggagc gccctggtgc ccggctgtgc ctccctgatg ggcccctgag aacagcagct
aaacgttgct atgggaagag gccagggcta gaggacacgg cacacatcct cattgcagct
cagctctgga agacatgtga cgctgatgcc tcaggcacct tccgaagttg ccctcctgag
gctctgggag acctgcctta ccacctgctc cagagcgagg accgtggact tctttcgaag
ttccttacca acctccatgt ggtggctgca cacttggaat tgggtctggt ctctcggctc
ttggaggccc atgccctcta tgcttcttca gtccccaaag aggaacaaaa gctcccgag
gctgacgttg cagtgtttcg caccttcctg aggcagcagg cttcaatcct cagccagtac
ccccggctcc tgccccagca ggcagccaac cagccccctg actcacctct ttgccaccaa
gcctcgctgc tctcccggag atggcacctc caacacacac tacgatggct taataaaccc
cggaccatga aaaatcagca aagctccagc ctgtctctgg cagtttcctc atccccttact
gctgtggcct tctccaccaa tgggcaaaga gcagctgtgg gcactgccaa tgggacagtt
tacctgttgg acctgagaac ttggcaggag gagaagtctg tggtgagtgg ctgtgatgga
atctctgctt gtttgttcct ctccgatgat acactctttc ttactgcctt cgacgggctc
ctggagctct gggacctgca gcatggttgt cgggtgctgc agactaaggc tcaccagtac
caaatcactg gctgctgcct gagcccagac tgccggctgc tagccaccgt gtgcttggga
ggatgcctaa agctgtggga cacagtccgt gggcagctgg ccttccagca cacctaccc
aagtccctga actgtgttgc cttccaccca gaggggcagg taatagccac aggcagctgg
gctggcagca tcagcttctt ccaggtggat gggctcaaag tcaccaagga cctgggggca
cccggagcct ctatccgtac cttggccttc aatgtgcctg ggggggttgt ggctgtgggc
cggctggaca gtatggtgga gctgtgggcc tggcgagaag gggcacggct ggctgccttc
cctgcccacc atggctttgt tgctgctgcg cttttcctgc atgcgggttg ccagttactg
acggctggag aggatggcaa ggttcaggtg tggtcagggt ctctgggtcg gccccgtggg
cacctgggtt ccctttctct ctctcctgcc ctctctgtgg cactcagccc agatggtgat
cgggtggctg ttggatatcg agcggatggc attaggatct acaaaatctc ttcaggttcc
caggggggctc agggtcaggc actggatgtg gcagtgtccg ccctggcctg gctaagcccc
aaggtattgg tgagtggtgc agaagatggg tccttgcagg gctgggcact caaggaatgc
tcccttcagt ccctctggct cctgtccaga ttccagaagc ctgtgctagg actgccact
tcccaggagc tcttggcttc tgcctcagag gatttcacag tgcagctgtg gccaaggcag
ctgctgacgc ggccacacaa ggcagaagac tttccctgtg gcactgagct gcggggacat
gagggccctg tgagctgctg tagtttcagc actgatggag gcagcctggc caccgggggc
cgggatcgga gtcctcctctg ctgggacgtg aggacccca aaaccctgt tttgatccac
tccttccctg cctgtcaccg tgactgggtc actggctgtg cctggaccaa agataaccta
ctgatatcct gctccagtga tggctctgtg gggctctggg accagagtc aggacagcga
cttggtcagt tcctgggtca tcagagtgct gtgagcgctg tggcagctgt ggaggagcac
gtggtgtctg tgagccggga tgggaccttg aaagtgtggg accatcaagg cgtggagctg
accagcatcc ctgctcactc aggacccatt agccactgtg cagctgccat ggagcccgt
gcagctggac agcctgggtc agagcttctg gtggtaaccg tcgggctaga tgggccaca
cggttatggc atccactctt ggtgtgccaa acccacaccc tcctgggaca cagcggccca
gtccgtgctg ctgctgtttc agaaacctca ggcctcatgc tgaccgcctc tgaggatggt
tctgtacggc tctggcaggt tcctaaggaa gcagatgaca catgtatacc aaggagttct
gcagccgtca ctgctgtggc ttgggcacca gatggttcca tgcagtatc tggaaatcaa
gctggggaac taatccttgtg gcaggaagct aaggctgtgg ccacagcaca ggctccaggc
cacattggtg ctctgatctg gtcctcggca cacacctttt ttgtcctcag tgctgatgag
aaaatcagca gtggcaagt gaaactgcgg aagggttcgg cacccggaaa tttgagtctt
cacctgaacc gaattctaca ggaggactta ggggtgctga caagtctgga ttgggctcct
gatggtcact ttctcatctt ggccaaagca gatttgaagt tactttgcat gaagccaggg
```

TABLE 1-continued

Sequences gatgctccat ctgaaatctg gagcagctat acagaaaatc ctatgatatt gtccacccac
aaggagtatg gcatatttgt cctgcagccc aaggatcctg gagttctttc tttcttgagg
caaaaggaat caggagagtt tgaagagagg ctgaacttg atataaactt agagaatcct
agtaggaccc taatatcgat aactcaagcc aaacctgaat ctgagtcctc attttttgtgt
gccagctctg atgggatcct atggaacctg gccaaatgca gcccagaagg agaatggacc
acaggtaaca tgtggcagaa aaaagcaaac actccagaaa cccaaactcc agggacagac
ccatctacct gcagggaatc tgatgccagc atggatagtg atgccagcat ggatagtgag
ccaacaccac atctaaagac acggcagcgt agaaagattc actcgggctc tgtcacagcc
ctccatgtgc tacctgagtt gctggtgaca gcttcgaagg acagagatgt taagctatgg
gagagaccca gtatgcagct gctgggcctg ttccgatgcg aagggtcagt gagctgcctg
gaaccttggc tgggcgctaa ctccaccctg cagcttgccg tgggagacgt gcagggcaat
gtgtactttc tgaattggga atga SEQ ID NO: 12 vRNA, Genbank #AF045143 ggcuggcuuu agcucagcgg uuacuucgac aguucuuuaa uugaaacaag caaccugucu
ggguuguucg agacccgcgg gcgcucucca guccuuuu SEQ ID NO: 13 vRNA, Genbank #AF045144 ggcuggcuuu agcucagcgg uuacuucgag uacauuguaa ccaccucucu ggugguucg
agacccgcgg gugcuuucca gcucuuuu SEQ ID NO: 14 vRNA, Genbank #AF045145 ggcuggcuuu agcucagcgg uuacuucgcg ugucaucaaa ccaccucucu ggguuguucg
agacccgcgg gcgcucucca gcccucuu SEQ ID NO: 15 INT protein sequence (residues 1473-1724 of human VPARP protein sequence)

Ala Asn Leu Arg Leu Pro Met ala Ser Ala Leu Pro Glu Ala Leu Cys Ser Gln
Ser Arg Thr Thr Pro Val Asp Leu Cys Leu Leu Glu Glu Ser Val Gly Ser Leu
Glu Gly Ser Arg Cys Pro Val Phe Ala Phe Gln Ser Ser Asp Thr Glu Ser Asp
Glu Leu Ser Glu Val Leu Gln Asp Ser Cys Phe Leu Gln Ile Lys Cys Asp Thr
Lys Asp Asp Ser Ile Pro Cys Phe Leu Glu Leu Gly Leu Asp Glu Ile Val
Cys Thr Gln His Trp Gln Asp Ala Val Pro Trp Thr Glu Leu Leu Ser Leu Gln
Thr Glu Asp Gly Phe Trp Lys Leu Thr Pro Glu Leu Gly Leu Ile Leu Asn Leu
Asn Thr Asn Gly Leu His Ser Phe Leu Lys Gln Lys Gly Ile Gln Ser Leu Gly
Val Leu Ser Gly Arg Glu Cys Leu Leu Asp Leu Ile Ala Thr Met Leu Val Leu Gln
Phe Ile Arg Thr Arg Leu Glu Lys Glu Gly Ile Val Phe Lys Ser Leu Met Lys
Met Asp Asp Pro Ser Ile Ser Arg Asn Ile Pro Trp Ala Phe Glu Ala Ile Lys
Gln Ala Ser Glu Trp Val Arg Arg Thr Glu Gly Gln Tyr Pro Ser Ile Cys Pro
Arg Leu Glu Leu Gly Asn Asp Trp Asp Ser Ala Thr Lys Gln Leu Leu Gly Leu
Gln Pro Ile Ser Thr Val Ser Pro Leu His Arg Val Leu His Tyr Ser Gln Gly SEQ ID NO: 16 NS5A1-31 from Hepatitis C Ser Gly Ser Trp Leu Arg Asp Ile Trp Asp Trp Ile Cys Glu Val Leu Ser Asp
Phe Lys Thr Trp Leu Lys Ala Lys Leu Met Pro Gln Leu SEQ ID NO: 17 NS5A2-29 from Hepatitis C as attached to MVP Met ala Gly Ser Trp Leu Arg Asp Ile Trp Asp Trp Ile Cys Glu Val Leu Ser
Asp Phe Lys Thr Trp Leu Lys Ala L TABLE 1-continued Sequences SEQ ID NO: 23 NS5A-rMVP partial sequence Met ala Gly Ser Trp Leu Arg Asp Ile Trp Asp Trp Ile Cys Glu Val Leu Ser
Asp Phe Lys Thr Trp Leu Lys Ala Lys Leu Met Pro Thr Met ala Thr Glu Glu SEQ ID NO: 24 rMVP, Genbank #AAC52161

Met ala Thr Glu Glu Ala Ile Ile Arg Ile Pro Pro Tyr His Tyr Ile His Val
Leu Asp Gln Asn Ser Asn Val Ser Arg Val Glu Val Gly Pro Lys Thr Tyr Ile
Arg Gln Asp Asn Glu Arg Val Leu Phe Ala Pro Val Arg Met Val Thr Val Pro
Pro Arg His Tyr Cys Ile Val Ala Asn Pro Val Ser Arg Asp Thr Gln Ser Ser
Val Leu Phe Asp Ile Thr Gly Gln Val Arg Leu Arg His Ala Asp Gln Glu Ile
Arg Leu Ala Gln Asp Pro Phe Pro Leu Tyr Pro Gly Glu Val Leu Glu Lys Asp
Ile Thr Pro Leu Gln Val Val Leu Pro Asn Thr Ala Leu His Leu Lys Ala Leu
Leu Asp Phe Glu Asp Lys Asn Gly Asp Lys Val Met ala Gly Asp Glu Trp Leu
Phe Glu Gly Pro Gly Thr Tyr Ile Pro Gln Lys Glu Val Val Val Glu Ile
Ile Gln Ala Thr Val Ile Lys Gln Asn Gln Ala Leu Arg Leu Arg Ala Arg Lys
Glu Cys Phe Asp Arg Glu Gly Lys Gly Arg Val Thr Gly Glu Glu Trp Leu Val
Arg Ser Val Gly Ala Tyr Leu Pro Ala Val Phe Glu Glu Val Leu Asp Leu Val
Asp Ala Val Ile Leu Thr Glu Lys Thr Ala Leu His Leu Arg Ala Leu Gln Asn
Phe Arg Asp Leu Arg Gly Val Leu His Arg Thr Gly Glu Glu Trp Leu Val Thr
Val Gln Asp Thr Glu Ala His Val Pro Asp Val Tyr Gly Val Leu Gly Val
Val Pro Ile Thr Thr Leu Gly Pro Arg His Tyr Cys Val Ile Leu Asp Pro Met
Gly Pro Asp Gly Lys Asn Gln Leu Gly Gln Lys Arg Val Val Lys Gly Glu Lys
Ser Phe Phe Leu Gln Pro Gly Glu Arg Leu Glu Arg Gly Ile Gln Asp Val Tyr
Val Leu Ser Glu Gln Gln Gly Leu Leu Leu Lys Ala Leu Gln Pro Leu Glu Glu
Gly Glu Ser Glu Glu Lys Val Ser His Gln Ala Gly Asp Cys Trp Leu Ile Arg
Gly Pro Leu Glu Tyr Val Pro Ser Ala Lys Val Glu Val Val Glu Glu Arg Gln
Ala Ile Pro Leu Asp Gln Asn Glu Gly Ile Tyr Val Gln Asp Val Lys Thr Gly
Lys Val Arg Ala Val Ile Gly Ser Thr Tyr Met Leu Thr Gln Asp Glu Val Leu
Trp Glu Lys Glu Leu Pro Ser Gly Val Glu Glu Leu Leu Asn Leu Gly His Asp
Pro Leu Ala Asp Arg Gly Gln Lys Gly Thr Ala Lys Pro Leu Gln Pro Ser Ala
Pro Arg Asn Lys Thr Arg Val Val Ser Tyr Arg Val Pro His Asn Ala Ala Val
Gln Val Tyr Asp Tyr Arg Ala Lys Arg Ala Arg Val Val Phe Gly Pro Glu Leu
Val Thr Leu Asp Pro Glu Glu Gln Phe Thr Val Leu Ser Leu Ser Ala Gly Arg
Pro Lys Arg Pro His Ala Arg Arg Ala Leu Cys Leu Leu Leu Gly Pro Asp Phe
Phe Thr Asp Val Ile Thr Ile Glu Thr Ala Asp His Ala Arg Leu Gln Leu Gln
Leu Ala Tyr Asn Trp His Phe Glu Leu Lys Asn Arg Asn Asp Pro Ala Glu Ala
Ala Lys Leu Phe Ser Val Pro Asp Phe Val Gly Asp Ala Cys Lys Ala Ile Ala
Ser Arg Val Arg Gly Ala Val Ala Ser Val Thr Phe Asp Asp Phe His Lys Asn
Ser Ala Arg Ile Ile Arg Met ala Val Phe Gly Phe Glu Met Ser Glu Asp Thr
Gly Pro Asp Gly Thr Leu Leu Pro Lys Ala Arg Asp Gln Ala Val Phe Pro Gln
Asn Gly Leu Val Val Ser Ser Val Asp Val Gln Pro Val Asp Glu
Arg Thr Arg Asp Ala Leu Gln Arg Ser Val Gln Leu Ala Ile Glu Ile Thr Thr
Asn Ser Gln Glu Ala Ala Ala Lys His Glu Ala Gln Arg Leu Glu Gln Glu Ala
Arg Gly Arg Leu Glu Arg Gln Lys Ile Leu Asp Gln Ser Glu Ala Glu Lys Ala
Arg Lys Glu Leu Leu Glu Leu Glu Ala Met Ser Met ala Val Glu Ser Thr Gly
Asn Ala Lys Ala Glu Ala Glu Ser Arg Ala Glu Ala Ala Arg Ile Glu Gly Glu
Gly Ser Val Leu Gln Ala Lys Leu Lys Ala Gln Ala Leu Ala Ile Glu Thr Glu
Ala Glu Leu Glu Arg Val Lys Lys Val Arg Glu Met Glu Leu Ile Tyr Ala Arg
Ala Gln Leu Glu Leu Glu Val Ser Lys Ala Gln Leu Ala Asn Val Ala Leu
Lys Lys Phe Lys Glu Met Thr Glu Ala Leu Gly Pro Gly Thr Ile Arg Asp Leu
Ala Val Ala Gly Pro Glu Met Gln Val Lys Leu Leu Gln Ser Leu Gly Leu Lys
Ser Thr Leu Ile Thr Asp Gly Ser Ser Pro Ile Asn Leu Phe Ser Thr Ala Phe
Gly Leu Leu Gly Leu Gly Ser Asp Gly Gln Pro Pro Ala Gln Lys SEQ ID NO: 25 rMVP cDNA, Genbank #U09870 atggcaactg aagaggccat catccgcatc cccccatacc actacatcca tgtgctggac
cagaacagta atgtgtcccg tgtggaggtt ggaccaaaga cctacatccg gcaggacaat
gagagggtac tgtttgcccc agttcgcatg gtgaccgtcc ccccacgcca ctactgcata
gtggccaacc ctgtgtcccg ggacacccag agttctgtgt tatttgacat cacaggacaa
gtccgactcc ggcacgctga ccaggagatc cgactagccc aggaccccct tccccctgtat
ccaggggagg tgctggaaaa ggacatcacc ccactgcagg tggttctgcc caacacagca
ctgcatctta aggcgttgct ggactttgag gataagaatg gagacaaggt catggcagga
gacgagtggc tatttgaggg acctggcacc tacatcccac agaaggaagt ggaagtcgtg
gagatcattc aggccacagt catcaaacag aaccaagcac tgcggctaag ggcccgaaag
gagtgctttg accgggaggg caaggggcgc gtgacagtg aggagtggct ggtccgatcc
gtggggcctt acctcccagc tgtctttgaa gaggtgctgg atctggtgga tgctgtgatc
cttacagaaa agactgccct gcacctccgg gctctgcaga acttcaggga ccttcgggga
gtgctccacc gcaccgggga ggaatggtta gtgacagtgc aggacacaga gcccatgtt
ccagatgtct atgaggaggt gcttgggta gtacccatca ccaccctggg acctcgacac
tactgtgtca ttcttgaccc aatgggacca gacggcaaga accagctggg acaaaagcgt
gttgtcaagg gagagaagtc cttttttcctc cagccaggag agaggctgga gcgaggcatc
caggatgtgt atgtgctgtc agagcagcag gggctgctac tgaaggcact gcagcccctg
gaggaggagg agagcgagga gaaggtctcc catcaggccg gagactgctg gctcatccgt
gggcccctgg agtatgtgcc atctgcaaaa gtggaggtgg tggaggagcg tcaggctatc TABLE 1-continued Sequences

```
cctctggacc aaaatgaggg catctatgtg caggatgtca agacggggaa ggtgcgggct
gtgattggaa gcacctacat gctgactcag gatgaagtcc tgtgggaaaa ggagctgcct
tctggggtgg aggagctgct gaacttgggg catgaccctc tggcagacag gggtcagaag
ggcacagcca agcccttca gccctcagct ccaaggaaca agacccgagt ggtcagctac
cgtgtcccgc acaatgcagc ggtgcaggtc tatgactaca gagccaagag agcccgtgtg
gtctttgggc ccgagctagt gacactggat cctgaggagc agttcacagt attgtccctt
tctgccgggc gacccaagcg tcctcatgcc cgccgtgcac tctgcctact gctgggacct
gatttcttta ctgatgtcat caccatcgaa actgcagatc atgccaggtt gcagctgcag
cttgcctaca actggcactt tgaactgaag aaccggaatg ccctgcaga ggcagccaag
cttttctccg tgcctgactt cgtgggtgac gcctgcaagg ccattgcatc ccgagtccgg
ggggctgtag cctctgtcac ctttgatgac ttccataaaa actcagcccg gatcattcga
atggctgttt ttggctttga gatgtctgaa gacacaggtc ctgatggcac actcctgccc
aaggctcgag accaggcagt cttcccccaa aacgggctgg tagtcagcag tgtggatgtg
cagtcagtgg agcccgtgga ccagaggacc cgggatgccc ttcagcgcag cgttcagctg
gccatcgaaa ttaccaccaa ctcccaggag gcagcagcca agcacgaggc tcagagactg
gaacaggaag cccgtggtcg gcttgagagg cagaagatct tggaccagtc agaagctgaa
aaagcccgca aggaactctt ggagcttgag gctatgagca tggctgtgga gagcacgggt
aatgccaaag cagaggctga gtcccgtgca gaggcagcga ggatcgaagg agaaggctct
gtgctgcagg ccaagctcaa ggcacaggcg ctagccattg agacggaggc tgagttggag
cgagtaaaga aagtacgaga gatgaactgt atctatgccc gggcccagtt ggagctggag
gtgagcaagg cgcagcagct tgccaatgtg gaggcaaaga agttcaagga gatgacagag
gcactgggcc ccggcaccat cagggacctg gctgtggccg ggccagagat gcaggtgaaa
cttctccagt ccctgggcct gaaatccact ctcatcaccg atggctcgtc tcccatcaac
ctcttcagca cagccttcgg gttgctgggg ctggggtctg atggtcagcc gccagcacag
aag
```

SEQ ID NO: 26 NS5A-rMVP fusion protein

```
Met ala Gly Ser Trp Leu Arg Asp Ile Trp Asp Trp Ile Cys Glu Val Leu Ser
Asp Phe Lys Thr Trp Leu Lys Ala Lys Leu Met Pro Thr Met ala Thr Glu Glu
Ala Ile Ile Arg Ile Pro Pro Tyr His Tyr Ile His Val Leu Asp Gln Asn Ser
Asn Val Ser Arg Val Glu Val Gly Pro Lys Thr Tyr Ile Arg Gln Asp Asn Glu
Arg Val Leu Phe Ala Pro Val Arg Met Val Thr Val Pro Pro Arg His Tyr Cys
Ile Val Ala Asn Pro Val Ser Arg Asp Thr Gln Ser Ser Val Leu Phe Asp Ile
Thr Gly Gln Val Arg Leu Arg His Ala Asp Gln Glu Ile Arg Leu Ala Gln Asp
Pro Phe Pro Leu Tyr Pro Gly Glu Val Leu Glu Lys Asp Ile Leu Pro Leu Gln
Val Val Leu Pro Asn Thr Ala Leu His Leu Lys Ala Leu Leu Asp Phe Glu Asp
Lys Asn Gly Asp Lys Val Met ala Gly Asp Glu Trp Leu Phe Glu Gly Pro Gly
Thr Tyr Ile Pro Gln Lys Glu Val Glu Val Val Glu Ile Ile Gln Ala Thr Val
Ile Lys Gln Asn Gln Ala Leu Arg Leu Arg Ala Lys Leu Gln Cys Phe Asp Arg
Glu Gly Lys Gly Arg Val Thr Gly Glu Glu Trp Leu Val Arg Ser Val Gly Ala
Tyr Leu Pro Ala Val Phe Glu Glu Val Leu Asp Leu Val Asp Ala Val Ile Leu
Thr Glu Lys Thr Ala Leu His Leu Arg Ala Leu Gln Asn Phe Arg Asp Leu Arg
Gly Val Leu His Arg Thr Gly Glu Glu Trp Leu Val Thr Val Gln Asn Thr Glu
Ala His Val Pro Asp Val Tyr Glu Glu Val Leu Gly Val Val Pro Ile Thr Thr
Leu Gly Pro Arg His Tyr Cys Val Ile Leu Asp Pro Met Gly Pro Asp Gly Lys
Asn Gln Leu Gly Gln Lys Arg Val Val Lys Gly Glu Lys Ser Phe Phe Leu Gln
Pro Gly Glu Arg Leu Glu Arg Gly Ile Gln Asp Val Tyr Val Leu Ser Glu Gln
Gln Gly Leu Leu Leu Lys Ala Leu Gln Pro Leu Glu Glu Gly Glu Ser Glu Glu
Lys Val Ser His Gln Ala Gly Asp Cys Trp Leu Ile Arg Gly Pro Leu Glu Tyr
Val Pro Ser Ala Lys Val Glu Val Val Glu Glu Arg Gln Ala Ile Pro Leu Asp
Gln Asn Glu Gly Ile Tyr Val Gln Asp Val Lys Thr Gly Lys Val Arg Ala Val
Ile Gly Ser Thr Tyr Met Leu Thr Gln Asp Glu Val Leu Trp Glu Lys Glu Leu
Pro Ser Gly Val Glu Glu Leu Leu Asn Leu Gly His Asp Pro Leu Ala Asp Arg
Gly Gln Lys Gly Thr Ala Lys Pro Leu Gln Pro Ser Ala Pro Arg Asn Lys Thr
Arg Val Val Ser Tyr Arg Val Pro His Asn Ala Ala Val Gln Val Tyr Asp Tyr
Arg Ala Lys Arg Ala Arg Val Val Phe Gly Pro Glu Leu Val Thr Leu Asp Pro
Glu Glu Gln Phe Thr Val Leu Ser Leu Ser Ala Gly Arg Pro Lys Arg Pro His
Ala Arg Arg Ala Leu Cys Leu Leu Leu Gly Pro Asp Phe Phe Thr Asp Val Ile
Thr Ile Glu Thr Ala Asp His Ala Arg Leu Gln Leu Gln Leu Ala Tyr Asn Trp
His Phe Glu Leu Lys Asn Arg Asn Asp Pro Ala Gly Ala Ala Lys Leu Phe Ser
Val Pro Asp Phe Val Gly Asp Ala Cys Lys Ala Ile Ala Ser Arg Val Arg Gly
Ala Val Ala Ser Val Thr Phe Asp Asp Phe His Lys Asn Ser Ala Arg Ile Ile
Arg Met ala Val Phe Gly Phe Glu Met Set Glu Asp Thr Gly Pro Asp Gly Thr
Leu Leu Pro Lys Ala Arg Asp Gln Ala Val Phe Pro Gln Asn Gly Leu Val Val
Ser Ser Val Asp Val Gln Ser Val Glu Pro Val Asp Gln Arg Thr Arg Asp Ala
Leu Gln Arg Ser Val Gln Leu Ala Ile Glu Ile Thr Thr Asn Ser Gln Glu Ala
Ala Ala Lys His Glu Ala Gln Arg Leu Glu Gln Glu Ala Arg Gly Arg Leu Glu
Arg Gln Lys Ile Leu Asp Gln Ser Glu Ala Glu Lys Ala Arg Lys Glu Leu Leu
Glu Leu Glu Ala Met Ser Met ala Val Glu Ser Thr Gly Asn Ala Lys Ala Glu
Ala Glu Ser Arg Ala Glu Ala Ala Arg Ile Glu Gly Glu Gly Ser Val Leu Gln
Ala Lys Leu Lys Ala Gln Ala Leu Ala Ile Glu Thr Glu Ala Glu Leu Glu Arg
Val Lys Lys Val Arg Glu Met Glu Leu Ile Tyr Ala Arg Ala Gln Leu Glu Leu
Glu Val Ser Lys Ala Gln Gln Leu Ala Asn Val Glu Ala Lys Lys Phe Lys Glu
Met Thr Glu Ala Leu Gly Pro Gly Thr Ile Arg Asp Leu Ala Val Ala Gly Pro
Glu Met Gln Val Lys Leu Leu Gln Ser Leu Gly Leu Lys Ser Thr Leu Ile Thr
Asp Gly Ser Ser Pro Ile Asn Leu Phe Ser Thr Ala Phe Gly Leu Leu Gly Leu
Gly Ser Asp Gly Gln Pro Pro Ala Gln Lys
```

TABLE 1-continued

Sequences

SEQ ID NO: 27 NS5A-rMVP cDNA atggccggtt cctggctaag ggacatctgg gactggatat gcgaggtgct gagcgacttt
aagacctggc tgaaagccaa gctcatgcca accatggcaa ctgaagaggc catcatccgc
atcccccat accactacat ccatgtgctg accagaaca gtaatgtgtc ccgtgtggag
gttggaccaa agacctacat ccggcaggac aatgagaggg tactgtttgc cccagttcgc
atggtgaccg tccccccacg ccactactgc atagtggcca accctgtgtc ccgggacacc
cagagttctg tgttatttga catcacagga caagtccgac tccggcacgc tgaccaggag
atccgactag cccaggaccc cttcccctg tatccagggg aggtgctgga aaaggacatc
accccactgc aggtggttct gcccaaacaca gcactgcatc ttaaggcgtt gctggactttt
gaggataaga atggagacaa ggtcatggca ggagacgagt ggctatttga gggacctggc
acctacatcc cacagaagga agtggaagtc gtggagatca ttcaggccac agtcatcaaa
cagaaccaag cactgcggct aagggcccga aggagtgctt tgaccgggga gggcaagggg
cgcgtgacag gtgaggagtg gctggtccga tccgtggggg cttacctccc agctgtcttt
gaagaggtgc tggatctggt ggatgctgtg atccttacag aaaagactgc cctgcacctc
cgggctctgc agaacttcag ggaccttcgg ggagtgctcc accgcaccgg ggaggaatgg
ttagtgacag tgcaggacac agaagcccat gttccagatg tctatgagga ggtgcttggg
gtagtaccca tcaccaccct gggacctcga cactactgtg tcattcttga cccaatggga
ccagacggca agaaccagct gggacaaaag cgtgttgtca agggagagaa gtccttttc
ctccagccag agagaggct ggagcgaggc atccaggatg tgtatgtgct gtcagagcag
caggggctgc tactgaaggc actgcagccc tggaggagg gagagagcga ggagaaggtc
tcccatcagg ccggagactg ctggctcatc cgtgggccc tggagtatgt gccatctgca
aaagtggagg tggtggagga gcgtcaggct atccctctgg accaaaatga gggcatctat
gtgcaggatg tcaagacggg gaaggtgcgg gctgtgattg aagcaccta catgctgact
caggatgaag tcctgtggga aaaggagctg ccttctgggg tggaggagct gctgaacttg
gggcatgacc ctctggcaga caggggtcag aagggcacag ccaagcccct tcagcccctg
gctccaagga acaagacccg agtggtcagc taccgtgtcc cgcacaatgc agcggtgcag
gtctatgact acagagccaa gagagcccgt gtggtctttg ggcccgagct agtgacactg
gatcctgagg agcagttcac agtattgtcc ctttctgccg ggcgacccaa gcgtcctcat
gcccgccgtg cactctgcct actgctggga cctgattct ttactgatgt catcaccatc
gaaactgcag atcatgccag gttgcagctg cagcttgcct acaactggca ctttgaactg
aagaaccgga atgaccctgc agaggcagcc aagcttttct ccgtgcctga cttcgtgggt
gacgcctgca aggccattgc atcccgagtc cggggggctg tagcctctgt cacctttgat
gacttccata aaaactcagc ccggatcatt cgaatggctg ttttggcctt tgagatgtct
gaagacacag tcctgatgg cacactcctg cccaaggctc gagaccaggc agtctttccc
caaaacgggc tggtagtcag cagtgtggat gtgcagtcag tggagcccgt ggaccagagg
acccgggatg cccttcagcg cagcgttcag ctggccatcg aaattaccac caactcccag
gaggcagcag ccaagcacga ggctcagaga ctggaacagg aagcccgtgg tcggcttgag
aggcagaaga tcttggacca gtcagaagct gaaaaagccc gcaaggaact cttggagctt
gaggctatga gcatggctgt ggagagcacg ggtaatgcca aagcagaggc tgagtcccgt
gcagaggcag cgaggatcga aggagaaggc tctgtgctgc aggccaagct caaggcacag
gcgctagcca ttgagacgga ggctgagttg gagcgagtaa agaaagtacg agagatggaa
ctgatctatg cccgggccca gttggagctg gaggtgagca aggcgcagca gcttgccaat
gtggaggcaa agaagttcaa ggagatgaca gaggcactgg cccccggcac catcagggac
ctggctgtgg ccgggccaga gatgcaggtg aaacttctcc agtccctggg cctgaaatcc
actctcatca ccgatggctc gtctcccatc aacctcttca gcacagcctt cgggttgctg
gggctggggt ctgatggtca gccgccagca cagaagtga SEQ ID NO: 28 NS5A-NS5A-rMVP fusion protein Met ala Gly Ser Trp Leu Arg Asp Ile Trp Asp Trp Ile Cys Glu Val Leu Ser
Asp Phe Lys Thr Trp Leu Lys Ala Lys Leu Met Pro Thr Met ala Gly Ser Trp
Leu Arg Asp Ile Trp Asp Trp Ile Cys Glu Val Leu Ser Asp Phe Lys Thr Trp
Leu Lys Ala Lys Leu Met Pro Thr Met ala Thr Glu Glu Ala Ile Ile Arg Ile
Pro Pro Tyr His Tyr Ile His Val Leu Asp Gln Asn Ser Asn Val Ser Arg Val
Glu Val Gly Pro Lys Thr Tyr Ile Arg Gln Asp Asn Glu Arg Val Leu Phe Ala
Pro Val Arg Met Val Thr Val Pro Pro Arg His Tyr Cys Ile Val Ala Asn Pro
Val Ser Arg Asp Thr Gln Ser Ser Val Leu Phe Asp Ile Thr Gly Gln Val Arg
Leu Arg His Ala Asp Gln Glu Ile Arg Leu Ala Gln Asp Pro Phe Pro Leu Tyr
Pro Gly Glu Val Leu Glu Lys Asp Ile Thr Pro Leu Val Val Leu Pro Asn
Thr Ala Leu His Leu Lys Ala Leu Leu Asp Phe Glu Asp Lys Asn Gly Asp Lys
Val Met ala Gly Asp Glu Trp Leu Phe Glu Gly Pro Gly Thr Tyr Ile Pro Gln
Lys Glu Val Glu Val Val Glu Ile Ile Gln Ala Thr Val Ile Lys Gln Asn Gln
Ala Leu Arg Leu Arg Ala Arg Lys Glu Cys Phe Asp Arg Gly Lys Gly Arg
Val Thr Gly Glu Glu Trp Leu Val Arg Ser Val Gly Ala Tyr Leu Pro Ala Val
Phe Glu Glu Val Leu Asp Leu Val Asp Ala Val Ile Leu Thr Glu Lys Thr Ala
Leu His Leu Arg Ala Leu Gln Asn Phe Arg Asp Leu Arg Gly Val Leu His Arg
Thr Gly Glu Glu Trp Leu Val Thr Val Gln Asp Thr Glu Ala His Val Pro Asp
Val Tyr Glu Glu Val Leu Gly Val Val Pro Ile Thr Thr Leu Gly Pro Arg His
Tyr Cys Val Ile Leu Asp Pro Met Gly Pro Asp Gly Lys Asn Gln Leu Gly Gln
Lys Arg Val Val Lys Gly Glu Lys Ser Phe Phe Leu Gln Pro Gly Glu Arg Leu
Glu Arg Gly Ile Gln Asp Val Tyr Val Leu Ser Glu Gln Gln Gly Leu Leu Leu
Lys Ala Leu Gln Pro Leu Glu Glu Gly Glu Ser Glu Glu Lys Val Ser His Gln
Ala Gly Asp Cys Trp Leu Ile Arg Gly Pro Leu Glu Tyr Val Pro Ser Ala Lys
Val Glu Val Val Glu Glu Arg Gln Ala Ile Pro Leu Asp Gln Asn Glu Gly Ile
Tyr Val Gln Asp Val Lys Thr Gly Lys Val Arg Ala Val Ile Gly Ser Thr Tyr
Met Leu Thr Gln Asp Glu Val Leu Trp Glu Lys Glu Leu Pro Ser Gly Val Glu TABLE 1-continued Sequences Glu Leu Leu Asn Leu Gly His Asp Pro Leu Ala Asp Arg Gly Gln Lys Gly Thr
Ala Lys Pro Leu Gln Pro Ser Ala Pro Arg Asn Lys Thr Arg Val Val Ser Tyr
Arg Val Pro His Asn Ala Ala Val Gln Val Tyr Asp Tyr Arg Ala Lys Arg Ala
Arg Val Phe Gly Pro Glu Leu Val Thr Leu Asp Pro Glu Glu Gln Phe Thr
Val Leu Ser Leu Ser Ala Gly Arg Pro Lys Arg Pro His Ala Arg Arg Ala Leu
Cys Leu Leu Leu Gly Pro Asp Phe Phe Thr Val Ile Thr Ile Glu Thr His Ala
Asp His Ala Arg Leu Gln Leu Gln Leu Ala Tyr Asn Trp His Phe Glu Leu Lys
Asn Arg Asn Asp Pro Ala Glu Ala Ala Lys Leu Phe Ser Val Pro Asp Phe Val
Gly Asp Ala Cys Lys Ala Ile Ala Ser Arg Val Arg Gly Ala Val Ala Ser Val
Thr Phe Asp Asp Phe His Lys Asn Ser Ala Arg Ile Ile Arg Met ala Val Phe
Gly Phe Glu Met Ser Glu Asp Thr Gly Pro Asp Gly Thr Leu Leu Pro Lys Ala
Arg Asp Gln Ala Val Phe Pro Gln Asn Gly Leu Val Val Ser Ser Val Asp Val
Gln Ser Val Glu Pro Val Asp Gln Arg Thr Arg Asp Ala Leu Gln Arg Ser Val
Gln Leu Ala Ile Glu Ile Thr Thr Asn Ser Gln Glu Ala Ala Ala Lys His Glu
Ala Arg Leu Glu Gln Glu Ala Arg Gly Arg Leu Glu Arg Gln Lys Ile Leu Leu
Asp Gln Ser Glu Ala Glu Lys Ala Arg Lys Glu Leu Leu Glu Leu Glu Ala Met
Ser Met ala Val Glu Ser Thr Gly Asn Ala Lys Ala Glu Ala Glu Ser Arg Ala
Glu Ala Ala Arg Ile Glu Gly Glu Gly Ser Val Leu Gln Ala Lys Leu Lys Ala
Gln Ala Leu Ala Ile Glu Thr Glu Ala Glu Leu Ala Arg Val Lys Lys Val Arg
Glu Met Glu Leu Ile Tyr Ala Arg Ala Gln Leu Glu Leu Glu Val Ser Lys Ala
Gln Gln Leu Ala Asn Val Glu Ala Lys Lys Phe Lys Glu Met Thr Glu Ala Leu
Gly Pro Gly Thr Ile Arg Asp Leu Ala Val Ala Gly Pro Glu Met Gln Val Lys
Leu Leu Gln Ser Leu Gly Leu Lys Ser Thr Leu Ile Thr Asp Gly Ser Ser Pro
Ile Asn Leu Phe Ser Thr Ala Phe Gly Leu Leu Gly Leu Gly Ser Asp Gly Gln
Pro Pro Ala Gln Lys SEQ ID NO: 29 NS5A-NS5A-rMVP cDNA

```
atggccggtt cctggctaag ggacatctgg gactggatat gcgaggtgct gagcgacttt
aagacctggc tgaaagccaa gctcatgcca accatggccg ttcctggct aagggacatc
tgggactgga tatgcgaggt gctgagcgac tttaagac TABLE 1-continued Sequences SEQ ID NO: 30 NS5A-rMVP-Z domain fusion protein Met ala Gly Ser TABLE 1-continued Sequences gtgcaggatg tcaagacggg gaaggtgcgg gctgtgattg aagcaccta catgctgact
caggatgaag tcctgtggga aaaggagctg ccttctgggg tggaggagct gctgaacttg
gggcatgacc ctctggcaga caggggtcag aagggcacag ccaagcccct tcagccctca
gctccaagga acaagacccg agtggtcagc taccgtgtcc cgcacaatgc agcggtgcag
gtctatgact acagagccaa gagagcccgt gtggtctttg ggcccgagct agtgacactg
gatcctgagg agcagttcac agtattgtcc ctttctgccg ggcgacccaa gcgtcctcat
gcccgccgtg cactctgcct actgctggga cctgatttct ttactgatgt catcaccatc
gaaactgcag atcatgccag gttgcagctg cagcttgcct acaactggca ctttgaactg
aagaaccgga atgaccctgc agaggcagcc aagcttttct ccgtgcctga cttcgtgggt
gacgcctgca aggccattgc atcccgagtc cgggggggctg tagcctctgt cacctttgat
gacttccata aaaactcagc ccggatcatt cgaatgctg tttttggctt tgagatgtct
gaagacacag gtcctgatgg cacactcctg cccaaggctc gagaccaggc agtctttccc
caaaacgggc tggtagtcag cagtgtggat gtgcagtcag tggagcccgt ggaccagagg
acccgggatg cccttcagcg cagcgttcag ctggccatcg aaattaccac caactcccag
gaggcagcag ccaagcacga ggctcagaga ctggaacagg aagcccgtgg tcggcttgag
aggcagaaga tcttggacca gtcagaagct gaaaaagccc gcaaggaact cttggagctt
gaggctatga gcatggctgt ggagagcacg ggtaatgcca aagcagaggc tgagtcccgt
gcagaggcag cgaggatcga aggagaaggc tctgtgctgc aggccaagct caaggcacag
gcgctagcca ttgagacgga ggctgagttg gagcgagtaa agaaagtacg agagatggaa
ctgatctatg cccgggccca gttggagctg gaggtgagca aggcgcagca gcttgccaat
gtggaggcaa agaagttcaa ggagatgaca gaggcactgg gccccggcac catcagggac
ctggctgtgg ccgggccaga gatgcaggtg aaacttctcc agtccctggg cctgaaatcc
actctcatca ccgatggctc gtctcccatc aacctcttca gcacagcctt cgggttgctg
gggctggggt ctgatggtca gccgccagca cagaagttta acatgcagca gcagcgccgc
ttttacgagg ccctgcacga ccccaacctg aacgaggagc agcgcaacgc caagattaag
agcattcgcg acgactag SEQ ID NO: 32 CP-rMVP fusion protein Met ala Gly Cys Gly Cys Pro Cys Gly Cys Gly Ala Met ala Thr Glu Glu Ala
Ile Arg Ile Pro Pro Tyr His Tyr Ile His Val Leu Asp Gln Asn Ser Asn
Val Ser Arg Val Glu Val Gly Pro Lys Thr Tyr Ile Arg Gln Asp Asn Glu Arg
Val Leu Phe Ala Pro Val Arg Met Val Thr Val Pro Pro Arg His Tyr Cys Ile
Val Ala Asn Pro Val Ser Arg Asp Thr Gln Ser Ser Val Leu Phe Asp Ile Thr
Gly Gln Val Arg Leu Arg His Ala Asp Gln Glu Ile Arg Leu Ala Gln Asp Pro
Phe Pro Leu Tyr Pro Gly Glu Val Leu Glu Lys Asp Ile Thr Pro Leu Gln Val
Val Leu Pro Asn Thr Ala Leu His Leu Lys Ala Leu Leu Asp Phe Glu Asp Lys
Asn Gly Asp Lys Val Met ala Gly Asp Glu Trp Leu Phe Glu Gly Pro Gly Thr
Tyr Ile Pro Gln Lys Glu Val Glu Val Val Glu Ile Ile Gln Ala Thr Val Ile
Lys Gln Asn Gln Ala Leu Arg Leu Arg Ala Arg Lys Glu Cys Phe Asp Arg Glu
Gly Lys Gly Arg Val Thr Gly Glu Glu Trp Leu Val Arg Ser Val Gly Ala Tyr
Leu Pro Ala Val Phe Glu Glu Val Leu Asp Leu Val Asp Ala Val Ile Leu Thr
Glu Lys Thr Ala Leu His Leu Arg Ala Leu Gln Asn Phe Arg Asp Leu Arg Gly
Val Leu His Arg Thr Gly Glu Trp Leu Val Thr Val Gln Asn Thr Gln Glu Ala
His Val Pro Asp Val Tyr Glu Glu Val Leu Gly Val Val Pro Ile Thr Thr Leu
Gly Pro Arg His Tyr Cys Val Ile Leu Asp Pro Met Gly Pro Asp Gly Lys Asn
Gln Leu Gly Gln Lys Arg Val Val Lys Gly Glu Lys Ser Phe Phe Leu Gln Pro
Gly Glu Arg Leu Glu Arg Gly Ile Gln Asp Val Tyr Val Leu Ser Glu Gln Gln
Gly Leu Leu Leu Lys Ala Leu Gln Pro Leu Glu Glu Gly Glu Ser Glu Glu Lys
Val Ser His Gln Ala Gly Asp Cys Trp Leu Ile Arg Gly Pro Leu Glu Tyr Val
Pro Ser Ala Lys Val Glu Val Val Glu Glu Arg Gln Ala Ile Pro Leu Asp Gln
Asn Glu Gly Ile Tyr Val Gln Asp Val Lys Thr Gly Lys Val Arg Ala Val Ile
Gly Ser Thr Tyr Met Leu Thr Gln Asp Glu Val Leu Trp Glu Lys Glu Leu Pro
Ser Gly Val Glu Glu Leu Leu Asn Leu Gly His Asp Pro Leu Ala Asp Arg Gly
Gln Lys Gly Thr Ala Lys Pro Leu Gln Pro Ser Ala Pro Arg Asn Lys Thr Arg
Val Val Ser Tyr Arg Val Pro His Asn Ala Ala Val Gln Val Tyr Asp Tyr Arg
Ala Lys Arg Ala Arg Val Val Phe Gly Pro Glu Leu Val Thr Leu Asp Pro Glu
Glu Gln Phe Thr Val Leu Ser Leu Ser Ala Gly Arg Pro Lys Arg Pro His Ala
Arg Arg Ala Leu Cys Leu Leu Leu Gly Pro Asp Phe Phe Thr Asp Val Ile Thr
Ile Glu Thr Ala Asp His Ala Arg Leu Gln Leu Gln Leu Ala Tyr Asn Trp His
Phe Glu Leu Lys Asn Arg Asn Asp Pro Ala Glu Ala Ala Lys Leu Phe Ser Val
Pro Asp Phe Val Gly Asp Ala Cys Lys Ala Ile Ala Ser Arg Val Arg Gly Ala
Val Ala Ser Val Thr Phe Asp Asp Phe His Lys Asn Ser Ala Arg Ile Ile Arg
Met ala Val Phe Gly Phe Glu Met Ser Glu Asp Thr Gly Pro Asp Gly Thr Leu
Leu Pro Lys Ala Arg Asp Gln Ala Val Phe Pro Asn Gly Leu Val Val Ser
Ser Val Asp Val Gln Ser Val Glu Pro Val Asp Gln Arg Thr Arg Asp Ala Leu
Gln Arg Ser Val Gln Leu Ala Ile Glu Ile Thr Thr Asn Ser Gln Glu Ala Ala
Ala Lys His Glu Ala Gln Arg Leu Glu Gln Glu Ala Arg Gly Arg Leu Glu Arg
Gln Lys Ile Leu Asp Gln Ser Glu Ala Glu Lys Ala Arg Lys Glu Leu Leu Glu
Leu Glu Ala Met Ser Met ala Val Glu Ser Thr Gly Asn Ala Lys Ala Glu Ala
Glu Ser Arg Ala Glu Ala Ala Arg Ile Glu Gly Glu Gly Ser Val Leu Gln Ala
Lys Leu Lys Ala Gln Ala Leu Ala Ile Glu Thr Glu Ala Glu Leu Glu Arg Val
Lys Lys Val Arg Glu Met Glu Leu Ile Tyr Ala Arg Ala Gln Leu Glu Leu Glu
Val Ser Lys Ala Gln Gln Leu Ala Asn Val Glu Ala Lys Lys Phe Lys Glu Met
Thr Glu Ala Leu Gly Pro Gly Thr Ile Arg Asp Leu Ala Val Ala Gly Pro Glu
Met Gln Val Lys Leu Leu Gln Ser Leu Gly Leu Lys Ser Thr Leu Ile Thr Asp
Gly Ser Ser Pro Ile Asn Leu Phe Ser Thr Ala Phe Gly Leu Leu Gly Leu Gly
Ser Asp Gly Gln Pro Pro Ala Gln Lys TABLE 1-continued Sequences SEQ ID NO: 33 CP-rMVP cDNA gaattcgcgg ccgcgtcgac tgtggcttgc agctgccagc taccctgcta aatgtttggt
gggaaaagct tgggattcac catggcaggc tgcggttgtc catgcggttg tggcgccatg
gcaactgaag aggccatcat ccgcatcccc ccataccact acatccatgt gctggaccag
aacagtaatg tgtcccgtgt ggaggttgga ccaaag acc tacatccggc aggacaatga
gagggtactg tttgccccag ttcgcatggt gaccgtcccc ccacgccact actgcatagt
ggccaaccct gtgtcccggg acacccagag ttctgtgtta tttgacatca caggacaagt
ccgactccgg cacgctgacc aggagatccg actagcccag gaccccttcc ccctgtatcc
aggggaggtg ctggaaaagg acatcacccc actgcaggtg gttctgccca acacagcact
gcatcttaag gcgttgctgg acttttgagga taagaatgga gacaaggtca tggcaggaga
cgagtggcta tttgagggac ctggcaccta catcccacag aaggaagtgg aagtcgtgga
gatcattcag gccacagtca tcaaacagaa ccaagcactg cggctaaggg cccgaaagga
gtgctttgac cgggagggca aggggcgcgt gacaggtgag gagtggctgg tccgatccgt
gggggcttac ctcccagctg tctttgaaga ggcgctggat ctggtggatg ctgtgatcct
tacagaaaag actgccctgc acctccgggc tctgcagaac ttcagggacc ttcggggagt
gctccaccgc accggggagg aatggttagt gacagtgcag gacacagaag cccatgttcc
agatgtctat gaggaggtgc ttggggtagt acccatcacc accctgggac ctcgacacta
ctgtgtcatt cttgacccaa tgggaccaga cggcaagaac cagctgggac aaaagcgtgt
tgtcaaggga gagaagtcct tttttcctcca gccaggagag aggctggagc gaggcatcca
ggatgtgtat gtgctgtcag agcagcaggg gctgctactg aaggcactgc agcccctgga
ggagggagag agcgaggaga aggtctccca tcaggccgga gactgctggc tcatccgtgg
gccccctggag tatgtgccat ctgcaaaagt ggaggtggtg gaggagcgtc aggctatccc
tctggaccaa aatgagggca tctatgtgca ggatgtcaag acggggaagg tgcgggctgt
gattggaagc acctacatgc tgactcagga tgaagtcctg tggggaaaagg agctgccttc
tggggtggag gagctgctga acttgggggca tgaccctctg gcagacaggg gtcagaaggg
cacagccaag ccccttcagc cctcagctcc aaggaacaag acccgagtgg tcagctaccg
tgtcccgcac aatgcagcgg tgcaggtcta tgactacaga gccaagagag cccgtgtggt
ctttgggccc gagctagtga cactggatcc tgaggagcag ttcacagtat tgtcccttttc
tgccgggcga cccaagcgtc ctcatgcccg ccgtgcactc tgcctactgc tgggacctga
tttcttttact gatgtcatca ccatcgaaac tgcagatcat gccaggttgc agctgcagct
tgcctacaac tggcactttg aactgaagaa ccggaatgac cctgcagagg cagccaagct
tttctccgtg cctgacttcg tgggtgacgc ctgcaaggcc attgcatccc gagtccgggg
ggctgtagcc tctgtcacct ttgatgactt ccataaaaaac tcagcccgga tcattcgaat
ggctgttttt ggctttgaga tgtctgaaga cacaggtcct gatggcacac tcctgcccaa
ggctcgagac caggcagtct ttcccccaaaa cgggctggta gtcagcagtg tggatgtgca
gtcagtggag cccgtggacc agaggacccg ggatgccctt cagcgcagcg ttcagctggc
catcgaaatt accaccaact cccaggaggc agcagccaag cacgaggctc agagactgga
acaggaagcc cgtggtcggc ttgagaggca gaagatcttg gaccagtcag aagctgaaaa
agcccgcaag gaactcttgg agcttgaggc tatgagcatg gctgtggaga gcacgggtaa
tgccaaagca gaggctgagt cccgtgcaga ggcagcgagg atcgaaggag aaggctctgt
gctgcaggcc aagctcaagg cacaggcgct agccattgag acggaggctg agttggagcg
agtaaagaaa gtacgagaga tggaactgat ctatgcccgg gcccagttgg agctggaggt
gagcaaggcg cagcagcttg ccaatgtgga ggcaaagaag ttcaaggaga tgacagaggc
actgggcccc ggcaccatca gggacctggc tgtggccggg ccagagatgc aggtgaaact
tctccagtcc ctgggcctga aatccactct catcaccgat ggctcgtctc ccatcaacct
cttcagcaca gccttcgggt tgctggggct ggggtctgat ggtcagccgc cagcagaca
gtgatccggc agcccgggga agacttgctc tcccaggctc tccgaagcag ccatgctgtg
ccttaggtca acactgactg cactgacaat ggataaaata aattgacaac tgtaaaaaaa
aaaaaaaagt cgacgcggcc gcgaattc SEQ ID NO: 34 CP-rMVP-Z domain fusion protein Met ala Gly Cys Gly Cys Pro Cys Gly Cys Gly Ala Met ala Thr Glu Glu Ala
Ile Ile Arg Ile Pro Tyr His Tyr Ile His Val Leu Asp Gln Asn Ser Asn
Val Ser Arg Val Glu Val Gly Pro Lys Thr Tyr Ile Arg Gln Asp Asn Glu Arg
Val Leu Phe Ala Pro Val Arg Met Val Thr Val Pro Pro Arg His Tyr Cys Ile
Val Ala Asn Pro Val Ser Arg Asp Thr Gln Ser Ser Val Leu Phe Asp Ile Thr
Gly Gln Val Arg Leu Arg His Ala Asp Gln Glu Ile Arg Leu Ala Gln Asp Pro
Phe Pro Leu Tyr Pro Gly Glu Val Leu Glu Lys Asp Ile Thr Pro Leu Gln Val
Val Leu Pro Asn Thr Ala Leu His Leu Lys Ala Leu Leu Asp Phe Glu Asp Lys
Asn Gly Asp Lys Val Met ala Gly Asp Glu Trp Leu Phe Glu Gly Pro Gly Thr
Tyr Ile Pro Gln Lys Glu Val Glu Val Glu Ile Ile Gln Ala Thr Val Ile
Lys Gln Asn Gln Ala Leu Arg Leu Arg Ala Arg Lys Glu Cys Phe Asp Lys Asp
Gly Lys Gly Arg Val Thr Gly Glu Glu Trp Leu Val Arg Ser Val Gly Ala Tyr
Leu Pro Ala Val Phe Glu Glu Val Leu Asp Leu Val Asp Ala Val Ile Leu Thr
Glu Lys Thr Ala Leu His Leu Arg Ala Leu Gln Asn Phe Arg Asp Leu Arg Gly
Val Leu His Arg Thr Gly Glu Glu Trp Leu Val Thr Val Gln Asp Thr Glu Ala
His Val Pro Asp Val Tyr Glu Glu Val Leu Gly Val Val Pro Ile Thr Thr Leu
Gly Pro Arg His Tyr Cys Val Ile Leu Asp Pro Met Gly Pro Asp Gly Lys Asn
Gln Leu Gly Gln Lys Arg Val Val Lys Gly Glu Lys Ser Phe Phe Leu Gln Pro
Gly Arg Leu Glu Arg Gly Ile Gln Asp Val Tyr Val Leu Ser Glu Glu Gln Gln
Gly Leu Leu Lys Ala Leu Gln Pro Leu Glu Glu Gly Glu Ser Glu Glu Lys
Val Ser His Gln Ala Gly Asp Cys Trp Leu Ile Arg Gly Pro Leu Glu Tyr Val
Pro Ser Ala Lys Val Glu Val Val Glu Glu Arg Gln Ala Ile Pro Leu Asp Gln
Asn Glu Gly Ile Tyr Val Gln Asp Val Lys Thr Gly Lys Val Arg Ala Val Ile
Gly Ser Thr Tyr Met Leu Thr Gln Asp Glu Val Leu Trp Glu Lys Glu Leu Pro TABLE 1-continued Sequences Ser Gly Val Glu Glu Leu Leu Asn Leu Gly His Asp Pro Leu Ala Asp Arg Gly
Gln Lys Gly Thr Ala Lys Pro Leu Gln Pro Ser Ala Pro Arg Asn Lys Thr Arg
Val Val Ser Tyr Arg Val Pro His Asn Ala Ala Val Gln Val Tyr Asp Tyr Arg
Ala Lys Arg Ala Arg Val Val Phe Gly Pro Glu Leu Val Thr Leu Asp Pro Glu
Glu Gln Phe Thr Val Leu Ser Leu Ser Ala Gly Arg Pro Lys Arg Pro His Ala
Arg Arg Ala Leu Cys Leu Leu Leu Gly Pro Asp Phe Phe Thr Asp Val Ile Thr
Ile Glu Thr Ala Asp His Ala Arg Leu Gln Leu Gln Leu Ala Tyr Asn Trp His
Phe Glu Leu Lys Asn Arg Asn Asp Pro Ala Glu Ala Ala Lys Leu Phe Ser Val
Pro Asp Phe Val Gly Asp Ala Cys Lys Ala Ile Ala Ser Arg Val Arg Gly Ala
Val Ala Ser Val Thr Phe Asp Asp Phe His Lys Asn Ser Ala Arg Ile Ile Arg
Met ala Val Phe Gly Phe Glu Met Ser Glu Asp Thr Gly Pro Asp Gly Thr Leu
Leu Pro Lys Ala Arg Asp Gln Ala Val Phe Pro Gln Asn Gly Leu Val Val Ser
Ser Val Asp Val Gln Ser Val Glu Pro Val Asp Gln Arg Thr Arg Asp Ala Leu
Gln Arg Ser Val Gln Leu Ala Ile Glu Ile Thr Thr Asn Ser Gln Glu Ala Ala
Ala Lys His Gly Ala Leu Arg Leu Gln Gly Leu Ala Arg Gly Arg Leu Glu Arg
Gln Lys Ile Leu Asp Gln Ser Glu Ala Glu Lys Ala Arg Lys Glu Leu Leu Glu
Leu Glu Ala Met Ser Met ala Val Glu Ser Thr Gly Asn Ala Lys Ala Glu Ala
Glu Ser Arg Ala Glu Ala Ala Arg Ile Glu Gly Glu Gly Ser Val Leu Gln Ala
Lys Leu Lys Ala Gln Ala Leu Ala Ile Glu Thr Val Ala Glu Leu Gln Arg Val
Lys Lys Val Arg Glu Met Glu Leu Ile Tyr Ala Arg Ala Gln Leu Glu Leu Glu
Val Ser Lys Ala Gln Gln Leu Asn Val Glu Ala Lys Lys Phe Lys Glu Met Thr
Glu Ala Leu Gly Pro Gly Thr Ile Arg Asp Leu Ala Val Ala Gly Pro Glu Met
Gln Val Lys Leu Leu Gln Ser Leu Gly Leu Lys Ser Thr Leu Ile Thr Asp Gly
Ser Ser Pro Ile Asn Leu Phe Ser Thr Ala Phe Gly Leu Leu Gly Leu Gly Ser
Asp Gly Gln Pro Pro Ala Gln Lys Phe Asn Met Gln Gln Gln Arg Arg Phe Tyr
Glu Ala Leu His Asp Pro Asn LeuA sn Glu Glu Gln Arg Asn Ala Lys Ile Lys
Ser Ile Arg Asp Asp SEQ ID NO: 35 CP-rMVP-Z cDNA gaattcgcgg ccgcgtcgac tgtggcttgc agctgccagc taccctgcta aatgtttggt
gggaaaagct tgggattcac catggcaggc tgcggttgtc catgcggttg tggcgccatg
gcaactgaag aggccatcat ccgcatcccc ccataccact acatccatgt gctggaccag
aacagtaatg tgtcccgtgt ggaggttgga ccaaagacct acatccggca ggacaatgag
agggtactgt ttgccccagt tcgcatggtg accgtccccc cacgccacta ctgcatagtg
gccaaccctg tgtcccggga cacccagagt tctgtgttat ttgacatcac aggacaagtc
cgactccggc acgctgacca ggagatccga ctagcccagg acccttccc cctgtatcca
gggagtgc tggaaaagga catcacccca ctgcaggtgg ttctgcccaa cacagcactg
catcttaagg cgttgctgga ctttgaggat aagaatggga caaggtcat ggcaggagac
gagtggctat ttgagggacc tggcacctac atcccacaga aggaagtgga agtcgtggga
atcattcagg ccacagtcat caaacagaac caagcactgc ggctaagggc ccgaaaggag
tgctttgacc gggagggcaa ggggcgcgtg acaggtgagg agtggctggt ccgatccgtg
ggggcttacc tcccagctgt ctttgaagag gtgctggatc tggtggatgc tgtgatcctt
acagaaaaga ctgccctgca cctccgggct ctgcagaact tcagggacct tcgggagtg
ctccaccgca ccggggagga atggttagtg acagtgcagg acacagaagc ccatgttcca
gatgtctatg aggaggtgct ggggtagta cccatcacca ccctgggacc tcgacactac
tgtgtcattc ttgacccaat gggaccagac ggcaagaacc agctgggaca aaagcgtgtt
gtcaagggag agaagtcctt tttcctccag ccaggagaga gtggagcg aggcatccag
gatgtgtatg tgctgtcaga gcagcagggg ctgctactga aggcactgca gcccctggag
gaggagaga gcgaggagaa ggtctcccat caggccggag actgctggct catccgtggg
cccctggagt atgtgccatc tgcaaaagtg gaggtggtgg aggagcgtca ggctatccct
ctggaccaaa atgagggcat ctatgtgcag gatgtcaaga cggggaaggt gcgggctgtg
attggaagca cctacatgct gactcaggat gaagtcctgt gggaaaagga gctgccttct
ggggtggagg agctgctgaa cttggggcat gaccctctgg cagacagggg tcagaagggc
acagccaagc cccttcagcc ctcagctcca aggaacaaga cccgagtggt cagctaccgt
gtcccgcaca atgcagcggt gcaggtctat gactacagag ccaagagagc ccgtgtggtc
tttggccccg agctagtgac actgatcct gaggagcagt tcacagtatt gtcccttct
gccgggcgac ccaagcgtcc tcatgcccgc cgtgcactct gcctactgct gggacctgat
ttctttactg atgtcatcac catcgaaact gcagatcatg ccaggttgca gctgcagctt
gcctacaact ggcactttga actgaagaac cggaatgacc ctgcagaggc agccaagctt
ttctccgtgc ctgacttcgt gggtgacgcc tgcaaggcca ttgcatcccg agtccggggg
gctgtagcct ctgtcacctt tgatgacttc cataaaaact cagcccggat cattcgaatg
gctgtttttg gctttgagat gtctgaagac acaggtcctg atggcacact cctgcccaag
gctcgagacc aggcagtctt tccccaaaac gggctggtag tcagcagtgt ggatgtgcag
tcagtgggagc ccgtggacca gaggacccgg gatgcccttc agcgcagcgt tcagctggcc
atcgaaatta ccaccaactc ccaggaggca gcagccaagc acgaggctca gagactggaa
caggaagccc gtggtcggct tgagaggcag aagatcttgg accagtcaga agctgaaaaa
gcccgcaagg aactcttgga gcttgaggct atgagcatgg ctgtggagag cacgggtaat
gccaaagcag aggctgagtc ccgtgcagag gcagcgagga tcgaaggaga aggctctgtg
ctgcaggcca agctcaaggc acaggcgcta gccattgaga cggaggctga gttggagcga
gtaaagaaag tacgagagat ggaactgatc tatgcccggg cccagttgga gctggaggtg
agcaaggcgc agcagcttgc caatgtggag gcaaagaagt tcaaggagat gacagaggca
ctgggcccg gcaccatcag ggacctggct gtggccgggc cagagatgca ggtgaaactt
ctccagtccc tgggcctgaa atccactctc atcaccgatg gctcgtctcc catcaacctc
ttcagcacag ccttcgggtt gctgggggctg ggtctgatg gtcagccgcc agcacagaag
tttaacatgc agcagcagcg ccgcttttac gaggccctgc acgaccccaa cctgaacgag
gagcagcgca acgccaagat taagagcatt cgcgacgact agggtacc

TABLE 1-continued

Sequences

SEQ ID NO: 36 NS5A-NS5A-rMVP-Z domain fusion protein

Met ala Gly Ser Trp Leu Arg Asp Ile Trp Asp Trp Ile Cys Glu Val Leu Ser
Asp Phe Lys Thr Trp Leu Lys Ala Lys Leu Met Pro Thr Met ala Gly Ser Trp
Leu Arg Asp Ile Trp Asp Trp Ile Cys Glu Val Leu Ser Asp Phe Lys Thr Trp
Leu Lys Ala Lys Leu Met Pro Thr Met ala Thr Glu Ala Ile Ile Arg Ile Ile
Pro Pro Tyr His Tyr Ile His Val Leu Asp Gln Asn Ser Asn Val Ser Arg Val
Glu Val Gly Pro Lys Thr Tyr Ile Arg Gln Asp Asn Glu Arg Val Leu Phe Ala
Pro Val Arg Met Val Thr Val Pro Pro Arg His Tyr Cys Ile Val Ala Asn Pro
Val Ser Arg Asp Thr Gln Ser Ser Val Leu Phe Asp Ile Thr Gly Gln Val Arg
Leu Arg His Ala Asp Gln Glu Ile Arg Leu Ala Gln Asp Pro Phe Pro Leu Tyr
Pro Gly Glu Val Leu Glu Lys Asp Ile Thr Pro Leu Gln Val Val Leu Pro Asn
Thr Ala Leu His Leu Lys Ala Leu Leu Asp Phe Glu Asp Lys Asn Gly Asp Lys
Val Met ala Gly Asp Glu Trp Leu Phe Glu Gly Pro Gly Thr Tyr Ile Pro Gln
Lys Glu Val Glu Val Val Glu Ile Ile Gln Ala Thr Val Ile Lys Gln Asn Gln
Ala Leu Arg Leu Arg Ala Arg Lys Glu Cys Phe Asp Arg Glu Gly Lys Gly Arg
Val Thr Gly Glu Glu Trp Leu Val Arg Ser Val Gly Ala Tyr Leu Pro Ala Val
Phe Glu Glu Val Leu Asp Leu Val Asp Ala Val Ile Leu Thr Glu Lys Thr Ala
Leu His Leu Arg Ala Leu Gln Asn Phe Arg Asp Leu Arg Gly Val Leu His Arg
Thr Gly Glu Glu Trp Leu Val Thr Val Gln Asp Thr Glu Ala His Val Pro Asp
Val Tyr Glu Glu Val Leu Gly Val Val Pro Ile Thr Thr Leu Gly Pro Arg His
Tyr Cys Val Ile Leu Asp Pro Met Gly Pro Asp Gly Lys Asn Gln Leu Gly Gln
Lys Arg Val Val Lys Gly Glu Lys Ser Phe Phe Leu Gln Pro Gly Glu Gln Leu
Glu Arg Gly Ile Gln Asp Val Tyr Val Leu Ser Glu Gln Gln Gly Leu Leu Leu
Lys Ala Leu Gln Pro Leu Glu Glu Gly Glu Ser Glu Glu Lys Val Ser His Gln
Ala Gly Asp Cys Trp Leu Ile Arg Gly Pro Leu Glu Tyr Val Pro Ser Ala Lys
Val Glu Val Val Glu Glu Arg Gln Ala Ile Pro Leu Asp Gln Asn Glu Gly Ile
Tyr Val Gln Asp Val Lys Thr Gly Lys Val Arg Ala Val Ile Gly Ser Thr Tyr
Met Leu Thr Gln Asp Glu Val Leu Trp Glu Lys Glu Leu Pro Ser Gly Val Glu
Glu Leu Leu Asn Leu Gly His Asp Pro Leu Ala Asp Arg Gly Gln Lys Gly Thr
Ala Lys Pro Leu Gln Pro Ser Ala Pro Arg Asn Lys Thr Arg Val Val Ser Tyr
Arg Val Pro His Asn Ala Ala Val Gln Val Tyr Asp Tyr Arg Glu Lys Arg Ala
Arg Val Val Phe Gly Pro Glu Leu Val Thr Leu Asp Pro Glu Glu Gln Phe Thr
Val Leu Ser Leu Ser Ala Gly Arg Pro Lys Arg Pro His Ala Arg Arg Ala Leu
Cys Leu Leu Leu Gly Pro Asp Phe Phe Thr Asp Val Ile Thr Ile Glu Thr Ala
Asp His Ala Arg Leu Gln Leu Gln Leu Ala Tyr Asn Trp His Phe Glu Leu Lys
Asn Arg Asn Asp Pro Ala Glu Ala Ala Lys Leu Phe Ser Val Pro Asp Phe Val
Gly Asp Ala Cys Lys Ala Ile Ala Ser Arg Val Arg Gly Ala Val Ala Ser Val
Thr Phe Asp Asp Phe His Lys Asn Ser Ala Arg Ile Ile Arg Met ala Val Phe
Gly Phe Glu Met Ser Glu Asp Thr Gly Pro Asp Gly Thr Leu Leu Pro Lys Ala
Arg Asp Gln Ala Val Phe Pro Gln Asn Gly Leu Val Val Ser Ser Val Asp Val
Gln Ser Val Glu Pro Val Asp Gln Arg Thr Arg Asp Ala Leu Gln Arg Ser Val
Gln Leu Ala Ile Glu Ile Thr Thr Asn Ser Gln Glu Ala Ala Ala Lys His Glu
Ala Gln Arg Leu Glu Gln Glu Ala Arg Gly Arg Leu Glu Arg Gln Lys Ile Leu
Asp Gln Ser Glu Ala Glu Lys Ala Arg Lys Glu Leu Leu Glu Leu Glu Ala Met
Ser Met ala Val Glu Ser Thr Gly Asn Ala Lys Ala Glu Ala Glu Ser Arg Ala
Glu Ala Ala Arg Ile Glu Gly Glu Gly Ser Val Leu Gln Ala Lys Leu Lys Ala
Gln Ala Leu Ala Ile Glu Thr Glu Ala Glu Leu Glu Arg Val Lys Lys Val Arg
Glu Met Glu Leu Ile Tyr Ala Arg Ala Gln Leu Glu Leu Glu Val Ser Lys Ala
Gln Gln Leu Ala Asn Val Glu Lys Lys Phe Lys Glu Met Thr Glu Ala Leu
Gly Pro Gly Thr Ile Arg Asp Leu Ala Val Ala Gly Pro Glu Met Gln Val Lys
Leu Leu Gln Ser Leu Gly Leu Lys Ser Thr Leu Ile Thr Asp Gly Ser Ser Pro
Ile Asn Leu Phe Ser Thr Ala Phe Gly Leu Leu Gly Leu Gly Ser Asp Gly Gln
Pro Pro Ala Gln Lys Phe Asn Met Gln Gln Arg Arg Phe Tyr Glu Ala Leu
His Asp Pro Asn Leu Asn Glu Glu Gln Arg Asn Ala Lys Ile Lys Ser Ile Arg
Asp Asp

---

SEQUENCE LISTING

<160> NUMBER OF SEQ ID NOS: 36

<210> SEQ ID NO 1
<211> LENGTH: 489
<212> TYPE: DNA
<213> ORGANISM: Homo sapiens

<400> SEQUENCE: 1

```
tgcacacaac actggcagga tgctgtgcct tggacagaac tcctcagtct acagacagag    60
gatggcttct ggaaacttac accagaactg ggacttatat taaatcttaa tacaaatggt   120
ttgcacagct ttcttaaaca aaaaggcatt caatctctag gtgtaaaagg aagagaatgt   180
```

```
ctcctggacc taattgccac aatgctggta ctacagttta ttcgcaccag gttggaaaaa      240
gagggaatag tgttcaaatc actgatgaaa atggatgacc cttctatttc aggaatatt       300 ccctgggctt tgaggcaat aaagcaagca agtgaatggg taagaagaac tgaaggacag       360
tacccatcta tctgcccacg gcttgaactg gggaacgact gggactctgc accaagcag       420 ttgctgggac tccagcccat aagcactgtg tccctcttc atagagtcct ccattacagt       480
caaggctaa                                                              489
```

<210> SEQ ID NO 2
<211> LENGTH: 162
<212> TYPE: PRT
<213> ORGANISM: Homo sapiens

<400> SEQUENCE: 2

Cys Thr Gln His Trp Gln Asp Ala Val Pro Trp Thr Glu Leu Leu Ser
1               5                   10                  15

Leu Gln Thr Glu Asp Gly Phe Trp Lys Leu Thr Pro Glu Leu Gly Leu
            20                  25                  30

Ile Leu Asn Leu Asn Thr Asn Gly Leu His Ser Phe Leu Lys Gln Lys
        35                  40                  45

Gly Ile Gln Ser Leu Gly Val Lys Gly Arg Glu Cys Leu Leu Asp Leu
    50                  55                  60

Ile Ala Thr Met Leu Val Leu Gln Phe Ile Arg Thr Arg Leu Glu Lys
65                  70                  75                  80

Glu Gly Ile Val Phe Lys Ser Leu Met Lys Met Asp Asp Pro Ser Ile
                85                  90                  95

Ser Arg Asn Ile Pro Trp Ala Phe Glu Ala Ile Lys Gln Ala Ser Glu
            100                 105                 110

Trp Val Arg Arg Thr Glu Gly Gln Tyr Pro Ser Ile Cys Pro Arg Leu
        115                 120                 125

Glu Leu Gly Asn Asp Trp Asp Ser Ala Thr Lys Gln Leu Leu Gly Leu
    130                 135                 140

Gln Pro Ile Ser Thr Val Ser Pro Leu His Arg Val Leu His Tyr Ser
145                 150                 155                 160

Gln Gly

<210> SEQ ID NO 3
<211> LENGTH: 1724
<212> TYPE: PRT
<213> ORGANISM: Homo sapiens

<400> SEQUENCE: 3

Met Val Met Gly Ile Phe Ala Asn Cys Ile Phe Cys Leu Lys Val Lys
1               5                   10                  15

Tyr Leu Pro Gln Gln Gln Lys Lys Leu Gln Thr Asp Ile Lys Glu
            20                  25                  30

Asn Gly Gly Lys Phe Ser Phe Ser Leu Asn Pro Gln Cys Thr His Ile
        35                  40                  45

Ile Leu Asp Asn Ala Asp Val Leu Ser Gln Tyr Gln Leu Asn Ser Ile
    50                  55                  60

Gln Lys Asn His Val His Ile Ala Asn Pro Asp Phe Ile Trp Lys Ser
65                  70                  75                  80

Ile Arg Glu Lys Arg Leu Leu Asp Val Lys Asn Tyr Asp Pro Tyr Lys
                85                  90                  95

-continued

```
Pro Leu Asp Ile Thr Pro Pro Asp Gln Lys Ala Ser Ser Ser Glu
            100                 105                 110

Val Lys Thr Glu Gly Leu Cys Pro Asp Ser Ala Thr Glu Glu Asp
        115                 120                 125

Thr Val Glu Leu Thr Glu Phe Gly Met Gln Asn Val Glu Ile Pro His
    130                 135                 140

Leu Pro Gln Asp Phe Glu Val Ala Lys Tyr Asn Thr Leu Glu Lys Val
145                 150                 155                 160

Gly Met Glu Gly Gly Gln Glu Ala Val Val Glu Leu Gln Cys Ser
                165                 170                 175

Arg Asp Ser Arg Asp Cys Pro Phe Leu Ile Ser Ser His Phe Leu Leu
            180                 185                 190

Asp Asp Gly Met Glu Thr Arg Arg Gln Phe Ala Ile Lys Lys Thr Ser
            195                 200                 205

Glu Asp Ala Ser Glu Tyr Phe Glu Asn Tyr Ile Glu Glu Leu Lys Lys
        210                 215                 220

Gln Gly Phe Leu Arg Glu His Phe Thr Pro Glu Ala Thr Gln Leu
225                 230                 235                 240

Ala Ser Glu Gln Leu Gln Ala Leu Leu Leu Glu Glu Val Met Asn Ser
                245                 250                 255

Ser Thr Leu Ser Gln Glu Val Ser Asp Leu Val Glu Met Ile Trp Ala
            260                 265                 270

Glu Ala Leu Gly His Leu Glu His Met Leu Leu Lys Pro Val Asn Arg
            275                 280                 285

Ile Ser Leu Asn Asp Val Ser Lys Ala Glu Gly Ile Leu Leu Leu Val
        290                 295                 300

Lys Ala Ala Leu Lys Asn Gly Glu Thr Ala Glu Gln Leu Gln Lys Met
305                 310                 315                 320

Met Thr Glu Phe Tyr Arg Leu Ile Pro His Lys Gly Thr Met Pro Lys
                325                 330                 335

Glu Val Asn Leu Gly Leu Leu Ala Lys Lys Ala Asp Leu Cys Gln Leu
            340                 345                 350

Ile Arg Asp Met Val Asn Val Cys Glu Thr Asn Leu Ser Lys Pro Asn
        355                 360                 365

Pro Pro Ser Leu Ala Lys Tyr Arg Ala Leu Arg Cys Lys Ile Glu His
    370                 375                 380

Val Glu Gln Asn Thr Glu Glu Phe Leu Arg Val Arg Lys Glu Val Leu
385                 390                 395                 400

Gln Asn His His Ser Lys Ser Pro Val Asp Val Leu Gln Ile Phe Arg
                405                 410                 415

Val Gly Arg Val Asn Glu Thr Thr Glu Phe Leu Ser Lys Leu Gly Asn
            420                 425                 430

Val Arg Pro Leu Leu His Gly Ser Pro Val Gln Asn Ile Val Gly Ile
        435                 440                 445

Leu Cys Arg Gly Leu Leu Leu Pro Lys Val Val Glu Asp Arg Gly Val
    450                 455                 460

Gln Arg Thr Asp Val Gly Asn Leu Gly Ser Gly Ile Tyr Phe Ser Asp
465                 470                 475                 480

Ser Leu Ser Thr Ser Ile Lys Tyr Ser His Pro Gly Glu Thr Asp Gly
                485                 490                 495

Thr Arg Leu Leu Leu Ile Cys Asp Val Ala Leu Gly Lys Cys Met Asp
            500                 505                 510

Leu His Glu Lys Asp Phe Pro Leu Thr Glu Ala Pro Pro Gly Tyr Asp
```

```
            515                 520                 525
Ser Val His Gly Val Ser Gln Thr Ala Ser Val Thr Thr Asp Phe Glu
530                 535                 540

Asp Asp Glu Phe Val Val Tyr Lys Thr Asn Gln Val Lys Met Lys Tyr
545                 550                 555                 560

Ile Ile Lys Phe Ser Met Pro Gly Asp Gln Ile Lys Asp Phe His Pro
                565                 570                 575

Ser Asp His Thr Glu Leu Glu Glu Tyr Arg Pro Glu Phe Ser Asn Phe
            580                 585                 590

Ser Lys Val Glu Asp Tyr Gln Leu Pro Asp Ala Lys Thr Ser Ser Ser
        595                 600                 605

Thr Lys Ala Gly Leu Gln Asp Ala Ser Gly Asn Leu Val Pro Leu Glu
    610                 615                 620

Asp Val His Ile Lys Gly Arg Ile Ile Asp Thr Val Ala Gln Val Ile
625                 630                 635                 640

Val Phe Gln Thr Tyr Thr Asn Lys Ser His Val Pro Ile Glu Ala Lys
                645                 650                 655

Tyr Ile Phe Pro Leu Asp Asp Lys Ala Ala Val Cys Gly Phe Glu Ala
            660                 665                 670

Phe Ile Asn Gly Lys His Ile Val Gly Glu Ile Lys Glu Lys Glu Glu
        675                 680                 685

Ala Gln Gln Glu Tyr Leu Glu Ala Val Thr Gln Gly His Gly Ala Tyr
    690                 695                 700

Leu Met Ser Gln Asp Ala Pro Asp Val Phe Thr Val Ser Val Gly Asn
705                 710                 715                 720

Leu Pro Pro Lys Ala Lys Val Leu Ile Lys Ile Thr Tyr Ile Thr Glu
                725                 730                 735

Leu Ser Ile Leu Gly Thr Val Gly Val Phe Phe Met Pro Ala Thr Val
            740                 745                 750

Ala Pro Trp Gln Gln Asp Lys Ala Leu Asn Glu Asn Leu Gln Asp Thr
        755                 760                 765

Val Glu Lys Ile Cys Ile Lys Glu Ile Gly Thr Lys Gln Ser Phe Ser
    770                 775                 780

Leu Thr Met Ser Ile Glu Met Pro Tyr Val Ile Glu Phe Ile Phe Ser
785                 790                 795                 800

Asp Thr His Glu Leu Lys Gln Lys Arg Thr Asp Cys Lys Ala Val Ile
                805                 810                 815

Ser Thr Met Glu Gly Ser Ser Leu Asp Ser Ser Gly Phe Ser Leu His
            820                 825                 830

Ile Gly Leu Ser Ala Ala Tyr Leu Pro Arg Met Trp Val Glu Lys His
        835                 840                 845

Pro Glu Lys Glu Ser Glu Ala Cys Met Leu Val Phe Gln Pro Asp Leu
    850                 855                 860

Asp Val Asp Leu Pro Asp Leu Ala Ser Glu Ser Glu Val Ile Ile Cys
865                 870                 875                 880

Leu Asp Cys Ser Ser Ser Met Glu Gly Val Thr Phe Leu Gln Ala Lys
                885                 890                 895

Gln Ile Thr Leu His Ala Leu Ser Leu Val Gly Glu Lys Gln Lys Val
            900                 905                 910

Asn Ile Ile Gln Phe Gly Thr Gly Tyr Lys Glu Leu Phe Ser Tyr Pro
        915                 920                 925

Lys His Ile Thr Ser Asn Thr Thr Ala Ala Glu Phe Ile Met Ser Ala
    930                 935                 940
```

-continued

```
Thr Pro Thr Met Gly Asn Thr Asp Phe Trp Lys Thr Leu Arg Tyr Leu
945                 950                 955                 960

Ser Leu Leu Tyr Pro Ala Arg Gly Ser Arg Asn Ile Leu Leu Val Ser
                965                 970                 975

Asp Gly His Leu Gln Asp Glu Ser Leu Thr Leu Gln Leu Val Lys Arg
            980                 985                 990

Ser Arg Pro His Thr Arg Leu Phe Ala Cys Gly Ile Gly Ser Thr Ala
        995                 1000                1005

Asn Arg His Val Leu Arg Ile Leu Ser Gln Cys Gly Ala Gly Val
    1010                1015                1020

Phe Glu Tyr Phe Asn Ala Lys Ser Lys His Ser Trp Arg Lys Gln
    1025                1030                1035

Ile Glu Asp Gln Met Thr Arg Leu Cys Ser Pro Ser Cys His Ser
    1040                1045                1050

Val Ser Val Lys Trp Gln Gln Leu Asn Pro Asp Ala Pro Glu Ala
    1055                1060                1065

Leu Gln Ala Pro Ala Gln Val Pro Ser Leu Phe Arg Asn Asp Arg
    1070                1075                1080

Leu Leu Val Tyr Gly Phe Ile Pro His Cys Thr Gln Ala Thr Leu
    1085                1090                1095

Cys Ala Leu Ile Gln Glu Lys Glu Phe Cys Thr Met Val Ser Thr
    1100                1105                1110

Thr Glu Leu Gln Lys Thr Thr Gly Thr Met Ile His Lys Leu Ala
    1115                1120                1125

Ala Arg Ala Leu Ile Arg Asp Tyr Glu Asp Gly Ile Leu His Glu
    1130                1135                1140

Asn Glu Thr Ser His Glu Met Lys Lys Gln Thr Leu Lys Ser Leu
    1145                1150                1155

Ile Ile Lys Leu Ser Lys Glu Asn Ser Leu Ile Thr Gln Phe Thr
    1160                1165                1170

Ser Phe Val Ala Val Glu Lys Arg Asp Glu Asn Glu Ser Pro Phe
    1175                1180                1185

Pro Asp Ile Pro Lys Val Ser Glu Leu Ile Ala Lys Glu Asp Val
    1190                1195                1200

Asp Phe Leu Pro Tyr Met Ser Trp Gln Gly Glu Pro Gln Glu Ala
    1205                1210                1215

Val Arg Asn Gln Ser Leu Leu Ala Ser Ser Glu Trp Pro Glu Leu
    1220                1225                1230

Arg Leu Ser Lys Arg Lys His Arg Lys Ile Pro Phe Ser Lys Arg
    1235                1240                1245

Lys Met Glu Leu Ser Gln Pro Glu Val Ser Glu Asp Phe Glu Glu
    1250                1255                1260

Asp Gly Leu Gly Val Leu Pro Ala Phe Thr Ser Asn Leu Glu Arg
    1265                1270                1275

Gly Gly Val Glu Lys Leu Leu Asp Leu Ser Trp Thr Glu Ser Cys
    1280                1285                1290

Lys Pro Thr Ala Thr Glu Pro Leu Phe Lys Lys Val Ser Pro Trp
    1295                1300                1305

Glu Thr Ser Thr Ser Ser Phe Phe Pro Ile Leu Ala Pro Ala Val
    1310                1315                1320

Gly Ser Tyr Leu Thr Pro Thr Arg Ala His Ser Pro Ala Ser
    1325                1330                1335
```

```
Leu Ser Phe Ala Ser Tyr Arg Gln Val Ala Ser Phe Gly Ser Ala
    1340            1345                1350

Ala Pro Pro Arg Gln Phe Asp Ala Ser Gln Phe Ser Gln Gly Pro
    1355            1360                1365

Val Pro Gly Thr Cys Ala Asp Trp Ile Pro Gln Ser Ala Ser Cys
    1370            1375                1380

Pro Thr Gly Pro Pro Gln Asn Pro Pro Ser Ala Pro Tyr Cys Gly
    1385            1390                1395

Ile Val Phe Ser Gly Ser Ser Leu Ser Ser Ala Gln Ser Ala Pro
    1400            1405                1410

Leu Gln His Pro Gly Gly Phe Thr Thr Arg Pro Ser Ala Gly Thr
    1415            1420                1425

Phe Pro Glu Leu Asp Ser Pro Gln Leu His Phe Ser Leu Pro Thr
    1430            1435                1440

Asp Pro Asp Pro Ile Arg Gly Phe Gly Ser Tyr His Pro Ser Ala
    1445            1450                1455

Tyr Ser Pro Phe His Phe Gln Pro Ser Ala Ala Ser Leu Thr Ala
    1460            1465                1470

Asn Leu Arg Leu Pro Met Ala Ser Ala Leu Pro Glu Ala Leu Cys
    1475            1480                1485

Ser Gln Ser Arg Thr Thr Pro Val Asp Leu Cys Leu Leu Glu Glu
    1490            1495                1500

Ser Val Gly Ser Leu Glu Gly Ser Arg Cys Pro Val Phe Ala Phe
    1505            1510                1515

Gln Ser Ser Asp Thr Glu Ser Asp Glu Leu Ser Glu Val Leu Gln
    1520            1525                1530

Asp Ser Cys Phe Leu Gln Ile Lys Cys Asp Thr Lys Asp Asp Ser
    1535            1540                1545

Ile Pro Cys Phe Leu Glu Leu Lys Glu Glu Asp Glu Ile Val Cys
    1550            1555                1560

Thr Gln His Trp Gln Asp Ala Val Pro Trp Thr Glu Leu Leu Ser
    1565            1570                1575

Leu Gln Thr Glu Asp Gly Phe Trp Lys Leu Thr Pro Glu Leu Gly
    1580            1585                1590

Leu Ile Leu Asn Leu Asn Thr Asn Gly Leu His Ser Phe Leu Lys
    1595            1600                1605

Gln Lys Gly Ile Gln Ser Leu Gly Val Lys Gly Arg Glu Cys Leu
    1610            1615                1620

Leu Asp Leu Ile Ala Thr Met Leu Val Leu Gln Phe Ile Arg Thr
    1625            1630                1635

Arg Leu Glu Lys Glu Gly Ile Val Phe Lys Ser Leu Met Lys Met
    1640            1645                1650

Asp Asp Pro Ser Ile Ser Arg Asn Ile Pro Trp Ala Phe Glu Ala
    1655            1660                1665

Ile Lys Gln Ala Ser Glu Trp Val Arg Arg Thr Glu Gly Gln Tyr
    1670            1675                1680

Pro Ser Ile Cys Pro Arg Leu Glu Leu Gly Asn Asp Trp Asp Ser
    1685            1690                1695

Ala Thr Lys Gln Leu Leu Gly Leu Gln Pro Ile Ser Thr Val Ser
    1700            1705                1710

Pro Leu His Arg Val Leu His Tyr Ser Gln Gly
    1715            1720
```

<210> SEQ ID NO 4
<211> LENGTH: 5175
<212> TYPE: DNA
<213> ORGANISM: Homo sapiens

<400> SEQUENCE: 4

| | | | | | |
|---|---|---|---|---|---|
| atggtgatgg | gaatctttgc | aaattgtatc | ttctgtttga | aagtgaagta | cttacctcag | 60 |
| cagcagaaga | aaaagctaca | aactgacatt | aaggaaaatg | gcggaaagtt | ttccttttcg | 120 |
| ttaaatcctc | agtgcacaca | tataatctta | gataatgctg | atgttctgag | tcagtaccaa | 180 |
| ctgaattcta | tccaaaagaa | ccacgttcat | attgcaaacc | cagattttat | atggaaatct | 240 |
| atcagagaaa | agagactctt | ggatgtaaag | aattatgatc | cttataagcc | cctggacatc | 300 |
| acaccacctc | ctgatcagaa | ggcgagcagt | tctgaagtga | aaacagaagg | tctatgcccg | 360 |
| gacagtgcca | cagaggagga | agacactgtg | gaactcactg | agtttggtat | gcagaatgtt | 420 |
| gaaattcctc | atcttcctca | agatttttgaa | gttgcaaaat | ataacacctt | ggagaaagtg | 480 |
| ggaatggagg | gaggccagga | agctgtggtg | gtggagcttc | agtgttcgcg | ggactccagg | 540 |
| gactgtcctt | tcctgatatc | ctcacacttc | ctcctggatg | atggcatgga | gactagaaga | 600 |
| cagttttgcta | taaagaaaac | ctctgaagat | gcaagtgaat | actttgaaaa | ttacattgaa | 660 |
| gaactgaaga | acaaggatt | tctactaaga | gaacatttca | cacctgaagc | aacccaatta | 720 |
| gcatctgaac | aattgcaagc | attgcttttg | gaggaagtca | tgaattcaag | cactctgagc | 780 |
| caagaggtga | gcgatttagt | agagatgatt | tgggcagagg | ccctgggcca | cctggaacac | 840 |
| atgcttctca | agccagtgaa | caggattagc | ctcaacgatg | tgagcaaggc | agaggggatt | 900 |
| ctccttctag | taaaggcagc | actgaaaaat | ggagaaacag | cagagcaatt | gcaaaagatg | 960 |
| atgacagagt | tttacagact | gatacctcac | aaaggcacaa | tgcccaaaga | agtgaacctg | 1020 |
| ggactattgg | ctaagaaagc | agacctctgc | cagctaataa | gagacatggt | taatgtctgt | 1080 |
| gaaactaatt | tgtccaaacc | caacccacca | tccctggcca | aataccgagc | tttgaggtgc | 1140 |
| aaaattgagc | atgttgaaca | gaatactgaa | gaatttctca | gggttagaaa | agaggttttg | 1200 |
| cagaatcatc | acagtaagag | cccagtggat | gtcttgcaga | tatttagagt | tggcagagtg | 1260 |
| aatgaaacca | cagagttttt | gagcaaactt | ggtaatgtga | ggcccttgtt | gcatggttct | 1320 |
| cctgtacaaa | acatcgtggg | aatcttgtgt | cgagggttgc | ttttacccaa | agtagtggaa | 1380 |
| gatcgtggtg | tgcaaagaac | agacgtcgga | aaccttggaa | gtgggattta | tttcagtgat | 1440 |
| tcgctcagta | caagtatcaa | gtactcacac | ccgggagaga | cagatggcac | cagactcctg | 1500 |
| ctcatttgtg | acgtagccct | cggaaagtgt | atggacttac | atgagaagga | ctttccctta | 1560 |
| actgaagcac | caccaggcta | cgacagtgtg | catggagttt | cacaaacagc | tctgtcacc | 1620 |
| acagactttg | aggatgatga | atttgttgtc | tataaaacca | atcaggttaa | aatgaaatat | 1680 |
| attattaaat | tttccatgcc | tggagatcag | ataaaggact | tcatcctag | tgatcatact | 1740 |
| gaattagagg | aatacagacc | tgagttttca | aattttttcaa | aggttgaaga | ttaccagtta | 1800 |
| ccagatgcca | aaacttccag | cagcaccaag | gccggcctcc | aggatgcctc | tgggaacttg | 1860 |
| gttcctctgg | aggatgtcca | catcaaaggg | agaatcatag | acactgtagc | ccaggtcatt | 1920 |
| gttttttcaga | catacacaaa | taaagtcac | gtgcccattg | aggcaaaata | tatctttcct | 1980 |
| ttggatgaca | aggccgctgt | gtgtggcttc | gaagccttca | tcaatgggaa | gcacatagtt | 2040 |
| ggagagatta | agagaaggga | agaagcccag | caagagtacc | tagaagccgt | gacccagggc | 2100 |
| catggcgctt | acctgatgag | tcaggatgct | ccggacgttt | ttactgtaag | tgttggaaac | 2160 |

```
ttacccccta aggctaaggt tcttataaaa attacctaca tcacagaact cagcatcctg    2220
ggcactgttg gtgtctttt  catgcccgcc accgtagcac cctggcaaca ggacaaggct    2280
ttgaatgaaa accttcagga tacagtagag aagatttgta taaaagaaat aggaacaaag    2340
caaagcttct ctttgactat gtctattgag atgccgtatg tgattgaatt cattttcagt    2400
gatacacatg aactgaaaca aaagcgcaca gactgcaaag ctgtcattag caccatggaa    2460
ggcagctcct tagacagcag tggatttttct ctccacatcg gtttgtctgc tgcctatctc   2520
ccaagaatgt gggttgaaaa acatccagaa aaagaaagcg aggcttgcat gcttgtcttt    2580
caacccgatc tcgatgtcga cctccctgac ctagccagtg agagcgaagt gattatttgt    2640
cttgactgct ccagttccat ggagggtgtg acattcttgc aagccaagca aatcaccttg    2700
catgcgctgt ccttggtggg tgagaagcag aaagtaaata ttatccagtt cggcacaggt    2760
tacaaggagc tattttcgta tcctaagcat atcacaagca ataccacggc agcagagttc    2820
atcatgtctg ccacacctac catggggaac acagacttct ggaaaacact ccgatatctt    2880
agcttattgt accctgctcg agggtcacgg aacatcctcc tggtgtctga tgggcacctc    2940
caggatgaga gcctgacatt acagctcgtg aagaggagcc gcccgcacac caggttattc    3000
gcctgcggta tcggttctac agcaaatcgt cacgtcttaa ggattttgtc ccagtgtggt    3060
gccggagtat ttgaatattt taatgcaaaa tccaagcata gttggagaaa acagatagaa    3120
gaccaaatga ccaggctatg ttctccgagt tgccactctg tctccgtcaa atggcagcaa    3180
ctcaatccag atgcgcccga ggccctgcag gccccagccc aggtgccatc cttgtttcgc    3240
aatgatcgac tccttgtcta tggattcatt cctcactgca caagcaac tctgtgtgca    3300 ctaattcaag agaaagaatt ttgtacaatg gtgtcgacta ctgagcttca gaagacaact    3360
ggaactatga tccacaagct ggcagcccga gctctaatca gagattatga agatggcatt    3420
cttcacgaaa atgaaaccag tcatgagatg aaaaaacaaa ccttgaaatc tctgattatt    3480
aaactcagta aagaaaactc tctcataaca caatttacaa gctttgtggc agttgagaaa    3540
agggatgaga atgagtcgcc ttttcctgat attccaaaag tttctgaact tattgccaaa    3600
gaagatgtag acttcctgcc ctacatgagc tggcaggggg agccccaaga agccgtcagg    3660
aaccagtctc ttttagcatc ctctgagtgg ccagaattac gtttatccaa acgaaaacat    3720
aggaaaattc cattttccaa aagaaaaatg gaattatctc agccagaagt ttctgaagat    3780
tttgaagagg atggcttagg tgtactacca gctttcacat caaatttgga acgtggaggt    3840
gtggaaaagc tattggattt aagttggaca gagtcatgta aaccaacagc aactgaacca    3900
ctatttaaga aagtcagtcc atgggaaaca tctacttcta gcttttttcc tattttggct    3960
ccggccgttg gttcctatct taccccgact acccgcgctc acagtcctgc ttccttgtct    4020
tttgcctcat atcgtcaggt agctagtttc ggttcagctg ctcctcccag acagtttgat    4080
gcatctcaat tcagccaagg ccctgtgcct ggcacttgtg ctgactggat cccacagtcg    4140
gcgtcttgtc ccacaggacc tccccagaac ccaccttctg cacccttattg tggcattgtt   4200 ttttcaggga gctcattaag ctctgcacag tctgctccac tgcaacatcc tggaggcttt    4260
actaccaggc cttctgctgg caccttccct gagctggatt ccccccagct tcatttctct    4320
cttcctacag accctgatcc catcagaggt tttgggtctt atcatccctc tgcttactct    4380
ccttttcatt ttcaaccttc cgcagcctct ttgactgcca accttaggct gccaatggcc    4440
tctgctttac ctgaggctct ttgcagtcag tcccggacta ccccagtaga tctctgtctt    4500
ctagaagaat cagtaggcag tctcgaagga agtcgatgtc ctgtctttgc ttttcaaagt    4560
```

-continued

```
tctgacacag aaagtgatga gctatcagaa gtacttcaag acagctgctt tttacaaata    4620
aagtgtgata caaaagatga cagtatcccg tgctttctgg aattaaaaga agaggatgaa    4680
atagtgtgca cacaacactg gcaggatgct gtgccttgga cagaactcct cagtctacag    4740
acagaggatg gcttctggaa acttacacca gaactgggac ttatattaaa tcttaataca    4800
aatggtttgc acagctttct taaacaaaaa ggcattcaat ctctaggtgt aaaaggaaga    4860
gaatgtctcc tggacctaat tgccacaatg ctggtactac agtttattcg caccaggttg    4920 gaaaagagg gaatagtgtt caaatcactg atgaaaatgg atgacccttc tatttccagg    4980
aatattccct gggcttttga ggcaataaag caagcaagtg aatgggtaag aagaactgaa    5040
ggacagtacc catctatctg cccacggctt gaactgggga acgactggga ctctgccacc    5100
aagcagttgc tgggactcca gcccataagc actgtgtccc ctcttcatag agtcctccat    5160
tacagtcaag gctaa                                                    5175

<210> SEQ ID NO 5
<211> LENGTH: 893
<212> TYPE: PRT
<213> ORGANISM: Homo sapiens

<400> SEQUENCE: 5

Met Ala Thr Glu Glu Phe Ile Ile Arg Ile Pro Pro Tyr His Tyr Ile
1               5                   10                  15

His Val Leu Asp Gln Asn Ser Asn Val Ser Arg Val Glu Val Gly Pro
            20                  25                  30

Lys Thr Tyr Ile Arg Gln Asp Asn Glu Arg Val Leu Phe Ala Pro Met
        35                  40                  45

Arg Met Val Thr Val Pro Pro Arg His Tyr Cys Thr Val Ala Asn Pro
    50                  55                  60

Val Ser Arg Asp Ala Gln Gly Leu Val Leu Phe Asp Val Thr Gly Gln
65                  70                  75                  80

Val Arg Leu Arg His Ala Asp Leu Glu Ile Arg Leu Ala Gln Asp Pro
                85                  90                  95

Phe Pro Leu Tyr Pro Gly Glu Val Leu Glu Lys Asp Ile Thr Pro Leu
            100                 105                 110

Gln Val Val Leu Pro Asn Thr Ala Leu His Leu Lys Ala Leu Leu Asp
        115                 120                 125

Phe Glu Asp Lys Asp Gly Asp Lys Val Val Ala Gly Asp Glu Trp Leu
    130                 135                 140

Phe Glu Gly Pro Gly Thr Tyr Ile Pro Arg Lys Glu Val Glu Val Val
145                 150                 155                 160

Glu Ile Ile Gln Ala Thr Ile Ile Arg Gln Asn Gln Ala Leu Arg Leu
                165                 170                 175

Arg Ala Arg Lys Glu Cys Trp Asp Arg Asp Gly Lys Glu Arg Val Thr
            180                 185                 190

Gly Glu Glu Trp Leu Val Thr Thr Val Gly Ala Tyr Leu Pro Ala Val
        195                 200                 205

Phe Glu Glu Val Leu Asp Leu Val Asp Ala Val Ile Leu Thr Glu Lys
    210                 215                 220

Thr Ala Leu His Leu Arg Ala Arg Arg Asn Phe Arg Asp Phe Arg Gly
225                 230                 235                 240

Val Ser Arg Arg Thr Gly Glu Glu Trp Leu Val Thr Val Gln Asp Thr
                245                 250                 255
```

```
Glu Ala His Val Pro Asp Val His Glu Val Leu Gly Val Val Pro
            260                 265                 270
Ile Thr Thr Leu Gly Pro His Asn Tyr Cys Val Ile Leu Asp Pro Val
        275                 280                 285
Gly Pro Asp Gly Lys Asn Gln Leu Gly Gln Lys Arg Val Val Lys Gly
290                 295                 300
Glu Lys Ser Phe Phe Leu Gln Pro Gly Glu Gln Leu Glu Gln Gly Ile
305                 310                 315                 320
Gln Asp Val Tyr Val Leu Ser Glu Gln Gln Gly Leu Leu Leu Arg Ala
                325                 330                 335
Leu Gln Pro Leu Glu Glu Gly Glu Asp Glu Glu Lys Val Ser His Gln
            340                 345                 350
Ala Gly Asp His Trp Leu Ile Arg Gly Pro Leu Glu Tyr Val Pro Ser
        355                 360                 365
Ala Lys Val Glu Val Val Glu Glu Arg Gln Ala Ile Pro Leu Asp Glu
    370                 375                 380
Asn Glu Gly Ile Tyr Val Gln Asp Val Lys Thr Gly Lys Val Arg Ala
385                 390                 395                 400
Val Ile Gly Ser Thr Tyr Met Leu Thr Gln Asp Glu Val Leu Trp Glu
                405                 410                 415
Lys Glu Leu Pro Pro Gly Val Glu Glu Leu Leu Asn Lys Gly Gln Asp
            420                 425                 430
Pro Leu Ala Asp Arg Gly Glu Lys Asp Thr Ala Lys Ser Leu Gln Pro
        435                 440                 445
Leu Ala Pro Arg Asn Lys Thr Arg Val Val Ser Tyr Arg Val Pro His
    450                 455                 460
Asn Ala Ala Val Gln Val Tyr Asp Tyr Arg Glu Lys Arg Ala Arg Val
465                 470                 475                 480
Val Phe Gly Pro Glu Leu Val Ser Leu Gly Pro Glu Glu Gln Phe Thr
                485                 490                 495
Val Leu Ser Leu Ser Ala Gly Arg Pro Lys Arg Pro His Ala Arg Arg
            500                 505                 510
Ala Leu Cys Leu Leu Leu Gly Pro Asp Phe Phe Thr Asp Val Ile Thr
        515                 520                 525
Ile Glu Thr Ala Asp His Ala Arg Leu Gln Leu Gln Leu Ala Tyr Asn
    530                 535                 540
Trp His Phe Glu Val Asn Asp Arg Lys Asp Pro Gln Glu Thr Ala Lys
545                 550                 555                 560
Leu Phe Ser Val Pro Asp Phe Val Gly Asp Ala Cys Lys Ala Ile Ala
                565                 570                 575
Ser Arg Val Arg Gly Ala Val Ala Ser Val Thr Phe Asp Asp Phe His
            580                 585                 590
Lys Asn Ser Ala Arg Ile Ile Arg Thr Ala Val Phe Gly Phe Glu Thr
        595                 600                 605
Ser Glu Ala Lys Gly Pro Asp Gly Met Ala Leu Pro Arg Pro Arg Asp
    610                 615                 620
Gln Ala Val Phe Pro Gln Asn Gly Leu Val Val Ser Ser Val Asp Val
625                 630                 635                 640
Gln Ser Val Glu Pro Val Asp Gln Arg Thr Arg Asp Ala Leu Gln Arg
                645                 650                 655
Ser Val Gln Leu Ala Ile Glu Ile Thr Thr Asn Ser Gln Glu Ala Ala
            660                 665                 670
Ala Lys His Glu Ala Gln Arg Leu Glu Gln Glu Ala Arg Gly Arg Leu
```

|     |     |     |     | 675 |     |     |     |     | 680 |     |     |     |     | 685 |     |
| --- | --- | --- | --- | --- | --- | --- | --- | --- | --- | --- | --- | --- | --- | --- | --- |
| Glu | Arg | Gln | Lys | Ile | Leu | Asp | Gln | Ser | Glu | Ala | Glu | Lys | Ala | Arg | Lys |
| 690 |     |     |     |     | 695 |     |     |     |     | 700 |     |     |     |     |     |
| Glu | Leu | Leu | Glu | Leu | Glu | Ala | Leu | Ser | Met | Ala | Val | Glu | Ser | Thr | Gly |
| 705 |     |     |     |     | 710 |     |     |     |     | 715 |     |     |     |     | 720 |
| Thr | Ala | Lys | Ala | Glu | Ala | Glu | Ser | Arg | Ala | Glu | Ala | Ala | Arg | Ile | Glu |
|     |     |     |     | 725 |     |     |     |     | 730 |     |     |     |     | 735 |     |
| Gly | Glu | Gly | Ser | Val | Leu | Gln | Ala | Lys | Leu | Lys | Ala | Gln | Ala | Leu | Ala |
|     |     |     | 740 |     |     |     |     | 745 |     |     |     |     | 750 |     |     |
| Ile | Glu | Thr | Glu | Ala | Glu | Leu | Gln | Arg | Val | Gln | Lys | Val | Arg | Glu | Leu |
|     |     | 755 |     |     |     |     | 760 |     |     |     |     | 765 |     |     |     |
| Glu | Leu | Val | Tyr | Ala | Arg | Ala | Gln | Leu | Glu | Leu | Glu | Val | Ser | Lys | Ala |
| 770 |     |     |     |     | 775 |     |     |     |     | 780 |     |     |     |     |     |
| Gln | Gln | Leu | Ala | Glu | Val | Glu | Val | Lys | Lys | Phe | Lys | Gln | Met | Thr | Glu |
| 785 |     |     |     |     | 790 |     |     |     |     | 795 |     |     |     |     | 800 |
| Ala | Ile | Gly | Pro | Ser | Thr | Ile | Arg | Asp | Leu | Ala | Val | Ala | Gly | Pro | Glu |
|     |     |     |     | 805 |     |     |     |     | 810 |     |     |     |     | 815 |     |
| Met | Gln | Val | Lys | Leu | Leu | Gln | Ser | Leu | Gly | Leu | Lys | Ser | Thr | Leu | Ile |
|     |     |     | 820 |     |     |     |     | 825 |     |     |     |     | 830 |     |     |
| Thr | Asp | Gly | Ser | Thr | Pro | Ile | Asn | Leu | Phe | Asn | Thr | Ala | Phe | Gly | Leu |
|     |     | 835 |     |     |     |     | 840 |     |     |     |     | 845 |     |     |     |
| Leu | Gly | Met | Gly | Pro | Glu | Gly | Gln | Pro | Leu | Gly | Arg | Arg | Val | Ala | Ser |
| 850 |     |     |     |     | 855 |     |     |     |     | 860 |     |     |     |     |     |
| Gly | Pro | Ser | Pro | Gly | Glu | Gly | Ile | Ser | Pro | Gln | Ser | Ala | Gln | Ala | Pro |
| 865 |     |     |     |     | 870 |     |     |     |     | 875 |     |     |     |     | 880 |
| Gln | Ala | Pro | Gly | Asp | Asn | His | Val | Val | Pro | Val | Leu | Arg |     |     |     |
|     |     |     |     | 885 |     |     |     |     | 890 |     |     |     |     |     |     |

<210> SEQ ID NO 6
<211> LENGTH: 2682
<212> TYPE: DNA
<213> ORGANISM: Homo sapiens

<400> SEQUENCE: 6

| atggcaactg | aagagttcat | catccgcatc | cccccatacc | actatatcca | tgtgctggac | 60 |
| cagaacagca | acgtgtcccg | tgtggaggtc | gggccaaaga | cctacatccg | gcaggacaat | 120 |
| gagagggtac | tgtttgcccc | catgcgcatg | gtgaccgtcc | ccccacgtca | ctactgcaca | 180 |
| gtggccaacc | ctgtgtctcg | ggatgcccag | ggcttggtgc | tgtttgatgt | cacagggcaa | 240 |
| gttcggcttc | gccacgctga | cctcgagatc | cggctggccc | aggacccctt | cccctgtac | 300 |
| ccaggggagg | tgctggaaaa | ggacatcaca | ccctgcagg | tggttctgcc | caacactgcc | 360 |
| ctccatctaa | aggcgctgct | tgattttgag | gataaagatg | gagacaaggt | ggtggcagga | 420 |
| gatgagtggc | ttttcgaggg | acctggcacg | tacatccccc | ggaaggaagt | ggaggtcgtg | 480 |
| gagatcattc | aggccaccat | catcaggcag | aaccaggctc | tgcggctcag | ggcccgcaag | 540 |
| gagtgctggg | accgggacgg | caaggagagg | gtgacagggg | aagaatggct | ggtcaccaca | 600 |
| gtagggcgt | acctcccagc | ggtgtttgag | gaggttctgg | atttggtgga | cgccgtcatc | 660 |
| cttacgaaa | agacagccct | gcacctccgg | gctcggcgga | acttccggga | cttcagggga | 720 |
| gtgtcccgcc | gcactgggga | ggagtggctg | gtaacagtgc | aggacacaga | ggcccacgtg | 780 |
| ccagatgtcc | acgaggaggt | gctggggggtt | gtgcccatca | ccaccctggg | ccccacaac | 840 |
| tactgcgtga | ttctcgaccc | tgtcggaccg | gatggcaaga | tcagctgggg | gcagaagcgc | 900 |

```
gtggtcaagg gagagaagtc ttttttcctc cagccaggag agcagctgga acaaggcatc    960
caggatgtgt atgtgctgtc ggagcagcag gggctgctgc tgaggccct gcagcccctg    1020 gaggaggggg aggatgagga aaggtctca caccaggctg gggaccactg gctcatccgc    1080 ggaccccctgg agtatgtgcc atctgccaaa gtggaggtgg tggaggagcg ccaggccatc    1140
cctctagacg agaacgaggg catctatgtg caggatgtca agaccggaaa ggtgcgcgct    1200
gtgattggaa gcacctacat gctgacccag gacgaagtcc tgtgggagaa agagctgcct    1260 cccgggggtgg aggagctgct gaacaagggg caggaccctc tggcagacag gggtgagaag    1320
gacacagcta agagcctcca gcccttggcg ccccggaaca agacccgtgt ggtcagctac    1380
cgcgtgcccc acaacgctgc ggtgcaggtg tacgactacc gagagaagcg agcccgcgtg    1440
gtcttcgggc ctgagctggt gtcgctgggt cctgaggagc agttcacagt gttgtccctc    1500
tcagctgggc ggcccaagcg tccccatgcc cgccgtgcgc tctgcctgct gctggggcct    1560
gacttcttca cagacgtcat caccatcgaa acggcggatc atgccaggct gcaactgcag    1620
ctggcctaca actggcactt tgaggtgaat gaccggaagg accccaaga gacggccaag    1680 ctcttttcag tgccagactt tgtaggtgat gcctgcaaag ccatcgcatc ccgggtgcgg    1740
ggggccgtgg cctctgtcac tttcgatgac ttccataaga actcagcccg catcattcgc    1800
actgctgtct ttggctttga gacctcggaa gcgaagggcc ccgatggcat ggccctgccc    1860
aggcccgcgg accaggctgt cttcccccaa aacgggctgg tggtcagcag tgtggacgtg    1920
cagtcagtgg agcctgtgga tcagaggacc cgggacgccc tgcaacgcag cgtccagctg    1980
gccatcgaga tcaccaccaa ctcccaggaa gcggcggcca gcatgaggc tcagagactg    2040 gagcaggaag cccgcggccg gcttgagcgg cagaagatcc tggaccagtc agaagccgag    2100
aaagctcgca aggaactttt ggagctggag gctctgagca tggccgtgga gagcaccggg    2160
actgccaagg cggaggccga gtccgtgcg gaggcagccc ggattgaggg agaagggtcc    2220
gtgctgcagg ccaagctaaa agcacaggcc ttggccattg aaacggaggc tgagctccag    2280
agggtccaga aggtccgaga gctggaactg gtctatgccc gggcccagct ggagctggag    2340
gtgagcaagg ctcagcagct ggctgaggtg gaggtgaaga agttcaagca gatgacagag    2400
gccataggcc ccagcaccat cagggacctt gctgtggctg ggcctgagat gcaggtaaaa    2460
ctgctccagt ccctgggcct gaaatcaacc ctcatcaccg atggctccac tcccatcaac    2520
ctcttcaaca cagcctttgg gctgctgggg atggggcccg agggtcagcc cctgggcaga    2580
agggtggcca gtgggcccag ccctgggggag gggatatccc cccagtctgc tcaggcccct    2640
caagctcctg gagacaacca cgtggtgcct gtactgcgct aa                       2682
```

<210> SEQ ID NO 7
<211> LENGTH: 12
<212> TYPE: PRT
<213> ORGANISM: Homo sapiens

<400> SEQUENCE: 7

Met Ala Gly Cys Gly Cys Pro Cys Gly Cys Gly Ala
1               5                   10

<210> SEQ ID NO 8
<211> LENGTH: 905
<212> TYPE: PRT
<213> ORGANISM: Artificial Sequence
<220> FEATURE:
<223> OTHER INFORMATION: CP-hMVP based on Homo sapien

```
<400> SEQUENCE: 8

Met Ala Gly Cys Gly Cys Pro Cys Gly Cys Gly Ala Met Ala Thr Glu
1               5                   10                  15

Glu Phe Ile Ile Arg Ile Pro Pro Tyr His Tyr Ile His Val Leu Asp
            20                  25                  30

Gln Asn Ser Asn Val Ser Arg Val Glu Val Gly Pro Lys Thr Tyr Ile
        35                  40                  45

Arg Gln Asp Asn Glu Arg Val Leu Phe Ala Pro Met Arg Met Val Thr
    50                  55                  60

Val Pro Pro Arg His Tyr Cys Thr Val Ala Asn Pro Val Ser Arg Asp
65                  70                  75                  80

Ala Gln Gly Leu Val Leu Phe Asp Val Thr Gly Gln Val Arg Leu Arg
                85                  90                  95

His Ala Asp Leu Glu Ile Arg Leu Ala Gln Asp Pro Phe Pro Leu Tyr
            100                 105                 110

Pro Gly Glu Val Leu Glu Lys Asp Ile Thr Pro Leu Gln Val Val Leu
        115                 120                 125

Pro Asn Thr Ala Leu His Leu Lys Ala Leu Leu Asp Phe Glu Asp Lys
    130                 135                 140

Asp Gly Asp Lys Val Val Ala Gly Asp Glu Trp Leu Phe Glu Gly Pro
145                 150                 155                 160

Gly Thr Tyr Ile Pro Arg Lys Glu Val Glu Val Glu Ile Ile Gln
                165                 170                 175

Ala Thr Ile Ile Arg Gln Asn Gln Ala Leu Arg Leu Arg Ala Arg Lys
            180                 185                 190

Glu Cys Trp Asp Arg Asp Gly Lys Glu Arg Val Thr Gly Glu Glu Trp
        195                 200                 205

Leu Val Thr Thr Val Gly Ala Tyr Leu Pro Ala Val Phe Glu Glu Val
    210                 215                 220

Leu Asp Leu Val Asp Ala Val Ile Leu Thr Glu Lys Thr Ala Leu His
225                 230                 235                 240

Leu Arg Ala Arg Arg Asn Phe Arg Asp Phe Arg Gly Val Ser Arg Arg
                245                 250                 255

Thr Gly Glu Glu Trp Leu Val Thr Val Gln Asp Thr Glu Ala His Val
            260                 265                 270

Pro Asp Val His Glu Glu Val Leu Gly Val Val Pro Ile Thr Thr Leu
        275                 280                 285

Gly Pro His Asn Tyr Cys Val Ile Leu Asp Pro Val Gly Pro Asp Gly
    290                 295                 300

Lys Asn Gln Leu Gly Gln Lys Arg Val Val Lys Gly Glu Lys Ser Phe
305                 310                 315                 320

Phe Leu Gln Pro Gly Glu Gln Leu Glu Gln Gly Ile Gln Asp Val Tyr
                325                 330                 335

Val Leu Ser Glu Gln Gln Gly Leu Leu Leu Arg Ala Leu Gln Pro Leu
            340                 345                 350

Glu Glu Gly Glu Asp Glu Glu Lys Val Ser His Gln Ala Gly Asp His
        355                 360                 365

Trp Leu Ile Arg Gly Pro Leu Glu Tyr Val Pro Ser Ala Lys Val Glu
    370                 375                 380

Val Val Glu Glu Arg Gln Ala Ile Pro Leu Asp Glu Asn Glu Gly Ile
385                 390                 395                 400

Tyr Val Gln Asp Val Lys Thr Gly Lys Val Arg Ala Val Ile Gly Ser
                405                 410                 415
```

```
Thr Tyr Met Leu Thr Gln Asp Glu Val Leu Trp Glu Lys Glu Leu Pro
            420                 425                 430

Pro Gly Val Glu Glu Leu Leu Asn Lys Gly Gln Asp Pro Leu Ala Asp
            435                 440                 445

Arg Gly Glu Lys Asp Thr Ala Lys Ser Leu Gln Pro Leu Ala Pro Arg
            450                 455                 460

Asn Lys Thr Arg Val Val Ser Tyr Arg Val Pro His Asn Ala Ala Val
465                 470                 475                 480

Gln Val Tyr Asp Tyr Arg Glu Lys Arg Ala Arg Val Val Phe Gly Pro
                    485                 490                 495

Glu Leu Val Ser Leu Gly Pro Glu Glu Gln Phe Thr Val Leu Ser Leu
            500                 505                 510

Ser Ala Gly Arg Pro Lys Arg Pro His Ala Arg Arg Ala Leu Cys Leu
            515                 520                 525

Leu Leu Gly Pro Asp Phe Phe Thr Asp Val Ile Thr Ile Glu Thr Ala
            530                 535                 540

Asp His Ala Arg Leu Gln Leu Gln Leu Ala Tyr Asn Trp His Phe Glu
545                 550                 555                 560

Val Asn Asp Arg Lys Asp Pro Gln Glu Thr Ala Lys Leu Phe Ser Val
                    565                 570                 575

Pro Asp Phe Val Gly Asp Ala Cys Lys Ala Ile Ala Ser Arg Val Arg
                    580                 585                 590

Gly Ala Val Ala Ser Val Thr Phe Asp Asp Phe His Lys Asn Ser Ala
            595                 600                 605

Arg Ile Ile Arg Thr Ala Val Phe Gly Phe Glu Thr Ser Glu Ala Lys
            610                 615                 620

Gly Pro Asp Gly Met Ala Leu Pro Arg Pro Arg Asp Gln Ala Val Phe
625                 630                 635                 640

Pro Gln Asn Gly Leu Val Val Ser Ser Val Asp Val Gln Ser Val Glu
                    645                 650                 655

Pro Val Asp Gln Arg Thr Arg Asp Ala Leu Gln Arg Ser Val Gln Leu
                    660                 665                 670

Ala Ile Glu Ile Thr Thr Asn Ser Gln Glu Ala Ala Lys His Glu
            675                 680                 685

Ala Gln Arg Leu Glu Gln Glu Ala Arg Gly Arg Leu Glu Arg Gln Lys
            690                 695                 700

Ile Leu Asp Gln Ser Glu Ala Glu Lys Ala Arg Lys Glu Leu Leu Glu
705                 710                 715                 720

Leu Glu Ala Leu Ser Met Ala Val Glu Ser Thr Gly Thr Ala Lys Ala
                    725                 730                 735

Glu Ala Glu Ser Arg Ala Glu Ala Arg Ile Glu Gly Glu Gly Ser
            740                 745                 750

Val Leu Gln Ala Lys Leu Lys Ala Gln Ala Leu Ala Ile Glu Thr Glu
            755                 760                 765

Ala Glu Leu Gln Arg Val Gln Lys Val Arg Glu Leu Glu Leu Val Tyr
            770                 775                 780

Ala Arg Ala Gln Leu Glu Leu Glu Val Ser Lys Ala Gln Gln Leu Ala
785                 790                 795                 800

Glu Val Glu Val Lys Lys Phe Lys Gln Met Thr Glu Ala Ile Gly Pro
                    805                 810                 815

Ser Thr Ile Arg Asp Leu Ala Val Ala Gly Pro Glu Met Gln Val Lys
            820                 825                 830
```

```
Leu Leu Gln Ser Leu Gly Leu Lys Ser Thr Leu Ile Thr Asp Gly Ser
            835                 840                 845

Thr Pro Ile Asn Leu Phe Asn Thr Ala Phe Gly Leu Leu Gly Met Gly
    850                 855                 860

Pro Glu Gly Gln Pro Leu Gly Arg Arg Val Ala Ser Gly Pro Ser Pro
865                 870                 875                 880

Gly Glu Gly Ile Ser Pro Gln Ser Ala Gln Ala Pro Gln Ala Pro Gly
                885                 890                 895

Asp Asn His Val Val Pro Val Leu Arg
            900                 905

<210> SEQ ID NO 9
<211> LENGTH: 2718
<212> TYPE: DNA
<213> ORGANISM: Artificial Sequence
<220> FEATURE:
<223> OTHER INFORMATION: CP-hMVP cDNA based on Homo sapien

<400> SEQUENCE: 9
atggcaggct gcggttgtcc atgcggttgt ggcgccatgg caactgaaga gttcatcatc      60
cgcatccccc cataccacta tatccatgtg ctggaccaga acagcaacgt gtcccgtgtg     120
gaggtcgggc aaagaccta catccggcag acaatgaga gggtactgtt tgcccccatg       180
cgcatggtga ccgtcccccc acgtcactac tgcacagtgg ccaaccctgt gtctcgggat     240
gcccagggct tggtgctgtt tgatgtcaca gggcaagttc ggcttcgcca cgctgacctc     300
gagatccggc tggcccagga ccccttcccc ctgtacccag gggaggtgct ggaaaaggac     360
atcacacccc tgcaggtggt tctgcccaac actgccctcc atctaaaggc gctgcttgat     420
tttgaggata agatggagca caaggtggtg gcaggagatg agtggctttt cgagggacct     480
ggcacgtaca tcccccggaa ggaagtggag gtcgtggaga tcattcaggc caccatcatc     540
aggcagaacc aggctctgcg gctcaggggc cgcaaggagt gctgggaccg ggacggcaag     600
gagagggtga caggggaaga atggctggtc accacagtag gggcgtacct cccagcggtg     660
tttgaggagg ttctggattt ggtggacgcc gtcatcctta cggaaaagac agccctgcac     720
ctccgggctc ggcggaactt ccgggacttc aggggagtgt cccgccgcac tggggaggag     780
tggctggtaa cagtgcagga cacagaggcc cacgtgccag atgtccacga ggaggtgctg     840
ggggttgtgc ccatcaccac cctgggcccc cacaactact gcgtgattct cgaccctgtc     900
ggaccggatg gcaagaatca gctggggcag aagcgcgtgg tcaagggaga gaagtctttt     960
ttcctccagc aggagagca gctggaacaa ggcatccagg atgtgtatgt gctgtcggag    1020
cagcaggggc tgctgctgag ggccctgcag cccctggagg aggggagga tgaggagaag    1080 gtctcacacc aggctgggga ccactggctc atccgcggac ccctggagta tgtgccatct    1140
gccaaagtgg aggtggtgga ggagcgccag gccatccctc tagacgagaa cgagggcatc    1200
tatgtgcagg atgtcaagac cggaaaggtg cgcgctgtga ttggaagcac ctacatgctg    1260
acccaggacg aagtcctgtg ggagaaagag ctgcctcccg ggtggagga gctgctgaac    1320 aaggggcagg accctctggc agacagggt gagaaggaca cagctaagag cctccagccc    1380
ttggcgcccc ggaacaagac ccgtgtggtc agctaccgcg tgccccacaa cgctgcggtg    1440
caggtgtacg actaccgaga gaagcgagcc cgcgtggtct tcgggcctga gctggtgtcg    1500
ctgggtcctg aggagcagtt cacagtgttg tccctctcag ctgggcggcc caagcgtccc    1560
catgcccgcc gtgcgctctg cctgctgctg gggcctgact tcttcacaga cgtcatcacc    1620
```

-continued

```
atcgaaacgg cggatcatgc caggctgcaa ctgcagctgg cctacaactg cactttgag    1680 gtgaatgacc ggaaggaccc ccaagagacg gccaagctct tttcagtgcc agactttgta    1740
ggtgatgcct gcaaagccat cgcatcccgg gtgcgggggg ccgtggcctc tgtcactttc    1800
gatgacttcc ataagaactc agcccgcatc attcgcactg ctgtctttgg ctttgagacc    1860
tcggaagcga agggccccga tggcatggcc ctgcccaggc ccgggaccca ggctgtcttc    1920
ccccaaaacg ggctggtggt cagcagtgtg gacgtgcagt cagtggagcc tgtggatcag    1980
aggacccggg acgccctgca acgcagcgtc cagctggcca tcgagatcac caccaactcc    2040
caggaagcgg cggccaagca tgaggctcag agactggagc aggaagcccg cggccggctt    2100
gagcggcaga agatcctgga ccagtcagaa gccgagaaag ctcgcaagga acttttggag    2160
ctggaggctc tgagcatggc cgtggagagc accgggactg ccaaggcgga ggccgagtcc    2220
cgtgcggagg cagcccggat tgaggagaa gggtccgtgc tgcaggccaa gctaaaagca    2280
caggccttgg ccattgaaac ggaggctgag ctccagaggg tccagaaggt ccgagagctg    2340
gaactggtct atgcccgggc ccagctggag ctggaggtga gcaaggctca gcagctggct    2400
gaggtggagg tgaagaagtt caagcagatg acagaggcca taggccccag caccatcagg    2460
gaccttgctg tggctgggcc tgagatgcag gtaaaactgc tccagtccct gggcctgaaa    2520
tcaaccctca tcaccgatgg ctccactccc atcaacctct tcaacacagc ctttgggctg    2580
ctggggatgg ggcccgaggg tcagcccctg ggcagaaggg tggccagtgg gcccagccct    2640
ggggagggga tatcccccca gtctgctcag gcccctcaag ctcctggaga caaccacgtg    2700
gtgcctgtac tgcgctaa                                                  2718
```

<210> SEQ ID NO 10
<211> LENGTH: 2627
<212> TYPE: PRT
<213> ORGANISM: Homo sapiens

<400> SEQUENCE: 10

```
Met Glu Lys Leu His Gly His Val Ser Ala His Pro Asp Ile Leu Ser
1               5                   10                  15

Leu Glu Asn Arg Cys Leu Ala Met Leu Pro Asp Leu Gln Pro Leu Glu
            20                  25                  30

Lys Leu His Gln His Val Ser Thr His Ser Asp Ile Leu Ser Leu Lys
        35                  40                  45

Asn Gln Cys Leu Ala Thr Leu Pro Asp Leu Lys Thr Met Glu Lys Pro
    50                  55                  60

His Gly Tyr Val Ser Ala His Pro Asp Ile Leu Ser Leu Glu Asn Gln
65                  70                  75                  80

Cys Leu Ala Thr Leu Ser Asp Leu Lys Thr Met Glu Lys Pro His Gly
                85                  90                  95

His Val Ser Ala His Pro Asp Ile Leu Ser Leu Glu Asn Arg Cys Leu
            100                 105                 110

Ala Thr Leu Pro Ser Leu Lys Ser Thr Val Ser Ala Ser Pro Leu Phe
        115                 120                 125

Gln Ser Leu Gln Ile Ser His Met Thr Gln Ala Asp Leu Tyr Arg Val
    130                 135                 140

Asn Asn Ser Asn Cys Leu Leu Ser Glu Pro Pro Ser Trp Arg Ala Gln
145                 150                 155                 160

His Phe Ser Lys Gly Leu Asp Leu Ser Thr Cys Pro Ile Ala Leu Lys
                165                 170                 175
```

```
Ser Ile Ser Ala Thr Glu Thr Ala Gln Glu Ala Thr Leu Gly Arg Trp
            180                 185                 190

Phe Asp Ser Glu Glu Lys Lys Gly Ala Glu Thr Gln Met Pro Ser Tyr
        195                 200                 205

Ser Leu Ser Leu Gly Glu Glu Glu Val Glu Asp Leu Ala Val Lys
        210                 215                 220

Leu Thr Ser Gly Asp Ser Glu Ser His Pro Glu Pro Thr Asp His Val
225                 230                 235                 240

Leu Gln Glu Lys Lys Met Ala Leu Leu Ser Leu Leu Cys Ser Thr Leu
                245                 250                 255

Val Ser Glu Val Asn Met Asn Asn Thr Ser Asp Pro Thr Leu Ala Ala
            260                 265                 270

Ile Phe Glu Ile Cys Arg Glu Leu Ala Leu Leu Glu Pro Glu Phe Ile
        275                 280                 285

Leu Lys Ala Ser Leu Tyr Ala Arg Gln Gln Leu Asn Val Arg Asn Val
        290                 295                 300

Ala Asn Asn Ile Leu Ala Ile Ala Ala Phe Leu Pro Ala Cys Arg Pro
305                 310                 315                 320

His Leu Arg Arg Tyr Phe Cys Ala Ile Val Gln Leu Pro Ser Asp Trp
                325                 330                 335

Ile Gln Val Ala Glu Leu Tyr Gln Ser Leu Ala Glu Gly Asp Lys Asn
            340                 345                 350

Lys Leu Val Pro Leu Pro Ala Cys Leu Arg Thr Ala Met Thr Asp Lys
        355                 360                 365

Phe Ala Gln Phe Asp Glu Tyr Gln Leu Ala Lys Tyr Asn Pro Arg Lys
        370                 375                 380

His Arg Ala Lys Arg His Pro Arg Arg Pro Arg Ser Pro Gly Met
385                 390                 395                 400

Glu Pro Pro Phe Ser His Arg Cys Phe Pro Arg Tyr Ile Gly Phe Leu
                405                 410                 415

Arg Glu Glu Gln Arg Lys Phe Glu Lys Ala Gly Asp Thr Val Ser Glu
            420                 425                 430

Lys Lys Asn Pro Pro Arg Phe Thr Leu Lys Lys Leu Val Gln Arg Leu
        435                 440                 445

His Ile His Lys Pro Ala Gln His Val Gln Ala Leu Leu Gly Tyr Arg
        450                 455                 460

Tyr Pro Ser Asn Leu Gln Leu Phe Ser Arg Ser Arg Leu Pro Gly Pro
465                 470                 475                 480

Trp Asp Ser Ser Arg Ala Gly Lys Arg Met Lys Leu Ser Arg Pro Glu
                485                 490                 495

Thr Trp Glu Arg Glu Leu Ser Leu Arg Gly Asn Lys Ala Ser Val Trp
            500                 505                 510

Glu Glu Leu Ile Glu Asn Gly Lys Leu Pro Phe Met Ala Met Leu Arg
        515                 520                 525

Asn Leu Cys Asn Leu Leu Arg Val Gly Ile Ser Ser Arg His His Glu
        530                 535                 540

Leu Ile Leu Gln Arg Leu Gln His Gly Lys Ser Val Ile His Ser Arg
545                 550                 555                 560

Gln Phe Pro Phe Arg Phe Leu Asn Ala His Asp Ala Ile Asp Ala Leu
                565                 570                 575

Glu Ala Gln Leu Arg Asn Gln Ala Leu Pro Phe Pro Ser Asn Ile Thr
            580                 585                 590

Leu Met Arg Arg Ile Leu Thr Arg Asn Glu Lys Asn Arg Pro Arg Arg
```

-continued

```
            595                 600                 605
Arg Phe Leu Cys His Leu Ser Arg Gln Gln Leu Arg Met Ala Met Arg
610                 615                 620

Ile Pro Val Leu Tyr Glu Gln Leu Lys Arg Glu Lys Leu Arg Val His
625                 630                 635                 640

Lys Ala Arg Gln Trp Lys Tyr Asp Gly Glu Met Leu Asn Arg Tyr Arg
                    645                 650                 655

Gln Ala Leu Glu Thr Ala Val Asn Leu Ser Val Lys His Ser Leu Pro
                660                 665                 670

Leu Leu Pro Gly Arg Thr Val Leu Val Tyr Leu Thr Asp Ala Asn Ala
            675                 680                 685

Asp Arg Leu Cys Pro Lys Ser Asn Pro Gln Gly Pro Pro Leu Asn Tyr
690                 695                 700

Ala Leu Leu Leu Ile Gly Met Met Ile Thr Arg Ala Glu Gln Val Asp
705                 710                 715                 720

Val Val Leu Cys Gly Gly Asp Thr Leu Lys Thr Ala Val Leu Lys Ala
                    725                 730                 735

Glu Glu Gly Ile Leu Lys Thr Ala Ile Lys Leu Gln Ala Gln Val Gln
                740                 745                 750

Glu Phe Asp Glu Asn Asp Gly Trp Ser Leu Asn Thr Phe Gly Lys Tyr
            755                 760                 765

Leu Leu Ser Leu Ala Gly Gln Arg Val Pro Val Asp Arg Val Ile Leu
770                 775                 780

Leu Gly Gln Ser Met Asp Asp Gly Met Ile Asn Val Ala Lys Gln Leu
785                 790                 795                 800

Tyr Trp Gln Arg Val Asn Ser Lys Cys Leu Phe Val Gly Ile Leu Leu
                    805                 810                 815

Arg Arg Val Gln Tyr Leu Ser Thr Asp Leu Asn Pro Asn Asp Val Thr
                820                 825                 830

Leu Ser Gly Cys Thr Asp Ala Ile Leu Lys Phe Ile Ala Glu His Gly
            835                 840                 845

Ala Ser His Leu Leu Glu His Val Gly Gln Met Asp Lys Ile Phe Lys
850                 855                 860

Ile Pro Pro Pro Pro Gly Lys Thr Gly Val Gln Ser Leu Arg Pro Leu
865                 870                 875                 880

Glu Glu Asp Thr Pro Ser Pro Leu Ala Pro Val Ser Gln Gln Gly Trp
                    885                 890                 895

Arg Ser Ile Arg Leu Phe Ile Ser Ser Thr Phe Arg Asp Met His Gly
                900                 905                 910

Glu Arg Asp Leu Leu Leu Arg Ser Val Leu Pro Ala Leu Gln Ala Arg
            915                 920                 925

Ala Ala Pro His Arg Ile Ser Leu His Gly Ile Asp Leu Arg Trp Gly
930                 935                 940

Val Thr Glu Glu Glu Thr Arg Arg Asn Arg Gln Leu Glu Val Cys Leu
945                 950                 955                 960

Gly Glu Val Glu Asn Ala Gln Leu Phe Val Gly Ile Leu Gly Ser Arg
                    965                 970                 975

Tyr Gly Tyr Ile Pro Pro Ser Tyr Asn Leu Pro Asp His Pro His Phe
                980                 985                 990

His Trp Ala Gln Gln Tyr Pro Ser Gly Arg Ser Val Thr Glu Met Glu
            995                 1000                1005

Val Met Gln Phe Leu Asn Arg Asn Gln Arg Leu Gln Pro Ser Ala
            1010                1015                1020
```

-continued

Gln Ala Leu Ile Tyr Phe Arg Asp Ser Ser Phe Leu Ser Ser Val
1025            1030                1035

Pro Asp Ala Trp Lys Ser Asp Phe Val Ser Glu Ser Glu Glu Ala
1040            1045                1050

Ala Cys Arg Ile Ser Glu Leu Lys Ser Tyr Leu Ser Arg Gln Lys
1055            1060                1065

Gly Ile Thr Cys Arg Arg Tyr Pro Cys Glu Trp Gly Gly Val Ala
1070            1075                1080

Ala Gly Arg Pro Tyr Val Gly Leu Glu Glu Phe Gly Gln Leu
1085            1090                1095

Val Leu Gln Asp Val Trp Asn Met Ile Gln Lys Leu Tyr Leu Gln
1100            1105                1110

Pro Gly Ala Leu Leu Glu Gln Pro Val Ser Ile Pro Asp Asp Asp
1115            1120                1125

Leu Val Gln Ala Thr Phe Gln Leu Gln Lys Pro Pro Ser Pro
1130            1135                1140

Ala Arg Pro Arg Leu Leu Gln Asp Thr Val Gln Gln Leu Met Leu
1145            1150                1155

Pro His Gly Arg Leu Ser Leu Val Thr Gly Gln Ser Gly Gln Gly
1160            1165                1170

Lys Thr Ala Phe Leu Ala Ser Leu Val Ser Ala Leu Gln Ala Pro
1175            1180                1185

Asp Gly Ala Lys Val Ala Pro Leu Val Phe Phe His Phe Ser Gly
1190            1195                1200

Ala Arg Pro Asp Gln Gly Leu Ala Leu Thr Leu Leu Arg Arg Leu
1205            1210                1215

Cys Thr Tyr Leu Arg Gly Gln Leu Lys Glu Pro Gly Ala Leu Pro
1220            1225                1230

Ser Thr Tyr Arg Ser Leu Val Trp Glu Leu Gln Gln Arg Leu Leu
1235            1240                1245

Pro Lys Ser Ala Glu Ser Leu His Pro Gly Gln Thr Gln Val Leu
1250            1255                1260

Ile Ile Asp Gly Ala Asp Arg Leu Val Asp Gln Asn Gly Gln Leu
1265            1270                1275

Ile Ser Asp Trp Ile Pro Lys Lys Leu Pro Arg Cys Val His Leu
1280            1285                1290

Val Leu Ser Val Ser Ser Asp Ala Gly Leu Gly Glu Thr Leu Glu
1295            1300                1305

Gln Ser Gln Gly Ala His Val Leu Ala Leu Gly Pro Leu Glu Ala
1310            1315                1320

Ser Ala Arg Ala Arg Leu Val Arg Glu Glu Leu Ala Leu Tyr Gly
1325            1330                1335

Lys Arg Leu Glu Glu Ser Pro Phe Asn Asn Gln Met Arg Leu Leu
1340            1345                1350

Leu Val Lys Arg Glu Ser Gly Arg Pro Leu Tyr Leu Arg Leu Val
1355            1360                1365

Thr Asp His Leu Arg Leu Phe Thr Leu Tyr Glu Gln Val Ser Glu
1370            1375                1380

Arg Leu Arg Thr Leu Pro Ala Thr Val Pro Leu Leu Leu Gln His
1385            1390                1395

Ile Leu Ser Thr Leu Glu Lys Glu His Gly Pro Asp Val Leu Pro
1400            1405                1410

-continued

```
Gln Ala Leu Thr Ala Leu Glu Val Thr Arg Ser Gly Leu Thr Val
1415                1420                1425

Asp Gln Leu His Gly Val Leu Ser Val Trp Arg Thr Leu Pro Lys
1430                1435                1440

Gly Thr Lys Ser Trp Glu Glu Ala Val Ala Ala Gly Asn Ser Gly
1445                1450                1455

Asp Pro Tyr Pro Met Gly Pro Phe Ala Cys Leu Val Gln Ser Leu
1460                1465                1470

Arg Ser Leu Leu Gly Glu Gly Pro Leu Glu Arg Pro Gly Ala Arg
1475                1480                1485

Leu Cys Leu Pro Asp Gly Pro Leu Arg Thr Ala Ala Lys Arg Cys
1490                1495                1500

Tyr Gly Lys Arg Pro Gly Leu Glu Asp Thr Ala His Ile Leu Ile
1505                1510                1515

Ala Ala Gln Leu Trp Lys Thr Cys Asp Ala Asp Ala Ser Gly Thr
1520                1525                1530

Phe Arg Ser Cys Pro Pro Glu Ala Leu Gly Asp Leu Pro Tyr His
1535                1540                1545

Leu Leu Gln Ser Gly Asn Arg Gly Leu Leu Ser Lys Phe Leu Thr
1550                1555                1560

Asn Leu His Val Val Ala Ala His Leu Glu Leu Gly Leu Val Ser
1565                1570                1575

Arg Leu Leu Glu Ala His Ala Leu Tyr Ala Ser Ser Val Pro Lys
1580                1585                1590

Glu Glu Gln Lys Leu Pro Glu Ala Asp Val Ala Val Phe Arg Thr
1595                1600                1605

Phe Leu Arg Gln Gln Ala Ser Ile Leu Ser Gln Tyr Pro Arg Leu
1610                1615                1620

Leu Pro Gln Gln Ala Ala Asn Gln Pro Leu Asp Ser Pro Leu Cys
1625                1630                1635

His Gln Ala Ser Leu Leu Ser Arg Arg Trp His Leu Gln His Thr
1640                1645                1650

Leu Arg Trp Leu Asn Lys Pro Arg Thr Met Lys Asn Gln Gln Ser
1655                1660                1665

Ser Ser Leu Ser Leu Ala Val Ser Ser Ser Pro Thr Ala Val Ala
1670                1675                1680

Phe Ser Thr Asn Gly Gln Arg Ala Ala Val Gly Thr Ala Asn Gly
1685                1690                1695

Thr Val Tyr Leu Leu Asp Leu Arg Thr Trp Gln Glu Glu Lys Ser
1700                1705                1710

Val Val Ser Gly Cys Asp Gly Ile Ser Ala Cys Leu Phe Leu Ser
1715                1720                1725

Asp Asp Thr Leu Phe Leu Thr Ala Phe Asp Gly Leu Leu Glu Leu
1730                1735                1740

Trp Asp Leu Gln His Gly Cys Arg Val Leu Gln Thr Lys Ala His
1745                1750                1755

Gln Tyr Gln Ile Thr Gly Cys Cys Leu Ser Pro Asp Cys Arg Leu
1760                1765                1770

Leu Ala Thr Val Cys Leu Gly Gly Cys Leu Lys Leu Trp Asp Thr
1775                1780                1785

Val Arg Gly Gln Leu Ala Phe Gln His Thr Tyr Pro Lys Ser Leu
1790                1795                1800

Asn Cys Val Ala Phe His Pro Glu Gly Gln Val Ile Ala Thr Gly
```

```
              1805                1810                1815
Ser Trp Ala Gly Ser Ile Ser Phe Phe Gln Val Asp Gly Leu Lys
    1820                1825                1830
Val Thr Lys Asp Leu Gly Ala Pro Gly Ala Ser Ile Arg Thr Leu
    1835                1840                1845
Ala Phe Asn Val Pro Gly Gly Val Val Ala Val Gly Arg Leu Asp
    1850                1855                1860
Ser Met Val Glu Leu Trp Ala Trp Arg Glu Gly Ala Arg Leu Ala
    1865                1870                1875
Ala Phe Pro Ala His His Gly Phe Val Ala Ala Leu Phe Leu
    1880                1885                1890
His Ala Gly Cys Gln Leu Leu Thr Ala Gly Glu Asp Gly Lys Val
    1895                1900                1905
Gln Val Trp Ser Gly Ser Leu Gly Arg Pro Arg Gly His Leu Gly
    1910                1915                1920
Ser Leu Ser Leu Ser Pro Ala Leu Ser Val Ala Leu Ser Pro Asp
    1925                1930                1935
Gly Asp Arg Val Ala Val Gly Tyr Arg Ala Asp Gly Ile Arg Ile
    1940                1945                1950
Tyr Lys Ile Ser Ser Gly Ser Gln Gly Ala Gln Gly Gln Ala Leu
    1955                1960                1965
Asp Val Ala Val Ser Ala Leu Ala Trp Leu Ser Pro Lys Val Leu
    1970                1975                1980
Val Ser Gly Ala Glu Asp Gly Ser Leu Gln Gly Trp Ala Leu Lys
    1985                1990                1995
Glu Cys Ser Leu Gln Ser Leu Trp Leu Leu Ser Arg Phe Gln Lys
    2000                2005                2010
Pro Val Leu Gly Leu Ala Thr Ser Gln Glu Leu Leu Ala Ser Ala
    2015                2020                2025
Ser Glu Asp Phe Thr Val Gln Leu Trp Pro Arg Gln Leu Leu Thr
    2030                2035                2040
Arg Pro His Lys Ala Glu Asp Phe Pro Cys Gly Thr Glu Leu Arg
    2045                2050                2055
Gly His Glu Gly Pro Val Ser Cys Cys Ser Phe Ser Thr Asp Gly
    2060                2065                2070
Gly Ser Leu Ala Thr Gly Gly Arg Asp Arg Ser Leu Leu Cys Trp
    2075                2080                2085
Asp Val Arg Thr Pro Lys Thr Pro Val Leu Ile His Ser Phe Pro
    2090                2095                2100
Ala Cys His Arg Asp Trp Val Thr Gly Cys Ala Trp Thr Lys Asp
    2105                2110                2115
Asn Leu Leu Ile Ser Cys Ser Ser Asp Gly Ser Val Gly Leu Trp
    2120                2125                2130
Asp Pro Glu Ser Gly Gln Arg Leu Gly Gln Phe Leu Gly His Gln
    2135                2140                2145
Ser Ala Val Ser Ala Val Ala Val Glu Glu His Val Val Ser
    2150                2155                2160
Val Ser Arg Asp Gly Thr Leu Lys Val Trp Asp His Gln Gly Val
    2165                2170                2175
Glu Leu Thr Ser Ile Pro Ala His Ser Gly Pro Ile Ser His Cys
    2180                2185                2190
Ala Ala Ala Met Glu Pro Arg Ala Ala Gly Gln Pro Gly Ser Glu
    2195                2200                2205
```

```
Leu Leu Val Val Thr Val Gly Leu Asp Gly Ala Thr Arg Leu Trp
2210                2215                2220

His Pro Leu Leu Val Cys Gln Thr His Thr Leu Leu Gly His Ser
    2225                2230                2235

Gly Pro Val Arg Ala Ala Ala Val Ser Glu Thr Ser Gly Leu Met
    2240                2245                2250

Leu Thr Ala Ser Glu Asp Gly Ser Val Arg Leu Trp Gln Val Pro
    2255                2260                2265

Lys Glu Ala Asp Asp Thr Cys Ile Pro Arg Ser Ser Ala Ala Val
    2270                2275                2280

Thr Ala Val Ala Trp Ala Pro Asp Gly Ser Met Ala Val Ser Gly
    2285                2290                2295

Asn Gln Ala Gly Glu Leu Ile Leu Trp Gln Glu Ala Lys Ala Val
    2300                2305                2310

Ala Thr Ala Gln Ala Pro Gly His Ile Gly Ala Leu Ile Trp Ser
    2315                2320                2325

Ser Ala His Thr Phe Phe Val Leu Ser Ala Asp Glu Lys Ile Ser
    2330                2335                2340

Glu Trp Gln Val Lys Leu Arg Lys Gly Ser Ala Pro Gly Asn Leu
    2345                2350                2355

Ser Leu His Leu Asn Arg Ile Leu Gln Glu Asp Leu Gly Val Leu
    2360                2365                2370

Thr Ser Leu Asp Trp Ala Pro Asp Gly His Phe Leu Ile Leu Ala
    2375                2380                2385

Lys Ala Asp Leu Lys Leu Leu Cys Met Lys Pro Gly Asp Ala Pro
    2390                2395                2400

Ser Glu Ile Trp Ser Ser Tyr Thr Glu Asn Pro Met Ile Leu Ser
    2405                2410                2415

Thr His Lys Glu Tyr Gly Ile Phe Val Leu Gln Pro Lys Asp Pro
    2420                2425                2430

Gly Val Leu Ser Phe Leu Arg Gln Lys Glu Ser Gly Glu Phe Glu
    2435                2440                2445

Glu Arg Leu Asn Phe Asp Ile Asn Leu Glu Asn Pro Ser Arg Thr
    2450                2455                2460

Leu Ile Ser Ile Thr Gln Ala Lys Pro Glu Ser Glu Ser Ser Phe
    2465                2470                2475

Leu Cys Ala Ser Ser Asp Gly Ile Leu Trp Asn Leu Ala Lys Cys
    2480                2485                2490

Ser Pro Glu Gly Glu Trp Thr Thr Gly Asn Met Trp Gln Lys Lys
    2495                2500                2505

Ala Asn Thr Pro Glu Thr Gln Thr Pro Gly Thr Asp Pro Ser Thr
    2510                2515                2520

Cys Arg Glu Ser Asp Ala Ser Met Asp Ser Asp Ala Ser Met Asp
    2525                2530                2535

Ser Glu Pro Thr Pro His Leu Lys Thr Arg Gln Arg Arg Lys Ile
    2540                2545                2550

His Ser Gly Ser Val Thr Ala Leu His Val Leu Pro Glu Leu Leu
    2555                2560                2565

Val Thr Ala Ser Lys Asp Arg Asp Val Lys Leu Trp Glu Arg Pro
    2570                2575                2580

Ser Met Gln Leu Leu Gly Leu Phe Arg Cys Glu Gly Ser Val Ser
    2585                2590                2595
```

| Cys | Leu | Glu | Pro | Trp | Leu | Gly | Ala | Asn | Ser | Thr | Leu | Gln | Leu | Ala |
|   | 2600 |   |   |   | 2605 |   |   |   |   | 2610 |   |   |   |   |

| Val | Gly | Asp | Val | Gln | Gly | Asn | Val | Tyr | Phe | Leu | Asn | Trp | Glu |
|   | 2615 |   |   |   | 2620 |   |   |   |   | 2625 |   |   |   |

<210> SEQ ID NO 11
<211> LENGTH: 7884
<212> TYPE: DNA
<213> ORGANISM: Homo sapiens

<400> SEQUENCE: 11

| | | | | | |
|---|---|---|---|---|---|
| atggaaaaac | tccatgggca | tgtgtctgcc | catccagaca | tcctctcctt | ggagaaccgg | 60 |
| tgcctggcta | tgctccctga | cttacagccc | ttggagaaac | tacatcagca | tgtatctacc | 120 |
| cactcagata | tcctctcctt | gaagaaccag | tgcctagcca | cgcttcctga | cctgaagacc | 180 |
| atggaaaaac | cacatggata | tgtgtctgcc | cacccagaca | tcctctcctt | ggagaaccag | 240 |
| tgcctggcca | cactttctga | cctgaagacc | atggagaaac | cacatggaca | tgtttctgcc | 300 |
| cacccagaca | tcctctcctt | ggagaaccgg | tgcctggcca | ccctccctag | tctaaagagc | 360 |
| actgtgtctg | ccagccccct | tgttccagagt | ctacagatat | ctcacatgac | gcaagctgat | 420 |
| ttgtaccgtg | tgaacaacag | caattgcctg | ctctctgagc | ctccaagttg | gagggctcag | 480 |
| catttctcta | agggactaga | cctttcaacc | tgccctatag | ccctgaaatc | catctctgcc | 540 |
| acagagacag | ctcaggaagc | aactttgggt | cgttggtttg | attcagaaga | gaagaaaggg | 600 |
| gcagagaccc | aaatgccttc | ttatagtctg | agcttgggag | aggaggagga | ggtggaggat | 660 |
| ctggccgtga | agctcaccct | ggagactct | gaatctcatc | cagagcctac | tgaccatgtc | 720 |
| cttcaggaaa | agaagatggc | tctactgagc | ttgctgtgct | ctactctggt | ctcagaagta | 780 |
| aacatgaaca | atacatctga | ccccaccctg | gctgccattt | ttgaaatctg | tcgtgaactt | 840 |
| gccctcctgg | agcctgagtt | tatcctcaag | gcatctttgt | atgccaggca | gcagctgaac | 900 |
| gtccggaatg | tggccaataa | catcttggcc | attgctgctt | tcttgccggc | gtgtcgcccc | 960 |
| cacctgcgac | gatatttctg | tgccattgtc | cagctgcctt | ctgactggat | ccaggtggct | 1020 |
| gagctttacc | agagcctggc | tgagggagat | aagaataagc | tggtgcccct | gccgccgtgt | 1080 |
| ctccgtactg | ccatgacgga | caaatttgcc | cagtttgacg | agtaccagct | ggctaagtac | 1140 |
| aaccctcgga | agcaccgggc | caagagacac | ccccgccggc | caccccgctc | tccagggatg | 1200 |
| gagcctccat | tttctcacag | atgttttcca | aggtacatag | ggtttctcag | agaagagcag | 1260 |
| agaaagtttg | agaaggccgg | tgatacagtg | tcagagaaaa | agaatcctcc | aaggttcacc | 1320 |
| ctgaagaagc | tggttcagcg | actgcacatc | cacaagcctg | cccagcacgt | tcaagccctg | 1380 |
| ctgggttaca | gataccccctc | caacctacag | ctctttttctc | gaagtcgcct | tcctgggcct | 1440 |
| tgggattcta | gcagagctgg | gaagaggatg | aagctgtcta | ggccagagac | ctgggagcgg | 1500 |
| gagctgagcc | tacgggggaa | caaagcgtcg | gtctgggagg | aactcattga | aaatgggaag | 1560 |
| cttcccttca | tggccatgct | tcggaacctg | tgcaacctgc | tgcgggttgg | aatcagttcc | 1620 |
| cgccaccatg | agctcattct | ccagagactc | cagcatggga | agtcggtgat | ccacagtcgg | 1680 |
| cagtttccat | tcagatttct | taacgcccat | gatgccattg | atgccctcga | ggctcaactc | 1740 |
| agaaatcaag | cattgccctt | tccttcgaat | ataacactga | tgaggcggat | actaactaga | 1800 |
| aatgaaaaga | accgtcccag | gcggaggttt | ctttgccacc | taagccgtca | gcagcttcgt | 1860 |
| atggcaatga | ggatacctgt | gttgtatgag | cagctcaaga | gggagaagct | gagagtacac | 1920 |
| aaggccagac | agtggaaata | tgatggtgag | atgctgaaca | ggtaccgaca | ggccctagag | 1980 |

```
acagctgtga acctctctgt gaagcacagc ctgcccctgc tgccaggccg cactgtcttg   2040
gtctatctga cagatgctaa tgcagacagg ctctgtccaa agagcaaccc acaagggccc   2100
ccgctgaact atgcactgct gttgattggg atgatgatca cgagggcgga gcaggtggac   2160
gtcgtgctgt gtggaggtga cactctgaag actgcagtgc ttaaggcaga agaaggcatc   2220
ctgaagactg ccatcaagct ccaggctcaa gtccaggagt ttgatgaaaa tgatggatgg   2280
tccctgaata cttttgggaa atacctgctg tctctggctg gccaaagggt tcctgtggac   2340
agggtcatcc tccttggcca aagcatggat gatggaatga taaatgtggc caaacagctt   2400
tactggcagc gtgtgaattc caagtgcctc tttgttggta tcctcctaag aagggtacaa   2460
tacctgtcaa cagatttgaa tcccaatgat gtgacactct caggctgtac tgatgcgata   2520
ctgaagttca ttgcagagca tggggcctcc catcttctgg aacatgtggg ccaaatggac   2580
aaaatattca agattccacc accccagga aagacagggg tccagtctct ccggccactg   2640
gaagaggaca ctccaagccc cttggctcct gtttcccagc aaggatggcg cagcatccgg   2700
cttttcattt catccacttt ccgagacatg cacggggagc gggacctgct gctgaggtct   2760
gtgctgccag cactgcaggc ccgagcggcc cctcaccgta tcagccttca cggaatcgac   2820
ctccgctggg gcgtcactga ggaggagacc cgtaggaaca gacaactgga agtgtgcctt   2880
ggggaggtgg agaacgcaca gctgtttgtg gggattctgg gctcccgtta tggatacatt   2940 cccccccagct acaaccttcc tgaccatcca cacttccact gggcccagca gtaccccttca   3000 gggcgctctg tgacagagat ggaggtgatg cagttcctga accggaacca acgtctgcag   3060
ccctctgccc aagctctcat ctacttccgg gattccagct cctcagctc tgtgccagat   3120 gcctggaaat ctgactttgt ttctgagtct gaagaggccg catgtcggat ctcagaactg   3180
aagagctacc taagcagaca gaaagggata acctgccgca gatacccctg tgagtggggg   3240
ggtgtggcag ctggccggcc ctatgttggc gggctggagg agtttgggca gttggttctg   3300
caggatgtat ggaatatgat ccagaagctc tacctgcagc ctggggccct gctggagcag   3360
ccagtgtcca tcccagacga tgacttggtc caggccacct tccagcagct gcagaagcca   3420
ccgagtcctg cccggccacg ccttcttcag gacacagtgc aacagctgat gctgccccac   3480
ggaaggctga gcctggtgac ggggcagtca ggacagggca agacagcctt cctggcatct   3540
cttgtgtcag ccctgcaggc tcctgatggg gccaaggtgg caccattagt cttcttccac   3600
ttttctgggg ctcgtcctga ccagggtctt gccctcactc tgctcagacg cctctgtacc   3660
tatctgcgtg gccaactaaa agagccaggt gccctcccca gcacctaccg aagcctggtg   3720
tgggagctgc agcagaggct gctgcccaag tctgctgagt ccctgcatcc tggccagacc   3780
caggtcctga tcatcgatgg ggctgatagg ttagtggacc agaatgggca gctgatttca   3840
gactggatcc caaagaagct tccccggtgt gtacacctgg tgctgagtgt gtctagtgat   3900
gcaggcctag gggagaccct tgagcagagc caggtgcccc acgtgctggc cttggggcct   3960
ctggaggcct ctgctcgggc ccggctggtg agagaggagc tggccctgta cgggaagcgg   4020
ctggaggagt caccatttaa caaccagatg cgactgctgc tggtgaagcg ggaatcaggc   4080
cggccgctct acctgcgctt ggtcaccgat cacctgagcc tcttcacgct gtatgagcag   4140
gtgtctgaga gactccggac cctgcctgcc actgtccccc tgctgctgca gcacatcctg   4200
agcacactgg agaaggagca cgggcctgat gtccttcccc aggcctttga ctgccctagaa   4260 gtcacacgga gtggtttgac tgtggaccag ctgcacggag tgctgagtgt gtggcggaca   4320
```

```
ctaccgaagg ggactaagag ctgggaagaa gcagtggctg ctggtaacag tggagacccc    4380 tacccccatgg gcccgtttgc ctgcctcgtc cagagtctgc gcagtttgct aggggagggc    4440
cctctggagc gccctggtgc ccggctgtgc ctccctgatg ggcccctgag aacagcagct    4500
aaacgttgct atgggaagag gccagggcta gaggacacgg cacacatcct cattgcagct    4560
cagctctgga agacatgtga cgctgatgcc tcaggcacct tccgaagttg ccctcctgag    4620
gctctgggag acctgcctta ccacctgctc cagagcggga accgtggact tctttcgaag    4680
ttccttacca acctccatgt ggtggctgca cacttggaat tgggtctggt ctctcggctc    4740
ttggaggccc atgccctcta tgcttcttca gtccccaaag aggaacaaaa gctccccgag    4800
gctgacgttg cagtgtttcg caccttcctg aggcagcagg cttcaatcct cagccagtac    4860
ccccggctcc tgccccagca ggcagccaac cagcccctgg actcacctct ttgccaccaa    4920
gcctcgctgc tctcccggag atggcacctc caacacacac tacgatggct aataaaccc    4980 cggaccatga aaaatcagca aagctccagc ctgtctctgg cagtttcctc atcccctact    5040
gctgtggcct tctccaccaa tgggcaaaga gcagctgtgg gcactgccaa tgggacagtt    5100
tacctgttgg acctgagaac ttggcaggag gagaagtctg tggtgagtgg ctgtgatgga    5160
atctctgctt gtttgttcct ctccgatgat cactctttc ttactgcctt cgacgggctc    5220
ctggagctct gggacctgca gcatggttgt cgggtgctgc agactaaggc tcaccagtac    5280
caaatcactg gctgctgcct gagcccagac tgccggctgc tagccaccgt gtgcttggga    5340
ggatgcctaa agctgtggga cacagtccgt gggcagctgg ccttccagca cacctacccc    5400
aagtccctga actgtgttgc cttccaccca gaggggcagg taatagccac aggcagctgg    5460
gctggcagca tcagcttctt ccaggtggat gggctcaaag tcaccaagga cctggggca    5520 cccggagcct ctatccgtac cttggccttc aatgtgcctg gggggttgt ggctgtgggc    5580 cggctggaca gtatggtgga gctgtgggcc tggcgagaag gggcacggct ggctgccttc    5640
cctgcccacc atggctttgt tgctgctgcg cttttcctgc atgcggggttg ccagttactg    5700 acggctggag aggatggcaa ggttcaggtg tggtcagggt ctctgggtcg gccccgtggg    5760 cacctggggtt ccctttctct ctctcctgcc ctctctgtgg cactcagccc agatggtgat    5820
cgggtggctg ttggatatcg agcggatggc attaggatct acaaaatctc ttcaggttcc    5880 caggggggctc agggtcaggc actggatgtg gcagtgtccg ccctggcctg gctaagcccc    5940
aaggtattgg tgagtggtgc agaagatggg tccttgcagg gctgggcact caaggaatgc    6000
tcccttcagt ccctctggct cctgtccaga ttccagaagc ctgtgctagg actgccact     6060 tcccaggagc tcttggcttc tgcctcagag gatttcacag tgcagctgtg gccaaggcag    6120
ctgctgacgc ggccacacaa ggcagaagac tttccctgtg gcactgagct gcggggacat    6180
gagggccctg tgagctgctg tagtttcagc actgatggag gcagcctggc caccggggc    6240 cgggatcgga gtctcctctg ctgggacgtg aggacaccca aaacccctgt tttgatccac    6300
tccttccctg cctgtcaccg tgactgggtc actggctgtg cctggaccaa agataaccta    6360
ctgatatcct gctccagtga tggctctgtg gggctctggg acccagagtc aggacagcgg    6420
cttggtcagt tcctgggtca tcagagtgct gtgagcgctg tggcagctgt ggaggagcac    6480
gtggtgtctg tgagccggga tgggaccttg aaagtgtggg accatcaagg cgtggagctg    6540
accagcatcc ctgctcactc aggaccatt agccactgtg cagctgccat ggagccccgt    6600
gcagctggac agcctgggtc agagcttctg gtggtaaccg tcgggctaga tggggccaca    6660
cggttatggc atccactctt ggtgtgccaa acccacaccc tcctgggaca cagcggccca    6720
```

```
gtccgtgctg ctgctgtttc agaaacctca ggcctcatgc tgaccgcctc tgaggatggt    6780
tctgtacggc tctggcaggt tcctaaggaa gcagatgaca catgtatacc aaggagttct    6840
gcagccgtca ctgctgtggc ttgggcacca gatggttcca tggcagtatc tggaaatcaa    6900
gctggggaac taatcttgtg caggaagct aaggctgtgg ccacagcaca ggctccaggc     6960
cacattggtg ctctgatctg gtcctcggca cacacctttt ttgtcctcag tgctgatgag    7020
aaaatcagcg agtggcaagt gaaactgcgg aagggttcgg cacccggaaa tttgagtctt    7080
cacctgaacc gaattctaca ggaggactta ggggtgctga caagtctgga ttgggctcct    7140
gatggtcact ttctcatctt ggccaaagca gatttgaagt tactttgcat gaagccaggg    7200
gatgctccat ctgaaatctg gagcagctat acagaaaatc ctatgatatt gtccacccac    7260
aaggagtatg gcatatttgt cctgcagccc aaggatcctg gagttctttc tttcttgagg    7320
caaaaggaat caggagagtt tgaagagagg ctgaactttg atataaactt agagaatcct    7380
agtaggaccc taatatcgat aactcaagcc aaacctgaat ctgagtcctc attttttgtgt   7440 gccagctctg atgggatcct atggaacctg gccaaatgca gcccagaagg agaatggacc    7500
acaggtaaca tgtggcagaa aaaagcaaac actccagaaa cccaaactcc agggacagac    7560
ccatctacct gcagggaatc tgatgccagc atggatagtg atgccagcat ggatagtgag    7620
ccaacaccac atctaaagac acggcagcgt agaaagattc actcgggctc tgtcacagcc    7680
ctccatgtgc tacctgagtt gctggtgaca gcttcgaagg acagagatgt taagctatgg    7740
gagagaccca gtatgcagct gctgggcctg ttccgatgcg aagggtcagt gagctgcctg    7800
gaaccttggc tgggcgctaa ctccaccctg cagcttgccg tgggagacgt gcagggcaat    7860
gtgtactttc tgaattggga atga                                          7884

<210> SEQ ID NO 12
<211> LENGTH: 98
<212> TYPE: RNA
<213> ORGANISM: Homo sapiens

<400> SEQUENCE: 12
ggcuggcuuu agcucagcgg uuacuucgac aguucuuuaa uugaaacaag caaccugucu     60
ggguuguucg agacccgcgg gcgcucucca guccuuuu                             98

<210> SEQ ID NO 13
<211> LENGTH: 88
<212> TYPE: RNA
<213> ORGANISM: Homo sapiens

<400> SEQUENCE: 13
ggcuggcuuu agcucagcgg uuacuucgag uacauuguaa ccaccucucu gggugguucg     60
agacccgcgg gugcuuucca gcucuuuu                                        88

<210> SEQ ID NO 14
<211> LENGTH: 88
<212> TYPE: RNA
<213> ORGANISM: Homo sapiens

<400> SEQUENCE: 14
ggcuggcuuu agcucagcgg uuacuucgcg ugucaucaaa ccaccucucu ggguuguucg     60
agacccgcgg gcgcucucca gcccucuu                                        88

<210> SEQ ID NO 15
```

```
<211> LENGTH: 252
<212> TYPE: PRT
<213> ORGANISM: Homo sapiens

<400> SEQUENCE: 15

Ala Asn Leu Arg Leu Pro Met Ala Ser Ala Leu Pro Glu Ala Leu Cys
1               5                   10                  15

Ser Gln Ser Arg Thr Thr Pro Val Asp Leu Cys Leu Leu Glu Glu Ser
            20                  25                  30

Val Gly Ser Leu Glu Gly Ser Arg Cys Pro Val Phe Ala Phe Gln Ser
        35                  40                  45

Ser Asp Thr Glu Ser Asp Glu Leu Ser Glu Val Leu Gln Asp Ser Cys
    50                  55                  60

Phe Leu Gln Ile Lys Cys Asp Thr Lys Asp Asp Ser Ile Pro Cys Phe
65                  70                  75                  80

Leu Glu Leu Lys Glu Glu Asp Glu Ile Val Cys Thr Gln His Trp Gln
                85                  90                  95

Asp Ala Val Pro Trp Thr Glu Leu Leu Ser Leu Gln Thr Glu Asp Gly
            100                 105                 110

Phe Trp Lys Leu Thr Pro Glu Leu Gly Leu Ile Leu Asn Leu Asn Thr
        115                 120                 125

Asn Gly Leu His Ser Phe Leu Lys Gln Lys Gly Ile Gln Ser Leu Gly
    130                 135                 140

Val Lys Gly Arg Glu Cys Leu Leu Asp Leu Ile Ala Thr Met Leu Val
145                 150                 155                 160

Leu Gln Phe Ile Arg Thr Arg Leu Glu Lys Glu Gly Ile Val Phe Lys
                165                 170                 175

Ser Leu Met Lys Met Asp Asp Pro Ser Ile Ser Arg Asn Ile Pro Trp
            180                 185                 190

Ala Phe Glu Ala Ile Lys Gln Ala Ser Glu Trp Val Arg Arg Thr Glu
        195                 200                 205

Gly Gln Tyr Pro Ser Ile Cys Pro Arg Leu Glu Leu Gly Asn Asp Trp
    210                 215                 220

Asp Ser Ala Thr Lys Gln Leu Leu Gly Leu Gln Pro Ile Ser Thr Val
225                 230                 235                 240

Ser Pro Leu His Arg Val Leu His Tyr Ser Gln Gly
                245                 250

<210> SEQ ID NO 16
<211> LENGTH: 31
<212> TYPE: PRT
<213> ORGANISM: Homo sapiens

<400> SEQUENCE: 16

Ser Gly Ser Trp Leu Arg Asp Ile Trp Asp Trp Ile Cys Glu Val Leu
1               5                   10                  15

Ser Asp Phe Lys Thr Trp Leu Lys Ala Lys Leu Met Pro Gln Leu
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: NS5A2-29 from Hepatitis C Virus as attached to
      MVP

<400> SEQUENCE: 17
```

Met Ala Gly Ser Trp Leu Arg Asp Ile Trp Asp Trp Ile Cys Glu Val
1               5                   10                  15

Leu Ser Asp Phe Lys Thr Trp Leu Lys Ala Lys Leu Met Pro Thr
            20                  25                  30

<210> SEQ ID NO 18
<211> LENGTH: 33
<212> TYPE: PRT
<213> ORGANISM: Staphylococcus aureus

<400> SEQUENCE: 18

Phe Asn Met Gln Gln Gln Arg Arg Phe Tyr Glu Ala Leu His Asp Pro
1               5                   10                  15

Asn Leu Asn Glu Glu Gln Arg Asn Ala Lys Ile Lys Ser Ile Arg Asp
            20                  25                  30

Asp

<210> SEQ ID NO 19
<211> LENGTH: 20
<212> TYPE: PRT
<213> ORGANISM: Hepatitis C virus

<400> SEQUENCE: 19

Arg Asp Ile Trp Asp Trp Ile Cys Glu Val Leu Ser Asp Phe Lys Thr
1               5                   10                  15

Trp Leu Lys Ala
            20

<210> SEQ ID NO 20
<211> LENGTH: 28
<212> TYPE: PRT
<213> ORGANISM: Hepatitis C virus

<400> SEQUENCE: 20

Gly Ser Trp Leu Arg Asp Ile Trp Asp Trp Ile Cys Glu Val Leu Ser
1               5                   10                  15

Asp Phe Lys Thr Trp Leu Lys Ala Lys Leu Met Pro
            20                  25

<210> SEQ ID NO 21
<211> LENGTH: 25
<212> TYPE: DNA
<213> ORGANISM: Artificial Sequence
<220> FEATURE:
<223> OTHER INFORMATION: Forward Primer based on based on Hepatitis C
      Virus and Rattus norvegicus

<400> SEQUENCE: 21
gaattcacca tggccggttc ctggc                                              25

<210> SEQ ID NO 22
<211> LENGTH: 26
<212> TYPE: DNA
<213> ORGANISM: Artificial Sequence
<220> FEATURE:
<223> OTHER INFORMATION: Reverse primer based on Hepatitis C Virus and
      Rattus norvegicus

<400> SEQUENCE: 22
ccttgctcac ccatggttgg catgag                                             26

<210> SEQ ID NO 23
<211> LENGTH: 36

<212> TYPE: PRT
<213> ORGANISM: Artificial Sequence
<220> FEATURE:
<223> OTHER INFORMATION: NS5A-rMVP partial sequence based on Hepatitis C Virus and Rattus norvegicus

<400> SEQUENCE: 23

```
Met Ala Gly Ser Trp Leu Arg Asp Ile Trp Asp Trp Ile Cys Glu Val
1               5                   10                  15

Leu Ser Asp Phe Lys Thr Trp Leu Lys Ala Lys Leu Met Pro Thr Met
            20                  25                  30

Ala Thr Glu Glu
        35
```

<210> SEQ ID NO 24
<211> LENGTH: 861
<212> TYPE: PRT
<213> ORGANISM: Rattus norvegicus

<400> SEQUENCE: 24

```
Met Ala Thr Glu Glu Ala Ile Ile Arg Ile Pro Pro Tyr His Tyr Ile
1               5                   10                  15

His Val Leu Asp Gln Asn Ser Asn Val Ser Arg Val Glu Val Gly Pro
            20                  25                  30

Lys Thr Tyr Ile Arg Gln Asp Asn Glu Arg Val Leu Phe Ala Pro Val
        35                  40                  45

Arg Met Val Thr Val Pro Pro Arg His Tyr Cys Ile Val Ala Asn Pro
    50                  55                  60

Val Ser Arg Asp Thr Gln Ser Ser Val Leu Phe Asp Ile Thr Gly Gln
65                  70                  75                  80

Val Arg Leu Arg His Ala Asp Gln Glu Ile Arg Leu Ala Gln Asp Pro
                85                  90                  95

Phe Pro Leu Tyr Pro Gly Glu Val Leu Glu Lys Asp Ile Thr Pro Leu
            100                 105                 110

Gln Val Val Leu Pro Asn Thr Ala Leu His Leu Lys Ala Leu Leu Asp
        115                 120                 125

Phe Glu Asp Lys Asn Gly Asp Lys Val Met Ala Gly Asp Glu Trp Leu
    130                 135                 140

Phe Glu Gly Pro Gly Thr Tyr Ile Pro Gln Lys Glu Val Glu Val Val
145                 150                 155                 160

Glu Ile Ile Gln Ala Thr Val Ile Lys Gln Asn Gln Ala Leu Arg Leu
                165                 170                 175

Arg Ala Arg Lys Glu Cys Phe Asp Arg Glu Gly Lys Gly Arg Val Thr
            180                 185                 190

Gly Glu Glu Trp Leu Val Arg Ser Val Gly Ala Tyr Leu Pro Ala Val
        195                 200                 205

Phe Glu Glu Val Leu Asp Leu Val Asp Ala Val Ile Leu Thr Glu Lys
    210                 215                 220

Thr Ala Leu His Leu Arg Ala Leu Gln Asn Phe Arg Asp Leu Arg Gly
225                 230                 235                 240

Val Leu His Arg Thr Gly Glu Glu Trp Leu Val Thr Val Gln Asp Thr
                245                 250                 255

Glu Ala His Val Pro Asp Val Tyr Glu Glu Val Leu Gly Val Val Pro
            260                 265                 270

Ile Thr Thr Leu Gly Pro Arg His Tyr Cys Val Ile Leu Asp Pro Met
        275                 280                 285
```

```
Gly Pro Asp Gly Lys Asn Gln Leu Gly Gln Lys Arg Val Val Lys Gly
    290                 295                 300

Glu Lys Ser Phe Phe Leu Gln Pro Gly Glu Arg Leu Glu Arg Gly Ile
305                 310                 315                 320

Gln Asp Val Tyr Val Leu Ser Glu Gln Gly Leu Leu Leu Lys Ala
                325                 330                 335

Leu Gln Pro Leu Glu Glu Gly Glu Ser Glu Lys Val Ser His Gln
            340                 345                 350

Ala Gly Asp Cys Trp Leu Ile Arg Gly Pro Leu Glu Tyr Val Pro Ser
            355                 360                 365

Ala Lys Val Glu Val Val Glu Glu Arg Gln Ala Ile Pro Leu Asp Gln
370                 375                 380

Asn Glu Gly Ile Tyr Val Gln Asp Val Lys Thr Gly Lys Val Arg Ala
385                 390                 395                 400

Val Ile Gly Ser Thr Tyr Met Leu Thr Gln Asp Glu Val Leu Trp Glu
                405                 410                 415

Lys Glu Leu Pro Ser Gly Val Glu Glu Leu Leu Asn Leu Gly His Asp
            420                 425                 430

Pro Leu Ala Asp Arg Gly Gln Lys Gly Thr Ala Lys Pro Leu Gln Pro
            435                 440                 445

Ser Ala Pro Arg Asn Lys Thr Arg Val Val Ser Tyr Arg Val Pro His
    450                 455                 460

Asn Ala Ala Val Gln Val Tyr Asp Tyr Arg Ala Lys Arg Ala Arg Val
465                 470                 475                 480

Val Phe Gly Pro Glu Leu Val Thr Leu Asp Pro Glu Glu Gln Phe Thr
                485                 490                 495

Val Leu Ser Leu Ser Ala Gly Arg Pro Lys Arg Pro His Ala Arg Arg
            500                 505                 510

Ala Leu Cys Leu Leu Leu Gly Pro Asp Phe Phe Thr Asp Val Ile Thr
            515                 520                 525

Ile Glu Thr Ala Asp His Ala Arg Leu Gln Leu Gln Leu Ala Tyr Asn
    530                 535                 540

Trp His Phe Glu Leu Lys Asn Arg Asn Asp Pro Ala Glu Ala Ala Lys
545                 550                 555                 560

Leu Phe Ser Val Pro Asp Phe Val Gly Asp Ala Cys Lys Ala Ile Ala
                565                 570                 575

Ser Arg Val Arg Gly Ala Val Ala Ser Val Thr Phe Asp Asp Phe His
            580                 585                 590

Lys Asn Ser Ala Arg Ile Ile Arg Met Ala Val Phe Gly Phe Glu Met
            595                 600                 605

Ser Glu Asp Thr Gly Pro Asp Gly Thr Leu Leu Pro Lys Ala Arg Asp
    610                 615                 620

Gln Ala Val Phe Pro Gln Asn Gly Leu Val Val Ser Ser Val Asp Val
625                 630                 635                 640

Gln Ser Val Glu Pro Val Asp Gln Arg Thr Arg Asp Ala Leu Gln Arg
                645                 650                 655

Ser Val Gln Leu Ala Ile Glu Ile Thr Thr Asn Ser Gln Glu Ala Ala
            660                 665                 670

Ala Lys His Glu Ala Gln Arg Leu Glu Gln Glu Ala Arg Gly Arg Leu
            675                 680                 685

Glu Arg Gln Lys Ile Leu Asp Gln Ser Glu Ala Glu Lys Ala Arg Lys
690                 695                 700

Glu Leu Leu Glu Leu Glu Ala Met Ser Met Ala Val Glu Ser Thr Gly
```

```
                705                 710                 715                 720
Asn Ala Lys Ala Glu Ala Glu Ser Arg Ala Glu Ala Ala Arg Ile Glu
                    725                 730                 735

Gly Glu Gly Ser Val Leu Gln Ala Lys Leu Lys Ala Gln Ala Leu Ala
            740                 745                 750

Ile Glu Thr Glu Ala Glu Leu Glu Arg Val Lys Lys Val Arg Glu Met
                755                 760                 765

Glu Leu Ile Tyr Ala Arg Ala Gln Leu Glu Leu Glu Val Ser Lys Ala
        770                 775                 780

Gln Gln Leu Ala Asn Val Glu Ala Lys Lys Phe Lys Glu Met Thr Glu
785                 790                 795                 800

Ala Leu Gly Pro Gly Thr Ile Arg Asp Leu Ala Val Ala Gly Pro Glu
                805                 810                 815

Met Gln Val Lys Leu Leu Gln Ser Leu Gly Leu Lys Ser Thr Leu Ile
            820                 825                 830

Thr Asp Gly Ser Ser Pro Ile Asn Leu Phe Ser Thr Ala Phe Gly Leu
        835                 840                 845

Leu Gly Leu Gly Ser Asp Gly Gln Pro Pro Ala Gln Lys
    850                 855                 860

<210> SEQ ID NO 25
<211> LENGTH: 2583
<212> TYPE: DNA
<213> ORGANISM: Rattus norvegicus

<400> SEQUENCE: 25
```

| | | | | | |
|---|---|---|---|---|---|
| atggcaactg | aagaggccat | catccgcatc | cccccatacc | actacatcca | tgtgctggac | 60 |
| cagaacagta | atgtgtcccg | tgtggaggtt | ggaccaaaga | cctacatccg | gcaggacaat | 120 |
| gagagggtac | tgtttgcccc | agttcgcatg | gtgaccgtcc | ccccacgcca | ctactgcata | 180 |
| gtggccaacc | ctgtgtcccg | ggacacccag | agttctgtgt | tatttgacat | acaggacaa | 240 |
| gtccgactcc | ggcacgctga | ccaggagatc | cgactagccc | aggacccctt | cccctgtat | 300 |
| ccagggagg | tgctggaaaa | ggacatcacc | ccactgcagg | tggttctgcc | caacacagca | 360 |
| ctgcatctta | aggcgttgct | ggactttgag | gataagaatg | gagacaaggt | catggcagga | 420 |
| gacgagtggc | tatttgaggg | aacctggcacc | tacatcccac | agaaggaagt | ggaagtcgtg | 480 |
| gagatcattc | aggccacagt | catcaaacag | aaccaagcac | tgcggctaag | ggcccgaaag | 540 |
| gagtgctttg | accgggaggg | caaggggcgc | gtgacaggtg | aggagtggct | ggtccgatcc | 600 |
| gtggggggctt | acctcccagc | tgtctttgaa | gaggtgctgg | atctggtgga | tgctgtgatc | 660 |
| cttacagaaa | agactgccct | gcacctccgg | gctctgcaga | acttcaggga | ccttcgggga | 720 |
| gtgctccacc | gcaccgggga | ggaatggtta | gtgacagtgc | aggacacaga | agcccatgtt | 780 |
| ccagatgtct | atgaggaggt | gcttgggggta | gtacccatca | ccaccctggg | acctcgacac | 840 |
| tactgtgtca | ttcttgaccc | aatgggacca | gacggcaaga | accagctggg | acaaaagcgt | 900 |
| gttgtcaagg | gagagaagtc | cttttttcctc | cagccaggag | agaggctgga | gcgaggcatc | 960 |
| caggatgtgt | atgtgctgtc | agagcagcag | gggctgctac | tgaaggcact | gcagcccctg | 1020 |
| gaggagggag | agagcgagga | gaaggtctcc | catcaggccg | gagactgctg | gctcatccgt | 1080 |
| gggccctgg | agtatgtgcc | atctgcaaaa | gtggaggtgg | tggaggagcg | tcaggctatc | 1140 |
| cctctggacc | aaaatgaggg | catctatgtg | caggatgtca | agacggggaa | ggtgcgggct | 1200 |
| gtgattggaa | gcacctacat | gctgactcag | gatgaagtcc | tgtgggaaaa | ggagctgcct | 1260 |

-continued

```
tctggggtgg aggagctgct gaacttgggg catgaccctc tggcagacag gggtcagaag    1320
ggcacagcca agcccttca gccctcagct ccaaggaaca agacccgagt ggtcagctac    1380
cgtgtcccgc acaatgcagc ggtgcaggtc tatgactaca gagccaagag agcccgtgtg    1440
gtctttgggc ccgagctagt gacactggat cctgaggagc agttcacagt attgtccctt    1500
tctgccgggc gacccaagcg tcctcatgcc cgccgtgcac tctgcctact gctgggacct    1560
gatttcttta ctgatgtcat caccatcgaa actgcagatc atgccaggtt gcagctgcag    1620
cttgcctaca actggcactt tgaactgaag aaccggaatg accctgcaga ggcagccaag    1680
cttttctccg tgcctgactt cgtgggtgac gcctgcaagg ccattgcatc ccgagtccgg    1740
ggggctgtag cctctgtcac ctttgatgac ttccataaaa actcagcccg gatcattcga    1800
atggctgttt ttggctttga gatgtctgaa gacacaggtc ctgatggcac actcctgccc    1860
aaggctcgag accaggcagt ctttccccaa acgggctgg tagtcagcag tgtggatgtg    1920
cagtcagtgg agcccgtgga ccagaggacc cgggatgccc ttcagcgcag cgttcagctg    1980
gccatcgaaa ttaccaccaa ctcccaggag gcagcagcca agcacgaggc tcagagactg    2040
gaacaggaag cccgtggtcg gcttgagagg cagaagatct tggaccagtc agaagctgaa    2100
aaagcccgca aggaactctt ggagcttgag gctatgagca tggctgtgga gagcacgggt    2160
aatgccaaag cagaggctga gtcccgtgca gaggcagcga ggatcgaagg agaaggctct    2220
gtgctgcagg ccaagctcaa ggcacaggcg ctagccattg agacggaggc tgagttggag    2280
cgagtaaaga agtacgaga gatggaactg atctatgccc gggcccagtt ggagctggag    2340
gtgagcaagg cgcagcagct tgccaatgtg gaggcaaaga agttcaagga gatgacagag    2400
gcactgggcc ccggcaccat cagggacctg gctgtggccg ggccagagat gcaggtgaaa    2460
cttctccagt ccctgggcct gaaatccact ctcatcaccg atggctcgtc tcccatcaac    2520
ctcttcagca cagccttcgg gttgctgggg ctggggtctg atggtcagcc gccagcacag    2580
aag                                                                  2583
```

<210> SEQ ID NO 26
<211> LENGTH: 892
<212> TYPE: PRT
<213> ORGANISM: Artificial Sequence
<220> FEATURE:
<223> OTHER INFORMATION: NS5A-rMVP fusion protein based on Hepatitis C
     Virus and Rattus norvegicus

<400> SEQUENCE: 26

Met Ala Gly Ser Trp Leu Arg Asp Ile Trp Asp Trp Ile Cys Glu Val
1               5                   10                  15

Leu Ser Asp Phe Lys Thr Trp Leu Lys Ala Lys Leu Met Pro Thr Met
            20                  25                  30

Ala Thr Glu Glu Ala Ile Ile Arg Ile Pro Pro Tyr His Tyr Ile His
        35                  40                  45

Val Leu Asp Gln Asn Ser Asn Val Ser Arg Val Glu Val Gly Pro Lys
    50                  55                  60

Thr Tyr Ile Arg Gln Asp Asn Glu Arg Val Leu Phe Ala Pro Val Arg
65                  70                  75                  80

Met Val Thr Val Pro Pro Arg His Tyr Cys Ile Val Ala Asn Pro Val
                85                  90                  95

Ser Arg Asp Thr Gln Ser Ser Val Leu Phe Asp Ile Thr Gly Gln Val
            100                 105                 110

Arg Leu Arg His Ala Asp Gln Glu Ile Arg Leu Ala Gln Asp Pro Phe

-continued

```
            115                 120                 125
Pro Leu Tyr Pro Gly Glu Val Leu Glu Lys Asp Ile Thr Pro Leu Gln
130                 135                 140

Val Val Leu Pro Asn Thr Ala Leu His Leu Lys Ala Leu Leu Asp Phe
145                 150                 155                 160

Glu Asp Lys Asn Gly Asp Lys Val Met Ala Gly Asp Glu Trp Leu Phe
                165                 170                 175

Glu Gly Pro Gly Thr Tyr Ile Pro Gln Lys Glu Val Glu Val Val Glu
                180                 185                 190

Ile Ile Gln Ala Thr Val Ile Lys Gln Asn Gln Ala Leu Arg Leu Arg
                195                 200                 205

Ala Arg Lys Glu Cys Phe Asp Arg Glu Gly Lys Gly Arg Val Thr Gly
210                 215                 220

Glu Glu Trp Leu Val Arg Ser Val Gly Ala Tyr Leu Pro Ala Val Phe
225                 230                 235                 240

Glu Glu Val Leu Asp Leu Val Asp Ala Val Ile Leu Thr Glu Lys Thr
                245                 250                 255

Ala Leu His Leu Arg Ala Leu Gln Asn Phe Arg Asp Leu Arg Gly Val
                260                 265                 270

Leu His Arg Thr Gly Glu Glu Trp Leu Val Thr Val Gln Asp Thr Glu
                275                 280                 285

Ala His Val Pro Asp Val Tyr Glu Glu Val Leu Gly Val Val Pro Ile
                290                 295                 300

Thr Thr Leu Gly Pro Arg His Tyr Cys Val Ile Leu Asp Pro Met Gly
305                 310                 315                 320

Pro Asp Gly Lys Asn Gln Leu Gly Gln Lys Arg Val Lys Gly Glu
                325                 330                 335

Lys Ser Phe Phe Leu Gln Pro Gly Glu Arg Leu Glu Arg Gly Ile Gln
                340                 345                 350

Asp Val Tyr Val Leu Ser Glu Gln Gln Gly Leu Leu Leu Lys Ala Leu
                355                 360                 365

Gln Pro Leu Glu Glu Gly Glu Ser Glu Glu Lys Val Ser His Gln Ala
370                 375                 380

Gly Asp Cys Trp Leu Ile Arg Gly Pro Leu Glu Tyr Val Pro Ser Ala
385                 390                 395                 400

Lys Val Glu Val Glu Glu Arg Gln Ala Ile Pro Leu Asp Gln Asn
                405                 410                 415

Glu Gly Ile Tyr Val Gln Asp Val Lys Thr Gly Lys Val Arg Ala Val
                420                 425                 430

Ile Gly Ser Thr Tyr Met Leu Thr Gln Asp Glu Val Leu Trp Glu Lys
                435                 440                 445

Glu Leu Pro Ser Gly Val Glu Leu Leu Asn Leu Gly His Asp Pro
450                 455                 460

Leu Ala Asp Arg Gly Gln Lys Gly Thr Ala Lys Pro Leu Gln Pro Ser
465                 470                 475                 480

Ala Pro Arg Asn Lys Thr Arg Val Val Ser Tyr Arg Val Pro His Asn
                485                 490                 495

Ala Ala Val Gln Val Tyr Asp Tyr Arg Ala Lys Arg Ala Arg Val Val
                500                 505                 510

Phe Gly Pro Glu Leu Val Thr Leu Asp Pro Glu Glu Gln Phe Thr Val
                515                 520                 525

Leu Ser Leu Ser Ala Gly Arg Pro Lys Arg Pro His Ala Arg Arg Ala
530                 535                 540
```

| | | | | | | | | | | | | |
|---|---|---|---|---|---|---|---|---|---|---|---|---|
| Leu | Cys | Leu | Leu | Leu | Gly | Pro | Asp | Phe | Phe | Thr | Asp | Val | Ile | Thr | Ile |
| 545 | | | | 550 | | | | | 555 | | | | | 560 | |

Leu Cys Leu Leu Leu Gly Pro Asp Phe Phe Thr Asp Val Ile Thr Ile
545                 550                 555                 560

Glu Thr Ala Asp His Ala Arg Leu Gln Leu Gln Leu Ala Tyr Asn Trp
                565                 570                 575

His Phe Glu Leu Lys Asn Arg Asn Asp Pro Ala Glu Ala Ala Lys Leu
            580                 585                 590

Phe Ser Val Pro Asp Phe Val Gly Asp Ala Cys Lys Ala Ile Ala Ser
        595                 600                 605

Arg Val Arg Gly Ala Val Ala Ser Val Thr Phe Asp Asp Phe His Lys
    610                 615                 620

Asn Ser Ala Arg Ile Ile Arg Met Ala Val Phe Gly Phe Glu Met Ser
625                 630                 635                 640

Glu Asp Thr Gly Pro Asp Gly Thr Leu Leu Pro Lys Ala Arg Asp Gln
                645                 650                 655

Ala Val Phe Pro Gln Asn Gly Leu Val Val Ser Ser Val Asp Val Gln
                660                 665                 670

Ser Val Glu Pro Val Asp Gln Arg Thr Arg Asp Ala Leu Gln Arg Ser
        675                 680                 685

Val Gln Leu Ala Ile Glu Ile Thr Thr Asn Ser Gln Glu Ala Ala Ala
    690                 695                 700

Lys His Glu Ala Gln Arg Leu Glu Gln Glu Ala Arg Gly Arg Leu Glu
705                 710                 715                 720

Arg Gln Lys Ile Leu Asp Gln Ser Glu Ala Glu Lys Ala Arg Lys Glu
                725                 730                 735

Leu Leu Glu Leu Glu Ala Met Ser Met Ala Val Glu Ser Thr Gly Asn
                740                 745                 750

Ala Lys Ala Glu Ala Glu Ser Arg Ala Glu Ala Ala Arg Ile Glu Gly
        755                 760                 765

Glu Gly Ser Val Leu Gln Ala Lys Leu Lys Ala Gln Ala Leu Ala Ile
    770                 775                 780

Glu Thr Glu Ala Glu Leu Glu Arg Val Lys Lys Val Arg Glu Met Glu
785                 790                 795                 800

Leu Ile Tyr Ala Arg Ala Gln Leu Glu Leu Glu Val Ser Lys Ala Gln
                805                 810                 815

Gln Leu Ala Asn Val Glu Ala Lys Lys Phe Lys Glu Met Thr Glu Ala
                820                 825                 830

Leu Gly Pro Gly Thr Ile Arg Asp Leu Ala Val Ala Gly Pro Glu Met
        835                 840                 845

Gln Val Lys Leu Leu Gln Ser Leu Gly Leu Lys Ser Thr Leu Ile Thr
    850                 855                 860

Asp Gly Ser Ser Pro Ile Asn Leu Phe Ser Thr Ala Phe Gly Leu Leu
865                 870                 875                 880

Gly Leu Gly Ser Asp Gly Gln Pro Pro Ala Gln Lys
                885                 890

<210> SEQ ID NO 27
<211> LENGTH: 2679
<212> TYPE: DNA
<213> ORGANISM: Artificial Sequence
<220> FEATURE:
<223> OTHER INFORMATION: NS5A-rMVP cDNA based on Hepatitis C Virus and
      Rattus norvegicus

<400> SEQUENCE: 27 atggcc

```
aagacctggc tgaaagccaa gctcatgcca accatggcaa ctgaagaggc catcatccgc    120
atccccccat accactacat ccatgtgctg gaccagaaca gtaatgtgtc ccgtgtggag    180
gttggaccaa agacctacat ccggcaggac aatgagaggg tactgttttgc cccagttcgc   240 atggtgaccg tcccccacg ccactactgc atagtggcca accctgtgtc ccgggacacc     300
cagagttctg tgttatttga catcacagga caagtccgac tccggcacgc tgaccaggag    360
atccgactag cccaggaccc cttccccctg tatccagggg aggtgctgga aaaggacatc    420
accccactgc aggtggttct gcccaacaca gcactgcatc ttaaggcgtt gctggacttt    480
gaggataaga atgagacaa ggtcatggca ggagacgagt ggctatttga gggacctggc     540
acctacatcc cacagaagga agtggaagtc gtggagatca ttcaggccac agtcatcaaa    600
cagaaccaag cactgcggct aagggcccga aaggagtgct tgaccgggga gggcaagggg    660
cgcgtgacag gtgaggagtg gctggtccga tccgtggggg cttacctccc agctgtcttt    720
gaagaggtgc tggatctggt ggatgctgtg atccttacag aaaagactgc cctgcacctc    780
cgggctctgc agaacttcag ggaccttcgg ggagtgctcc accgcaccgg ggaggaatgg    840
ttagtgacag tgcaggacac agaagcccat gttccagatg tctatgagga ggtgcttggg    900
gtagtaccca tcaccaccct gggacctcga cactactgtg tcattcttga cccaatggga    960
ccagacggca agaaccagct gggacaaaag cgtgttgtca agggagagaa gtccttttc     1020 ctccagccag agagaggct ggagcgaggc atccaggatg tgtatgtgct gtcagagcag     1080
caggggctgc tactgaaggc actgcagccc ctggaggagg agagagcga ggagaaggtc     1140 tcccatcagg ccggagactg ctggctcatc cgtgggcccc tggagtatgt gccatctgca   1200
aaagtggagg tggtggagga gcgtcaggct atccctctgg accaaaatga gggcatctat    1260
gtgcaggatg tcaagacggg gaaggtgcgg gctgtgattg aagcaccta catgctgact    1320 caggatgaag tcctgtggga aaaggagctg ccttctgggg tggaggagct gctgaacttg    1380
gggcatgacc ctctggcaga caggggtcag aagggcacag ccaagcccct tcagccctca    1440
gctccaagga acaagacccg agtggtcagc taccgtgtcc cgcacaatgc agcggtgcag    1500
gtctatgact acagagccaa agagagcccgt gtggtctttg gcccgagct agtgacactg    1560 gatcctgagg agcagttcac agtattgtcc ctttctgccg gcgacccaa gcgtcctcat     1620 gcccgccgtg cactctgcct actgctggga cctgatttct ttactgatgt catcaccatc   1680
gaaactgcag atcatgccag gttgcagctg cagcttgcct caaactggca ctttgaactg   1740
aagaaccgga atgaccctgc agaggcagcc aagcttttct ccgtgcctga cttcgtgggt   1800
gacgcctgca aggccattgc atcccgagtc cggggggctg tagcctctgt cacctttgat   1860
gacttccata aaaactcagc ccggatcatt cgaatgctgc tttttggctt tgagatgtct   1920
gaagacacag gtcctgatgg cacactcctg cccaaggctc gagaccaggc agtctttccc   1980
caaaacgggc tggtagtcag cagtgtggat gtgcagtcag tggagcccgt ggaccagagg   2040
acccgggatg cccttcagcg cagcgttcag ctggccatcg aaattaccac caactcccag   2100
gaggcagcag ccaagcacga ggctcagaga ctgaacagg aagcccgtgg tcggcttgag    2160
aggcagaaga tcttggacca gtcagaagct gaaaaagccc gcaaggaact cttggagctt   2220
gaggctatga gcatggctgt ggagagcacg ggtaatgcca aagcagaggc tgagtcccgt   2280
gcagaggcag cgaggatcga aggagaaggc tctgtgctgc aggccaagct caaggcacag   2340
gcgctagcca ttgagacgga ggctgagttg gagcgagtaa agaaagtacg agagatggaa   2400
```

```
ctgatctatg cccgggccca gttggagctg gaggtgagca aggcgcagca gcttgccaat    2460
gtggaggcaa agaagttcaa ggagatgaca gaggcactgg gccccggcac catcagggac    2520
ctggctgtgg ccgggccaga gatgcaggtg aaacttctcc agtccctggg cctgaaatcc    2580
actctcatca ccgatggctc gtctcccatc aacctcttca gcacagcctt cgggttgctg    2640
gggctggggt ctgatggtca gccgccagca cagaagtga                           2679
```

<210> SEQ ID NO 28
<211> LENGTH: 923
<212> TYPE: PRT
<213> ORGANISM: Artificial Sequence
<220> FEATURE:
<223> OTHER INFORMATION: NS5A-NS5A-rMVP fusion protein based on
      Hepatitis C Virus and Rattus norvegicus

<400> SEQUENCE: 28

```
Met Ala Gly Ser Trp Leu Arg Asp Ile Trp Asp Trp Ile Cys Glu Val
1               5                   10                  15

Leu Ser Asp Phe Lys Thr Trp Leu Lys Ala Lys Leu Met Pro Thr Met
            20                  25                  30

Ala Gly Ser Trp Leu Arg Asp Ile Trp Asp Trp Ile Cys Glu Val Leu
        35                  40                  45

Ser Asp Phe Lys Thr Trp Leu Lys Ala Lys Leu Met Pro Thr Met Ala
    50                  55                  60

Thr Glu Glu Ala Ile Ile Arg Ile Pro Pro Tyr His Tyr Ile His Val
65                  70                  75                  80

Leu Asp Gln Asn Ser Asn Val Ser Arg Val Glu Val Gly Pro Lys Thr
                85                  90                  95

Tyr Ile Arg Gln Asp Asn Glu Arg Val Leu Phe Ala Pro Val Arg Met
            100                 105                 110

Val Thr Val Pro Pro Arg His Tyr Cys Ile Val Ala Asn Pro Val Ser
        115                 120                 125

Arg Asp Thr Gln Ser Ser Val Leu Phe Asp Ile Thr Gly Gln Val Arg
    130                 135                 140

Leu Arg His Ala Asp Gln Glu Ile Arg Leu Ala Gln Asp Pro Phe Pro
145                 150                 155                 160

Leu Tyr Pro Gly Glu Val Leu Glu Lys Asp Ile Thr Pro Leu Gln Val
                165                 170                 175

Val Leu Pro Asn Thr Ala Leu His Leu Lys Ala Leu Leu Asp Phe Glu
            180                 185                 190

Asp Lys Asn Gly Asp Lys Val Met Ala Gly Asp Glu Trp Leu Phe Glu
        195                 200                 205

Gly Pro Gly Thr Tyr Ile Pro Gln Lys Glu Val Glu Val Val Glu Ile
    210                 215                 220

Ile Gln Ala Thr Val Ile Lys Gln Asn Gln Ala Leu Arg Leu Arg Ala
225                 230                 235                 240

Arg Lys Glu Cys Phe Asp Arg Glu Gly Lys Gly Arg Val Thr Gly Glu
                245                 250                 255

Glu Trp Leu Val Arg Ser Val Gly Ala Tyr Leu Pro Ala Val Phe Glu
            260                 265                 270

Glu Val Leu Asp Leu Val Asp Ala Val Ile Leu Thr Glu Lys Thr Ala
        275                 280                 285

Leu His Leu Arg Ala Leu Gln Asn Phe Arg Asp Leu Arg Gly Val Leu
    290                 295                 300

His Arg Thr Gly Glu Glu Trp Leu Val Thr Val Gln Asp Thr Glu Ala
```

-continued

```
                305                 310                 315                 320
            His Val Pro Asp Val Tyr Glu Val Leu Gly Val Val Pro Ile Thr
                            325                 330                 335

Thr Leu Gly Pro Arg His Tyr Cys Val Ile Leu Asp Pro Met Gly Pro
                            340                 345                 350

Asp Gly Lys Asn Gln Leu Gly Gln Lys Arg Val Val Lys Gly Glu Lys
                            355                 360                 365

Ser Phe Phe Leu Gln Pro Gly Glu Arg Leu Glu Arg Gly Ile Gln Asp
                370                 375                 380

Val Tyr Val Leu Ser Glu Gln Gln Gly Leu Leu Leu Lys Ala Leu Gln
            385                 390                 395                 400

Pro Leu Glu Glu Gly Glu Ser Glu Glu Lys Val Ser His Gln Ala Gly
                            405                 410                 415

Asp Cys Trp Leu Ile Arg Gly Pro Leu Glu Tyr Val Pro Ser Ala Lys
                            420                 425                 430

Val Glu Val Val Glu Glu Arg Gln Ala Ile Pro Leu Asp Gln Asn Glu
                            435                 440                 445

Gly Ile Tyr Val Gln Asp Val Lys Thr Gly Lys Val Arg Ala Val Ile
                450                 455                 460

Gly Ser Thr Tyr Met Leu Thr Gln Asp Glu Val Leu Trp Glu Lys Glu
            465                 470                 475                 480

Leu Pro Ser Gly Val Glu Glu Leu Leu Asn Leu Gly His Asp Pro Leu
                            485                 490                 495

Ala Asp Arg Gly Gln Lys Gly Thr Ala Lys Pro Leu Gln Pro Ser Ala
                            500                 505                 510

Pro Arg Asn Lys Thr Arg Val Val Ser Tyr Arg Val Pro His Asn Ala
                            515                 520                 525

Ala Val Gln Val Tyr Asp Tyr Arg Ala Lys Arg Ala Arg Val Val Phe
                            530                 535                 540

Gly Pro Glu Leu Val Thr Leu Asp Pro Glu Glu Gln Phe Thr Val Leu
            545                 550                 555                 560

Ser Leu Ser Ala Gly Arg Pro Lys Arg Pro His Ala Arg Arg Ala Leu
                            565                 570                 575

Cys Leu Leu Leu Gly Pro Asp Phe Phe Thr Asp Val Ile Thr Ile Glu
                            580                 585                 590

Thr Ala Asp His Ala Arg Leu Gln Leu Gln Leu Ala Tyr Asn Trp His
                            595                 600                 605

Phe Glu Leu Lys Asn Arg Asn Asp Pro Ala Glu Ala Ala Lys Leu Phe
                            610                 615                 620

Ser Val Pro Asp Phe Val Gly Asp Ala Cys Lys Ala Ile Ala Ser Arg
            625                 630                 635                 640

Val Arg Gly Ala Val Ala Ser Val Thr Phe Asp Asp Phe His Lys Asn
                            645                 650                 655

Ser Ala Arg Ile Ile Arg Met Ala Val Phe Gly Phe Glu Met Ser Glu
                            660                 665                 670

Asp Thr Gly Pro Asp Gly Thr Leu Leu Pro Lys Ala Arg Asp Gln Ala
                            675                 680                 685

Val Phe Pro Gln Asn Gly Leu Val Val Ser Ser Val Asp Val Gln Ser
                            690                 695                 700

Val Glu Pro Val Asp Gln Arg Thr Arg Asp Ala Leu Gln Arg Ser Val
            705                 710                 715                 720

Gln Leu Ala Ile Glu Ile Thr Thr Asn Ser Gln Glu Ala Ala Ala Lys
                            725                 730                 735
```

```
His Glu Ala Gln Arg Leu Glu Gln Glu Ala Arg Gly Arg Leu Glu Arg
            740                 745                 750

Gln Lys Ile Leu Asp Gln Ser Glu Ala Glu Lys Ala Arg Lys Glu Leu
        755                 760                 765

Leu Glu Leu Glu Ala Met Ser Met Ala Val Glu Ser Thr Gly Asn Ala
    770                 775                 780

Lys Ala Glu Ala Glu Ser Arg Ala Glu Ala Ala Arg Ile Glu Gly Glu
785                 790                 795                 800

Gly Ser Val Leu Gln Ala Lys Leu Lys Ala Gln Ala Leu Ala Ile Glu
                805                 810                 815

Thr Glu Ala Glu Leu Glu Arg Val Lys Lys Val Arg Glu Met Glu Leu
            820                 825                 830

Ile Tyr Ala Arg Ala Gln Leu Glu Leu Glu Val Ser Lys Ala Gln Gln
        835                 840                 845

Leu Ala Asn Val Glu Ala Lys Lys Phe Lys Glu Met Thr Glu Ala Leu
    850                 855                 860

Gly Pro Gly Thr Ile Arg Asp Leu Ala Val Ala Gly Pro Glu Met Gln
865                 870                 875                 880

Val Lys Leu Leu Gln Ser Leu Gly Leu Lys Ser Thr Leu Ile Thr Asp
                885                 890                 895

Gly Ser Ser Pro Ile Asn Leu Phe Ser Thr Ala Phe Gly Leu Leu Gly
            900                 905                 910

Leu Gly Ser Asp Gly Gln Pro Pro Ala Gln Lys
        915                 920
```

<210> SEQ ID NO 29
<211> LENGTH: 2772
<212> TYPE: DNA
<213> ORGANISM: Artificial Sequence
<220> FEATURE:
<223> OTHER INFORMATION: NS5A-NS5A-rMVP cDNA based on Hepatitis C Virus
      and Rattus norvegicus

<400> SEQUENCE: 29

```
atggccggtt cctggctaag ggacatctgg gactggatat gcgaggtgct gagcgacttt      60
aagacctggc tgaaagccaa gctcatgcca accatggccg ttcctggct aagggacatc     120 tgggactgga tatgcgaggt gctgagcgac tttaagacct ggctgaaagc caagctcatg     180
ccaaccatgg caactgaaga ggccatcatc cgcatccccc ataccacta catccatgtg     240 ctggaccaga cagtaatgt gtcccgtgtg gaggttggac caaagaccta catccggcag     300
gacaatgaga gggtactgtt tgccccagtt cgcatggtga ccgtcccccc acgccactac     360
tgcatagtgg ccaaccctgt gtcccgggac acccagagtt ctgtgttatt tgacatcaca     420
ggacaagtcc gactccggca cgctgaccag gagatccgac tagcccagga ccccttcccc     480
ctgtatccag gggaggtgct ggaaaaggac atcaccccac tgcaggtggt tctgcccaac     540
acagcactgc atcttaaggc gttgctggac tttgaggata gaatggaga caaggtcatg     600 gcaggagacg agtggctatt tgagggacct ggcacctaca tcccacagaa ggaagtggaa     660
gtcgtggaga tcattcaggc cacagtcatc aaacagaacc aagcactgcg gctaagggcc     720
cgaaaggagt gctttgaccg ggagggcaag gggcgcgtga caggtgagga gtggctggtc     780
cgatccgtgg gggcttacct cccagctgtc tttgaagagg tgctggatct ggtggatgct     840
gtgatcctta cagaaaagac tgccctgcac ctccgggctc tgcagaactt cagggacctt     900
cggggagtgc tccaccgcac cggggaggaa tggttagtga cagtgcagga cacagaagcc     960
```

```
catgttccag atgtctatga ggaggtgctt ggggtagtac ccatcaccac cctgggacct    1020
cgacactact gtgtcattct tgacccaatg ggaccagacg caagaacca gctgggacaa    1080 aagcgtgttg tcaagggaga gaagtccttt ttcctccagc caggagagag gctggagcga    1140
ggcatccagg atgtgtatgt gctgtcagag cagcaggggc tgctactgaa ggcactgcag    1200
cccctggagg agggagagag cgaggagaag gtctcccatc aggccggaga ctgctggctc    1260
atccgtgggc ccctggagta tgtgccatct gcaaaagtgg aggtggtgga ggagcgtcag    1320
gctatccctc tggaccaaaa tgagggcatc tatgtgcagg atgtcaagac ggggaaggtg    1380
cgggctgtga ttggaagcac ctacatgctg actcaggatg aagtcctgtg ggaaaaggag    1440
ctgccttctg gggtggagga gctgctgaac ttggggcatg accctctggc agacaggggt    1500
cagaagggca cagccaagcc ccttcagccc tcagctccaa ggaacaagac ccgagtggtc    1560
agctaccgtg tcccgcacaa tgcagcggtg caggtctatg actacagagc caagagagcc    1620
cgtgtggtct ttgggcccga gctagtgaca ctggatcctg aggagcagtt cacagtattg    1680
tccctttctg ccgggcgacc caagcgtcct catgcccgcc gtgcactctg cctactgctg    1740
ggacctgatt tctttactga tgtcatcacc atcgaaactg cagatcatgc caggttgcag    1800
ctgcagcttg cctacaactg gcactttgaa ctgaagaacc ggaatgaccc tgcagaggca    1860
gccaagcttt tctccgtgcc tgacttcgtg ggtgacgcct gcaaggccat tgcatcccga    1920
gtccgggggg ctgtagcctc tgtcaccttt gatgacttcc ataaaaactc agcccggatc    1980
attcgaatgg ctgttttgg ctttgagatg tctgaagaca caggtcctga tggcacactc    2040
ctgcccaagg ctcgagacca ggcagtcttt ccccaaaacg ggctggtagt cagcagtgtg    2100
gatgtgcagt cagtggagcc cgtggaccag aggacccggg atgcccttca gcgcagcgtt    2160
cagctggcca tcgaaattac caccaactcc caggaggcag cagccaagca cgaggctcag    2220
agactggaac aggaagcccg tggtcggctt gagaggcaga agatcttgga ccagtcagaa    2280
gctgaaaaag cccgcaagga actcttggag cttgaggcta tgagcatggc tgtggagagc    2340
acgggtaatg ccaaagcaga ggctgagtcc cgtgcagagg cagcgaggat cgaaggagaa    2400
ggctctgtgc tgcaggccaa gctcaaggca caggcgctag ccattgagac ggaggctgag    2460
ttggagcgag taaagaaagt acgagagatg gaactgatct atgcccgggc ccagttggag    2520
ctggaggtga gcaaggcgca gcagcttgcc aatgtggagg caaagaagtt caaggagatg    2580
acagaggcac tgggccccgg caccatcagg gacctggctg tggccgggcc agagatgcag    2640
gtgaaacttc tccagtccct gggcctgaaa tccactctca tcaccgatgg ctcgtctccc    2700
atcaacctct tcagcacagc cttcgggttg ctggggctgg ggtctgatgg tcagccgcca    2760
gcacagaagt ga                                                        2772
```

<210> SEQ ID NO 30
<211> LENGTH: 925
<212> TYPE: PRT
<213> ORGANISM: Artificial Sequence
<220> FEATURE:
<223> OTHER INFORMATION: NS5A-rMVP-Z domain fusion protein based on
      Hepatitis C Virus and Rattus norvegicus

<400> SEQUENCE: 30

```
Met Ala Gly Ser Trp Leu Arg Asp Ile Trp Asp Trp Ile Cys Glu Val
1               5                   10                  15

Leu Ser Asp Phe Lys Thr Trp Leu Lys Ala Lys Leu Met Pro Thr Met
                20                  25                  30
```

```
Ala Thr Glu Glu Ala Ile Ile Arg Ile Pro Pro Tyr His Tyr Ile His
         35                  40                  45

Val Leu Asp Gln Asn Ser Asn Val Ser Arg Val Glu Val Gly Pro Lys
 50                  55                  60

Thr Tyr Ile Arg Gln Asp Asn Glu Arg Val Leu Phe Ala Pro Val Arg
 65                  70                  75                  80

Met Val Thr Val Pro Pro Arg His Tyr Cys Ile Val Ala Asn Pro Val
                 85                  90                  95

Ser Arg Asp Thr Gln Ser Ser Val Leu Phe Asp Ile Thr Gly Gln Val
             100                 105                 110

Arg Leu Arg His Ala Asp Gln Glu Ile Arg Leu Ala Gln Asp Pro Phe
             115                 120                 125

Pro Leu Tyr Pro Gly Glu Val Leu Glu Lys Asp Ile Thr Pro Leu Gln
         130                 135                 140

Val Val Leu Pro Asn Thr Ala Leu His Leu Lys Ala Leu Leu Asp Phe
145                 150                 155                 160

Glu Asp Lys Asn Gly Asp Lys Val Met Ala Gly Asp Glu Trp Leu Phe
                 165                 170                 175

Glu Gly Pro Gly Thr Tyr Ile Pro Gln Lys Glu Val Glu Val Val Glu
             180                 185                 190

Ile Ile Gln Ala Thr Val Ile Lys Gln Asn Gln Ala Leu Arg Leu Arg
             195                 200                 205

Ala Arg Lys Glu Cys Phe Asp Arg Glu Gly Lys Gly Arg Val Thr Gly
         210                 215                 220

Glu Glu Trp Leu Val Arg Ser Val Gly Ala Tyr Leu Pro Ala Val Phe
225                 230                 235                 240

Glu Glu Val Leu Asp Leu Val Asp Ala Val Ile Leu Thr Glu Lys Thr
                 245                 250                 255

Ala Leu His Leu Arg Ala Leu Gln Asn Phe Arg Asp Leu Arg Gly Val
             260                 265                 270

Leu His Arg Thr Gly Glu Glu Trp Leu Val Thr Val Gln Asp Thr Glu
         275                 280                 285

Ala His Val Pro Asp Val Tyr Glu Glu Val Leu Gly Val Val Pro Ile
         290                 295                 300

Thr Thr Leu Gly Pro Arg His Tyr Cys Val Ile Leu Asp Pro Met Gly
305                 310                 315                 320

Pro Asp Gly Lys Asn Gln Leu Gly Gln Lys Arg Val Lys Gly Glu
                 325                 330                 335

Lys Ser Phe Phe Leu Gln Pro Gly Glu Arg Leu Glu Arg Gly Ile Gln
             340                 345                 350

Asp Val Tyr Val Leu Ser Glu Gln Gly Leu Leu Leu Lys Ala Leu
             355                 360                 365

Gln Pro Leu Glu Glu Gly Glu Ser Glu Glu Lys Val Ser His Gln Ala
 370                 375                 380

Gly Asp Cys Trp Leu Ile Arg Gly Pro Leu Glu Tyr Val Pro Ser Ala
385                 390                 395                 400

Lys Val Glu Val Glu Glu Arg Gln Ala Ile Pro Leu Asp Gln Asn
                 405                 410                 415

Glu Gly Ile Tyr Val Gln Asp Val Lys Thr Gly Lys Val Arg Ala Val
             420                 425                 430

Ile Gly Ser Thr Tyr Met Leu Thr Gln Asp Glu Val Leu Trp Glu Lys
             435                 440                 445
```

```
Glu Leu Pro Ser Gly Val Glu Glu Leu Leu Asn Leu Gly His Asp Pro
450                 455                 460

Leu Ala Asp Arg Gly Gln Lys Gly Thr Ala Lys Pro Leu Gln Pro Ser
465                 470                 475                 480

Ala Pro Arg Asn Lys Thr Arg Val Val Ser Tyr Arg Val Pro His Asn
                485                 490                 495

Ala Ala Val Gln Val Tyr Asp Tyr Arg Ala Lys Arg Ala Arg Val Val
            500                 505                 510

Phe Gly Pro Glu Leu Val Thr Leu Asp Pro Glu Glu Gln Phe Thr Val
        515                 520                 525

Leu Ser Leu Ser Ala Gly Arg Pro Lys Arg Pro His Ala Arg Arg Ala
530                 535                 540

Leu Cys Leu Leu Leu Gly Pro Asp Phe Phe Thr Asp Val Ile Thr Ile
545                 550                 555                 560

Glu Thr Ala Asp His Ala Arg Leu Gln Leu Gln Leu Ala Tyr Asn Trp
                565                 570                 575

His Phe Glu Leu Lys Asn Arg Asn Asp Pro Ala Glu Ala Ala Lys Leu
            580                 585                 590

Phe Ser Val Pro Asp Phe Val Gly Asp Ala Cys Lys Ala Ile Ala Ser
        595                 600                 605

Arg Val Arg Gly Ala Val Ala Ser Val Thr Phe Asp Asp Phe His Lys
610                 615                 620

Asn Ser Ala Arg Ile Ile Arg Met Ala Val Phe Gly Phe Glu Met Ser
625                 630                 635                 640

Glu Asp Thr Gly Pro Asp Gly Thr Leu Leu Pro Lys Ala Arg Asp Gln
                645                 650                 655

Ala Val Phe Pro Gln Asn Gly Leu Val Val Ser Ser Val Asp Val Gln
            660                 665                 670

Ser Val Glu Pro Val Asp Gln Arg Thr Arg Asp Ala Leu Gln Arg Ser
        675                 680                 685

Val Gln Leu Ala Ile Glu Ile Thr Thr Asn Ser Gln Glu Ala Ala Ala
690                 695                 700

Lys His Glu Ala Gln Arg Leu Glu Gln Glu Ala Arg Gly Arg Leu Glu
705                 710                 715                 720

Arg Gln Lys Ile Leu Asp Gln Ser Glu Ala Glu Lys Ala Arg Lys Glu
                725                 730                 735

Leu Leu Glu Leu Glu Ala Met Ser Met Ala Val Glu Ser Thr Gly Asn
            740                 745                 750

Ala Lys Ala Glu Ala Glu Ser Arg Ala Glu Ala Ala Arg Ile Glu Gly
        755                 760                 765

Glu Gly Ser Val Leu Gln Ala Lys Leu Lys Ala Gln Ala Leu Ala Ile
770                 775                 780

Glu Thr Glu Ala Glu Leu Glu Arg Val Lys Lys Val Arg Glu Met Glu
785                 790                 795                 800

Leu Ile Tyr Ala Arg Ala Gln Leu Glu Leu Glu Val Ser Lys Ala Gln
                805                 810                 815

Gln Leu Ala Asn Val Glu Ala Lys Lys Phe Lys Glu Met Thr Glu Ala
            820                 825                 830

Leu Gly Pro Gly Thr Ile Arg Asp Leu Ala Val Ala Gly Pro Glu Met
        835                 840                 845

Gln Val Lys Leu Leu Gln Ser Leu Gly Leu Lys Ser Thr Leu Ile Thr
850                 855                 860

Asp Gly Ser Ser Pro Ile Asn Leu Phe Ser Thr Ala Phe Gly Leu Leu
```

```
                865                 870                 875                 880
Gly Leu Gly Ser Asp Gly Gln Pro Pro Ala Gln Lys Phe Asn Met Gln
                        885                 890                 895

Gln Gln Arg Arg Phe Tyr Glu Ala Leu His Asp Pro Asn Leu Asn Glu
            900                 905                 910

Glu Gln Arg Asn Ala Lys Ile Lys Ser Ile Arg Asp Asp
        915                 920                 925

<210> SEQ ID NO 31
<211> LENGTH: 2778
<212> TYPE: DNA
<213> ORGANISM: Artificial Sequence
<220> FEATURE:
<223> OTHER INFORMATION: NS5A-rMVP-Z domain cDNA based on Hepatitis C
      Virus and Rattus norvegicus

<400> SEQUENCE: 31
atggccggtt cctggctaag ggacatctgg gactggatat gcgaggtgct gagcgacttt      60
aagacctggc tgaaagccaa gctcatgcca accatggcaa ctgaagaggc catcatccgc     120 atcccccat accactacat ccatgtgctg accagaaca gtaatgtgtc ccgtgtggag       180
gttggaccaa agacctacat ccggcaggac aatgagaggg tactgtttgc cccagttcgc     240
atggtgaccg tccccccacg ccactactgc atagtggcca accctgtgtc ccgggacacc     300
cagagttctg tgttatttga catcacagga caagtccgac tccggcacgc tgaccaggag     360
atccgactag cccaggaccc cttcccctg tatccagggg aggtgctgga aaaggacatc      420
accccactgc aggtggttct gcccaacaca gcactgcatc ttaaggcgtt gctggacttt     480
gaggataaga atggagacaa ggtcatggca ggagacgagt ggctatttga gggacctggc     540
acctacatcc cacagaagga agtggaagtc gtggagatca ttcaggccac agtcatcaaa     600
cagaaccaag cactgcggct aagggcccga aggagtgct ttgaccggga gggcaagggg      660
cgcgtgacag tgaggagtg gctggtccga tccgtggggg cttacctccc agctgtcttt     720
gaagaggtgc tggatctggt ggatgctgtg atccttacag aaaagactgc cctgcacctc     780
cgggctctgc agaacttcag ggaccttcgg ggagtgctcc accgcaccgg ggaggaatgg     840
ttagtgacag tgcaggacac agaagcccat gttccagatg tctatgagga ggtgcttggg     900
gtagtaccca tcaccaccct gggacctcga cactactgtg tcattcttga cccaatggga     960
ccagacggca agaaccagct gggacaaaag cgtgttgtca agggagagaa gtccttttc    1020 ctccagccag agagaggct ggagcgaggc atccaggatg tgtatgtgct gtcagagcag    1080
caggggctgc tactgaaggc actgcagccc ctggaggagg gagagagcga ggagaaggtc    1140
tcccatcagg ccggagactg ctggctcatc cgtgggcccc tggagtatgt gccatctgca    1200
aaagtggagg tggtggagga gcgtcaggct atccctctgg accaaaatga gggcatctat    1260
gtgcaggatg tcaagacggg gaaggtgcgg gctgtgattg aagcaccta catgctgact    1320 caggatgaag tcctgtggga aaaggagctg cccttctgggg tggaggagct gctgaacttg    1380
gggcatgacc ctctggcaga caggggtcag aagggcacag ccaagccctt cagccctca    1440 gctccaagga caagacccg agtggtcagc taccgtgtcc cgcacaatgc agcggtgcag    1500
gtctatgact acagagccaa gagagcccgt gtggtctttg gcccgagct agtgacactg    1560 gatcctgagg agcagttcac agtattgtcc ctttctgccg ggcgaccaa gcgtcctcat    1620 gccgccgtg cactctgcct actgctggga cctgatttct ttactgatgt catcaccatc    1680
gaaactgcag atcatgccag gttgcagctg cagcttgcct acaactggca ctttgaactg    1740
```

-continued

```
aagaaccgga atgaccctgc agaggcagcc aagcttttct ccgtgcctga cttcgtgggt   1800
gacgcctgca aggccattgc atcccgagtc cggggggctg tagcctctgt cacctttgat   1860
gacttccata aaaactcagc ccggatcatt cgaatggctg tttttggctt tgagatgtct   1920
gaagacacag gtcctgatgg cacactcctg cccaaggctc gagaccaggc agtctttccc   1980
caaaacgggc tggtagtcag cagtgtggat gtgcagtcag tggagcccgt ggaccagagg   2040
acccgggatg cccttcagcg cagcgttcag ctggccatcg aaattaccac caactcccag   2100
gaggcagcag ccaagcacga ggctcagaga ctggaacagg aagcccgtgg tcggcttgag   2160
aggcagaaga tcttggacca gtcagaagct gaaaaagccc gcaaggaact cttggagctt   2220
gaggctatga gcatggctgt ggagagcacg ggtaatgcca aagcagaggc tgagtcccgt   2280
gcagaggcag cgaggatcga aggagaaggc tctgtgctgc aggccaagct caaggcacag   2340
gcgctagcca ttgagacgga ggctgagttg gagcgagtaa agaaagtacg agagatggaa   2400
ctgatctatg cccgggccca gttggagctg gaggtgagca aggcgcagca gcttgccaat   2460
gtggaggcaa agaagttcaa ggagatgaca gaggcactgg gccccggcac catcagggac   2520
ctggctgtgg ccgggccaga gatgcaggtg aaacttctcc agtccctggg cctgaaatcc   2580
actctcatca ccgatggctc gtctcccatc aacctcttca gcacagcctt cgggttgctg   2640
gggctggggt ctgatggtca gccgccagca cagaagttta acatgcagca gcagcgccgc   2700
ttttacgagg ccctgcacga ccccaacctg aacgaggagc agcgcaacgc caagattaag   2760
agcattcgcg acgactag                                                 2778
```

<210> SEQ ID NO 32
<211> LENGTH: 873
<212> TYPE: PRT
<213> ORGANISM: Artificial Sequence
<220> FEATURE:
<223> OTHER INFORMATION: CP-rMVP fusion protein based on Rattus norvegicus

<400> SEQUENCE: 32

```
Met Ala Gly Cys Gly Cys Pro Cys Gly Cys Gly Ala Met Ala Thr Glu
1               5                   10                  15

Glu Ala Ile Ile Arg Ile Pro Pro Tyr His Tyr Ile His Val Leu Asp
            20                  25                  30

Gln Asn Ser Asn Val Ser Arg Val Glu Val Gly Pro Lys Thr Tyr Ile
        35                  40                  45

Arg Gln Asp Asn Glu Arg Val Leu Phe Ala Pro Val Arg Met Val Thr
    50                  55                  60

Val Pro Pro Arg His Tyr Cys Ile Val Ala Asn Pro Val Ser Arg Asp
65                  70                  75                  80

Thr Gln Ser Ser Val Leu Phe Asp Ile Thr Gly Gln Val Arg Leu Arg
                85                  90                  95

His Ala Asp Gln Glu Ile Arg Leu Ala Gln Asp Pro Phe Pro Leu Tyr
            100                 105                 110

Pro Gly Glu Val Leu Glu Lys Asp Ile Thr Pro Leu Gln Val Val Leu
        115                 120                 125

Pro Asn Thr Ala Leu His Leu Lys Ala Leu Leu Asp Phe Glu Asp Lys
    130                 135                 140

Asn Gly Asp Lys Val Met Ala Gly Asp Glu Trp Leu Phe Glu Gly Pro
145                 150                 155                 160

Gly Thr Tyr Ile Pro Gln Lys Glu Val Glu Val Val Glu Ile Ile Gln
```

-continued

```
                165                 170                 175
Ala Thr Val Ile Lys Gln Asn Gln Ala Leu Arg Leu Arg Ala Arg Lys
                    180                 185                 190

Glu Cys Phe Asp Arg Glu Gly Lys Gly Arg Val Thr Gly Glu Glu Trp
                195                 200                 205

Leu Val Arg Ser Val Gly Ala Tyr Leu Pro Ala Val Phe Glu Glu Val
    210                 215                 220

Leu Asp Leu Val Asp Ala Val Ile Leu Thr Glu Lys Thr Ala Leu His
225                 230                 235                 240

Leu Arg Ala Leu Gln Asn Phe Arg Asp Leu Arg Gly Val Leu His Arg
                245                 250                 255

Thr Gly Glu Glu Trp Leu Val Thr Val Gln Asp Thr Glu Ala His Val
                260                 265                 270

Pro Asp Val Tyr Glu Glu Val Leu Gly Val Val Pro Ile Thr Thr Leu
                275                 280                 285

Gly Pro Arg His Tyr Cys Val Ile Leu Asp Pro Met Gly Pro Asp Gly
                290                 295                 300

Lys Asn Gln Leu Gly Gln Lys Arg Val Val Lys Gly Glu Lys Ser Phe
305                 310                 315                 320

Phe Leu Gln Pro Gly Glu Arg Leu Glu Arg Gly Ile Gln Asp Val Tyr
                325                 330                 335

Val Leu Ser Glu Gln Gln Gly Leu Leu Leu Lys Ala Leu Gln Pro Leu
                340                 345                 350

Glu Glu Gly Glu Ser Glu Glu Lys Val Ser His Gln Ala Gly Asp Cys
                355                 360                 365

Trp Leu Ile Arg Gly Pro Leu Glu Tyr Val Pro Ser Ala Lys Val Glu
                370                 375                 380

Val Val Glu Glu Arg Gln Ala Ile Pro Leu Asp Gln Asn Glu Gly Ile
385                 390                 395                 400

Tyr Val Gln Asp Val Lys Thr Gly Lys Val Arg Ala Val Ile Gly Ser
                405                 410                 415

Thr Tyr Met Leu Thr Gln Asp Glu Val Leu Trp Glu Lys Glu Leu Pro
                420                 425                 430

Ser Gly Val Glu Glu Leu Leu Asn Leu Gly His Asp Pro Leu Ala Asp
                435                 440                 445

Arg Gly Gln Lys Gly Thr Ala Lys Pro Leu Gln Pro Ser Ala Pro Arg
                450                 455                 460

Asn Lys Thr Arg Val Val Ser Tyr Arg Val Pro His Asn Ala Ala Val
465                 470                 475                 480

Gln Val Tyr Asp Tyr Arg Ala Lys Arg Ala Arg Val Val Phe Gly Pro
                485                 490                 495

Glu Leu Val Thr Leu Asp Pro Glu Glu Gln Phe Thr Val Leu Ser Leu
                500                 505                 510

Ser Ala Gly Arg Pro Lys Arg Pro His Ala Arg Arg Ala Leu Cys Leu
                515                 520                 525

Leu Leu Gly Pro Asp Phe Phe Thr Asp Val Ile Thr Ile Glu Thr Ala
                530                 535                 540

Asp His Ala Arg Leu Gln Leu Gln Leu Ala Tyr Asn Trp His Phe Glu
545                 550                 555                 560

Leu Lys Asn Arg Asn Asp Pro Ala Glu Ala Lys Leu Phe Ser Val
                565                 570                 575

Pro Asp Phe Val Gly Asp Ala Cys Lys Ala Ile Ala Ser Arg Val Arg
                580                 585                 590
```

```
Gly Ala Val Ala Ser Val Thr Phe Asp Asp Phe His Lys Asn Ser Ala
            595                 600                 605
Arg Ile Ile Arg Met Ala Val Phe Gly Phe Glu Met Ser Glu Asp Thr
        610                 615                 620
Gly Pro Asp Gly Thr Leu Leu Pro Lys Ala Arg Asp Gln Ala Val Phe
625                 630                 635                 640
Pro Gln Asn Gly Leu Val Val Ser Ser Val Asp Val Gln Ser Val Glu
                645                 650                 655
Pro Val Asp Gln Arg Thr Arg Asp Ala Leu Gln Arg Ser Val Gln Leu
            660                 665                 670
Ala Ile Glu Ile Thr Thr Asn Ser Gln Glu Ala Ala Lys His Glu
        675                 680                 685
Ala Gln Arg Leu Glu Gln Glu Ala Arg Gly Arg Leu Glu Arg Gln Lys
    690                 695                 700
Ile Leu Asp Gln Ser Glu Ala Glu Lys Ala Arg Lys Glu Leu Leu Glu
705                 710                 715                 720
Leu Glu Ala Met Ser Met Ala Val Glu Ser Thr Gly Asn Ala Lys Ala
                725                 730                 735
Glu Ala Glu Ser Arg Ala Glu Ala Ala Arg Ile Glu Gly Glu Gly Ser
            740                 745                 750
Val Leu Gln Ala Lys Leu Lys Ala Gln Ala Leu Ala Ile Glu Thr Glu
        755                 760                 765
Ala Glu Leu Glu Arg Val Lys Lys Val Arg Glu Met Glu Leu Ile Tyr
    770                 775                 780
Ala Arg Ala Gln Leu Glu Leu Glu Val Ser Lys Ala Gln Gln Leu Ala
785                 790                 795                 800
Asn Val Glu Ala Lys Lys Phe Lys Glu Met Thr Glu Ala Leu Gly Pro
                805                 810                 815
Gly Thr Ile Arg Asp Leu Ala Val Ala Gly Pro Glu Met Gln Val Lys
            820                 825                 830
Leu Leu Gln Ser Leu Gly Leu Lys Ser Thr Leu Ile Thr Asp Gly Ser
        835                 840                 845
Ser Pro Ile Asn Leu Phe Ser Thr Ala Phe Gly Leu Leu Gly Leu Gly
    850                 855                 860
Ser Asp Gly Gln Pro Pro Ala Gln Lys
865                 870

<210> SEQ ID NO 33
<211> LENGTH: 2847
<212> TYPE: DNA
<213> ORGANISM: Artificial Sequence
<220> FEATURE:
<223> OTHER INFORMATION: CP-rMVP cDNA based on Rattus norvegicus

<400> SEQUENCE: 33
gaattcgcgg ccgcgtcgac tgtggcttgc agctgccagc taccctgcta aatgtttggt      60
gggaaaagct tgggattcac catggcaggc tgcggttgtc catgcggttg tggcgccatg     120
gcaactgaag aggccatcat ccgcatcccc ccataccact acatccatgt gctggaccag     180
aacagtaatg tgtcccgtgt ggaggttgga ccaaagacct acatccggca ggacaatgag     240
agggtactgt ttgccccagt tcgcatggtg accgtccccc cacgccacta ctgcatagtg     300
gccaaccctg tgtcccggga cacccagagt tctgtgttat ttgacatcac aggacaagtc     360
cgactccggc acgctgacca ggagatccga ctagcccagg accccttccc cctgtatcca     420
```

```
ggggaggtgc tggaaaagga catcacccca ctgcaggtgg ttctgcccaa cacagcactg    480
catcttaagg cgttgctgga cttttgaggat aagaatggag acaaggtcat ggcaggagac   540
gagtggctat ttgagggacc tggcacctac atcccacaga aggaagtgga agtcgtggag    600
atcattcagg ccacagtcat caaacagaac caagcactgc ggctaagggc ccgaaaggag    660
tgctttgacc gggagggcaa ggggcgcgtg acaggtgagg agtggctggt ccgatccgtg    720
ggggcttacc tcccagctgt cttttgaagag gtgctggatc tggtggatgc tgtgatcctt    780
acagaaaaga ctgccctgca cctccgggct ctgcagaact tcagggacct tcggggagtg    840
ctccaccgca ccggggagga atggttagtg acagtgcagg acacagaagc ccatgttcca    900
gatgtctatg aggaggtgct tggggtagta cccatcacca ccctgggacc tcgacactac    960
tgtgtcattc ttgacccaat gggaccagac ggcaagaacc agctgggaca aaagcgtgtt   1020
gtcaagggag agaagtcctt tttcctccag ccaggagaga ggctggagcg aggcatccag   1080
gatgtgtatg tgctgtcaga gcagcagggg ctgctactga aggcactgca gccctggag   1140 gagggagaga gcgaggagaa ggtctcccat caggccggag actgctggct catccgtggg   1200
cccctggagt atgtgccatc tgcaaaagtg gaggtggtgg aggagcgtca ggctatccct   1260
ctggaccaaa atgagggcat ctatgtgcag gatgtcaaga cggggaaggt gcgggctgtg   1320
attggaagca cctacatgct gactcaggat gaagtcctgt gggaaaagga gctgccttct   1380
ggggtggagg agctgctgaa cttggggcat gaccctctgg cagacagggg tcagaagggc   1440
acagccaagc cccttcagcc ctcagctcca aggaacaaga cccgagtggt cagctaccgt   1500
gtcccgcaca atgcagcggt gcaggtctat gactacagag ccaagagagc ccgtgtggtc   1560
tttgggcccg agctagtgac actggatcct gaggagcagt tcacagtatt gtccctttct   1620
gccgggcgac ccaagcgtcc tcatgcccgc cgtgcactct gcctactgct gggacctgat   1680
ttctttactg atgtcatcac catcgaaact gcagatcatg ccaggttgca gctgcagctt   1740
gcctacaact ggcactttga actgaagaac cggaatgacc ctgcagaggc agccaagctt   1800
ttctccgtgc ctgacttcgt gggtgacgcc tgcaaggcca ttgcatcccg agtccggggg   1860
gctgtagcct ctgtcacctt tgatgacttc cataaaaact cagcccggat cattcgaatg   1920
gctgtttttg gctttgagat gtctgaagac acaggtcctg atggcacact cctgcccaag   1980
gctcgagacc aggcagtctt tccccaaaac gggctggtag tcagcagtgt ggatgtgcag   2040
tcagtggagc ccgtggacca gaggacccgg gatgcccttc agcgcagcgt tcagctggcc   2100
atcgaaatta ccaccaactc ccaggaggca cagccaagc acgaggctca gagactggaa   2160
caggaagccc gtggtcggct tgagaggcag aagatcttgg accagtcaga agctgaaaaa   2220
gcccgcaagg aactcttgga gcttgaggct atgagcatgg ctgtggagag cacgggtaat   2280
gccaaagcag aggctgagtc ccgtgcagag gcagcgagga tcgaaggaga aggctctgtg   2340
ctgcaggcca agctcaaggc acaggcgcta gccattgaga cggaggctga gttggagcga   2400
gtaaagaaag tacgagagat ggaactgatc tatgcccggg cccagttgga gctggaggtg   2460
agcaaggcgc agcagcttgc caatgtggag gcaaagaagt tcaaggagat gacagaggca   2520
ctgggccccg gcaccatcag ggacctggct gtggccgggc cagagatgca ggtgaaactt   2580
ctccagtccc tgggcctgaa atccactctc atcaccgatg gctcgtctcc catcaacctc   2640
ttcagcacag ccttcgggtt gctggggctg gggtctgatg gtcagccgcc agcacagaag   2700
tgatccggca gcccggggaa gacttgctct cccaggctct ccgaagcagc catgctgtgc   2760
cttaggtcaa cactgactgc actgacaatg gataaaataa attgacaact gtaaaaaaaa   2820
```
aaaaaaagtc gacgcggccg cgaattc                                    2847

<210> SEQ ID NO 34
<211> LENGTH: 905
<212> TYPE: PRT
<213> ORGANISM: Artificial Sequence
<220> FEATURE:
<223> OTHER INFORMATION: CP-rMVP-Z domain fusion protein based on Rattus
       norvegicus

<400> SEQUENCE: 34

Met Ala Gly Cys Gly Cys Pro Cys Gly Cys Gly Ala Met Ala Thr Glu
1 5 10 15

Glu Ala Ile Ile Arg Ile Pro Pro Tyr His Tyr Ile His Val Leu Asp
20 25 30

Gln Asn Ser Asn Val Ser Arg Val Glu Val Gly Pro Lys Thr Tyr Ile
35 40 45

Arg Gln Asp Asn Glu Arg Val Leu Phe Ala Pro Val Arg Met Val Thr
50 55 60

Val Pro Pro Arg His Tyr Cys Ile Val Ala Asn Pro Val Ser Arg Asp
65 70 75 80

Thr Gln Ser Ser Val Leu Phe Asp Ile Thr Gly Gln Val Arg Leu Arg
85 90 95

His Ala Asp Gln Glu Ile Arg Leu Ala Gln Asp Pro Phe Pro Leu Tyr
100 105 110

Pro Gly Glu Val Leu Glu Lys Asp Ile Thr Pro Leu Gln Val Val Leu
115 120 125

Pro Asn Thr Ala Leu His Leu Lys Ala Leu Leu Asp Phe Glu Asp Lys
130 135 140

Asn Gly Asp Lys Val Met Ala Gly Asp Glu Trp Leu Phe Glu Gly Pro
145 150 155 160

Gly Thr Tyr Ile Pro Gln Lys Glu Val Glu Val Val Glu Ile Ile Gln
165 170 175

Ala Thr Val Ile Lys Gln Asn Gln Ala Leu Arg Leu Arg Ala Arg Lys
180 185 190

Glu Cys Phe Asp Arg Glu Gly Lys Gly Arg Val Thr Gly Glu Glu Trp
195 200 205

Leu Val Arg Ser Val Gly Ala Tyr Leu Pro Ala Val Phe Glu Glu Val
210 215 220

Leu Asp Leu Val Asp Ala Val Ile Leu Thr Glu Lys Thr Ala Leu His
225 230 235 240

Leu Arg Ala Leu Gln Asn Phe Arg Asp Leu Arg Gly Val Leu His Arg
245 250 255

Thr Gly Glu Glu Trp Leu Val Thr Val Gln Asp Thr Glu Ala His Val
260 265 270

Pro Asp Val Tyr Glu Glu Val Leu Gly Val Val Pro Ile Thr Thr Leu
275 280 285

Gly Pro Arg His Tyr Cys Val Ile Leu Asp Pro Met Gly Pro Asp Gly
290 295 300

Lys Asn Gln Leu Gly Gln Lys Arg Val Val Lys Gly Glu Lys Ser Phe
305 310 315 320

Phe Leu Gln Pro Gly Glu Arg Leu Glu Arg Gly Ile Gln Asp Val Tyr
325 330 335

Val Leu Ser Glu Gln Gln Gly Leu Leu Leu Lys Ala Leu Gln Pro Leu
340 345 350

-continued

```
Glu Gly Glu Ser Glu Lys Val Ser His Gln Ala Gly Asp Cys
    355             360             365
Trp Leu Ile Arg Gly Pro Leu Glu Tyr Val Pro Ser Ala Lys Val Glu
    370             375             380
Val Val Glu Glu Arg Gln Ala Ile Pro Leu Asp Gln Asn Glu Gly Ile
385             390             395             400
Tyr Val Gln Asp Val Lys Thr Gly Lys Val Arg Ala Val Ile Gly Ser
            405             410             415
Thr Tyr Met Leu Thr Gln Asp Glu Val Leu Trp Lys Glu Leu Pro
            420             425             430
Ser Gly Val Glu Glu Leu Leu Asn Leu Gly His Asp Pro Leu Ala Asp
            435             440             445
Arg Gly Gln Lys Gly Thr Ala Lys Pro Leu Gln Pro Ser Ala Pro Arg
    450             455             460
Asn Lys Thr Arg Val Val Ser Tyr Arg Val Pro His Asn Ala Ala Val
465             470             475             480
Gln Val Tyr Asp Tyr Arg Ala Lys Arg Ala Arg Val Val Phe Gly Pro
            485             490             495
Glu Leu Val Thr Leu Asp Pro Glu Glu Gln Phe Thr Val Leu Ser Leu
            500             505             510
Ser Ala Gly Arg Pro Lys Arg Pro His Ala Arg Arg Ala Leu Cys Leu
            515             520             525
Leu Leu Gly Pro Asp Phe Phe Thr Asp Val Ile Thr Ile Glu Thr Ala
    530             535             540
Asp His Ala Arg Leu Gln Leu Gln Leu Ala Tyr Asn Trp His Phe Glu
545             550             555             560
Leu Lys Asn Arg Asn Asp Pro Ala Glu Ala Lys Leu Phe Ser Val
            565             570             575
Pro Asp Phe Val Gly Asp Ala Cys Lys Ala Ile Ala Ser Arg Val Arg
            580             585             590
Gly Ala Val Ala Ser Val Thr Phe Asp Asp Phe His Lys Asn Ser Ala
            595             600             605
Arg Ile Ile Arg Met Ala Val Phe Gly Phe Glu Met Ser Glu Asp Thr
    610             615             620
Gly Pro Asp Gly Thr Leu Leu Pro Lys Ala Arg Asp Gln Ala Val Phe
625             630             635             640
Pro Gln Asn Gly Leu Val Val Ser Ser Val Asp Val Gln Ser Val Glu
            645             650             655
Pro Val Asp Gln Arg Thr Arg Asp Ala Leu Gln Arg Ser Val Gln Leu
            660             665             670
Ala Ile Glu Ile Thr Thr Asn Ser Gln Glu Ala Ala Lys His Glu
            675             680             685
Ala Gln Arg Leu Glu Gln Glu Ala Arg Gly Arg Leu Glu Arg Gln Lys
    690             695             700
Ile Leu Asp Gln Ser Glu Ala Glu Lys Ala Arg Lys Glu Leu Leu Glu
705             710             715             720
Leu Glu Ala Met Ser Met Ala Val Glu Ser Thr Gly Asn Ala Lys Ala
            725             730             735
Glu Ala Glu Ser Arg Ala Glu Ala Arg Ile Glu Gly Glu Gly Ser
            740             745             750
Val Leu Gln Ala Lys Leu Lys Ala Gln Ala Leu Ala Ile Glu Thr Glu
            755             760             765
```

| Ala | Glu | Leu | Glu | Arg | Val | Lys | Lys | Val | Arg | Glu | Met | Glu | Leu | Ile | Tyr |
| | 770 | | | | 775 | | | | | 780 | | | | | |

| Ala | Arg | Ala | Gln | Leu | Glu | Leu | Glu | Val | Ser | Lys | Ala | Gln | Gln | Leu | Asn |
| 785 | | | | | 790 | | | | | 795 | | | | | 800 |

| Val | Glu | Ala | Lys | Lys | Phe | Lys | Glu | Met | Thr | Glu | Ala | Leu | Gly | Pro | Gly |
| | | | | 805 | | | | | 810 | | | | | 815 | |

| Thr | Ile | Arg | Asp | Leu | Ala | Val | Ala | Gly | Pro | Glu | Met | Gln | Val | Lys | Leu |
| | | | 820 | | | | | 825 | | | | | 830 | | |

| Leu | Gln | Ser | Leu | Gly | Leu | Lys | Ser | Thr | Leu | Ile | Thr | Asp | Gly | Ser | Ser |
| | | | 835 | | | | | 840 | | | | | 845 | | |

| Pro | Ile | Asn | Leu | Phe | Ser | Thr | Ala | Phe | Gly | Leu | Leu | Gly | Leu | Gly | Ser |
| 850 | | | | | 855 | | | | | 860 | | | | | |

| Asp | Gly | Gln | Pro | Pro | Ala | Gln | Lys | Phe | Asn | Met | Gln | Gln | Gln | Arg | Arg |
| 865 | | | | | 870 | | | | | 875 | | | | | 880 |

| Phe | Tyr | Glu | Ala | Leu | His | Asp | Pro | Asn | Leu | Asn | Glu | Glu | Gln | Arg | Asn |
| | | | | | 885 | | | | | 890 | | | | | 895 |

| Ala | Lys | Ile | Lys | Ser | Ile | Arg | Asp | Asp |
| | | | | 900 | | | | 905 |

<210> SEQ ID NO 35
<211> LENGTH: 2808
<212> TYPE: DNA
<213> ORGANISM: Artificial Sequence
<220> FEATURE:
<223> OTHER INFORMATION: CP-rMVP-Z cDNA based on Rattus norvegicus

<400> SEQUENCE: 35

```
gaattcgcgg ccgcgtcgac tgtggcttgc agctgccagc taccctgcta atgtttggt      60
gggaaaagct tgggattcac catggcaggc tgcggttgtc catgcggttg tggcgccatg    120
gcaactgaag aggccatcat ccgcatcccc ccataccact acatccatgt gctggaccag    180
aacagtaatg tgtcccgtgt ggaggttgga ccaaagacct acatccggca ggacaatgag    240
agggtactgt ttgccccagt tcgcatggtg accgtccccc cacgccacta ctgcatagtg    300
gccaaccctg tgtcccggga cacccagagt tctgtgttat ttgacatcac aggacaagtc    360
cgactccggc acgctgacca ggagatccga ctagcccagg accccttccc cctgtatcca    420
ggggaggtgc tggaaaagga catcacccca ctgcaggtgg ttctgcccaa cacagcactg    480
catcttaagg cgttgctgga ctttgaggat aagaatggag acaaggtcat ggcaggagac    540
gagtggctat ttgagggacc tggcacctac atcccacaga aggaagtgga agtcgtggag    600
atcattcagg ccacagtcat caaacagaac caagcactgc ggctaagggc ccgaaaggag    660
tgctttgacc gggagggcaa ggggcgcgtg acaggtgagg agtggctggt ccgatccgtg    720
ggggcttacc tcccagctgt ctttgaagag gtgctggatc tggtggatgc tgtgatcctt    780
acagaaaaga ctgccctgca cctccgggct ctgcagaact tcagggacct tcggggagtg    840
ctccaccgca ccggggagga atggttagta acagtgcagg acacagaagc ccatgttcca    900
gatgtctatg aggaggtgct tgggtagta cccatcacca ccctgggacc tcgacactac    960
tgtgtcattc ttgacccaat gggaccagac ggcaagaacc agctgggaca aaagcgtgtt   1020
gtcaaggag agaagtcctt tttcctccag ccaggagaga ggctggagcg aggcatccag   1080
gatgtgtatg tgctgtcaga gcagcagggg ctgctactga aggcactgca gcccctggag   1140
gagggagaga gcgaggagaa ggtctcccat caggccggag actgctggct catccgtggg   1200
ccccctggagt atgtgccatc tgcaaaagtg gaggtggtgg aggagcgtca ggctatccct   1260
```

```
ctggaccaaa atgagggcat ctatgtgcag gatgtcaaga cggggaaggt gcgggctgtg   1320
attggaagca cctacatgct gactcaggat gaagtcctgt gggaaaagga gctgccttct   1380
ggggtggagg agctgctgaa cttggggcat gaccctctgg cagacagggg tcagaagggc   1440
acagccaagc cccttcagcc ctcagctcca aggaacaaga cccgagtggt cagctaccgt   1500
gtcccgcaca atgcagcggt gcaggtctat gactacagag ccaagagagc ccgtgtggtc   1560
tttgggcccg agctagtgac actggatcct gaggagcagt tcacagtatt gtcccttttct   1620
gccgggcgac ccaagcgtcc tcatgcccgc cgtgcactct gcctactgct gggacctgat   1680
ttctttactg atgtcatcac catcgaaact gcagatcatg ccaggttgca gctgcagctt   1740
gcctacaact ggcactttga actgaagaac cggaatgacc ctgcagaggc agccaagctt   1800
ttctccgtgc ctgacttcgt gggtgacgcc tgcaaggcca ttgcatcccg agtccggggg   1860
gctgtagcct ctgtcacctt tgatgacttc cataaaaact cagcccggat cattcgaatg   1920
gctgttttg gctttgagat gtctgaagac acaggtcctg atggcacact cctgcccaag   1980
gctcgagacc aggcagtctt tccccaaaac gggctggtag tcagcagtgt ggatgtgcag   2040
tcagtggagc ccgtggacca gaggacccgg gatgcccttc agcgcagcgt tcagctggcc   2100
atcgaaatta ccaccaactc ccaggaggca gcagccaagc acgaggctca gagactggaa   2160
caggaagccc gtggtcggct tgagaggcag aagatcttgg accagtcaga agctgaaaaa   2220
gcccgcaagg aactcttgga gcttgaggct atgagcatgg ctgtggagag cacgggtaat   2280
gccaaagcag aggctgagtc ccgtgcagag gcagcgagga tcgaaggaga aggctctgtg   2340
ctgcaggcca agctcaaggc acaggcgcta gccattgaga cggaggctga gttggagcga   2400
gtaaagaaag tacgagagat ggaactgatc tatgcccggg cccagttgga gctggaggtg   2460
agcaaggcgc agcagcttgc caatgtggag gcaaagaagt tcaaggagat gacagaggca   2520
ctgggccccg gcaccatcag ggacctggct gtggccgggc cagagatgca ggtgaaactt   2580
ctccagtccc tgggcctgaa atccactctc atcaccgatg gctcgtctcc catcaacctc   2640
ttcagcacag ccttcgggtt gctggggctg ggtctgatg gtcagccgcc agcacagaag   2700
tttaacatgc agcagcagcg ccgcttttac gaggccctgc acgaccccaa cctgaacgag   2760
gagcagcgca acgccaagat taagagcatt cgcgacgact agggtacc             2808
```

<210> SEQ ID NO 36
<211> LENGTH: 956
<212> TYPE: PRT
<213> ORGANISM: Artificial Sequence
<220> FEATURE:
<223> OTHER INFORMATION: NS5A-NS5A-rMVP-Z domain fusion protein based on
      Hepatitis C Virus and Rattus norvegicus

<400> SEQUENCE: 36

```
Met Ala Gly Ser Trp Leu Arg Asp Ile Trp Asp Trp Ile Cys Glu Val
1               5                   10                  15

Leu Ser Asp Phe Lys Thr Trp Leu Lys Ala Lys Leu Met Pro Thr Met
            20                  25                  30

Ala Gly Ser Trp Leu Arg Asp Ile Trp Asp Trp Ile Cys Glu Val Leu
        35                  40                  45

Ser Asp Phe Lys Thr Trp Leu Lys Ala Lys Leu Met Pro Thr Met Ala
    50                  55                  60

Thr Glu Glu Ala Ile Ile Arg Ile Pro Pro Tyr His Tyr Ile His Val
65                  70                  75                  80

Leu Asp Gln Asn Ser Asn Val Ser Arg Val Glu Val Gly Pro Lys Thr
```

```
                    85                  90                  95
Tyr Ile Arg Gln Asp Asn Glu Arg Val Leu Phe Ala Pro Val Arg Met
                100                 105                 110
Val Thr Val Pro Pro Arg His Tyr Cys Ile Val Ala Asn Pro Val Ser
                115                 120                 125
Arg Asp Thr Gln Ser Ser Val Leu Phe Asp Ile Thr Gly Gln Val Arg
                130                 135                 140
Leu Arg His Ala Asp Gln Glu Ile Arg Leu Ala Gln Asp Pro Phe Pro
145                 150                 155                 160
Leu Tyr Pro Gly Glu Val Leu Glu Lys Asp Ile Thr Pro Leu Gln Val
                165                 170                 175
Val Leu Pro Asn Thr Ala Leu His Leu Lys Ala Leu Leu Asp Phe Glu
                180                 185                 190
Asp Lys Asn Gly Asp Lys Val Met Ala Gly Asp Glu Trp Leu Phe Glu
                195                 200                 205
Gly Pro Gly Thr Tyr Ile Pro Gln Lys Glu Val Glu Val Glu Ile
                210                 215                 220
Ile Gln Ala Thr Val Ile Lys Gln Asn Gln Ala Leu Arg Leu Arg Ala
225                 230                 235                 240
Arg Lys Glu Cys Phe Asp Arg Glu Gly Lys Gly Arg Val Thr Gly Glu
                245                 250                 255
Glu Trp Leu Val Arg Ser Val Gly Ala Tyr Leu Pro Ala Val Phe Glu
                260                 265                 270
Glu Val Leu Asp Leu Val Asp Ala Val Ile Leu Thr Glu Lys Thr Ala
                275                 280                 285
Leu His Leu Arg Ala Leu Gln Asn Phe Arg Asp Leu Arg Gly Val Leu
                290                 295                 300
His Arg Thr Gly Glu Glu Trp Leu Val Thr Val Gln Asp Thr Glu Ala
305                 310                 315                 320
His Val Pro Asp Val Tyr Glu Glu Val Leu Gly Val Val Pro Ile Thr
                325                 330                 335
Thr Leu Gly Pro Arg His Tyr Cys Val Ile Leu Asp Pro Met Gly Pro
                340                 345                 350
Asp Gly Lys Asn Gln Leu Gly Gln Lys Arg Val Val Lys Gly Glu Lys
                355                 360                 365
Ser Phe Phe Leu Gln Pro Gly Glu Arg Leu Glu Arg Gly Ile Gln Asp
                370                 375                 380
Val Tyr Val Leu Ser Glu Gln Gln Gly Leu Leu Leu Lys Ala Leu Gln
385                 390                 395                 400
Pro Leu Glu Glu Gly Glu Ser Glu Glu Lys Val Ser His Gln Ala Gly
                    405                 410                 415
Asp Cys Trp Leu Ile Arg Gly Pro Leu Glu Tyr Val Pro Ser Ala Lys
                420                 425                 430
Val Glu Val Glu Glu Arg Gln Ala Ile Pro Leu Asp Gln Asn Glu
                435                 440                 445
Gly Ile Tyr Val Gln Asp Val Lys Thr Gly Lys Val Arg Ala Val Ile
                450                 455                 460
Gly Ser Thr Tyr Met Leu Thr Gln Asp Glu Val Leu Trp Glu Lys Glu
465                 470                 475                 480
Leu Pro Ser Gly Val Glu Glu Leu Leu Asn Leu Gly His Asp Pro Leu
                    485                 490                 495
Ala Asp Arg Gly Gln Lys Gly Thr Ala Lys Pro Leu Gln Pro Ser Ala
                500                 505                 510
```

```
Pro Arg Asn Lys Thr Arg Val Ser Tyr Arg Val Pro His Asn Ala
        515                 520                 525

Ala Val Gln Val Tyr Asp Tyr Arg Ala Lys Arg Ala Arg Val Val Phe
    530                 535                 540

Gly Pro Glu Leu Val Thr Leu Asp Pro Glu Glu Gln Phe Thr Val Leu
545                 550                 555                 560

Ser Leu Ser Ala Gly Arg Pro Lys Arg Pro His Ala Arg Arg Ala Leu
            565                 570                 575

Cys Leu Leu Leu Gly Pro Asp Phe Phe Thr Asp Val Ile Thr Ile Glu
            580                 585                 590

Thr Ala Asp His Ala Arg Leu Gln Leu Gln Leu Ala Tyr Asn Trp His
        595                 600                 605

Phe Glu Leu Lys Asn Arg Asn Asp Pro Ala Glu Ala Lys Leu Phe
        610                 615                 620

Ser Val Pro Asp Phe Val Gly Asp Ala Cys Lys Ala Ile Ala Ser Arg
625                 630                 635                 640

Val Arg Gly Ala Val Ala Ser Val Thr Phe Asp Asp Phe His Lys Asn
                645                 650                 655

Ser Ala Arg Ile Ile Arg Met Ala Val Phe Gly Phe Glu Met Ser Glu
                660                 665                 670

Asp Thr Gly Pro Asp Gly Thr Leu Leu Pro Lys Ala Arg Asp Gln Ala
            675                 680                 685

Val Phe Pro Gln Asn Gly Leu Val Val Ser Ser Val Asp Val Gln Ser
    690                 695                 700

Val Glu Pro Val Asp Gln Arg Thr Arg Asp Ala Leu Gln Arg Ser Val
705                 710                 715                 720

Gln Leu Ala Ile Glu Ile Thr Thr Asn Ser Gln Glu Ala Ala Ala Lys
                725                 730                 735

His Glu Ala Gln Arg Leu Glu Gln Glu Ala Arg Gly Arg Leu Glu Arg
            740                 745                 750

Gln Lys Ile Leu Asp Gln Ser Glu Ala Glu Lys Ala Arg Lys Glu Leu
    755                 760                 765

Leu Glu Leu Glu Ala Met Ser Met Ala Val Glu Ser Thr Gly Asn Ala
770                 775                 780

Lys Ala Glu Ala Glu Ser Arg Ala Glu Ala Ala Arg Ile Glu Gly Glu
785                 790                 795                 800

Gly Ser Val Leu Gln Ala Lys Leu Lys Ala Gln Ala Leu Ala Ile Glu
                805                 810                 815

Thr Glu Ala Glu Leu Glu Arg Val Lys Lys Val Arg Glu Met Glu Leu
            820                 825                 830

Ile Tyr Ala Arg Ala Gln Leu Glu Leu Glu Val Ser Lys Ala Gln Gln
    835                 840                 845

Leu Ala Asn Val Glu Ala Lys Lys Phe Lys Glu Met Thr Glu Ala Leu
850                 855                 860

Gly Pro Gly Thr Ile Arg Asp Leu Ala Val Ala Gly Pro Glu Met Gln
865                 870                 875                 880

Val Lys Leu Leu Gln Ser Leu Gly Leu Lys Ser Thr Leu Ile Thr Asp
                885                 890                 895

Gly Ser Ser Pro Ile Asn Leu Phe Ser Thr Ala Phe Gly Leu Leu Gly
            900                 905                 910

Leu Gly Ser Asp Gly Gln Pro Pro Ala Gln Lys Phe Asn Met Gln Gln
            915                 920                 925
```

-continued

```
Gln Arg Arg Phe Tyr Glu Ala Leu His Asp Pro Asn Leu Asn Glu Glu
        930             935             940

Gln Arg Asn Ala Lys Ile Lys Ser Ile Arg Asp Asp
945             950             955
```

What is claimed is:

1. A major vault protein having a non-structural protein 5A (NS5A) amphipathic a-helix structure fused to its N-terminus, wherein the sequence of the major vault protein has at least 90% sequence identity to SEQ ID NO: 5.

2. The major vault protein of claim 1, wherein the NS5A amphipathic α-helix structure comprises SEQ ID NO: 19.

3. The major vault protein of claim 1, wherein the NS5A amphipathic comprises SEQ ID NO: 17.

4. The major vault protein of claim 1, further comprising a peptide fused to its C-terminus.

5. The major vault protein of claim 4, wherein the peptide comprises the Z domain of Staphylococcal Protein A (SpA) or a sequence having SEQ ID NO:18.

6. The major vault protein of claim 1, wherein the major vault protein has at least 95% sequence identity to SEQ ID NO: 5.

7. The major vault protein of claim 1, wherein the major vault protein has at least 90% sequence identity to SEQ ID NO: 5 and the NSSA amphipathic α-helix structure comprises SEQ ID NO: 19.

8. A composition comprising the major vault protein according to claim 1.

9. The composition of claim 8, further comprising a therapeutic compound and/or a lipophilic substance.

10. The composition of claim 9, wherein therapeutic compound is selected from the group consisting of All-trans Retinoic Acid (ATRA), amphotericin B, bryostatin 1, GSK744, MK-2048, IQP0528, 5-chloro-3-phenylsulfonylindole-2-carboxamide (CSIS), and dapivirine.

11. The composition of claim 8, further comprising a hydrogel.

12. The composition of claim 8, further comprising a thermally responsive polymer.

13. A method of delivering a peptide to a subject which comprises administering the major vault protein according to claim 4 to the subject.

14. A method of delivering a therapeutic compound and/or a lipophilic substance to a subject, which comprises administering the composition according to claim 9 to the subject.

* * * * *